United States Patent
Won et al.

(10) Patent No.: US 12,144,249 B2
(45) Date of Patent: Nov. 12, 2024

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Jongwoo Won, Suwon-si (KR); Dong Wan Ryu, Suwon-si (KR); Hayun Song, Suwon-si (KR); Eunhye An, Suwon-si (KR); Hyung Sun Kim, Suwon-si (KR); Jinhyun Lui, Suwon-si (KR); Mijin Lee, Suwon-si (KR); Hyungyu Lee, Suwon-si (KR); Sung-Hyun Jung, Suwon-si (KR); Ho Kuk Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 720 days.

(21) Appl. No.: 17/371,257

(22) Filed: Jul. 9, 2021

(65) Prior Publication Data

US 2022/0020933 A1 Jan. 20, 2022

(30) Foreign Application Priority Data

Jul. 17, 2020 (KR) .......................... 10-2020-0088630

(51) Int. Cl.
*C07D 491/147* (2006.01)
*C07D 209/86* (2006.01)
*C09K 11/06* (2006.01)
*H10K 85/60* (2023.01)
*H10K 50/11* (2023.01)
*H10K 101/10* (2023.01)

(52) U.S. Cl.
CPC ......... *H10K 85/654* (2023.02); *C07D 209/86* (2013.01); *C07D 491/147* (2013.01); *C09K 11/06* (2013.01); *H10K 85/657* (2023.02); *H10K 85/6572* (2023.02); *C09K 2211/1018* (2013.01); *H10K 50/11* (2023.02); *H10K 2101/10* (2023.02)

(58) Field of Classification Search
None
See application file for complete search history.

(56) References Cited

U.S. PATENT DOCUMENTS

| 5,061,569 | A | 10/1991 | VanSlyke et al. |
| 9,755,157 | B2 | 9/2017 | Lee et al. |
| 2016/0155955 | A1* | 6/2016 | Yokoyama ............ C09B 57/007 548/417 |
| 2017/0237017 | A1 | 8/2017 | Parham et al. |
| 2018/0339994 | A1 | 11/2018 | Kudo et al. |
| 2021/0163427 | A1* | 6/2021 | Kim ..................... H10K 85/657 |

FOREIGN PATENT DOCUMENTS

| CN | 102754238 A | 10/2012 |
| CN | 106397398 A | 2/2017 |
| CN | 106467516 A | 3/2017 |
| CN | 106661007 A | 5/2017 |
| CN | 111269243 A | 6/2020 |
| CN | 112851687 A | 5/2021 |
| EP | 2535958 A1 | 12/2012 |
| EP | 3009438 A1 | 4/2016 |
| JP | 1993-009471 A | 1/1993 |
| JP | 1995-126615 A | 5/1995 |
| JP | 1998-095973 A | 4/1998 |
| JP | 5581341 B2 | 7/2014 |
| JP | 2014-528942 A | 10/2014 |
| JP | 6387311 B2 | 9/2018 |
| JP | 2019-201042 A | 11/2019 |
| KR | 10-2011-0016288 A | 2/2011 |
| KR | 10-2011-0102055 A | 9/2011 |
| KR | 10-1108512 B1 | 1/2012 |
| KR | 10-2013-0052485 A | 5/2013 |
| KR | 10-2013-0114785 A | 10/2013 |
| KR | 10-2014-0009838 A | 1/2014 |
| KR | 10-2014-0136722 A | 12/2014 |
| KR | 10-2015-0095186 A | 8/2015 |
| KR | 10-2015-0136452 A | 12/2015 |
| KR | 10-2015-0143553 A | 12/2015 |

(Continued)

OTHER PUBLICATIONS

Machine translation of KR-20160028737-A, translation generated Apr. 2024, 30 pages. (Year: 2024).*

Chinese Office Action (including a search report) dated May 24, 2023, of the corresponding Chinese Patent Application No. 202110806850.0.

*Primary Examiner* — Robert S Loewe
(74) *Attorney, Agent, or Firm* — Lee IP Law, P.C.

(57) ABSTRACT

A compound for an organic optoelectronic device, a composition for an organic optoelectronic device including the same, an organic optoelectronic device, and a display device, the compound being represented by Chemical Formula 1:

[Chemical Formula 1]

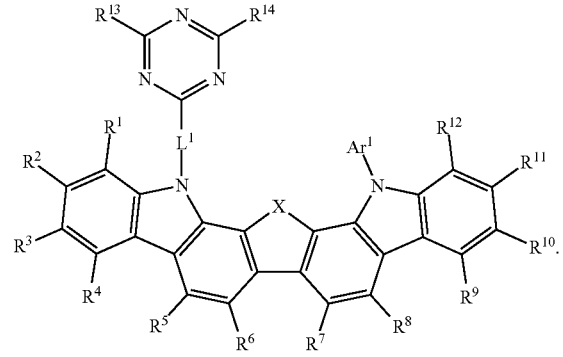

20 Claims, 1 Drawing Sheet

(56) References Cited

FOREIGN PATENT DOCUMENTS

| KR | 10-2016-0019486 A | 2/2016 |
|----|-------------------|--------|
| KR | 10-2016-0026136 A | 3/2016 |
| KR | 10-2016-0028737 A | 3/2016 |
| KR | 10-1680093 B1 | 11/2016 |
| KR | 10-2017-0041886 A | 4/2017 |
| KR | 10-1777883 B1 | 9/2017 |
| KR | 10-1793392 B1 | 11/2017 |
| KR | 10-2018-0023625 A | 3/2018 |
| KR | 10-2018-0042146 A | 4/2018 |
| KR | 10-2019-0007968 A | 1/2019 |
| KR | 10-2020-0076817 A | 6/2020 |
| KR | 10-2021-0066708 A | 6/2021 |
| WO | WO 1995/09147 A1 | 4/1995 |
| WO | WO 2011/000455 A1 | 1/2011 |
| WO | WO 2013/041176 A1 | 3/2013 |
| WO | WO 2014-010910 A1 | 1/2014 |
| WO | WO 2014/057684 A1 | 4/2014 |
| WO | WO 2014/166585 A1 | 10/2014 |
| WO | WO 2017/038728 A1 | 3/2017 |

\* cited by examiner

COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

CROSS-REFERENCE TO RELATED APPLICATION

Korean Patent Application No. 10-2020-0088630, filed on Jul. 17, 2020, in the Korean Intellectual Property Office, and entitled: "Compound for Organic Optoelectronic Device, Composition for Organic Optoelectronic Device, Organic Optoelectronic Device and Display Device," is incorporated by reference herein in its entirety.

BACKGROUND

1. Field

Embodiments relate to a compound for an organic optoelectronic device, a composition for an organic optoelectronic device, an organic optoelectronic device, and a display device.

2. Description of the Related Art

An organic optoelectronic device (e.g., organic optoelectronic diode) is a device capable of converting electrical energy and optical energy to each other.

Organic optoelectronic devices may be divided into two types according to a principle of operation. One is a photoelectric device that generates electrical energy by separating excitons formed by light energy into electrons and holes, and transferring the electrons and holes to different electrodes, respectively and the other is light emitting device that generates light energy from electrical energy by supplying voltage or current to the electrodes.

Examples of the organic optoelectronic device may include an organic photoelectric device, an organic light emitting diode, an organic solar cell, and an organic photoconductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode is greatly influenced by an organic material between electrodes.

SUMMARY

The embodiments may be realized by providing a compound for an organic optoelectronic device, the compound being represented by Chemical Formula 1:

[Chemical Formula 1]

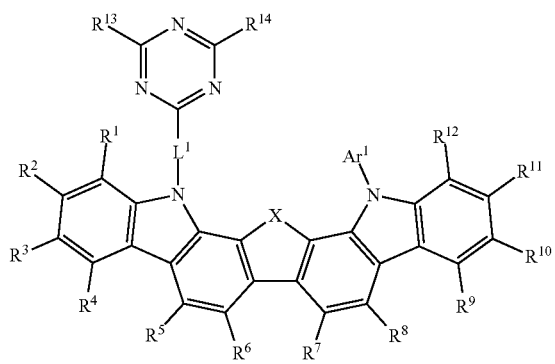

wherein, in Chemical Formula 1, X is O or S, $L^1$ is a single bond or a substituted or unsubstituted C6 to C20 arylene group, $R^1$ to $R^{12}$ are each independently hydrogen, deuterium, a substituted or unsubstituted C1 to C30 alkyl group, or a substituted or unsubstituted C6 to C20 aryl group, $R^{13}$ and $R^{14}$ are each independently a substituted or unsubstituted C6 to C30 aryl group, a substituted or unsubstituted dibenzofuranyl group, or a substituted or unsubstituted dibenzothiophenyl group, and $Ar^1$ is a substituted or unsubstituted C6 to C30 aryl group.

The embodiments may be realized by providing an organic optoelectronic device including an anode and a cathode facing each other, and at least one organic layer between the anode and the cathode, wherein the at least one organic layer includes the compound for an organic optoelectronic device according to an embodiment.

The embodiments may be realized by providing a display device including the organic optoelectronic device according to an embodiment.

The embodiments may be realized by providing an organic optoelectronic device including an anode and a cathode facing each other, and at least one organic layer between the anode and the cathode, wherein the at least one organic layer includes the composition for an organic optoelectronic device according to an embodiment.

The embodiments may be realized by providing a display device including the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
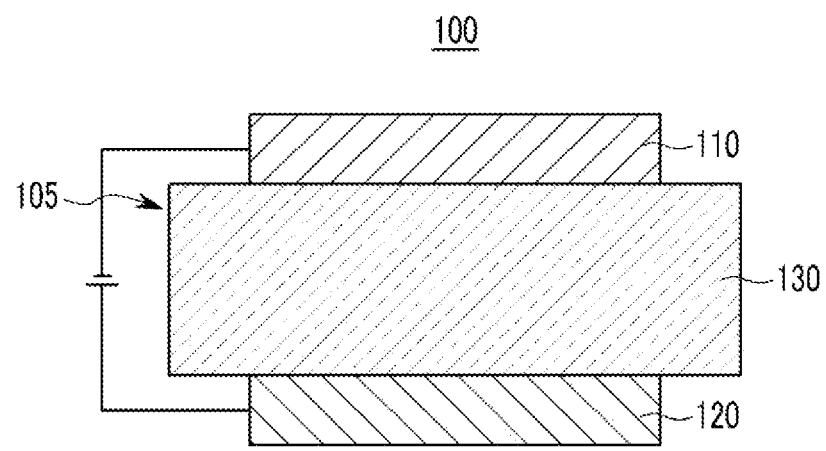
FIGS. 1 and 2 are cross-sectional views each illustrating an organic light emitting diode according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

In one example of the present disclosure, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof. As used herein, the term "or" is not an exclusive term, e.g., "A or B" would include A, B, or A and B.

In specific example of the present disclosure, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In specific example of the present disclosure, the "substituted" refers to replacement of at least one hydrogen of a substituent or a compound by deuterium, a C1 to C20 alkyl group, a C6 to C30 aryl group, or a cyano group. In specific example of the present disclosure, the "substituted" refers to replacement of at least one hydrogen of a substituent or a compound by deuterium, a C1 to C5 alkyl group, a C6 to C18 aryl group, or a cyano group. In specific example of the present disclosure, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, when a definition is not otherwise provided, "hetero" refers to one including one to three heteroatoms selected from N, O, S, P, and Si, and remaining carbons in one functional group.

As used herein, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic, or fused ring polycyclic (i.e., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

A compound for an organic optoelectronic device according to an one embodiment may be, e.g., represented by Chemical Formula 1.

[Chemical Formula 1]

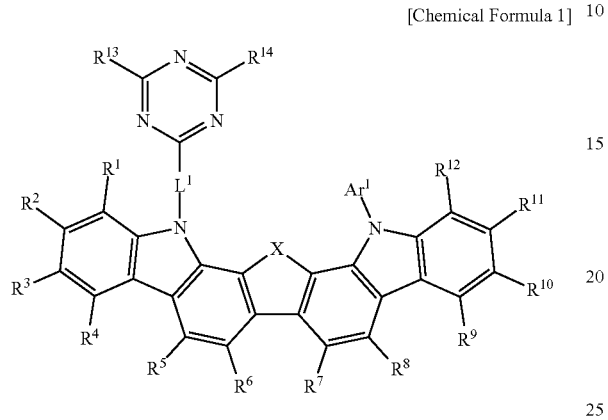

In Chemical Formula 1, X may be, e.g., O or S.

$L^1$ may be or may include, e.g., a single bond or a substituted or unsubstituted C6 to C20 arylene group.

$R^1$ to $R^{12}$ may each independently be or include, e.g., hydrogen, deuterium, a substituted or unsubstituted C1 to C30 alkyl group, or a substituted or unsubstituted C6 to C20 aryl group.

$R^{13}$ and $R^{14}$ may each independently be or include, e.g., a substituted or unsubstituted C6 to C30 aryl group, a substituted or unsubstituted dibenzofuranyl group, or a substituted or unsubstituted dibenzothiophenyl group.

$Ar^1$ may be or may include, e.g., a substituted or unsubstituted C6 to C30 aryl group.

The compound represented by Chemical Formula 1 may include a skeleton or moiety in which two carbazoles are fused centered on furan (or thiophene) at positions 1 and 2, respectively, and any one carbazole of the two carbazoles may be substituted with triazine in an N-direction (e.g., at a N-position of the carbazole).

A HOMO electron cloud may be distributed in the N direction of the carbazole on one side of the furan (or thiophene), a LUMO electron cloud may be distributed in the N direction of the carbazole on the other side of the furan (or thiophene), and the HOMO/LUMO cloud may be divided and distributed. Accordingly, the compound represented by Chemical Formula 1 may have a small ΔEST energy level, thereby securing life-span performance of an organic light emitting diode including the compound.

In an implementation, carbazole moieties may be fused around furan (or thiophene) at positions 1 and 2, respectively, separation of the HOMO/LUMO compartment may be made more clearly, and the hole transport region may be expanded to increase a life-span of a device, and improve a driving voltage and efficiency.

In an implementation, $L^1$ may be, e.g., a single bond or a substituted or unsubstituted phenylene group.

In an implementation, $L^1$ may be, e.g., a single bond, a substituted or unsubstituted ortho-phenylene group, a substituted or unsubstituted meta-phenylene group, or a substituted or unsubstituted para-phenylene group.

In an implementation, $L^1$ may be, e.g., a single bond, a substituted or unsubstituted meta-phenylene group, or a substituted or unsubstituted para-phenylene group.

In an implementation, $R^{13}$ and $R^{14}$ may each independently be, e.g., a substituted or unsubstituted phenyl group or a substituted or unsubstituted biphenyl group.

In an implementation, $R^{13}$ and $R^{14}$ may each independently be, e.g., a substituent of Group I.

[Group I]

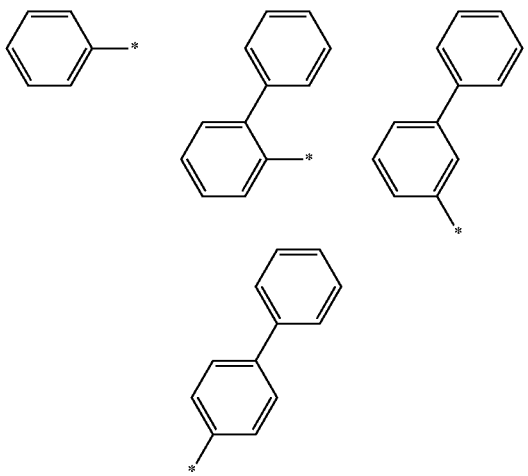

In Group I, * is a linking point.

In an implementation, $Ar^1$ may be, e.g., a substituted or unsubstituted phenyl group, a substituted or unsubstituted biphenyl group, or a substituted or unsubstituted naphthyl group.

In an implementation, $Ar^1$ may be, e.g., a substituted or unsubstituted phenyl group.

In an implementation, $R^1$ to $R^{12}$ may each independently be, e.g., hydrogen, deuterium, a substituted or unsubstituted C1 to C10 alkyl group, or a substituted or unsubstituted C6 to C12 aryl group.

In an implementation, each of $R^1$ to $R^{12}$ may be hydrogen.

In an implementation, the compound for an organic optoelectronic device represented by Chemical Formula 1 may be, e.g., a compound of Group 1.

[Group 1]

[1]

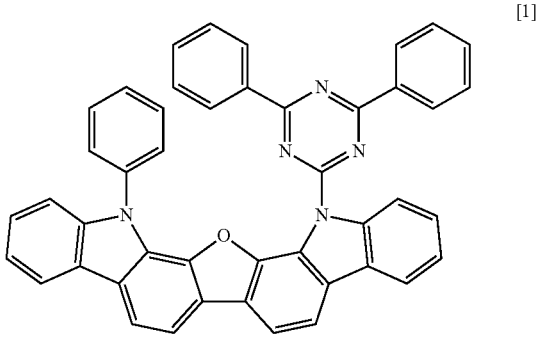

[2]
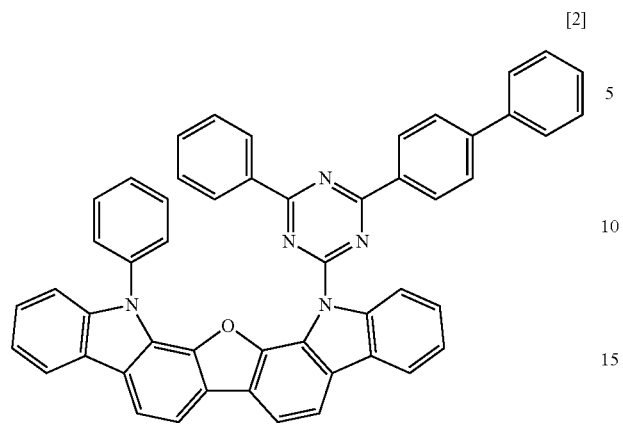
[3]
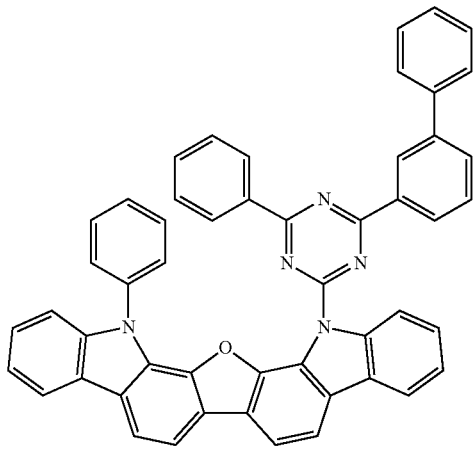
[4]
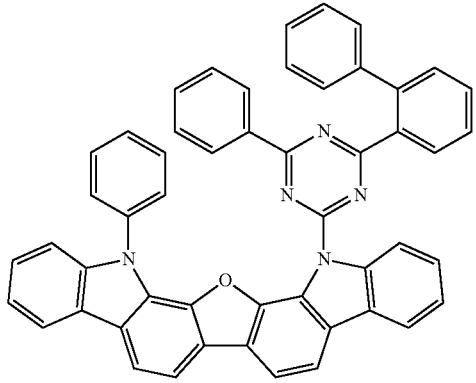
[5]
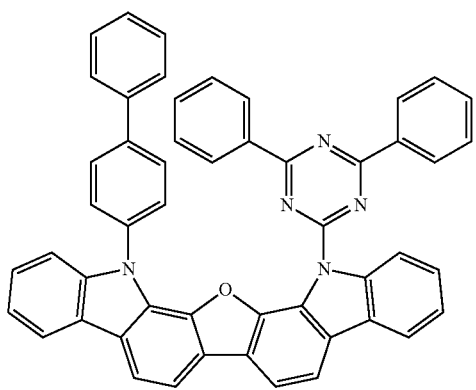
[6]
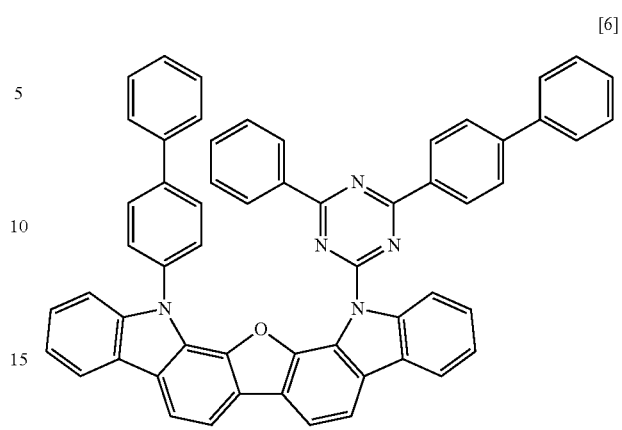
[7]
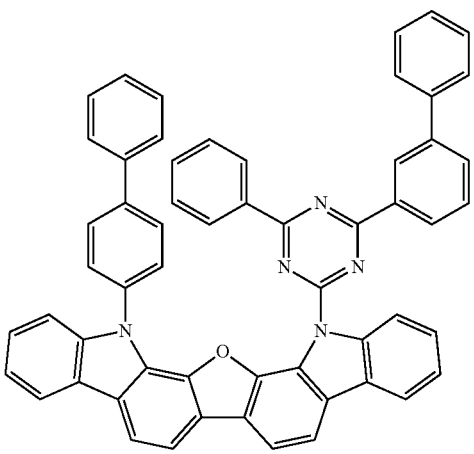
[8]
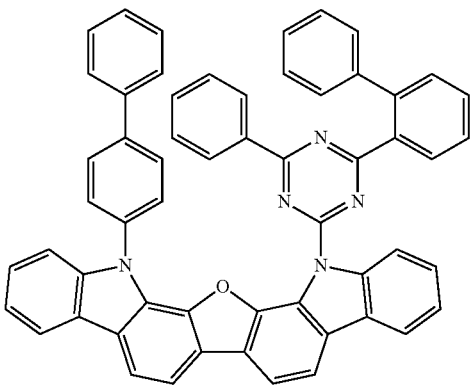
[9]
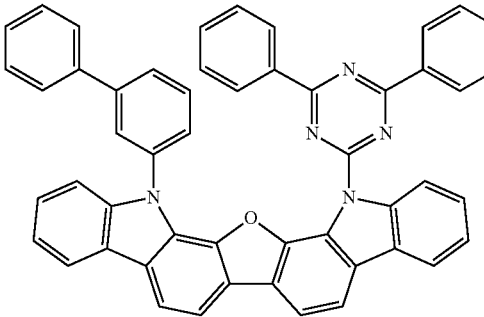

[10]
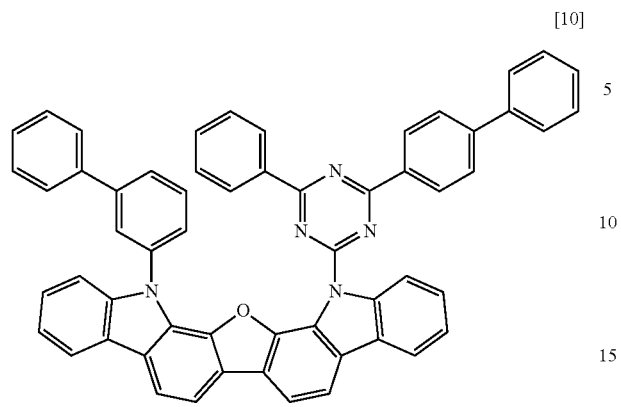
[11]
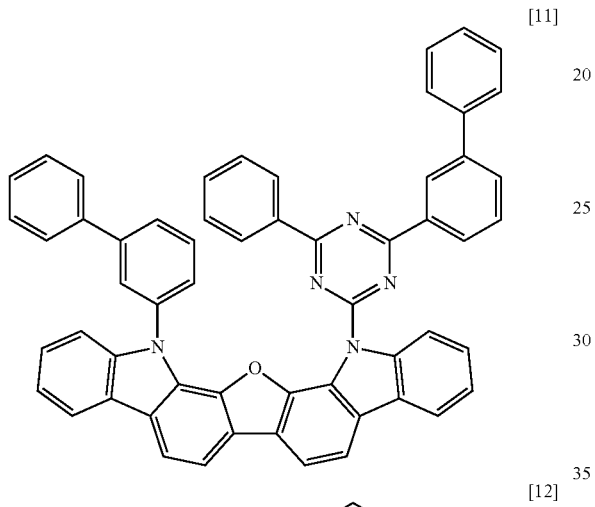
[12]
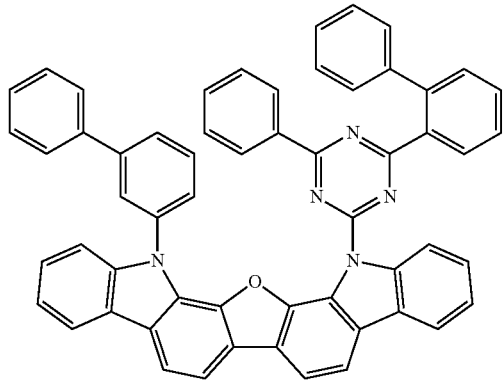
[13]
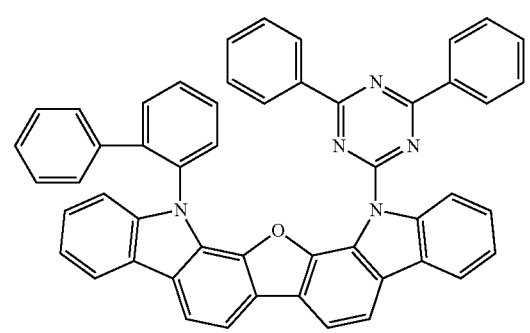
[14]
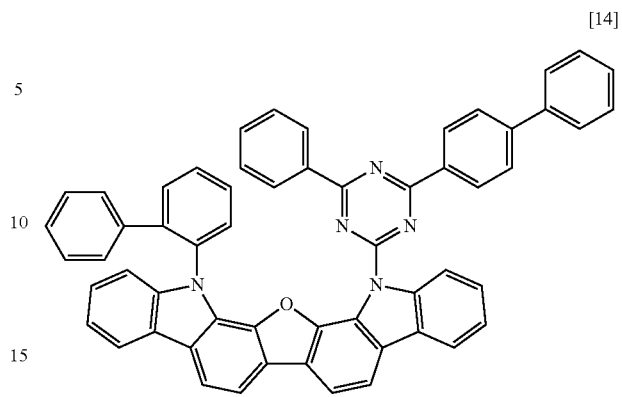
[15]
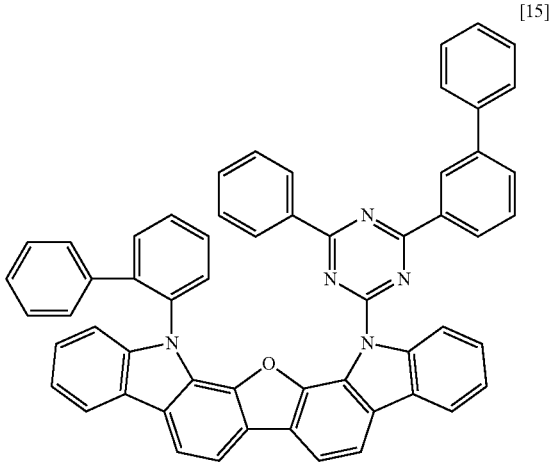
[16]
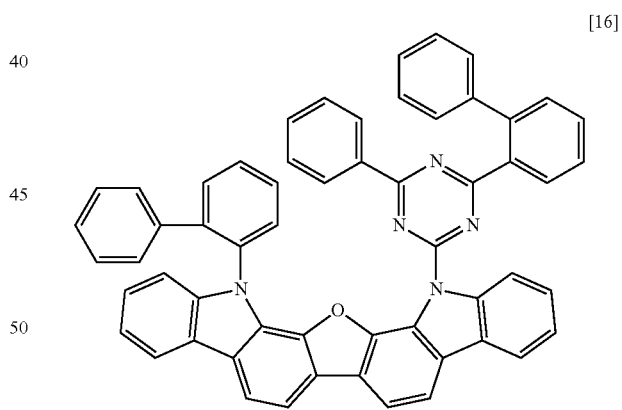
[17]
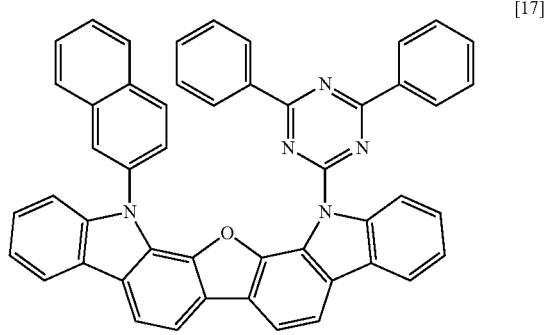

-continued
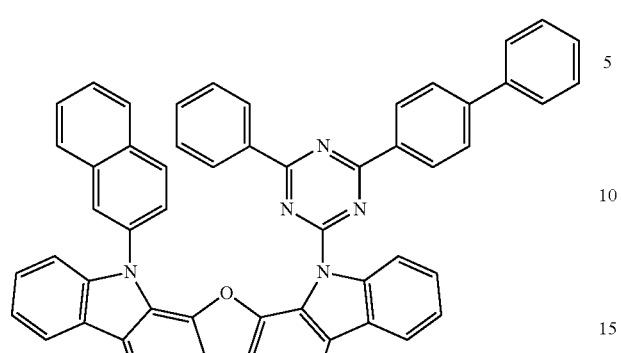
[18]
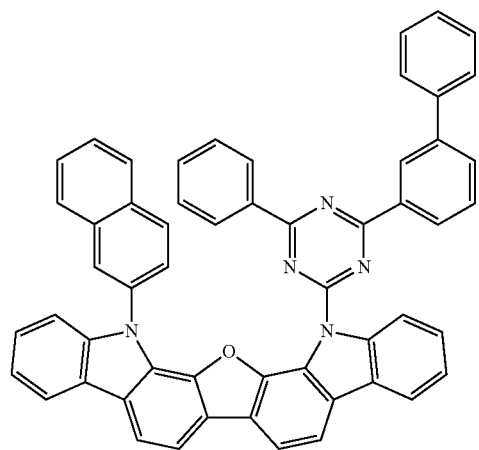
[19]
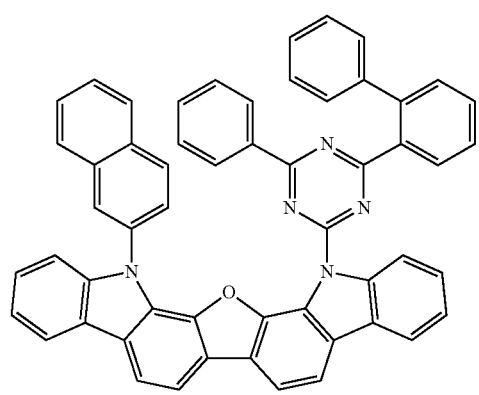
[20]
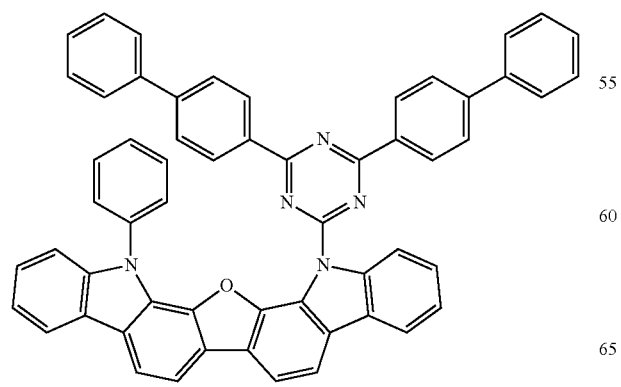
[21]
-continued
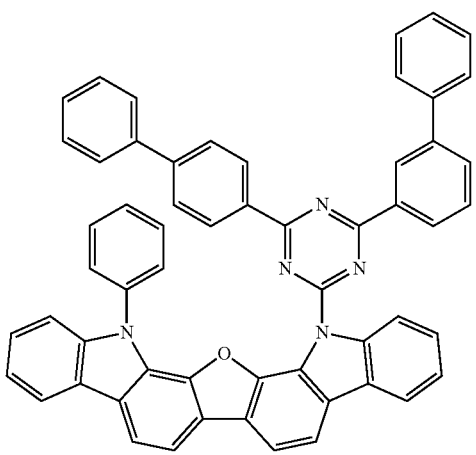
[22]
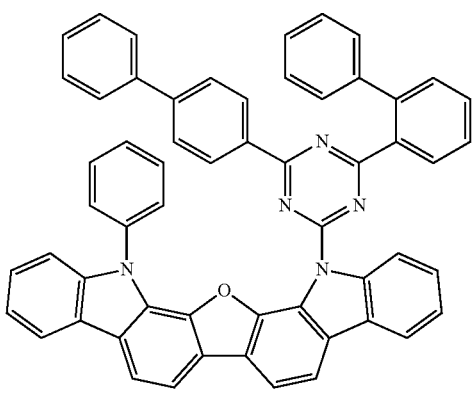
[23]
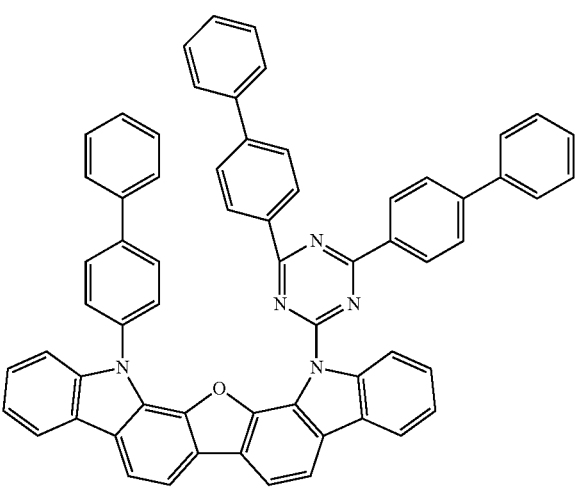
[24]

[25]
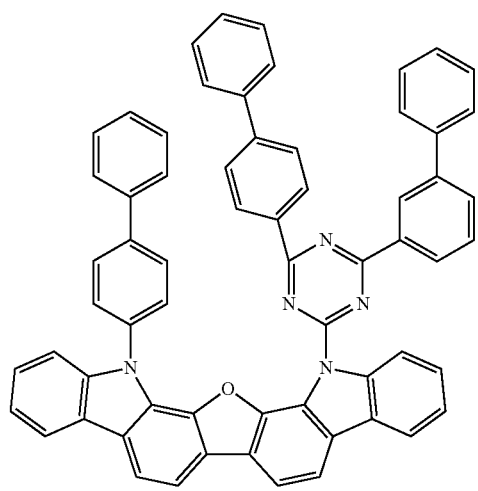
[26]
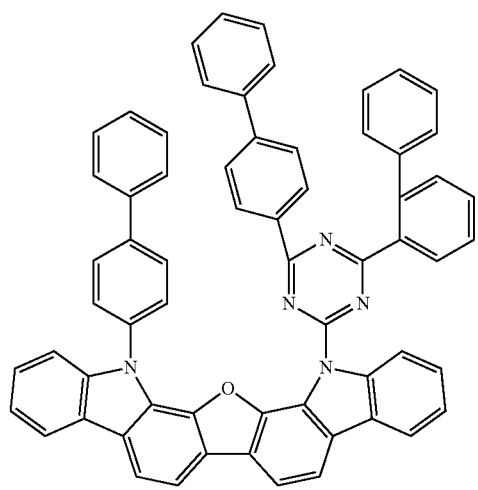
[27]
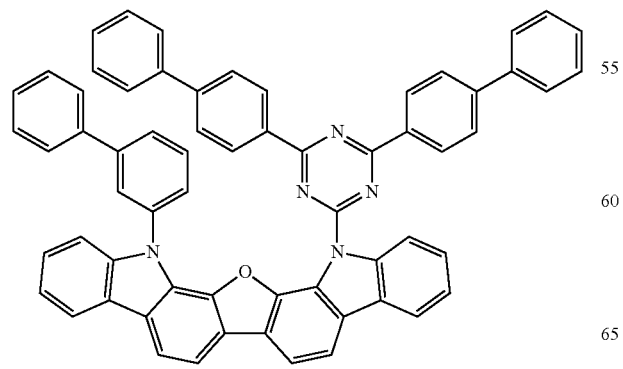
[28]
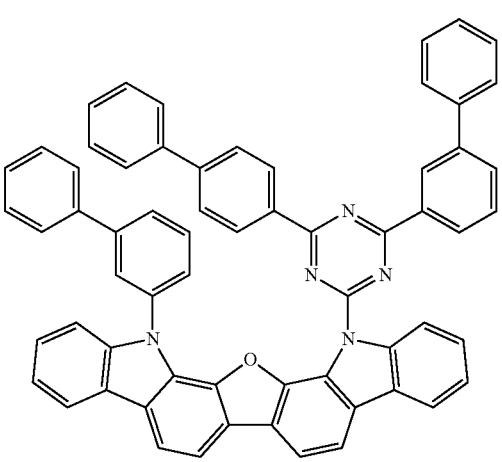
[29]
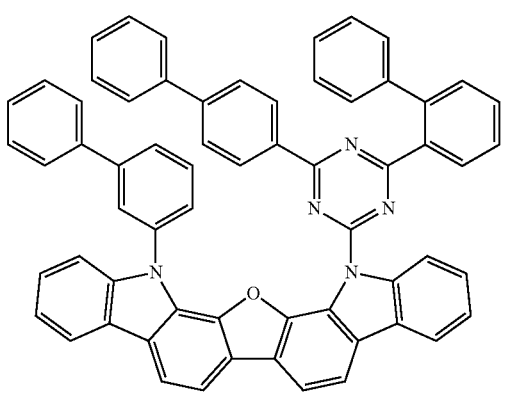
[30]

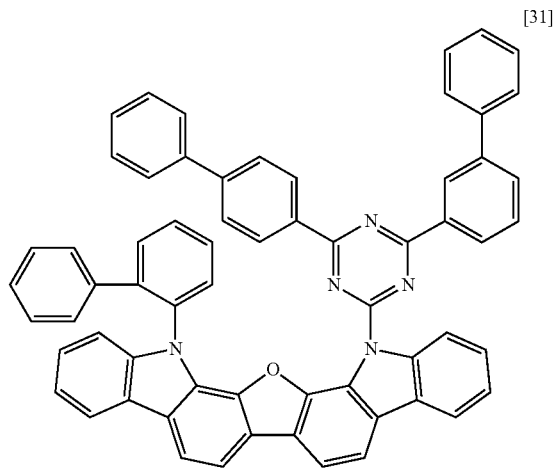
[31]
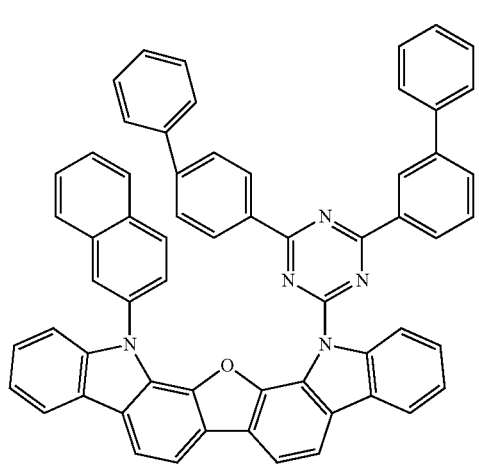
[34]
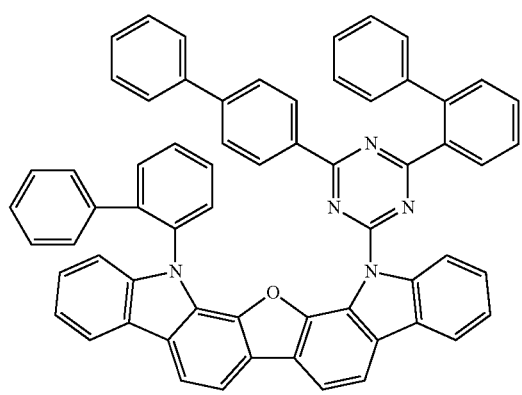
[32]
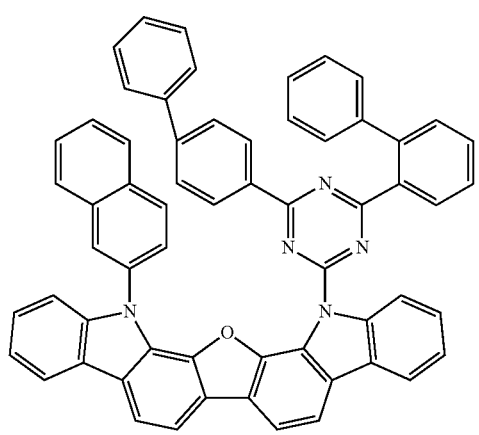
[35]
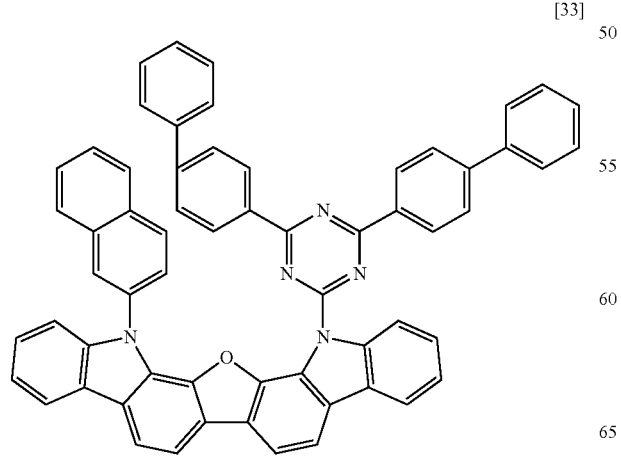
[33]
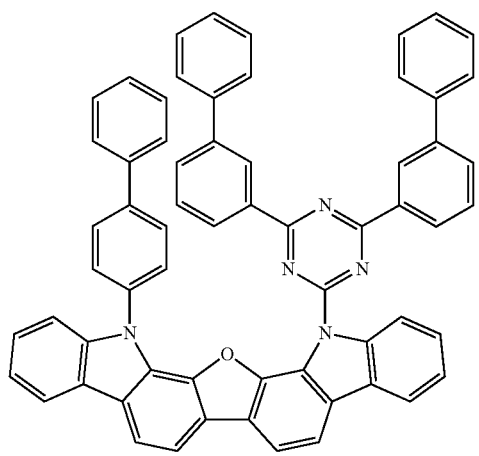
[36]

[37]
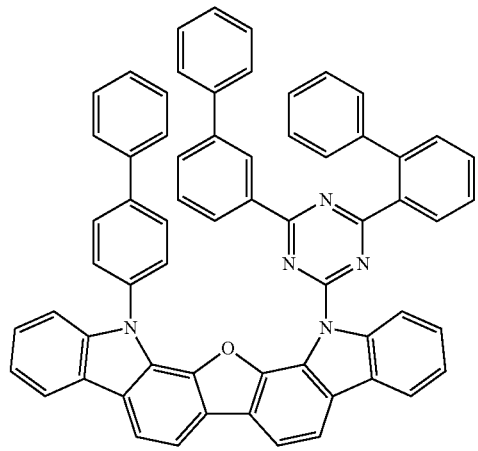
[38]
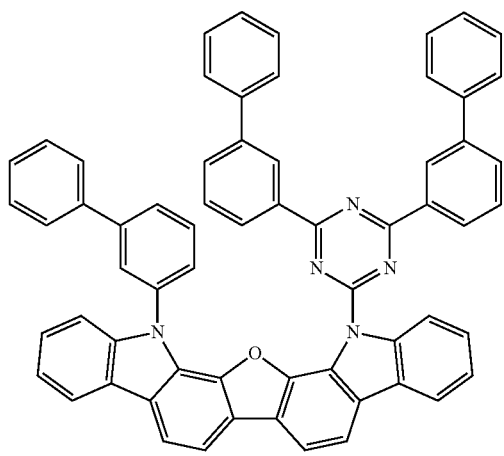
[39]
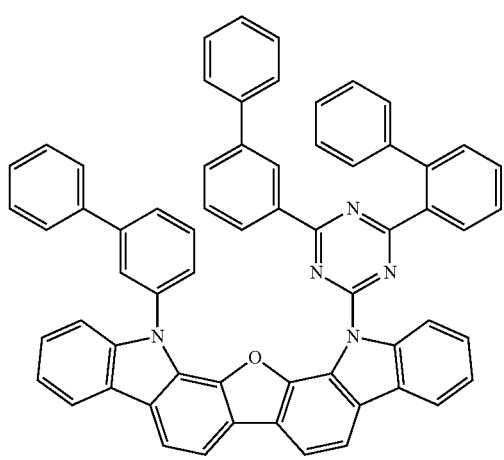
[40]
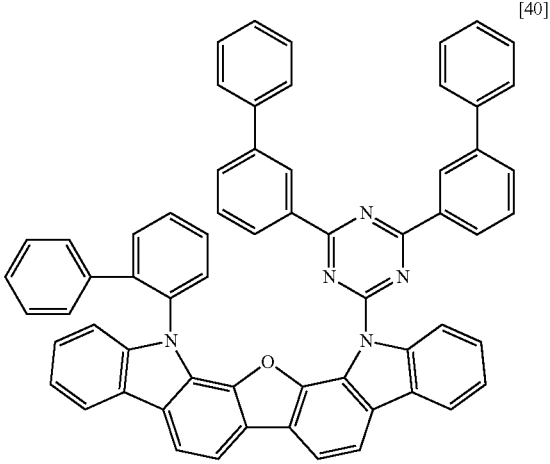
[41]
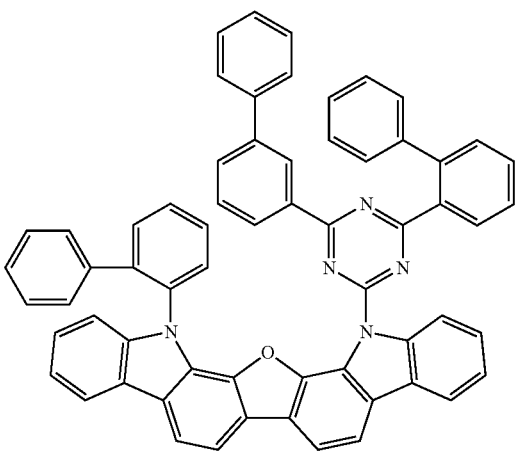
[42]
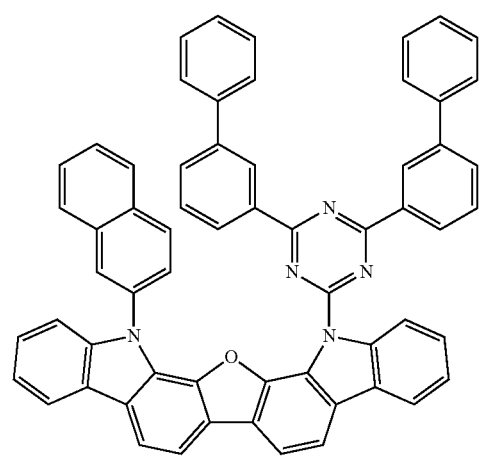

[43]
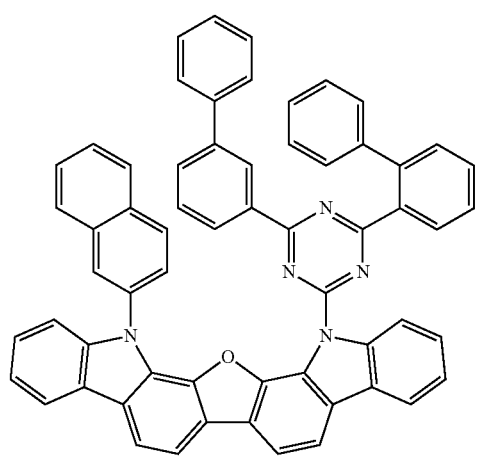
[44]
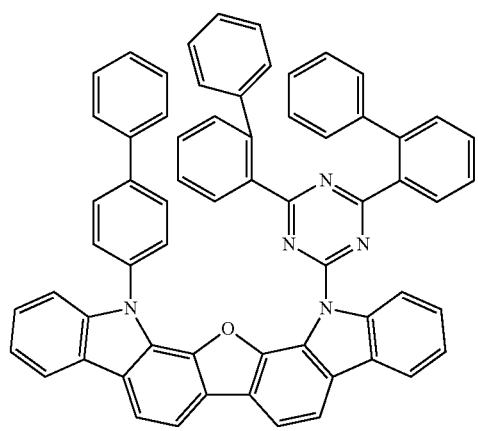
[45]
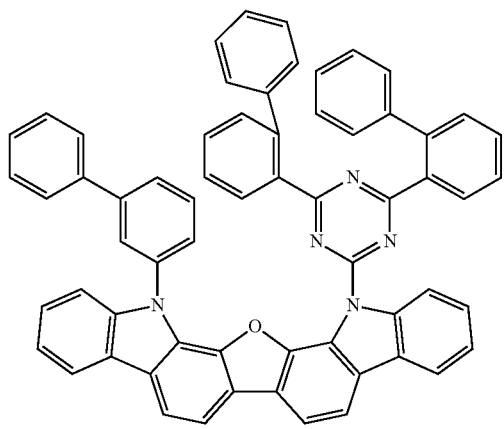
[46]
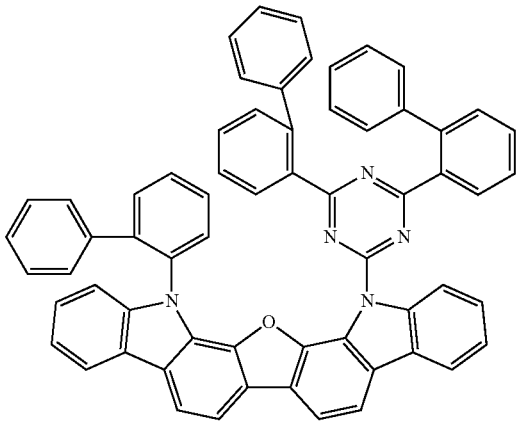
[47]
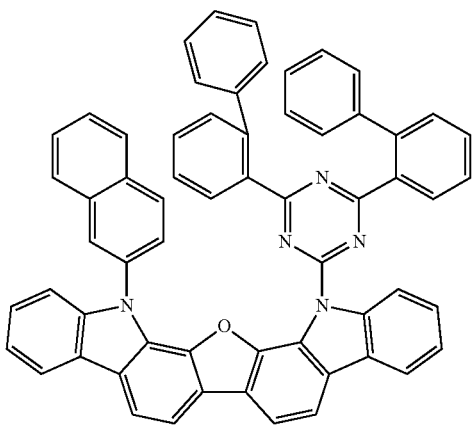
[48]
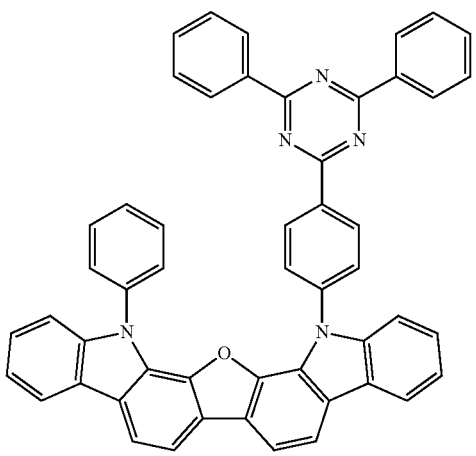

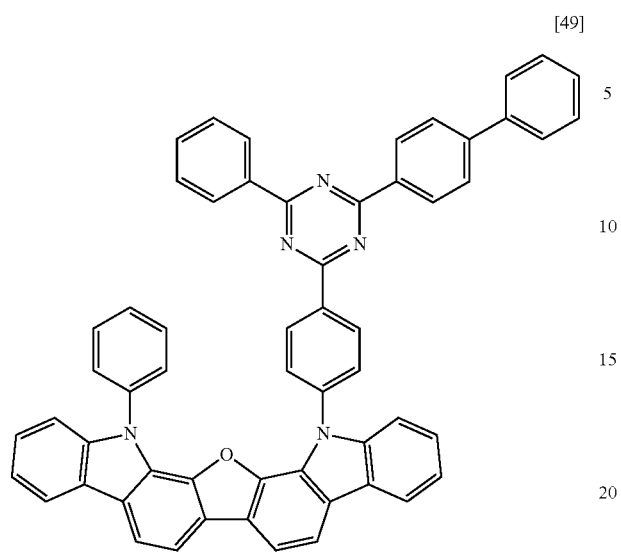
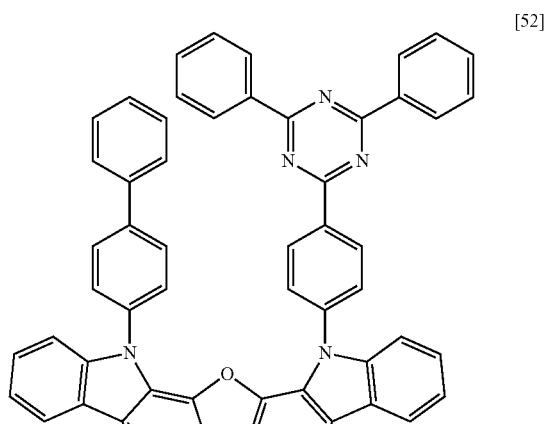
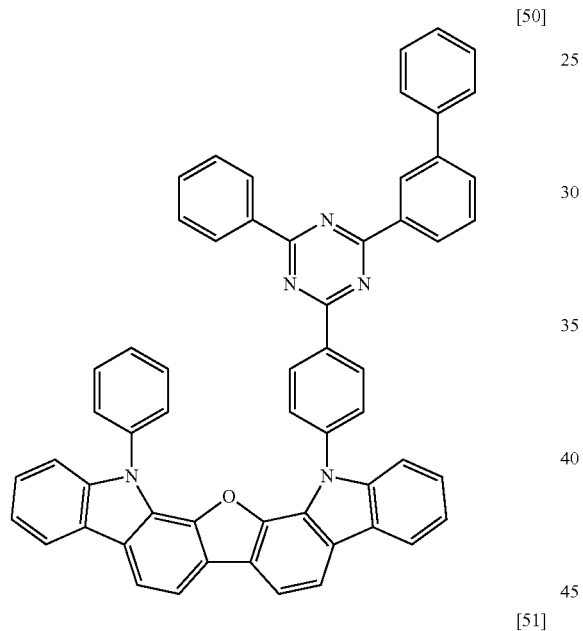
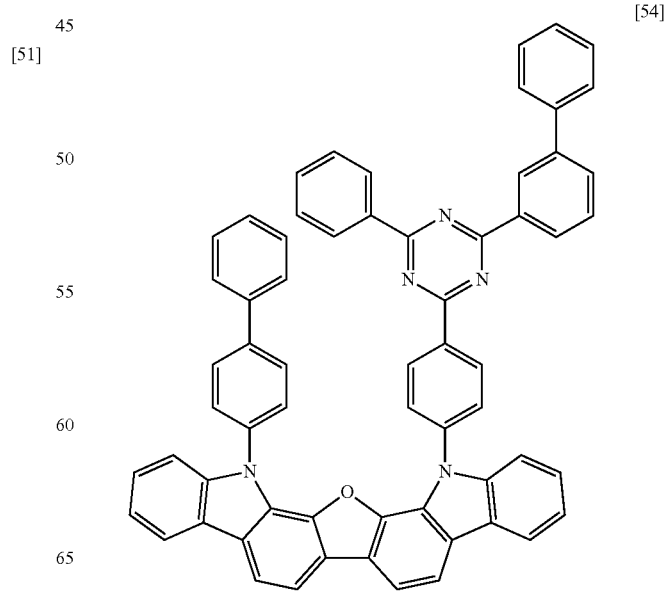

[55]
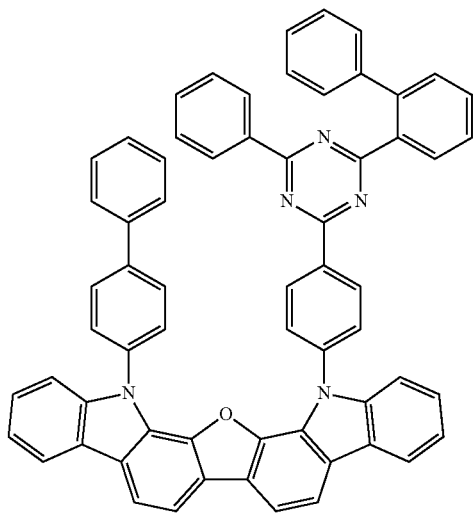
[56]
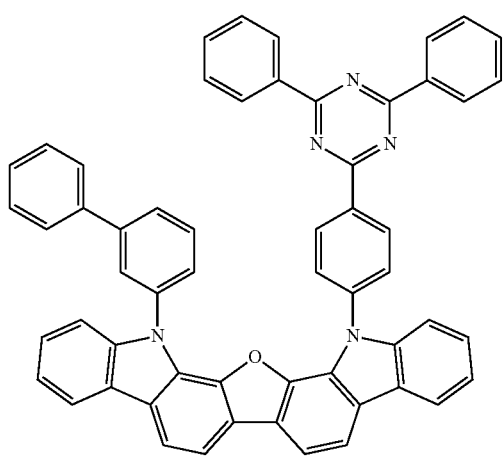
[57]
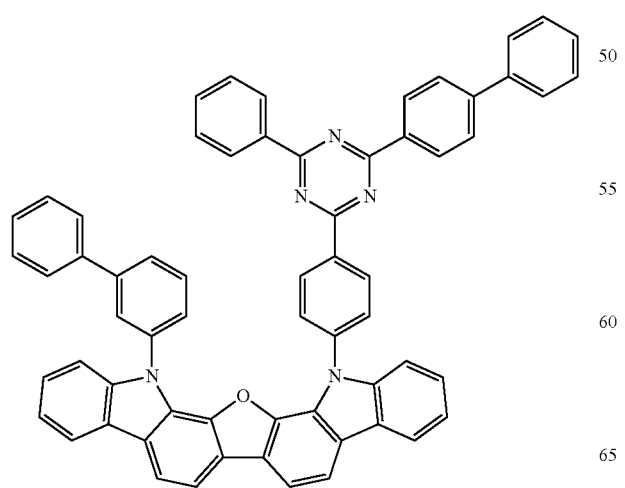
[58]
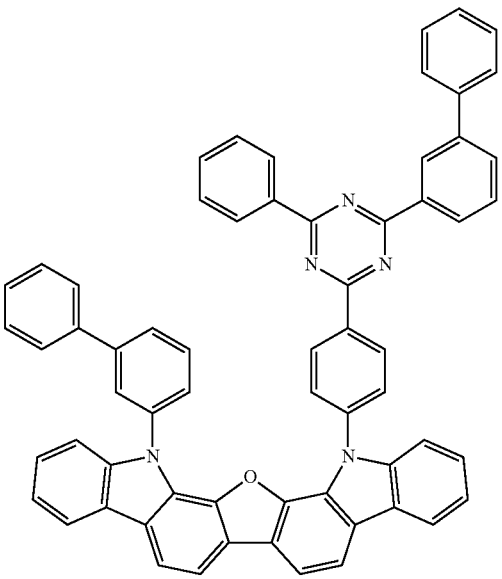
[59]
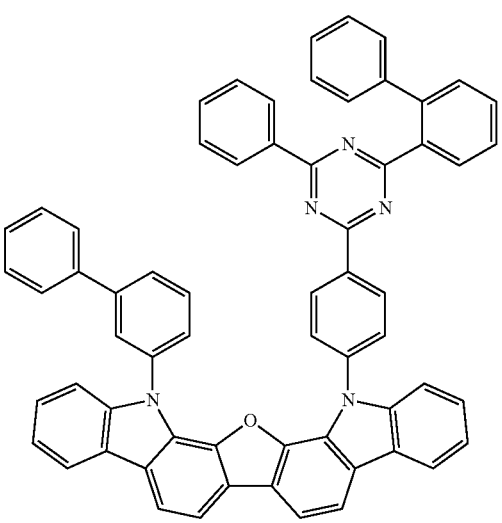
[60]
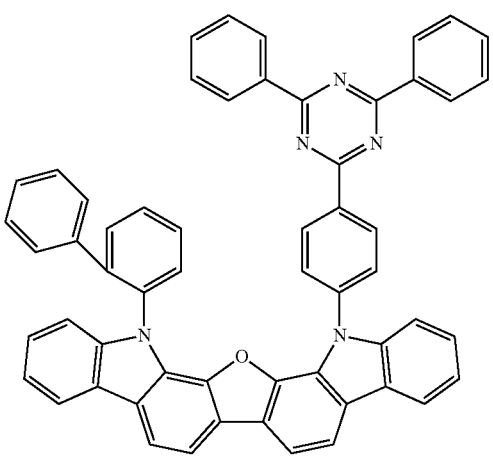

[61]
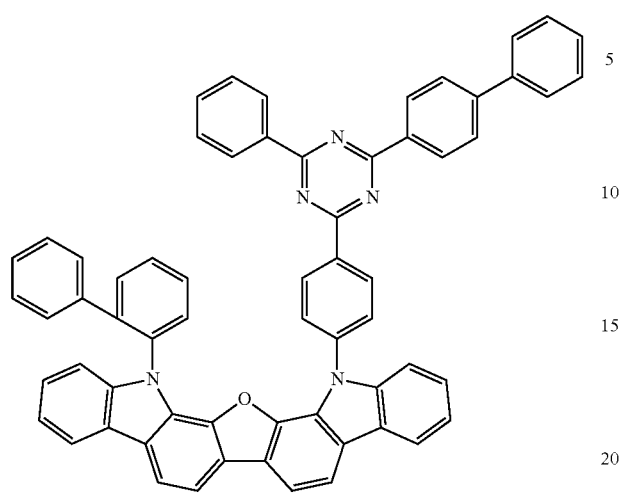
[62]
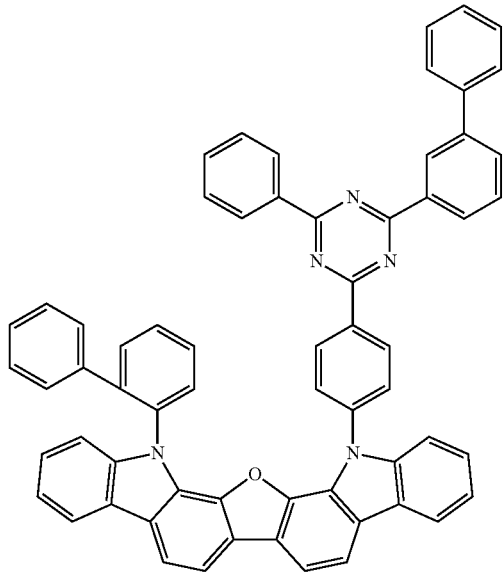
[63]
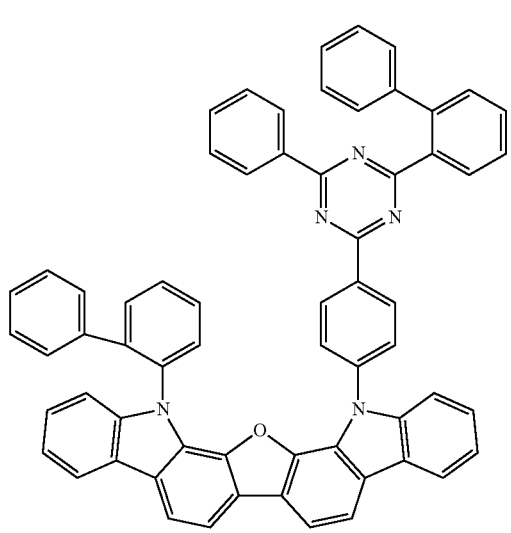
[64]
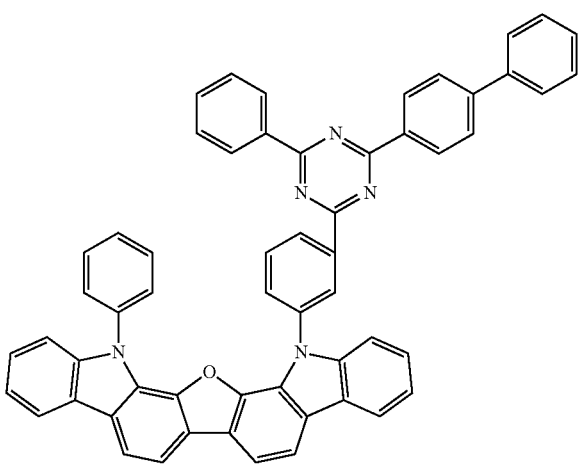
[65]
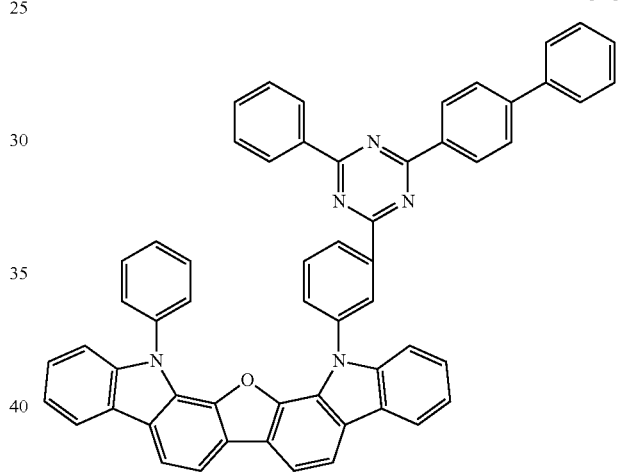
[66]
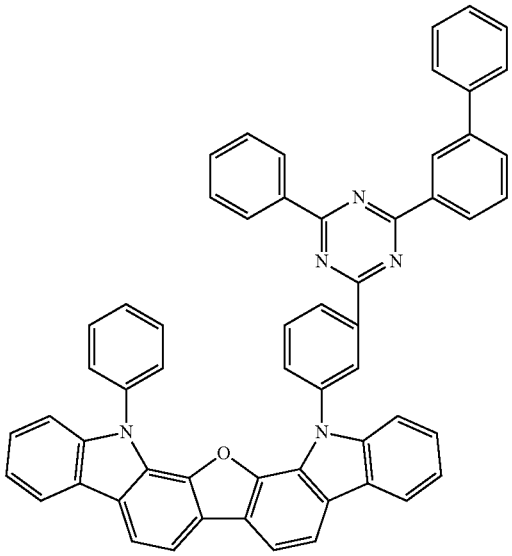

[67]
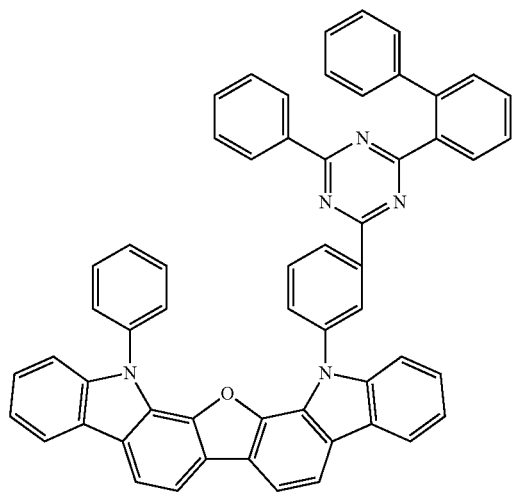
[68]
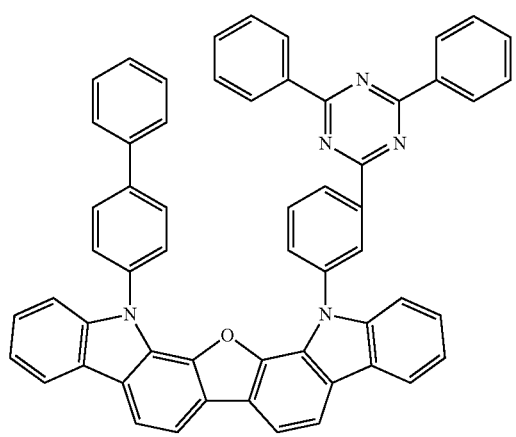
[69]
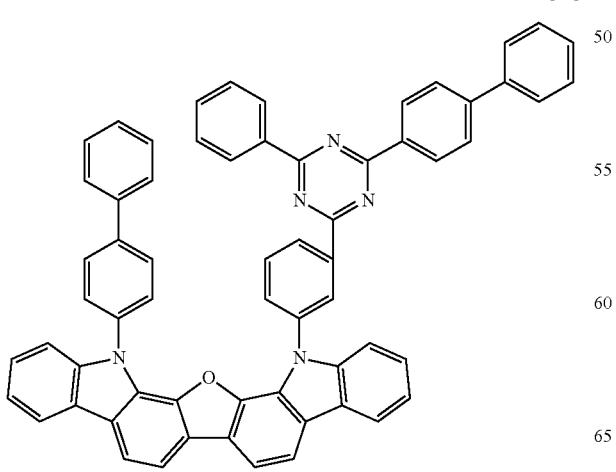
[70]
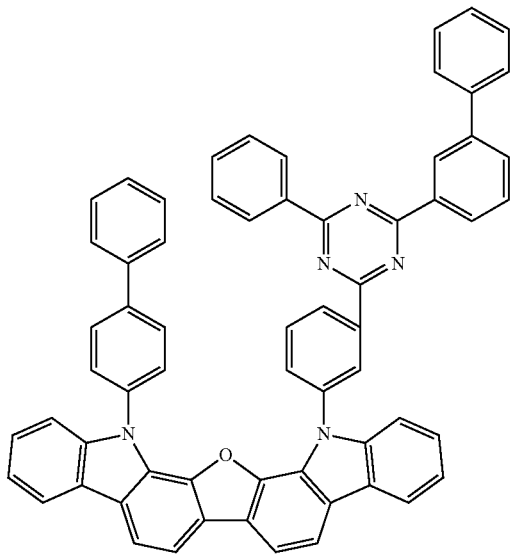
[71]
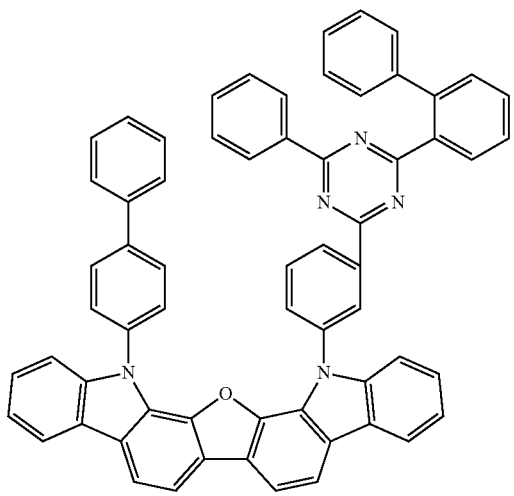
[72]
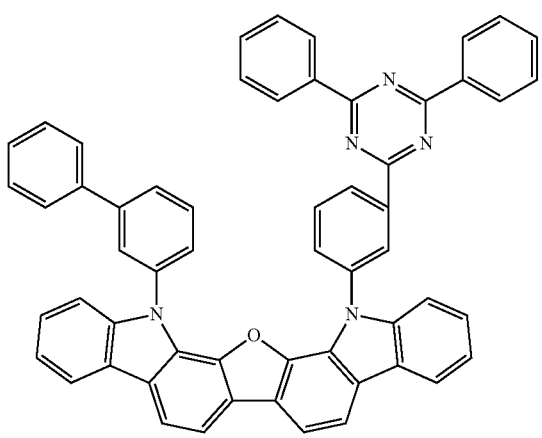

[73]
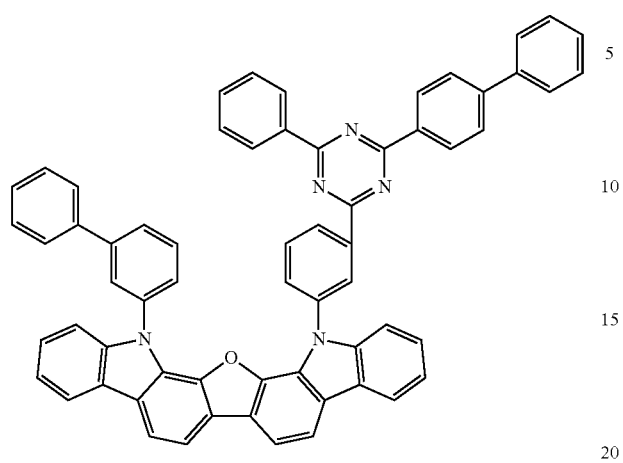
[74]
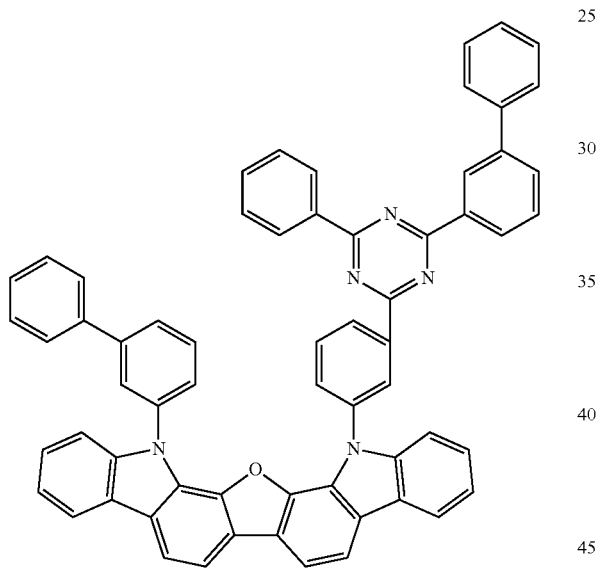
[75]
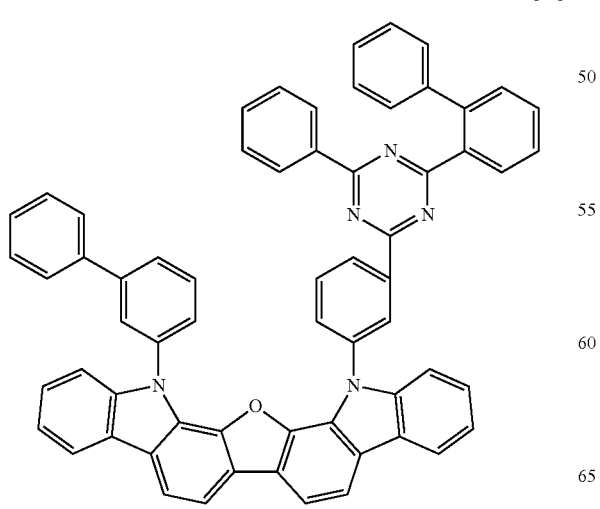
[76]
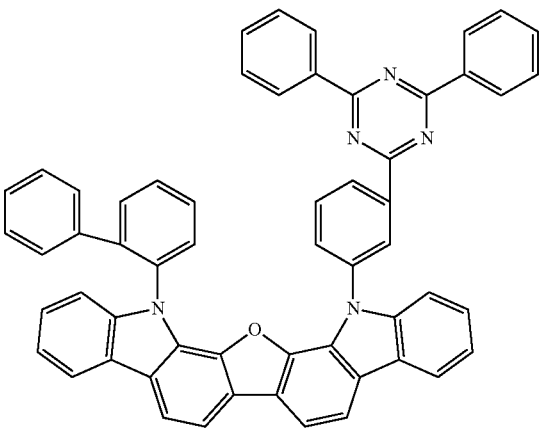
[77]
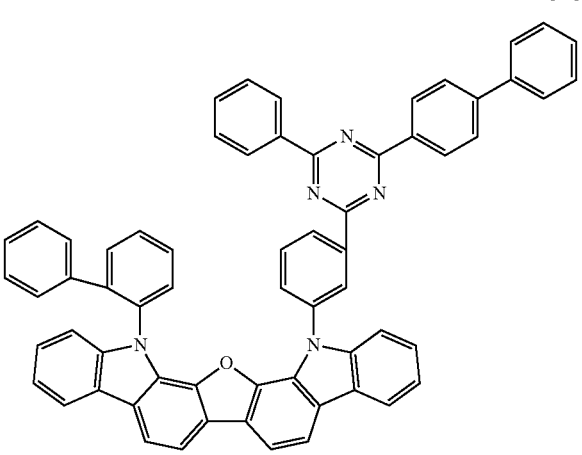
[78]
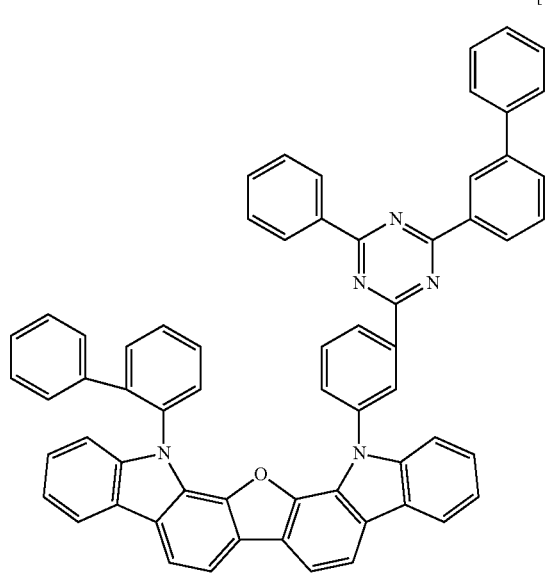

-continued
[79]
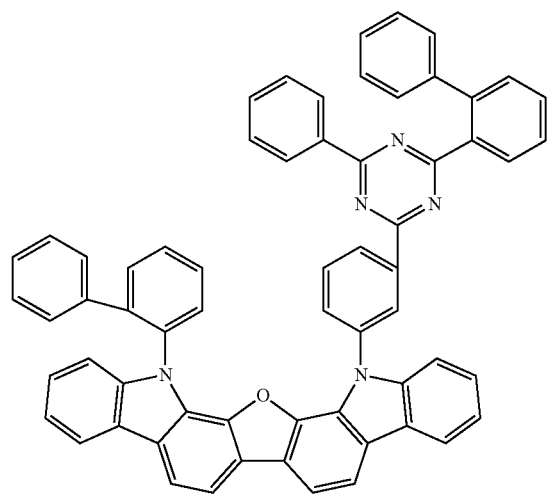
[80]
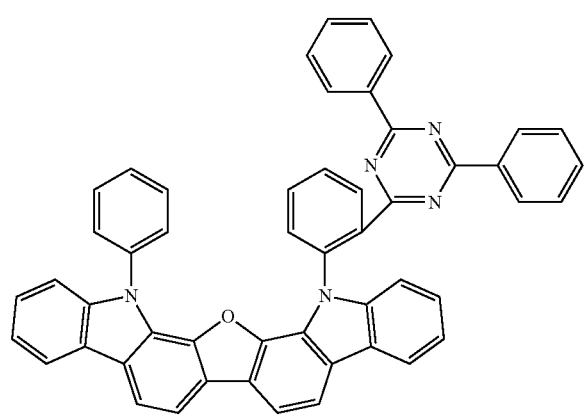
[81]
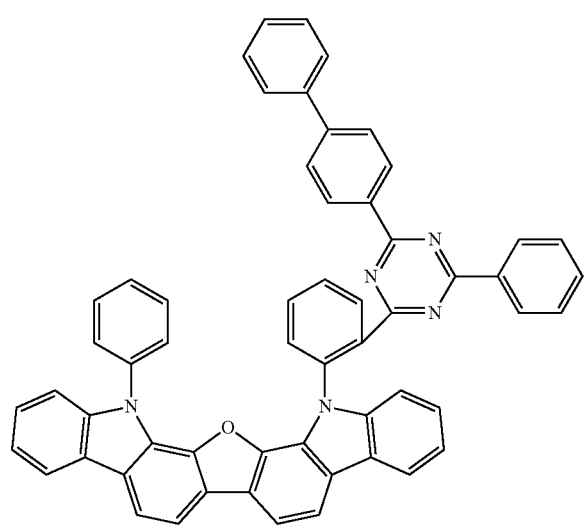
-continued
[82]
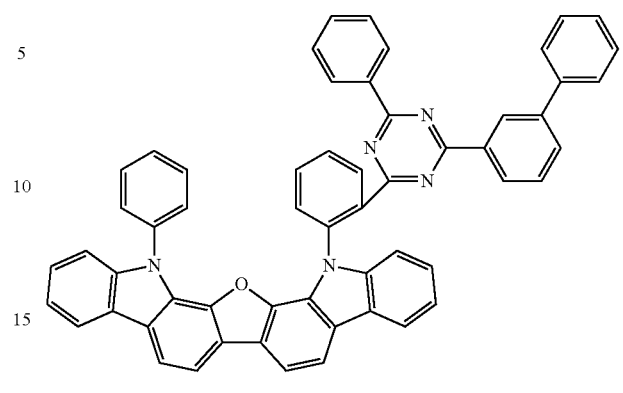
[83]
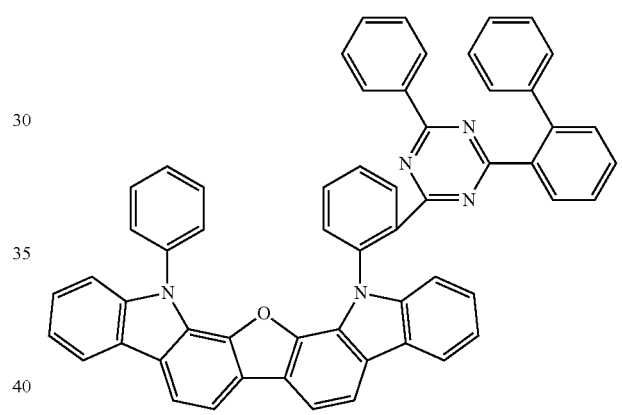
[84]
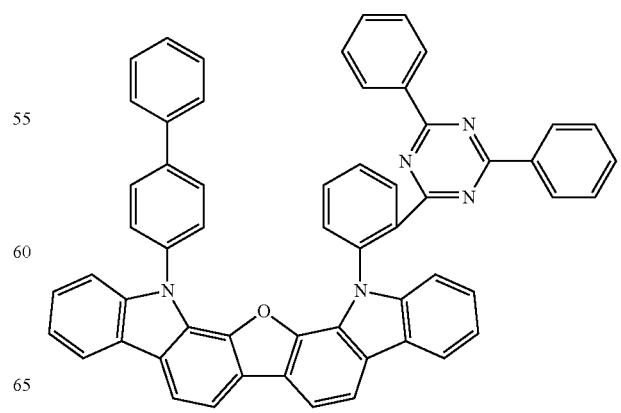

[85]
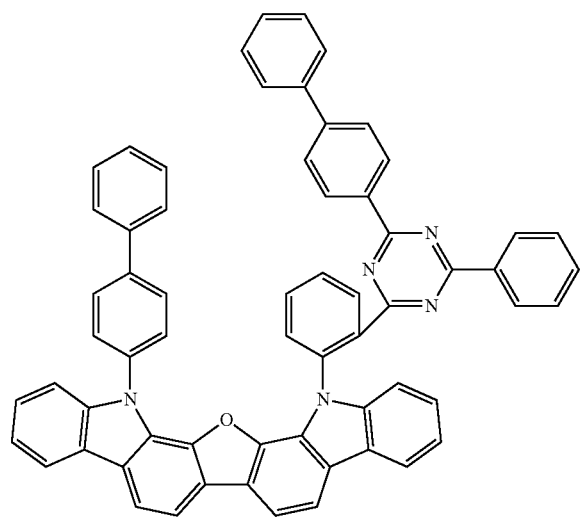
[88]
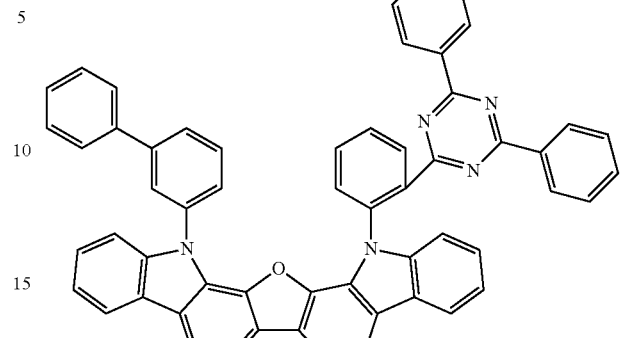
[86]
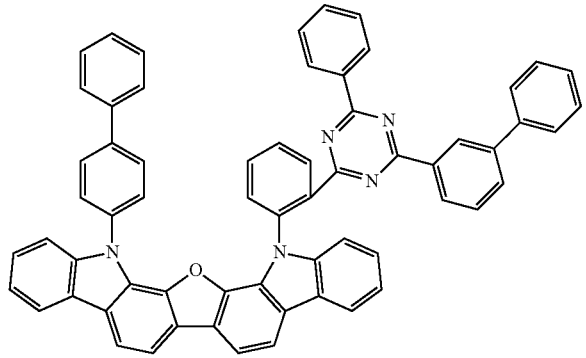
[89]
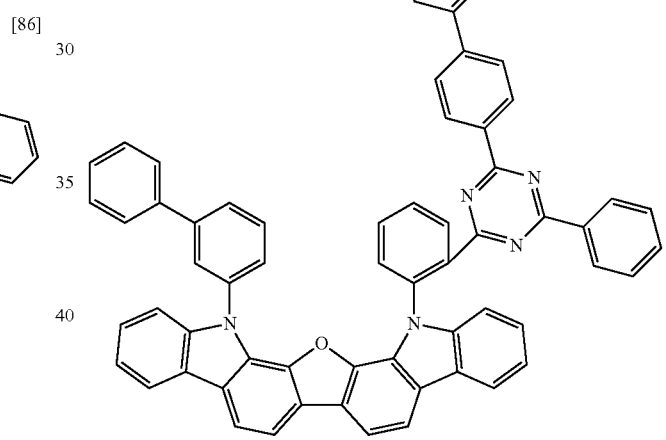
[87]
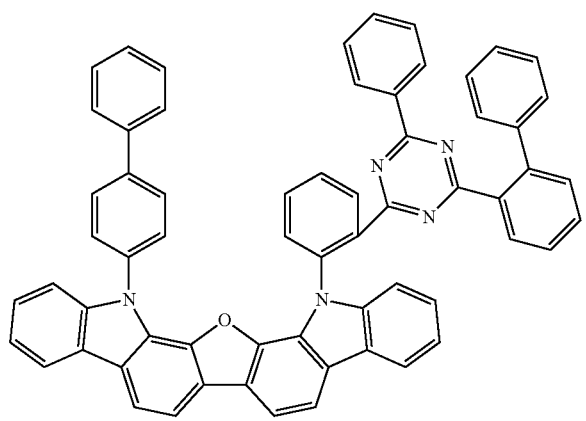
[90]
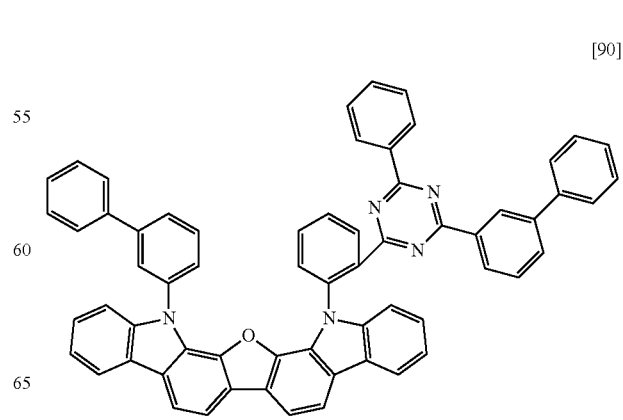

[91]
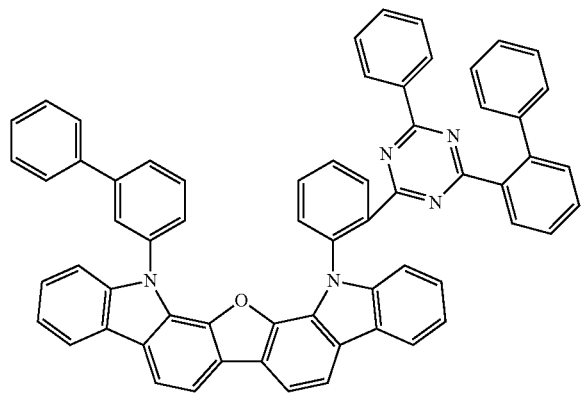
[92]
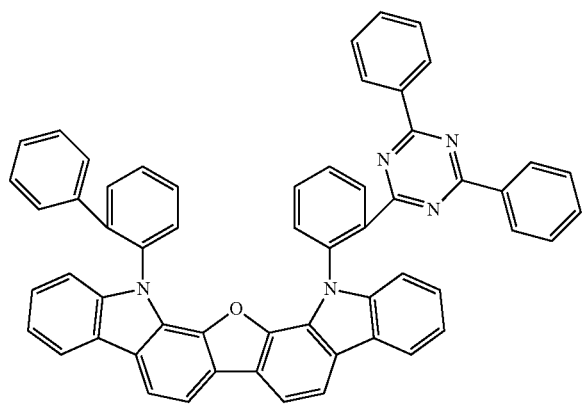
[93]
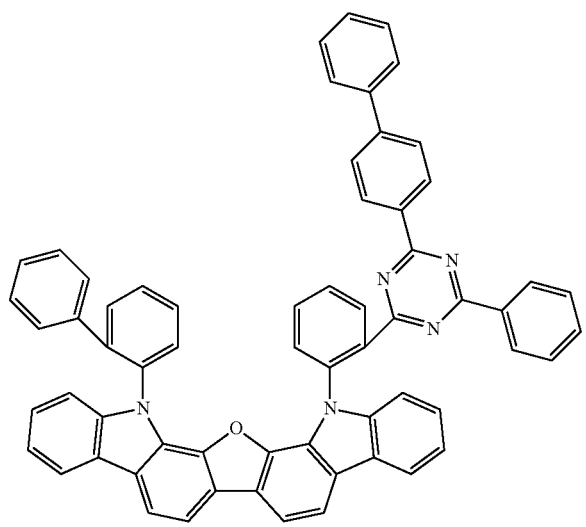
[94]
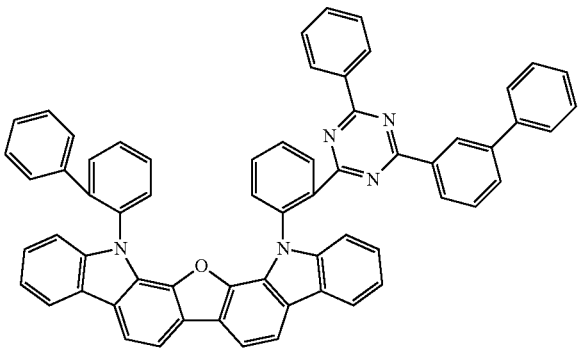
[95]
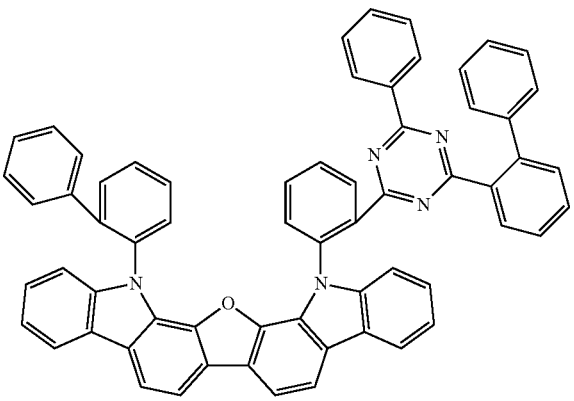
[96]
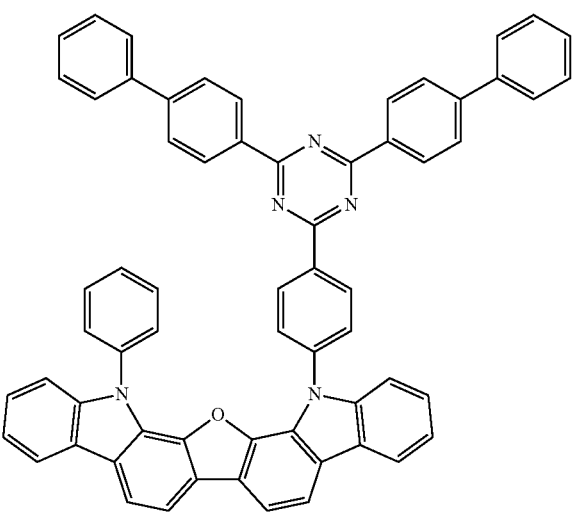

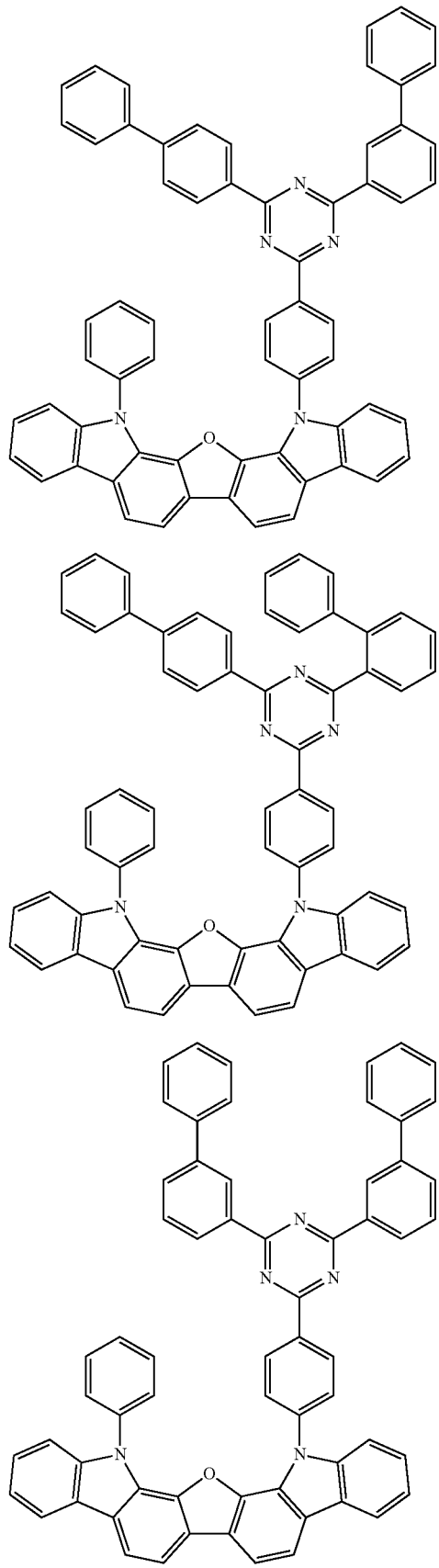
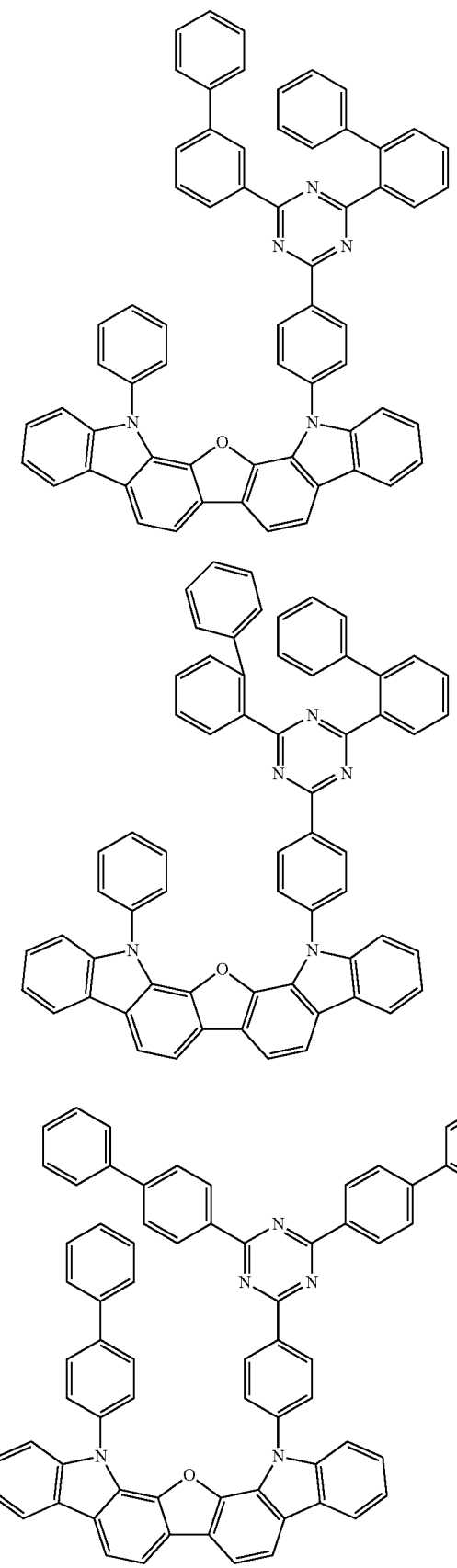

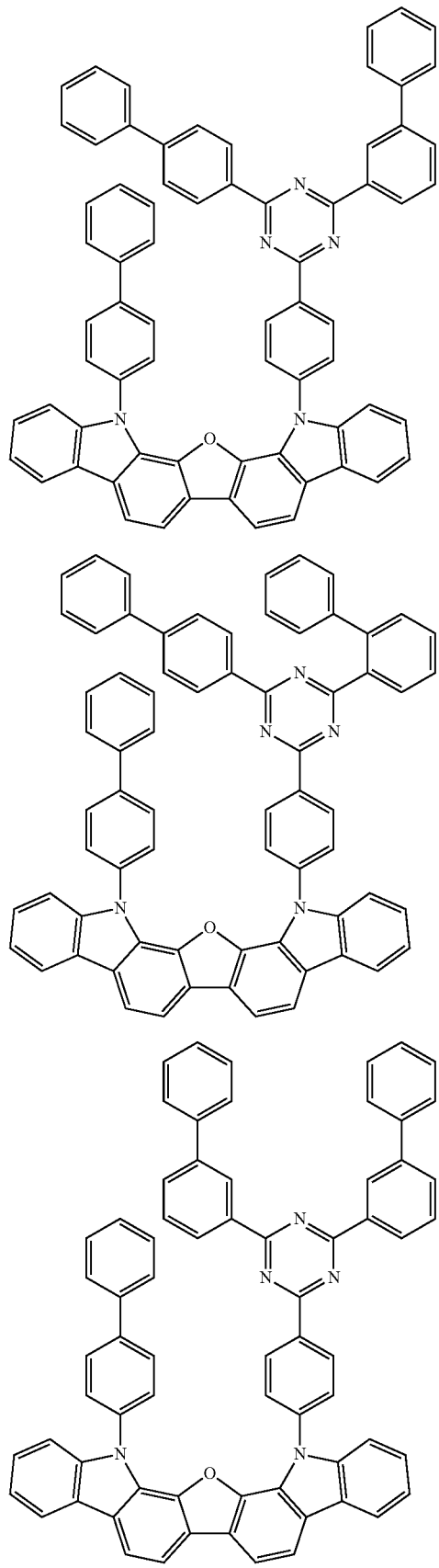
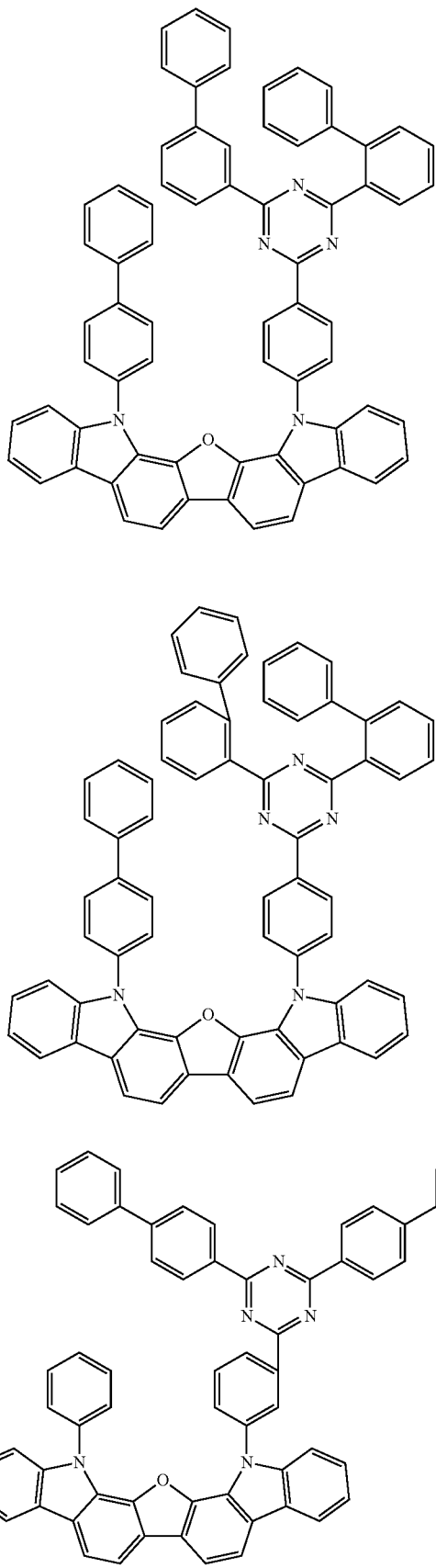

[109]
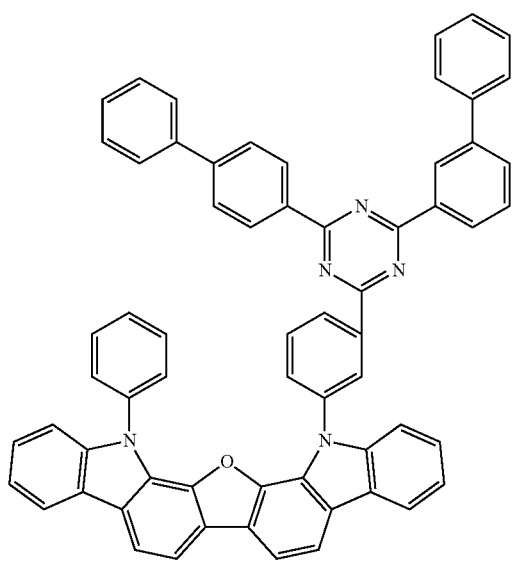
[110]
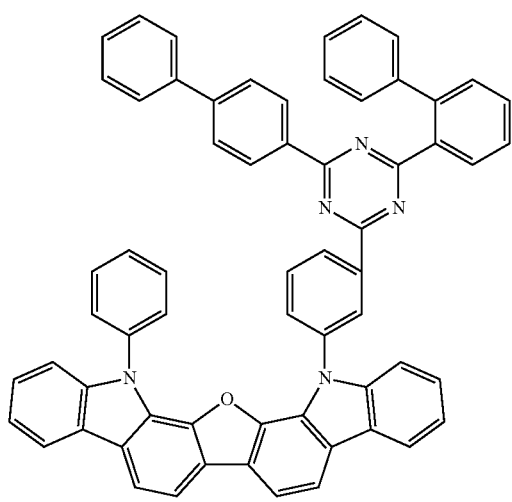
[111]
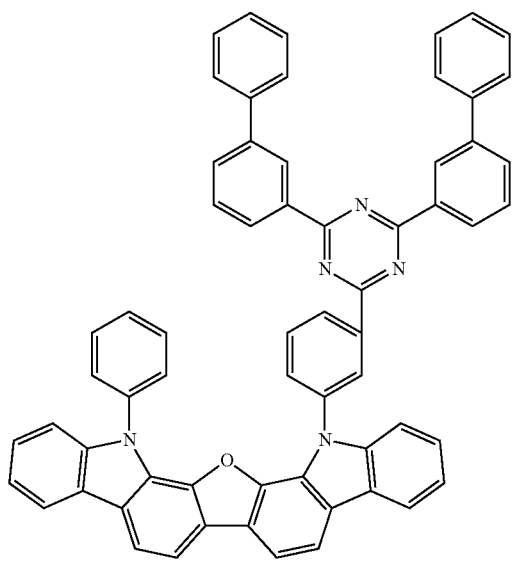
[112]
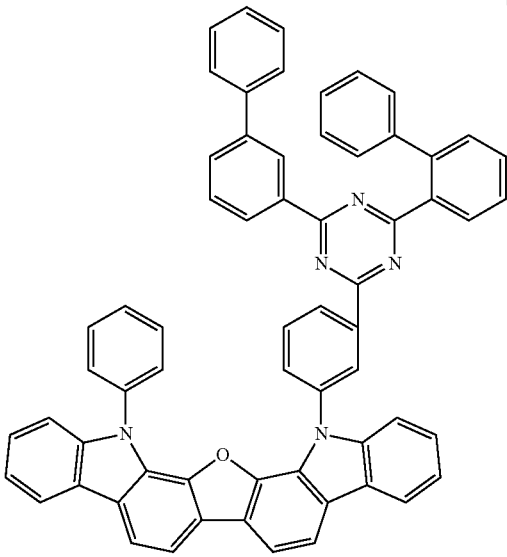
[113]
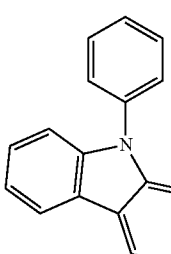
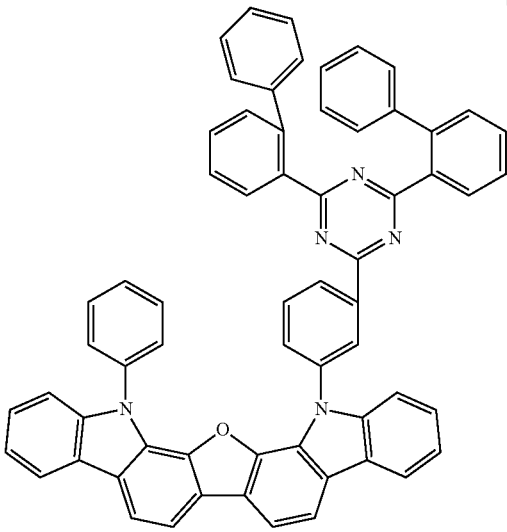
[114]
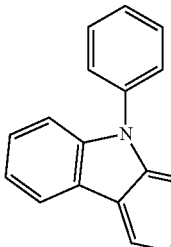
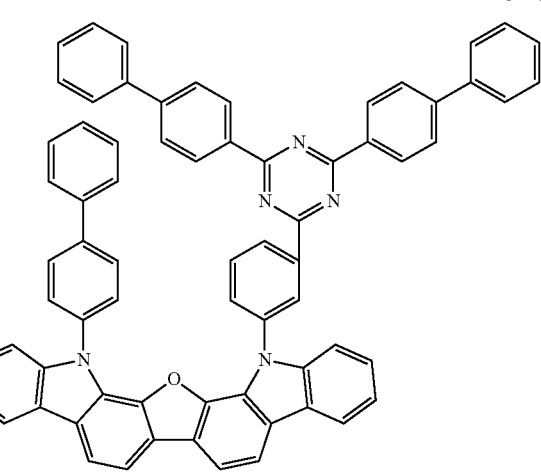

[115]
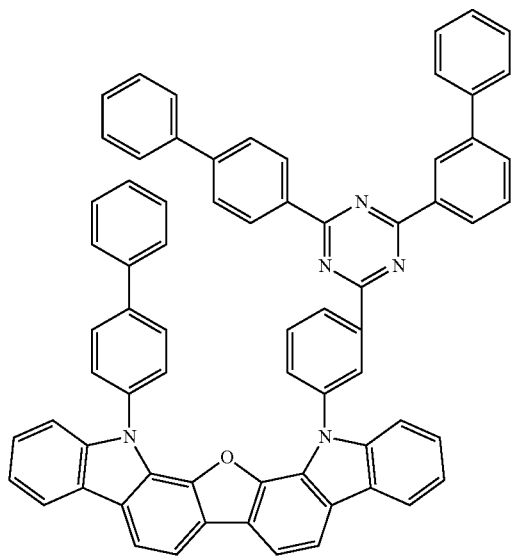
[116]
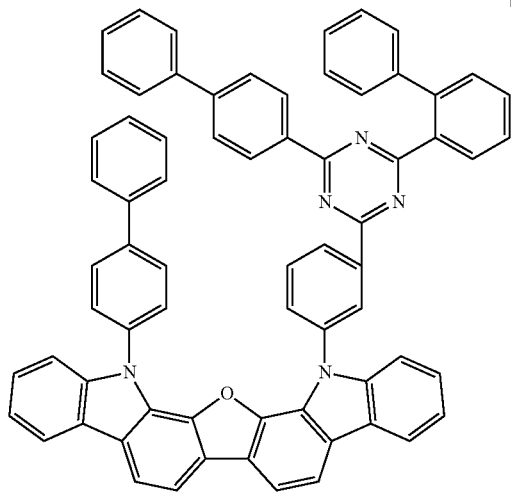
[117]
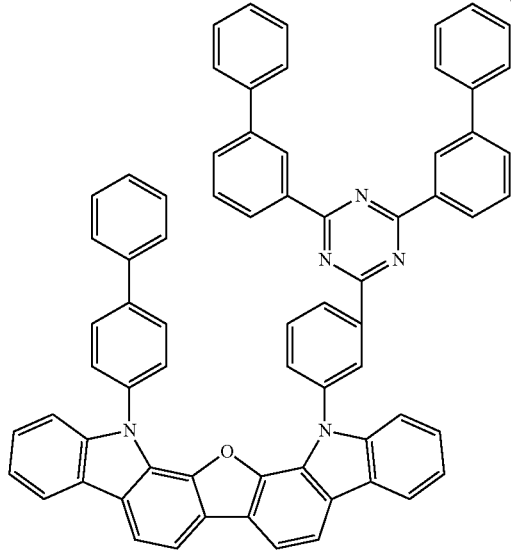
[118]
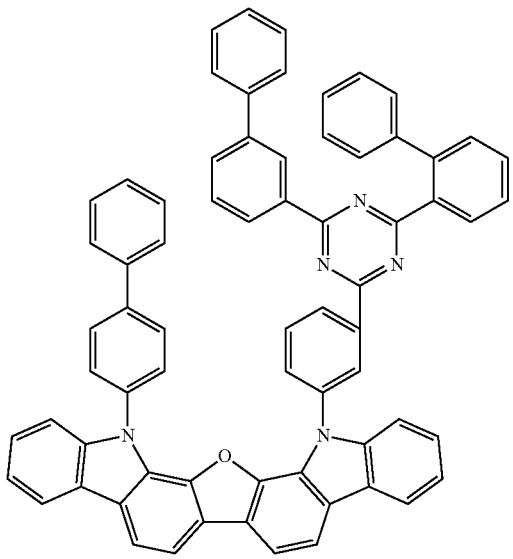
[119]
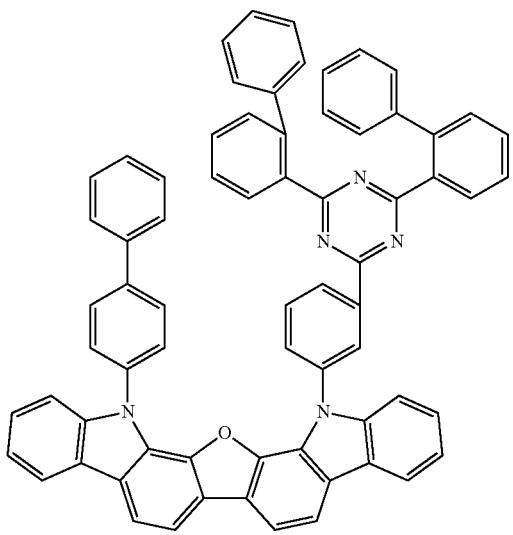
[120]
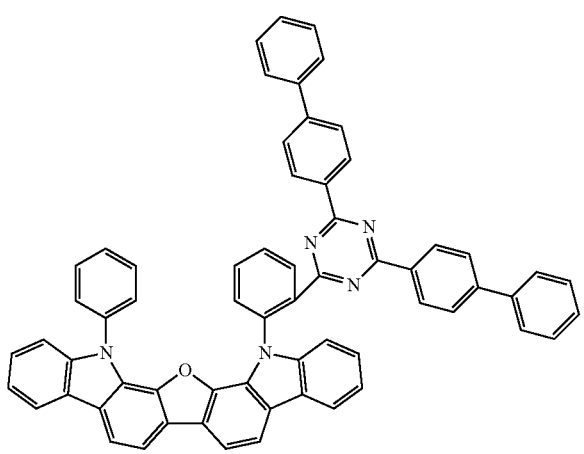

[121]
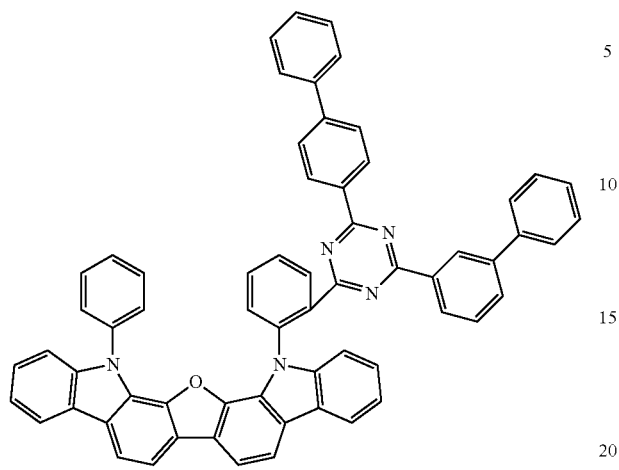
[122]
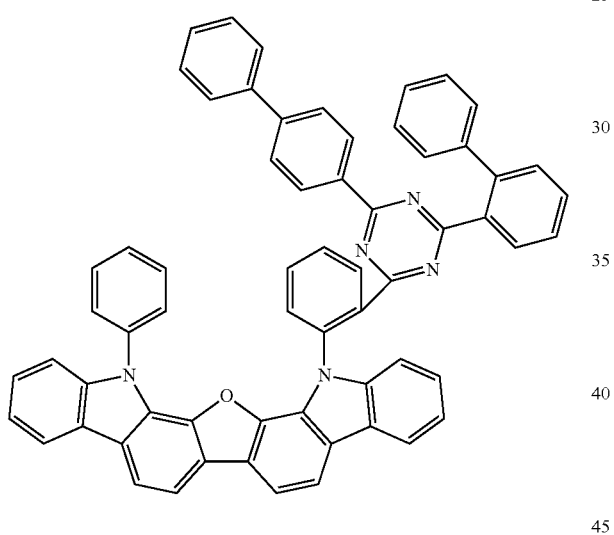
[123]
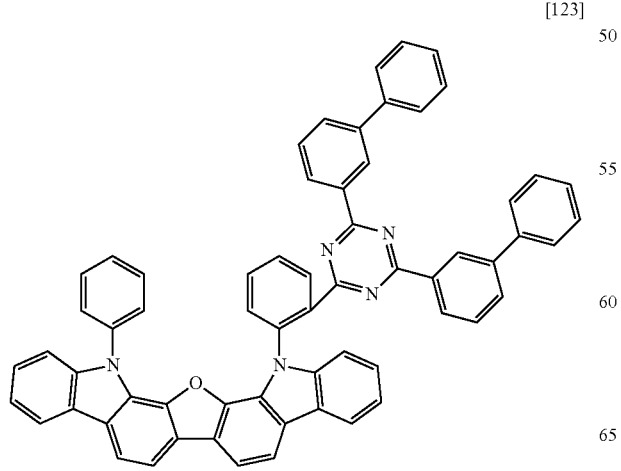
[124]
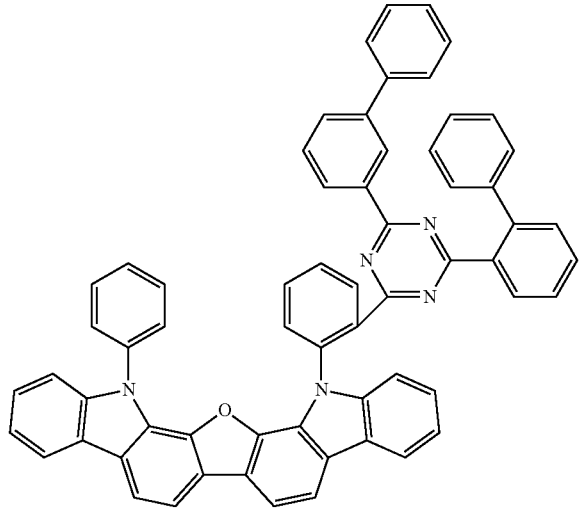
[125]
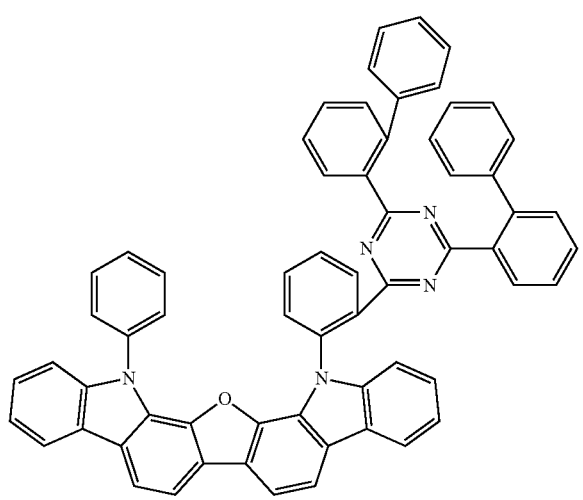
[126]
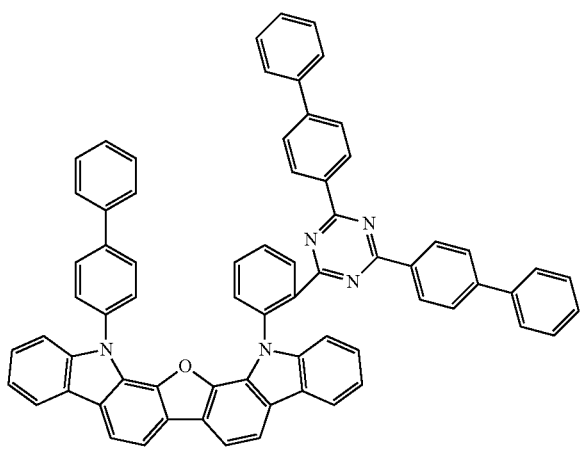

[127]
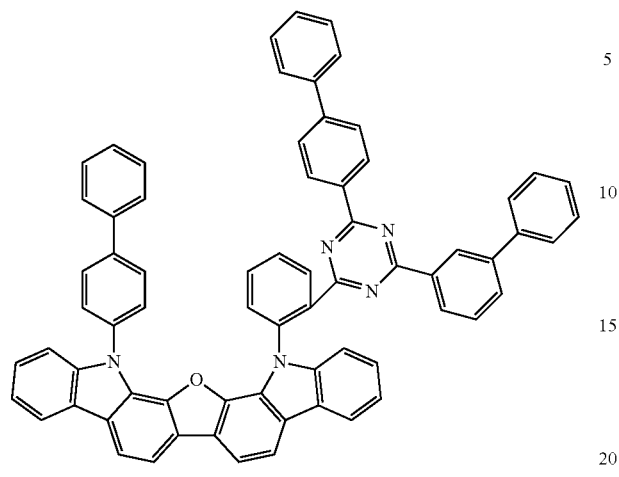
[128]
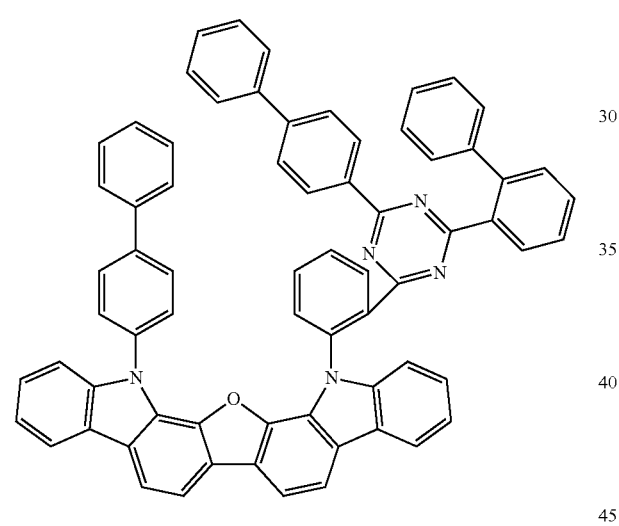
[129]
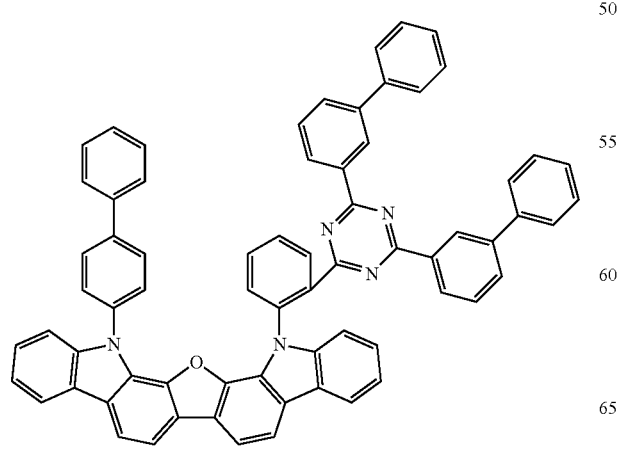
[130]
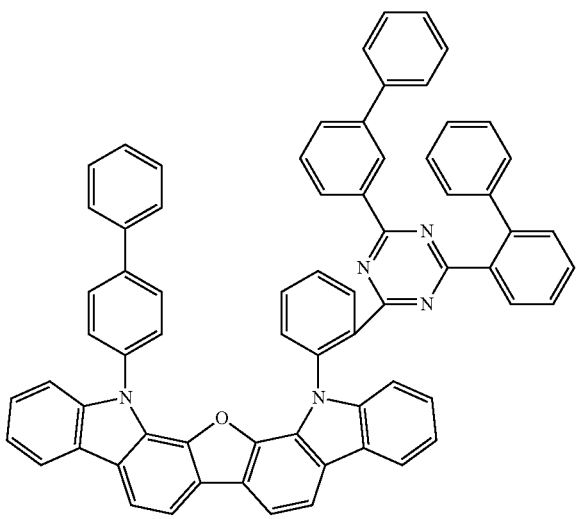
[131]
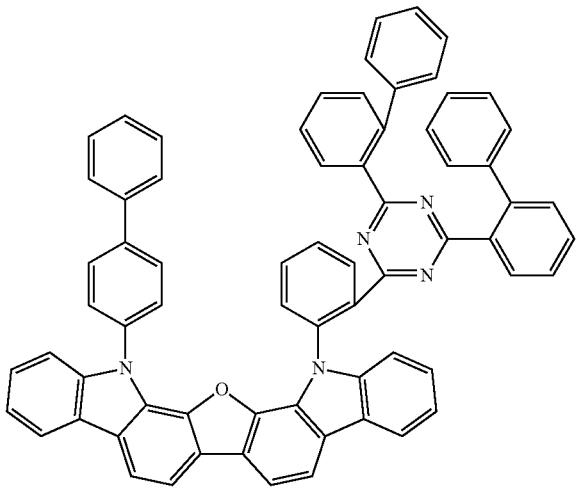
[132]
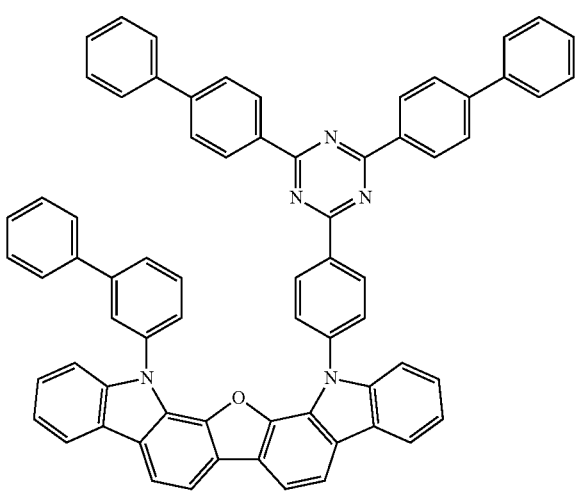

[133]
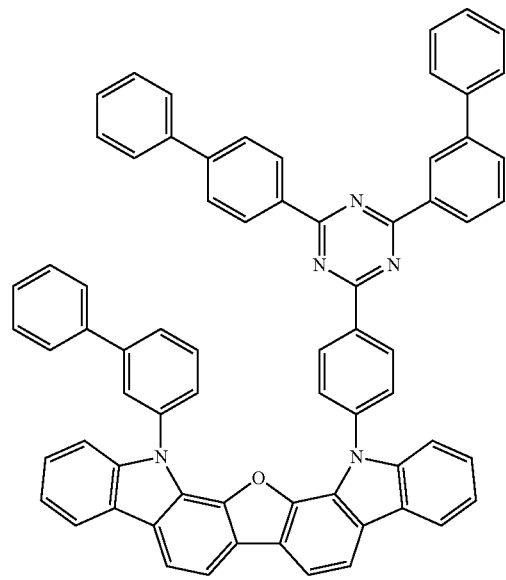
[134]
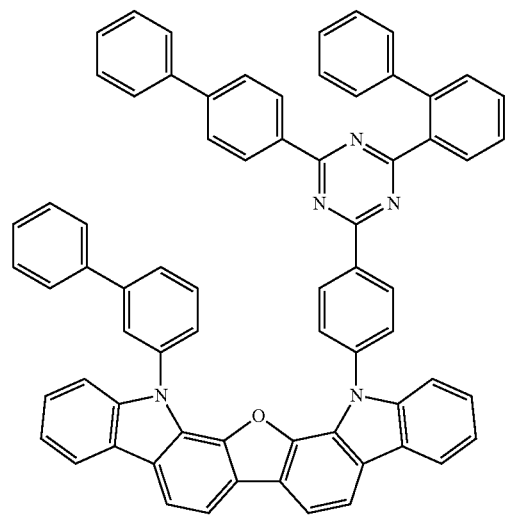
[135]
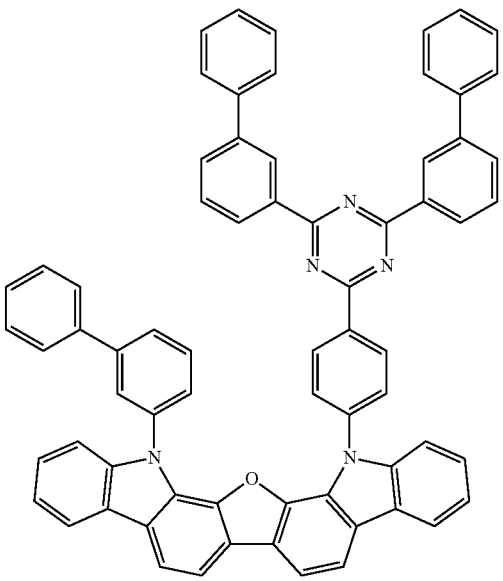
[136]
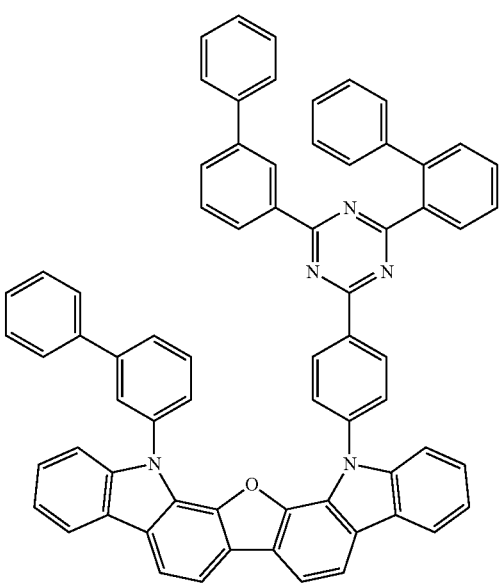

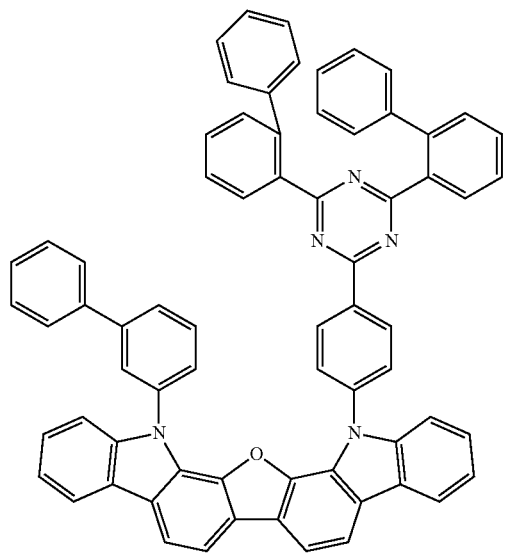
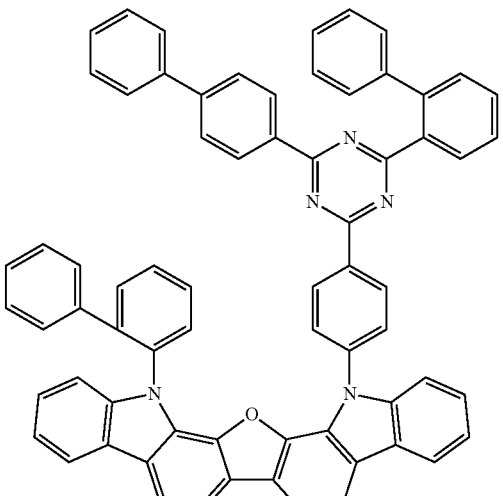
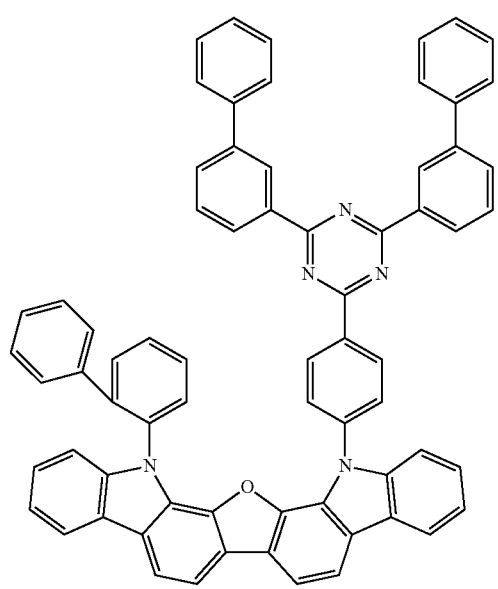

[142]
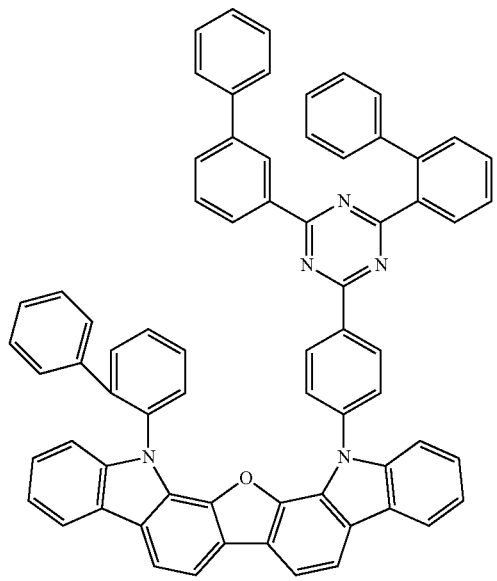
[143]
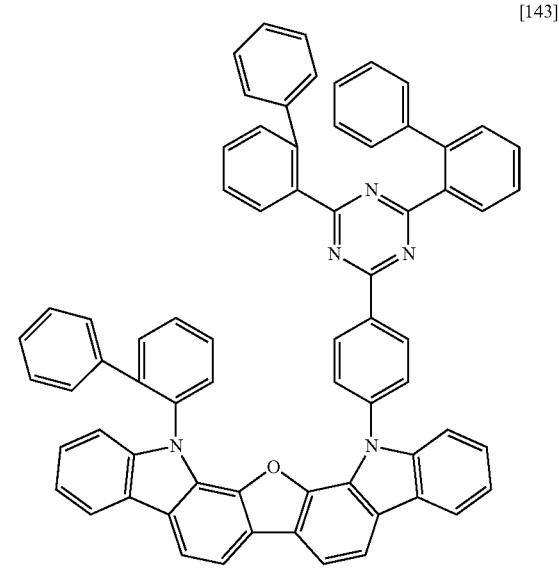
[144]
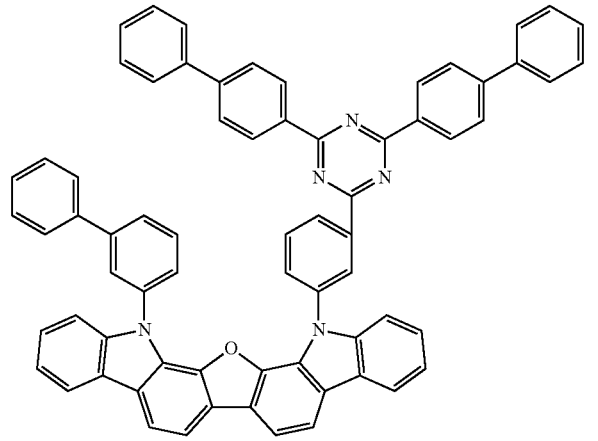
[145]
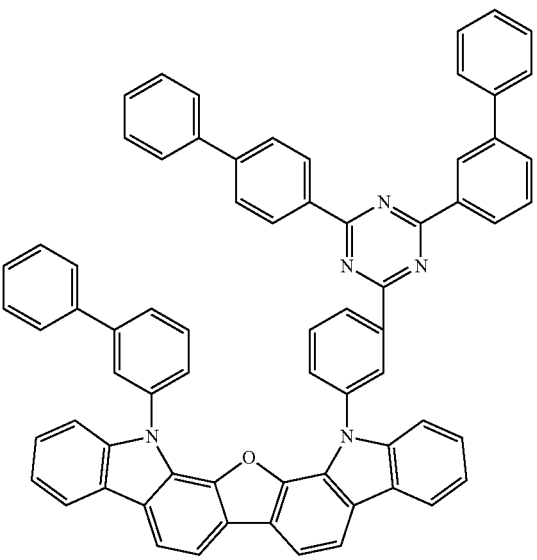
[146]
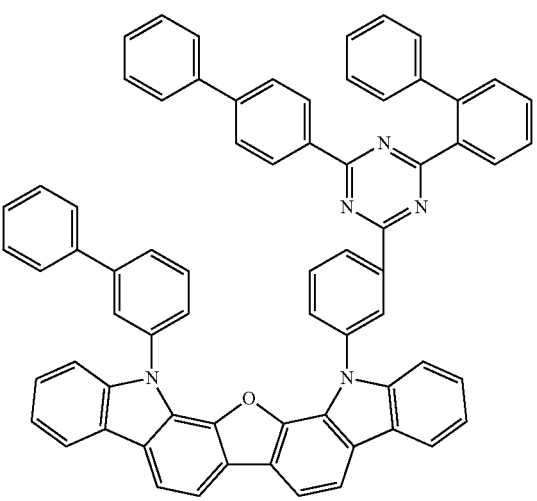
[147]
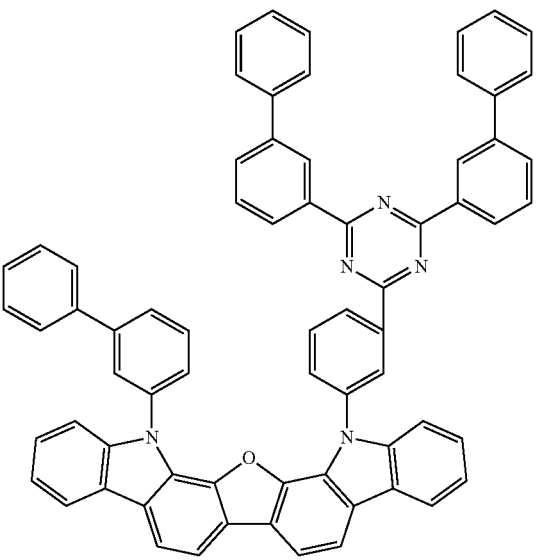

[148]
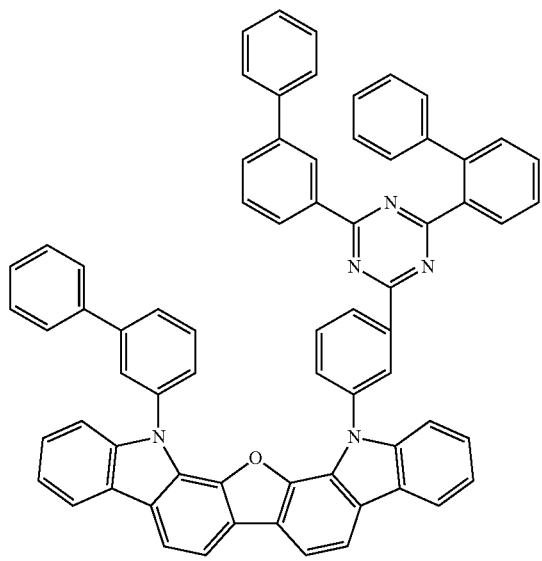
[149]
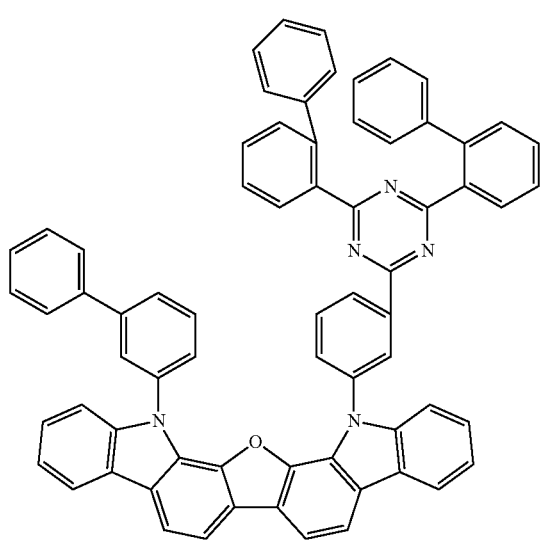
[150]
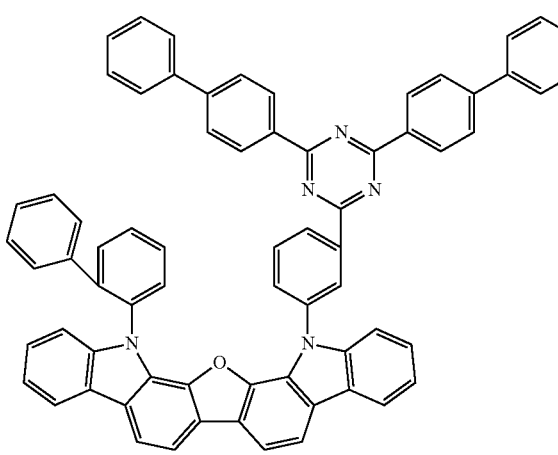
[151]
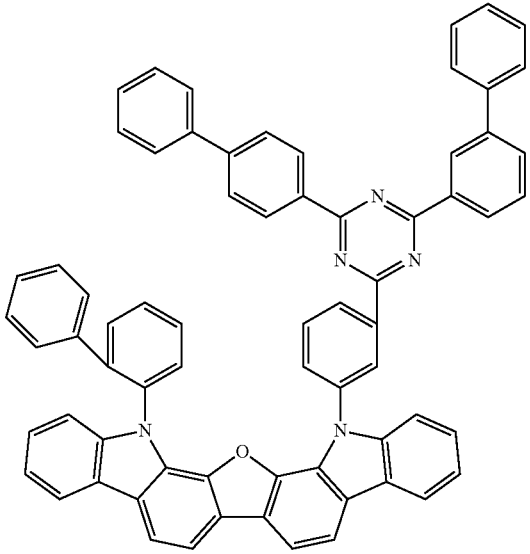
[152]
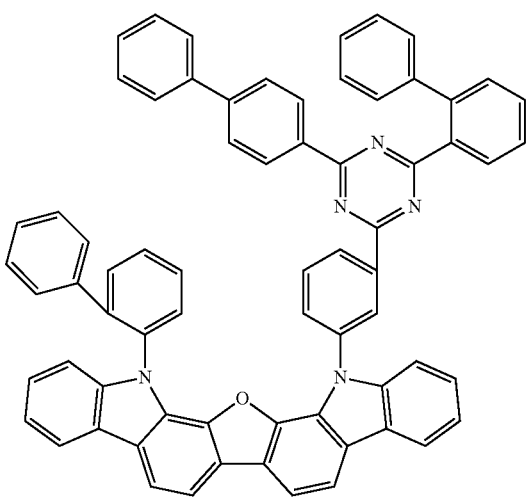
[153]
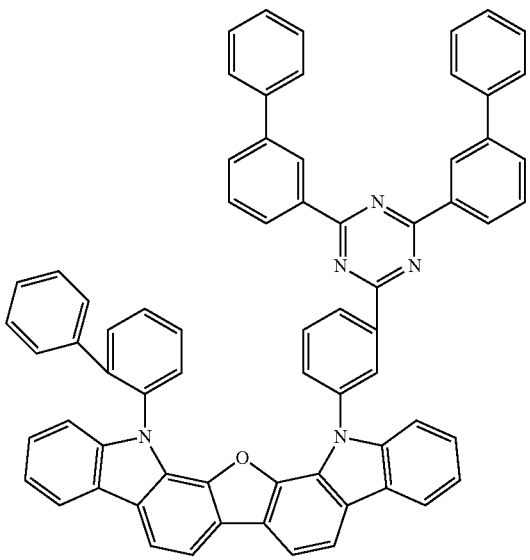

[154]
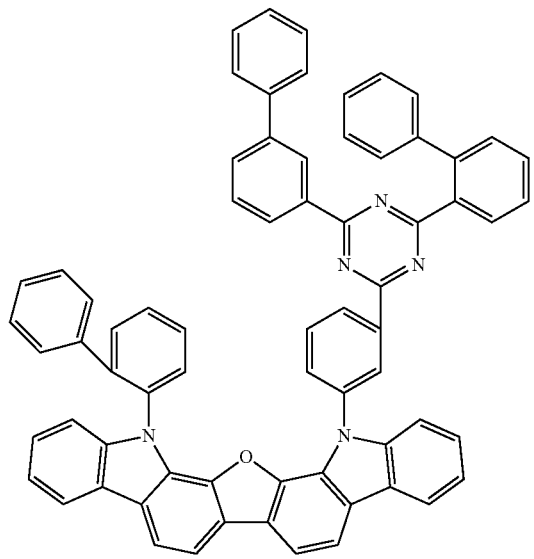
[155]
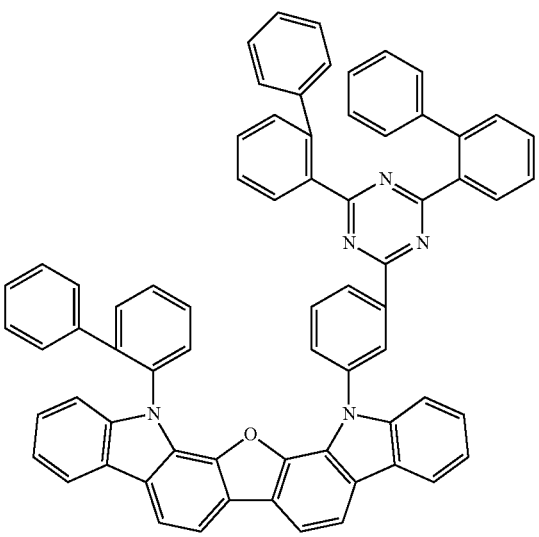
[156]
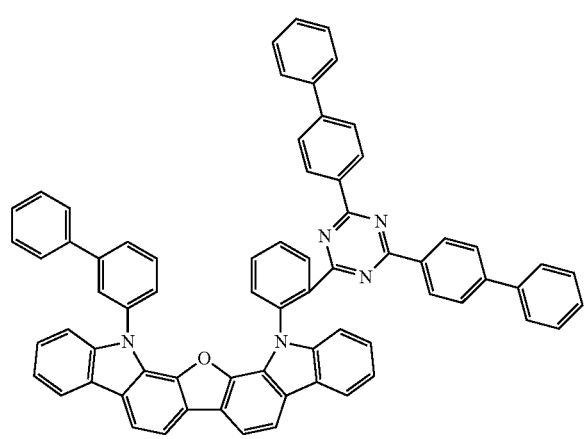
[157]
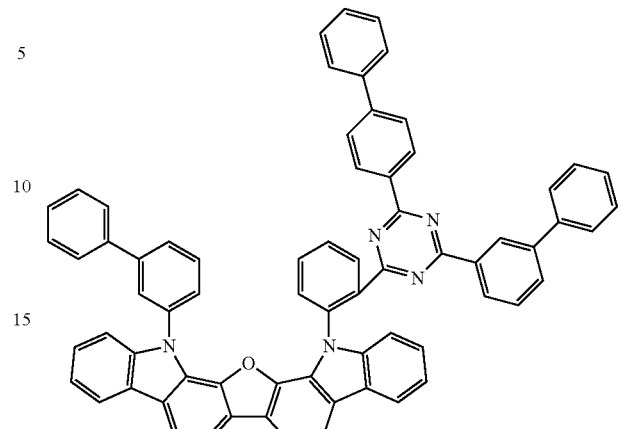
[158]
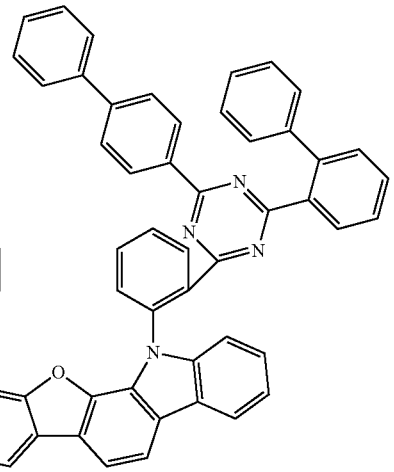
[159]
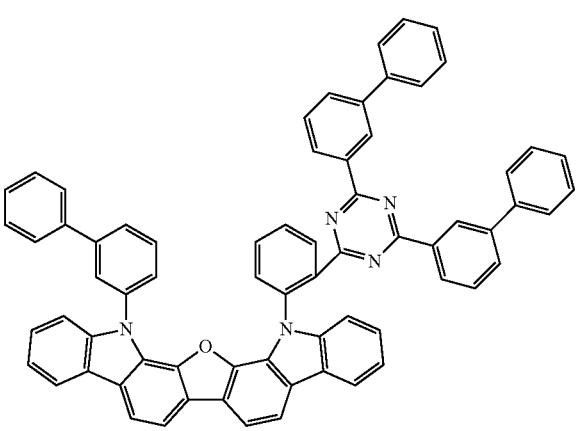

[160]
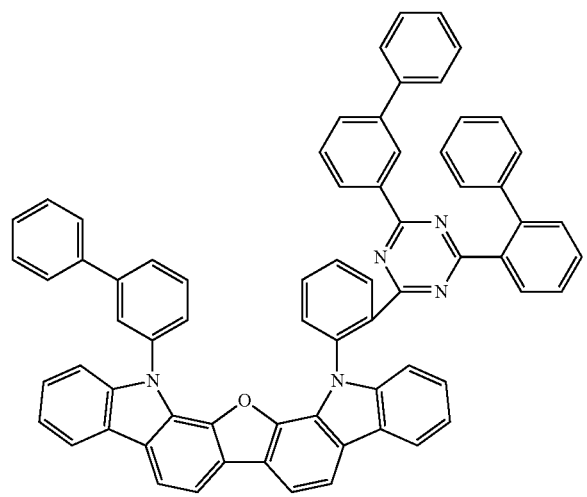
[161]
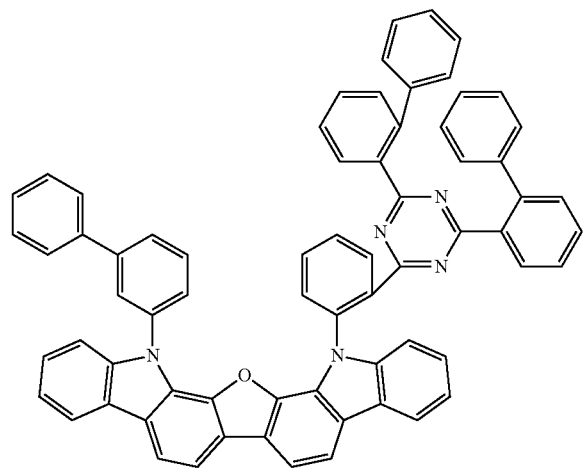
[162]
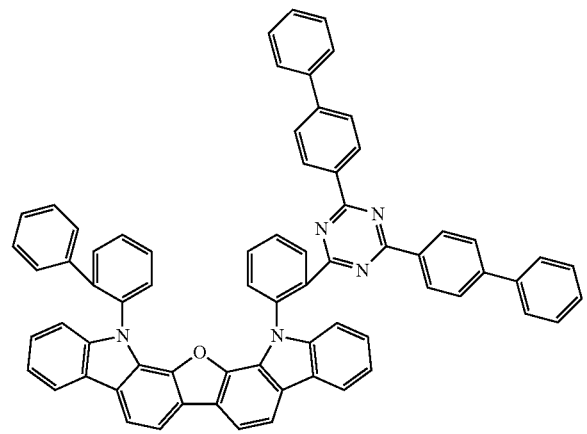
[163]
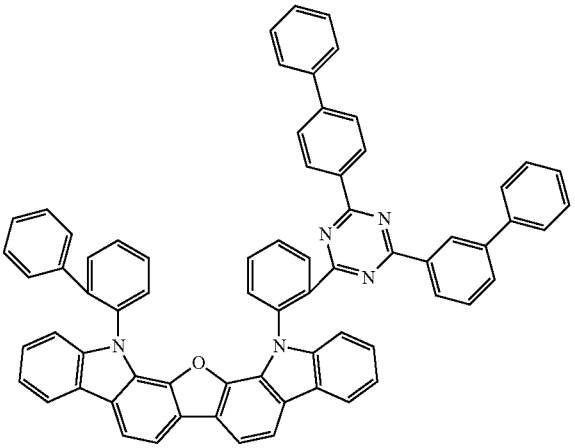
[164]
[165]
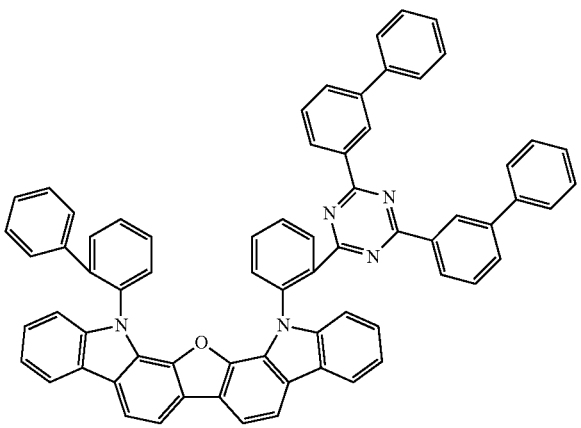

[166]
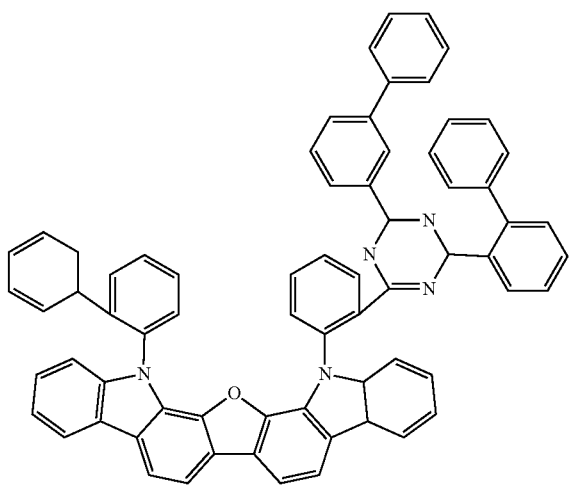
[167]
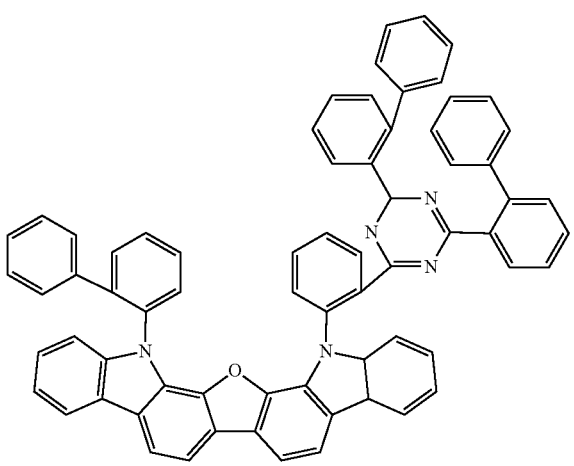
[168]
-continued
[169]
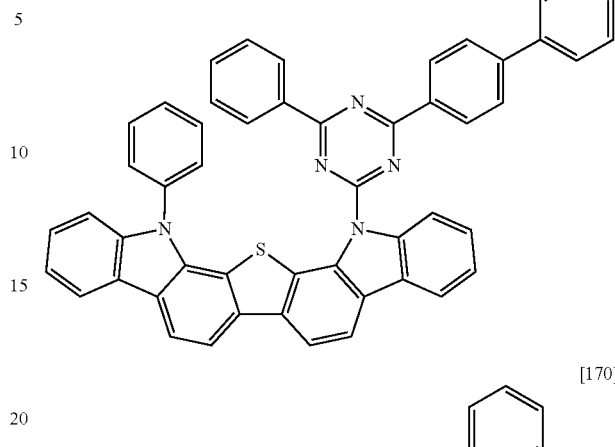
[170]
[171]
[172]
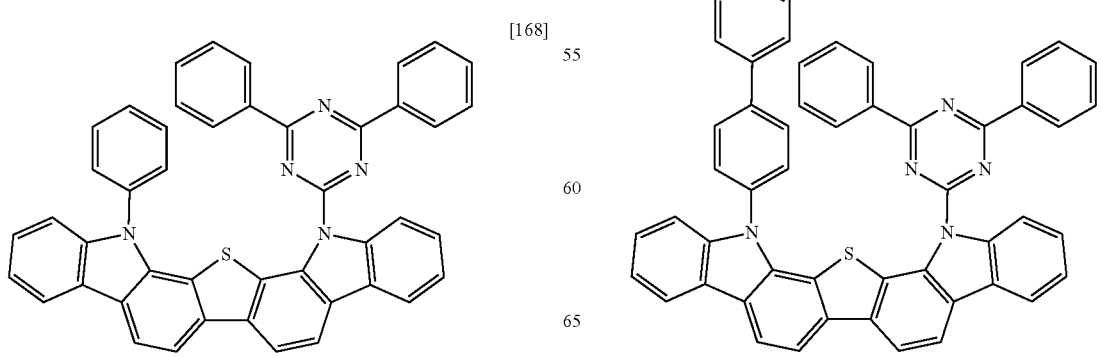

[173]
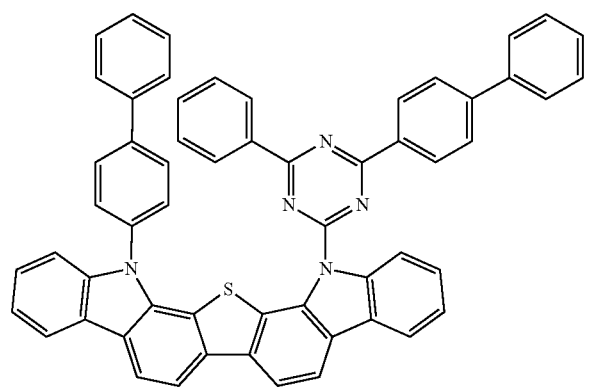
[174]
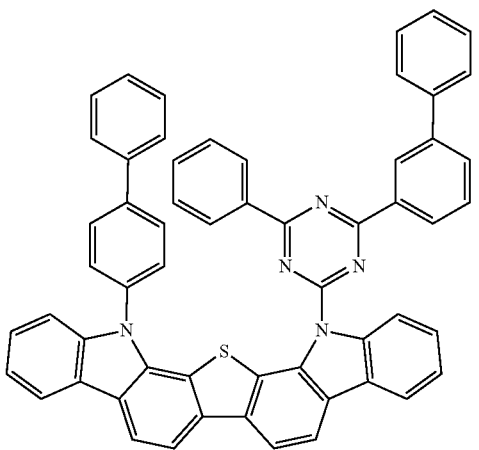
[175]
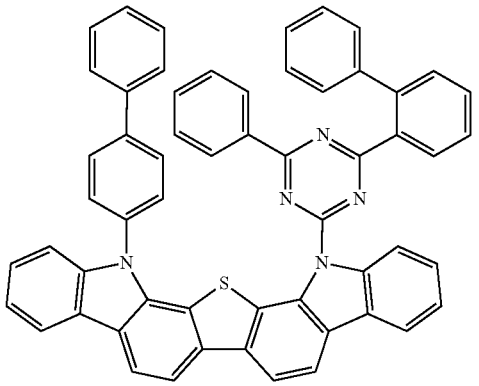
[176]
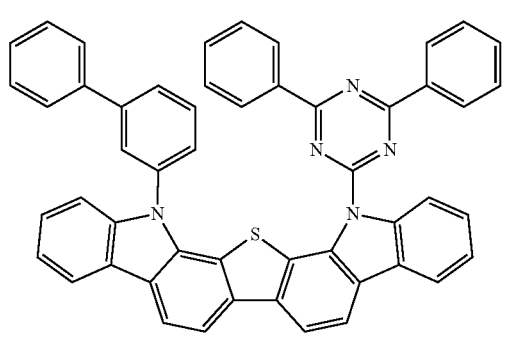
[177]
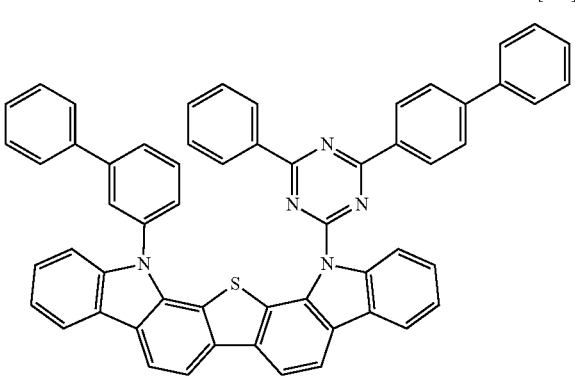
[178]
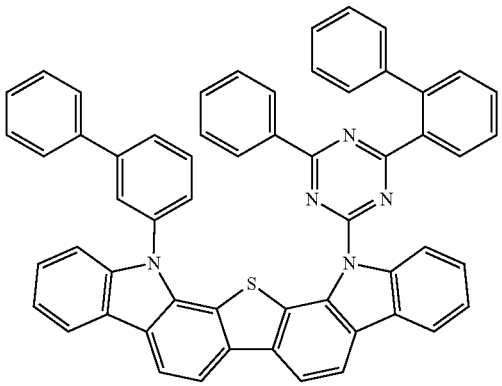
[179]
[180]
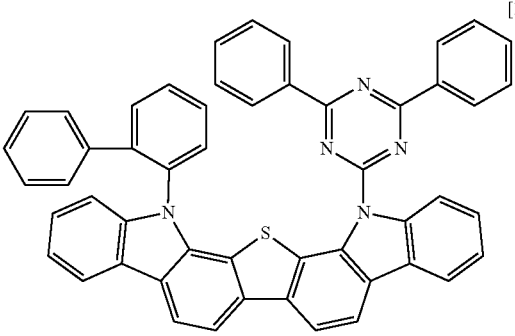

-continued
[181]
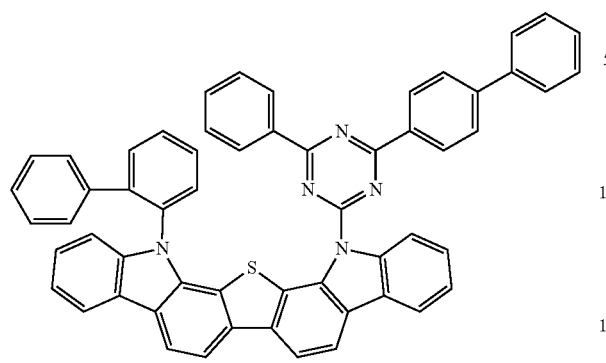
[182]
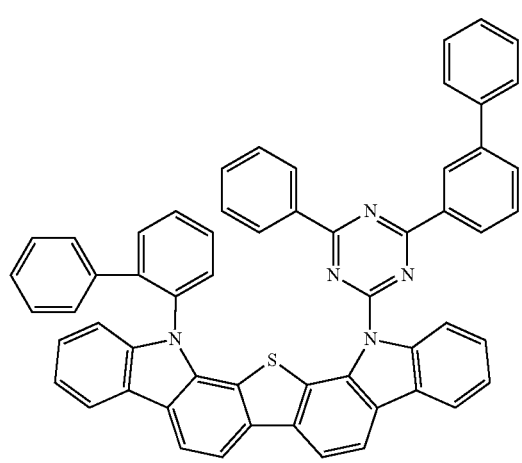
[183]
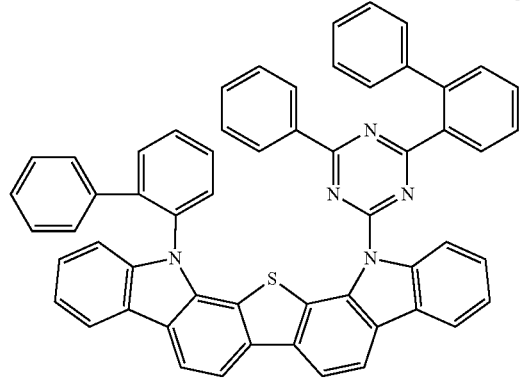
[184]
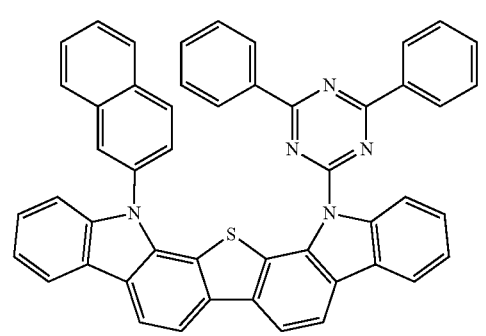
-continued
[185]
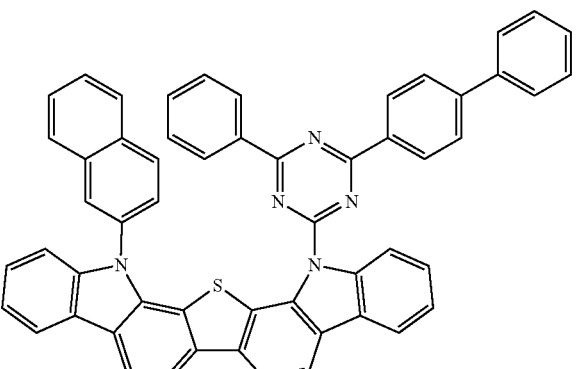
[186]
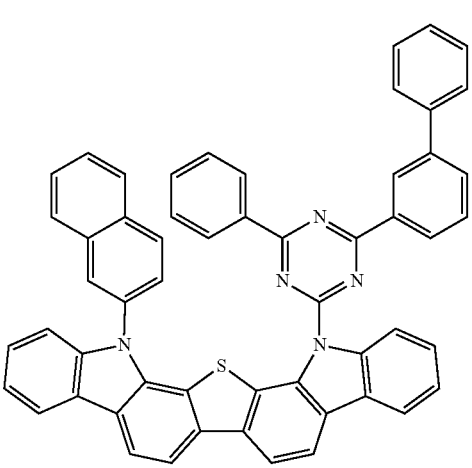
[187]
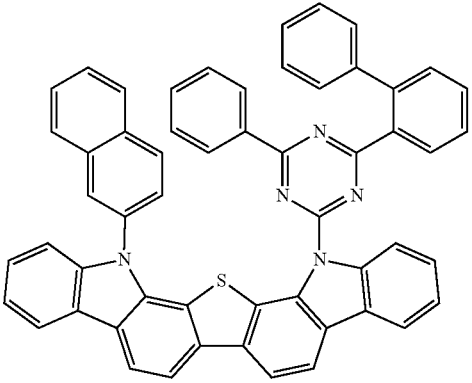
[188]
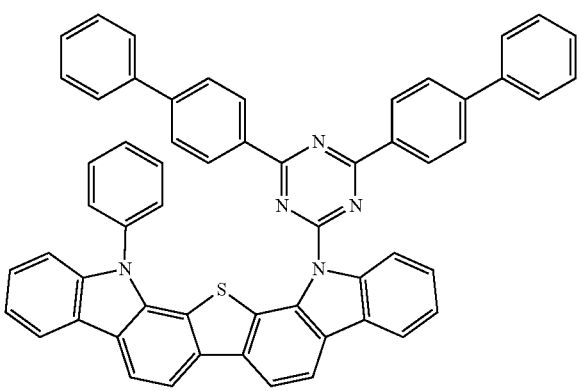

-continued
[189]
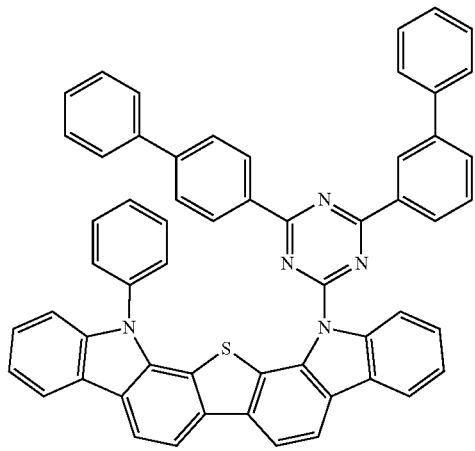
[190]
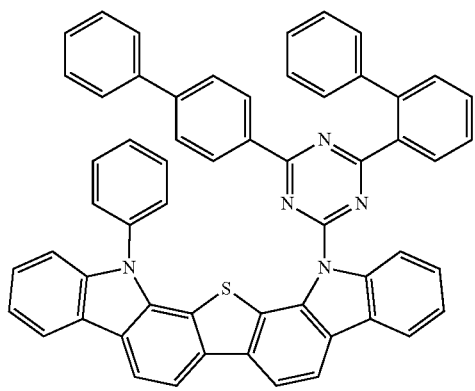
[191]
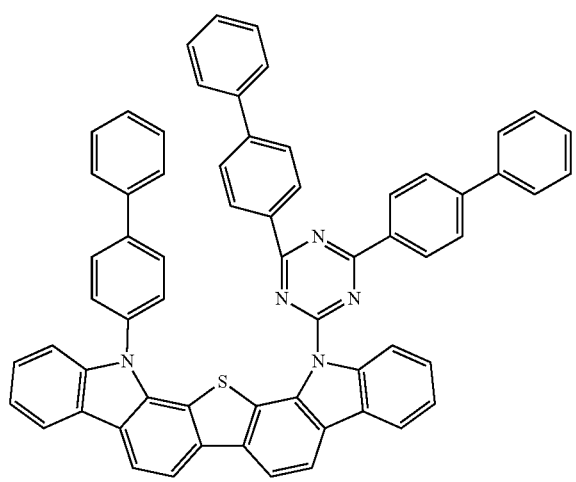
-continued
[192]
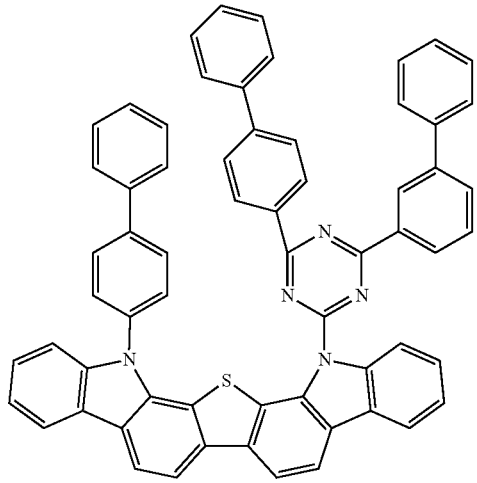
[193]
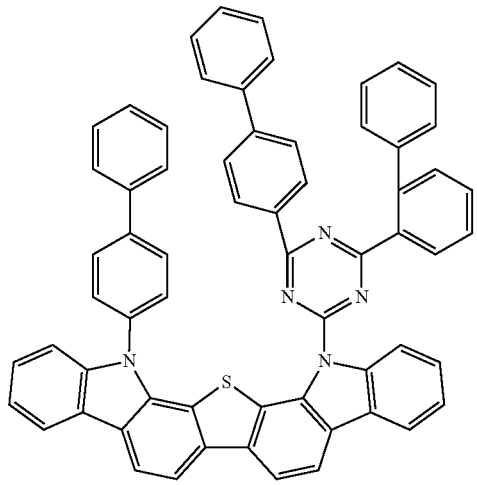
[194]
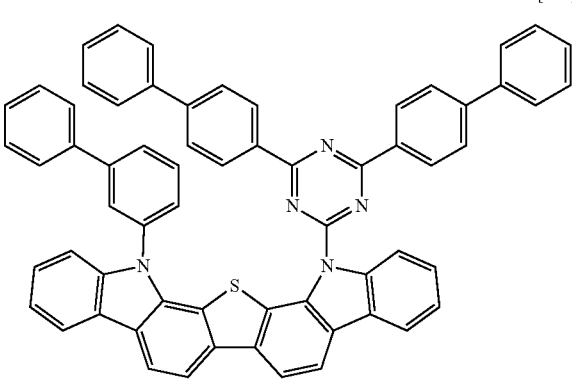

[195]
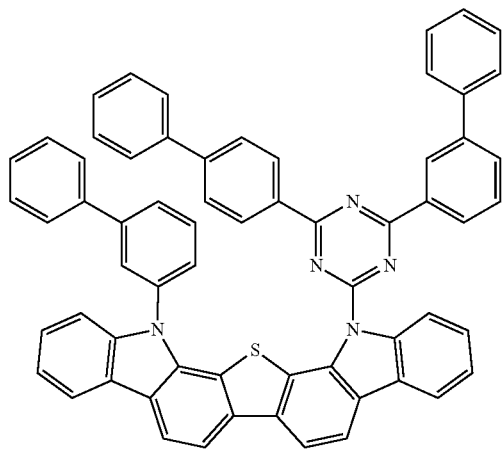
[196]
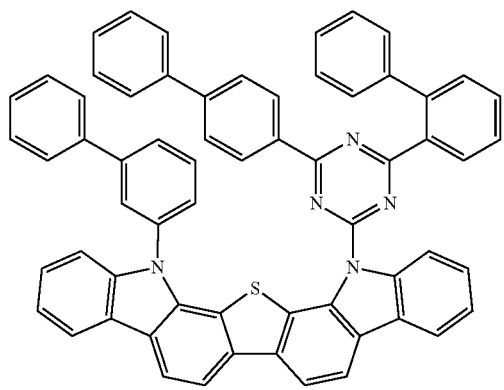
[197]
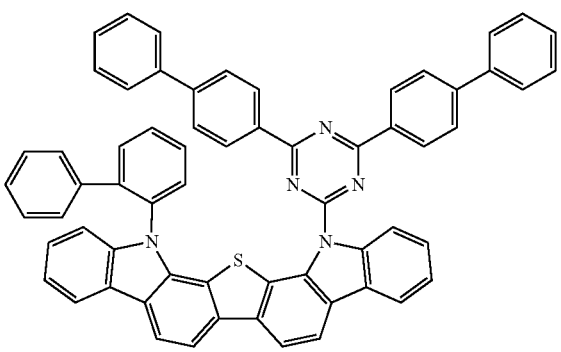
[198]
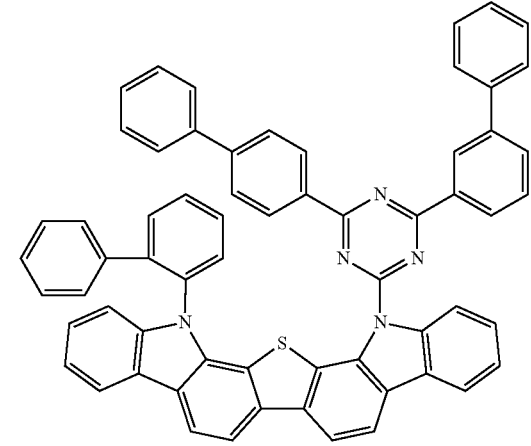
[199]
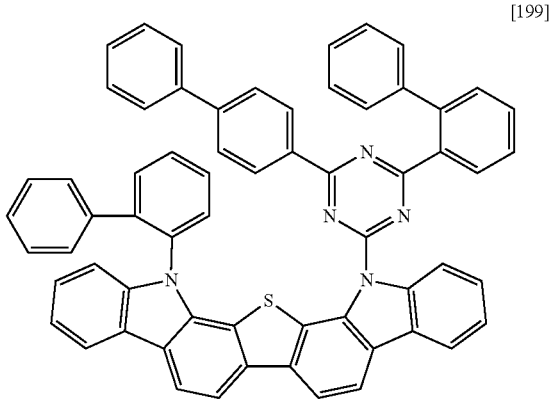
[200]
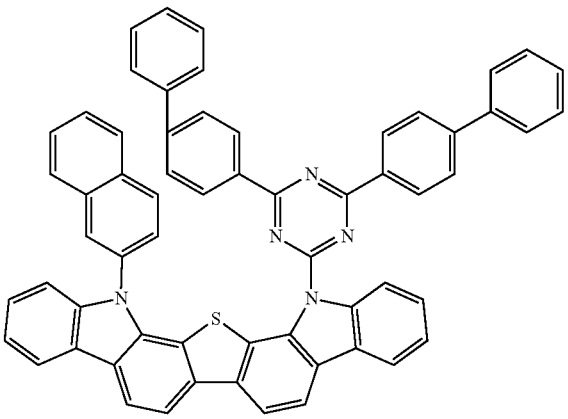
[201]
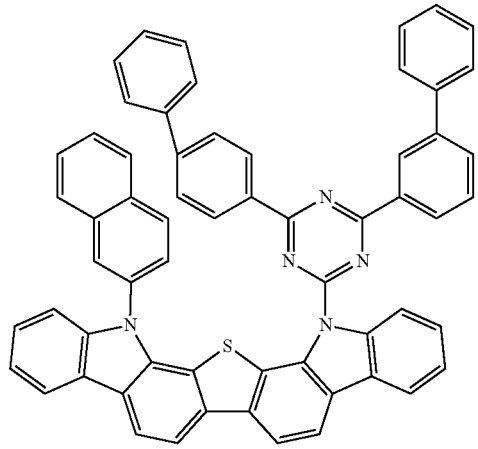

[202]
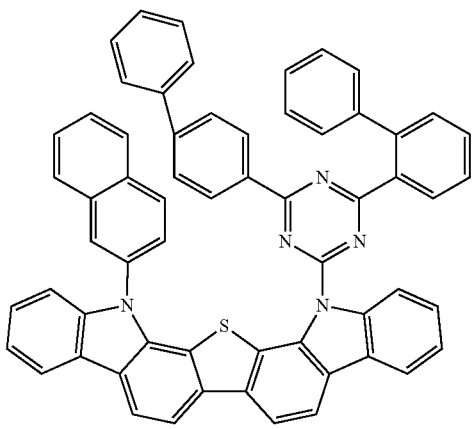
[203]
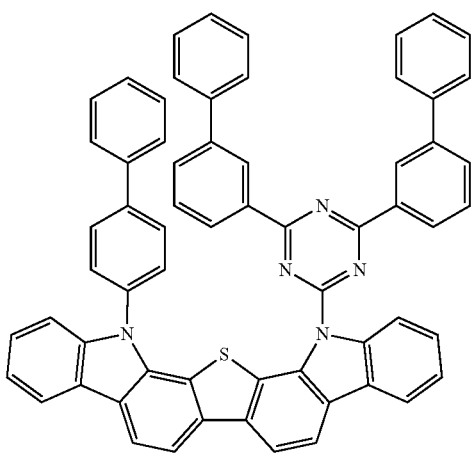
[204]
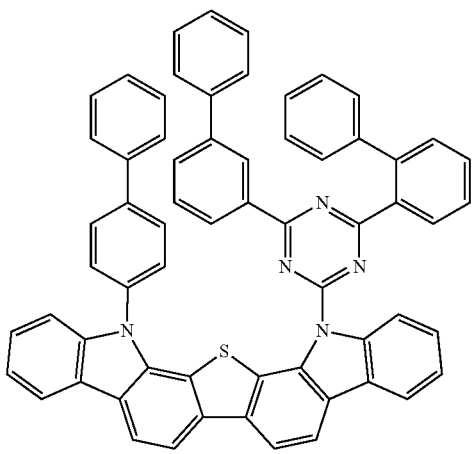
[205]
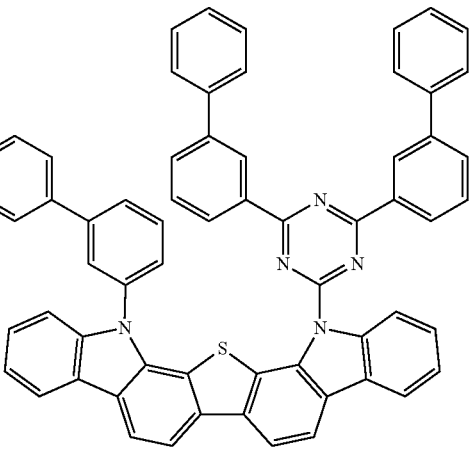
[206]
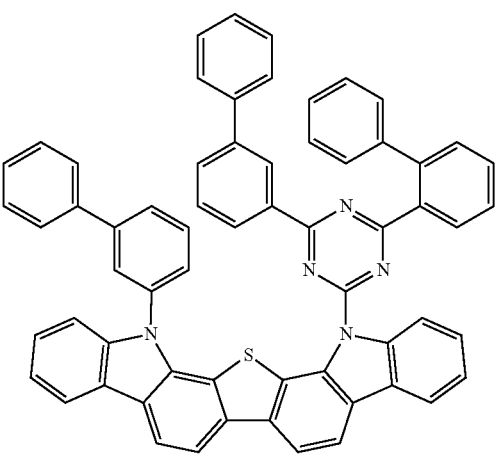
[207]
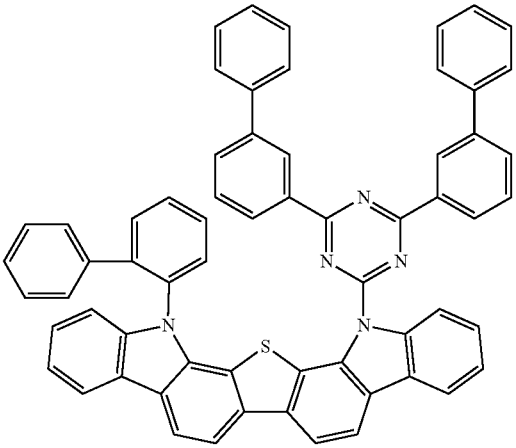

[208]
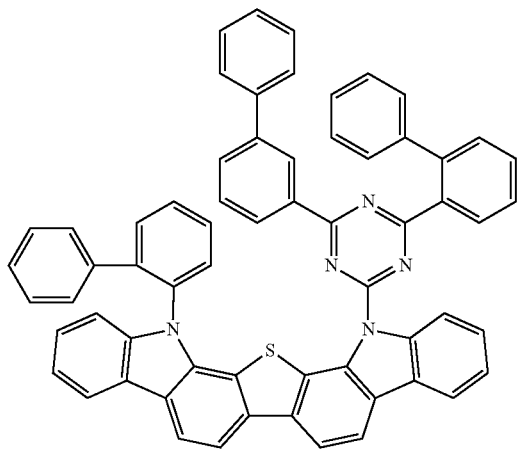
[209]
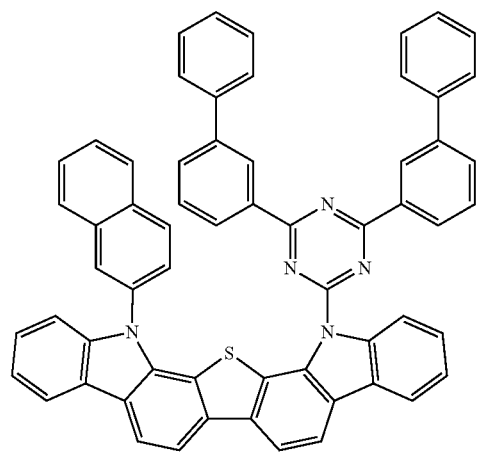
[210]
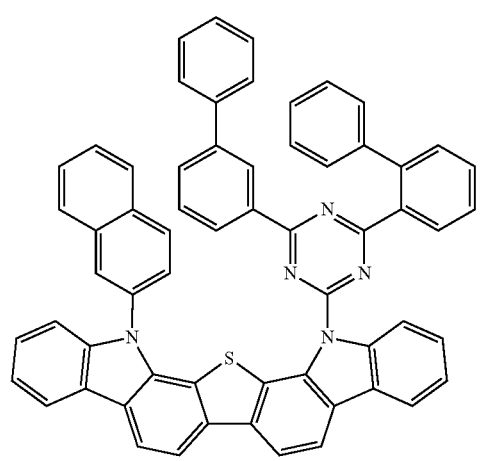
[211]
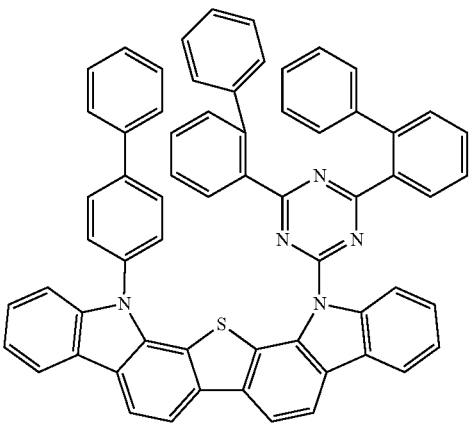
[212]
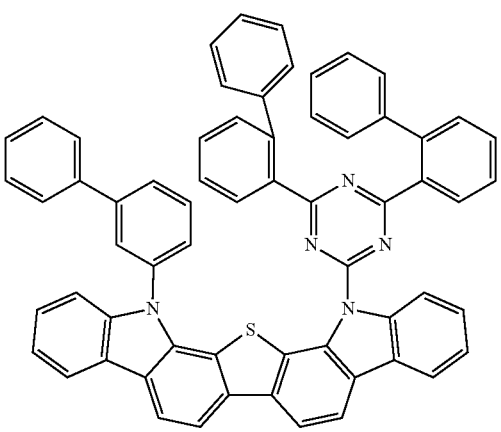
[213]
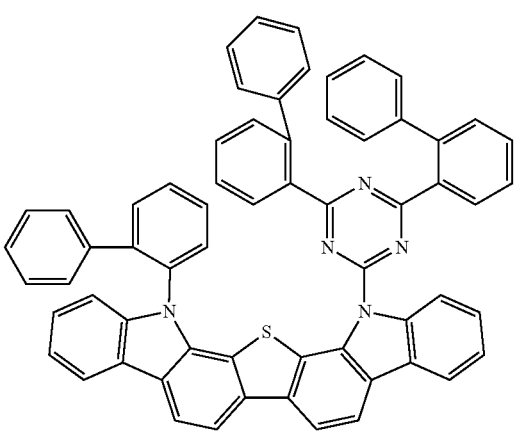

[214]
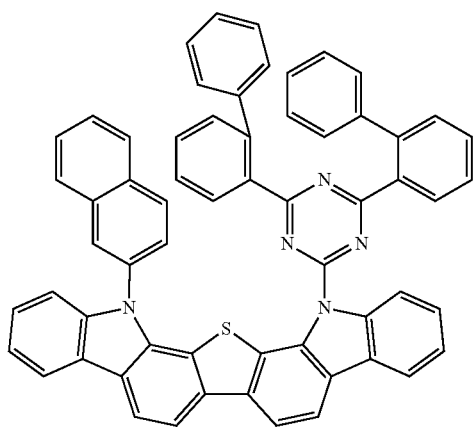
[215]
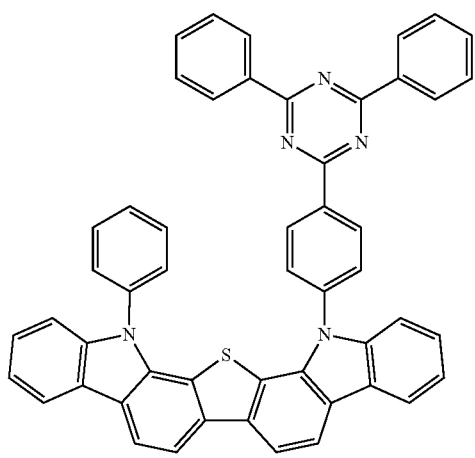
[216]
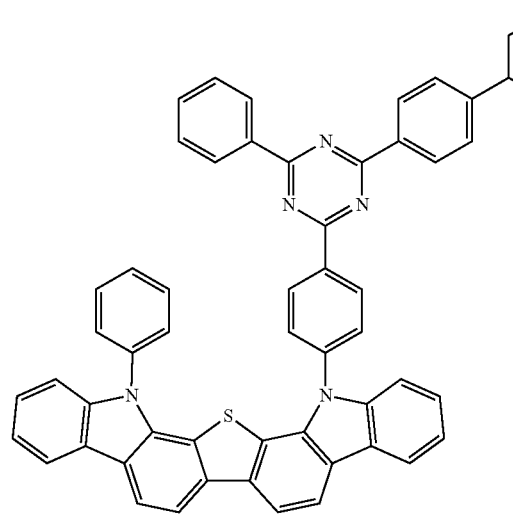
[217]
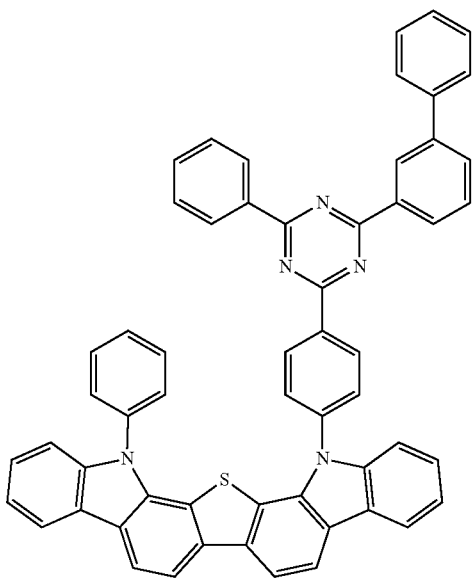
[218]
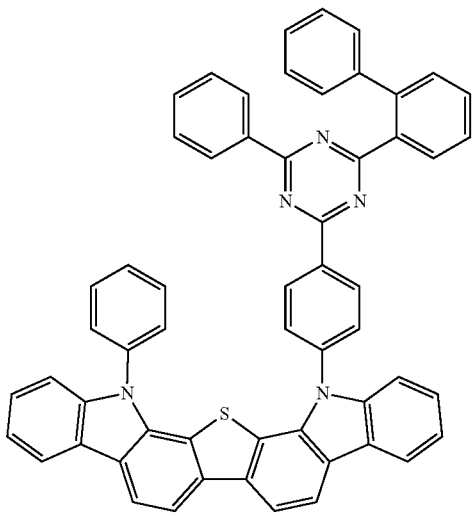
[219]
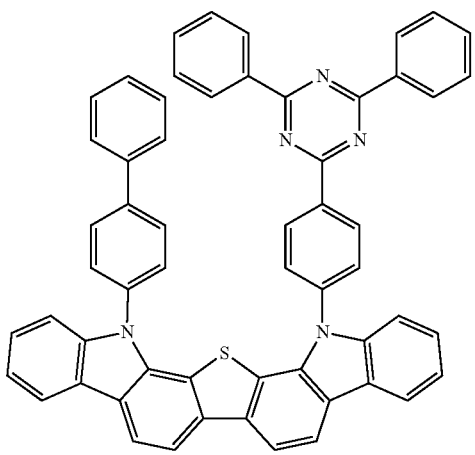

[220]
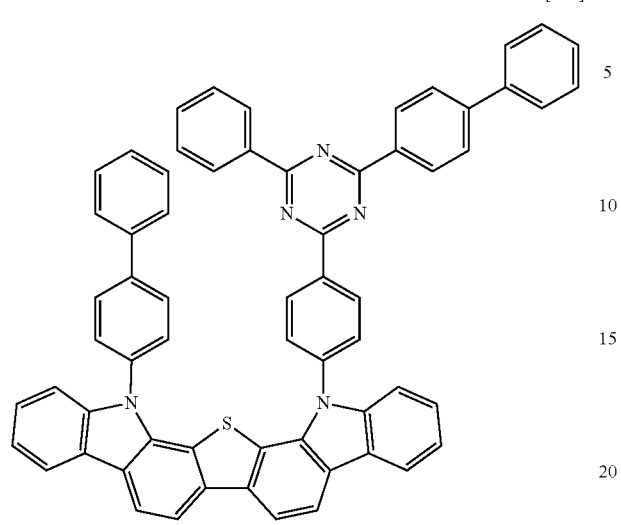
[221]
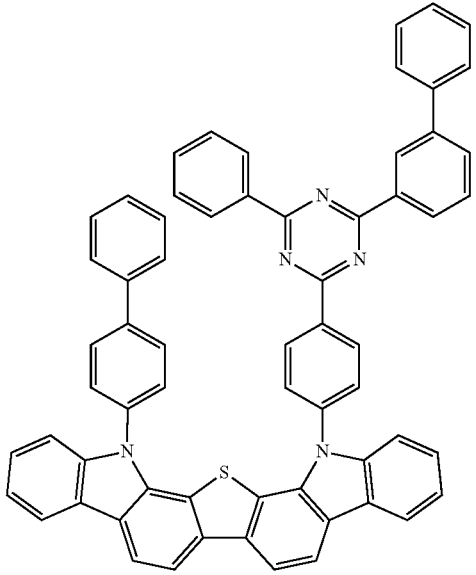
[222]
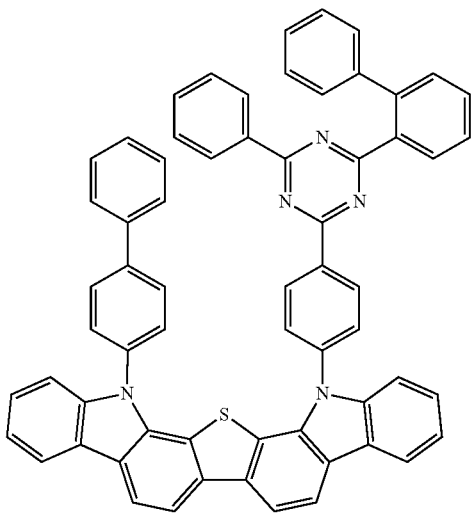
[223]
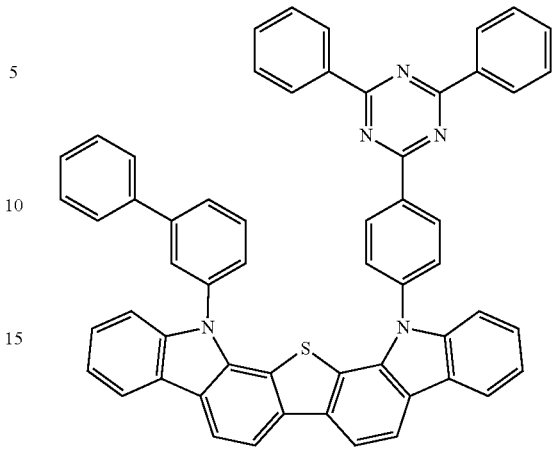
[224]
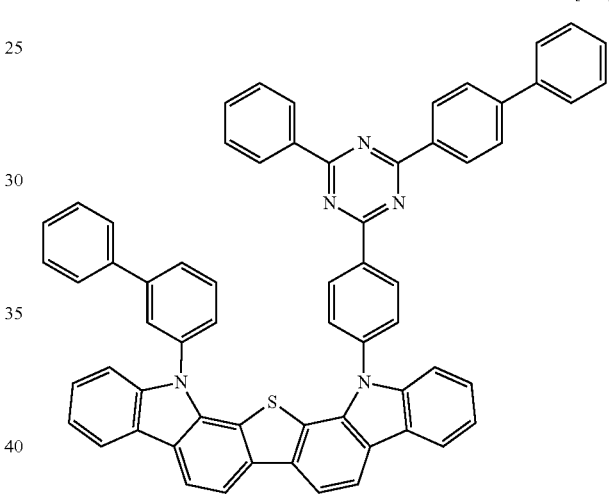
[225]
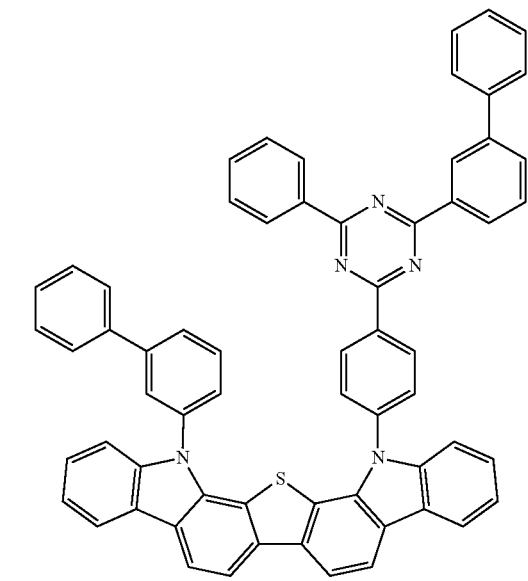

[226]
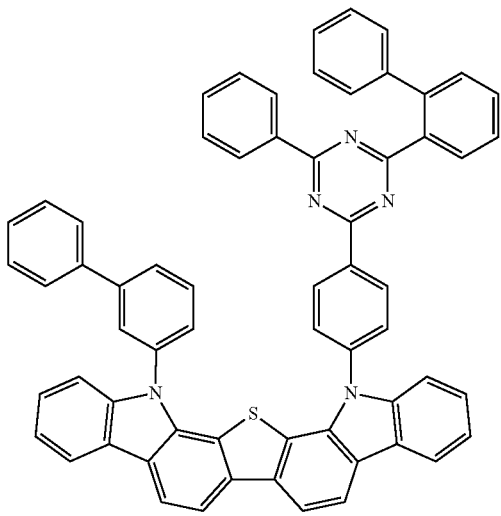
[227]
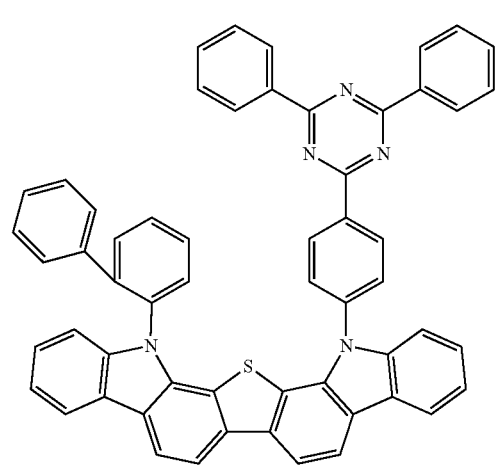
[228]
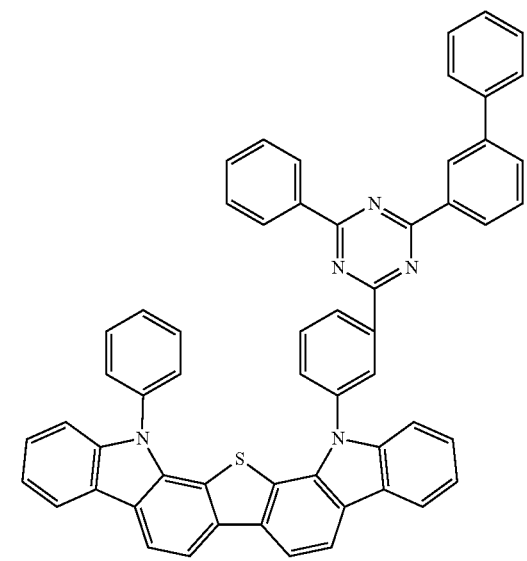
[229]
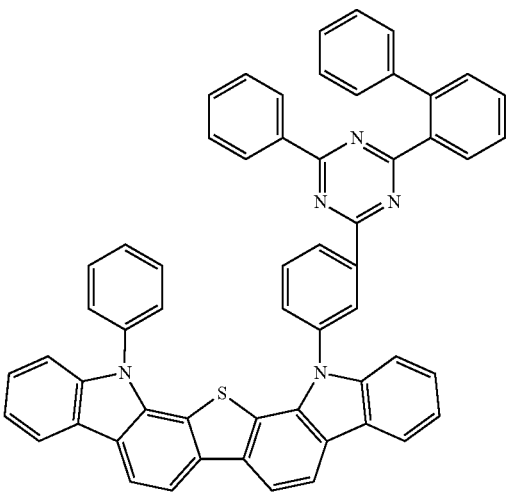
[230]
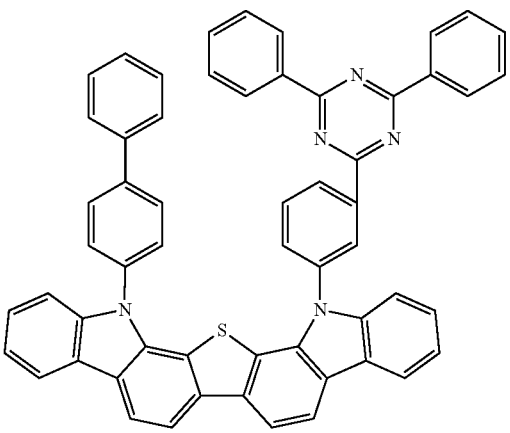
[231]
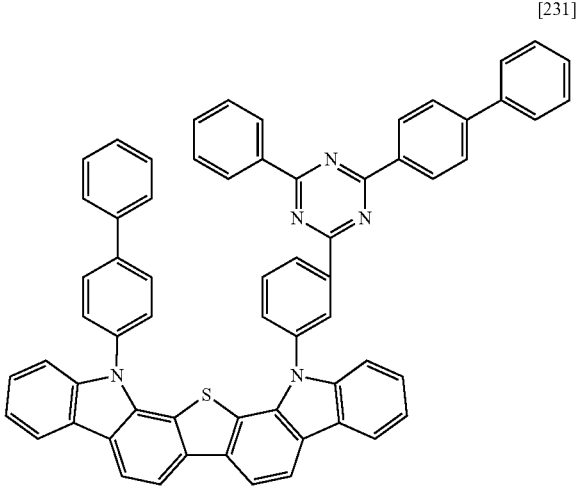

[232]
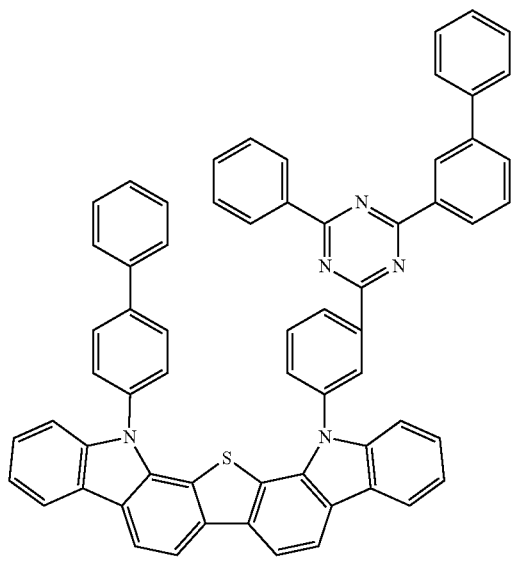
[233]
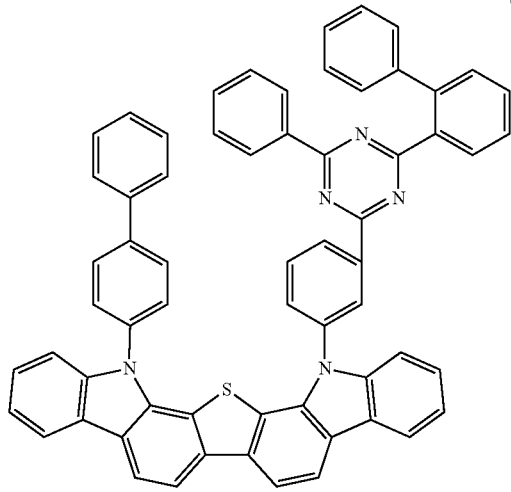
[234]
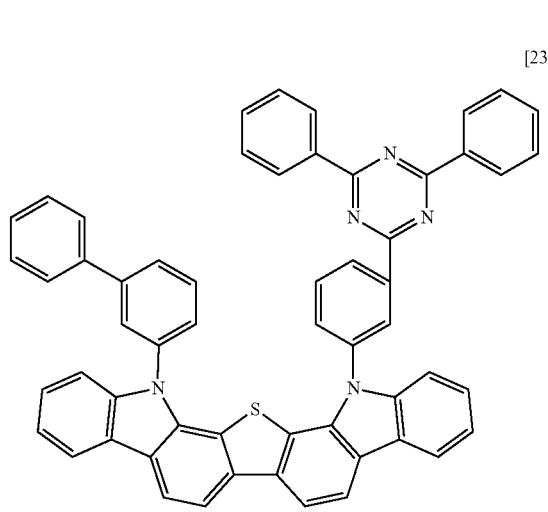
[235]
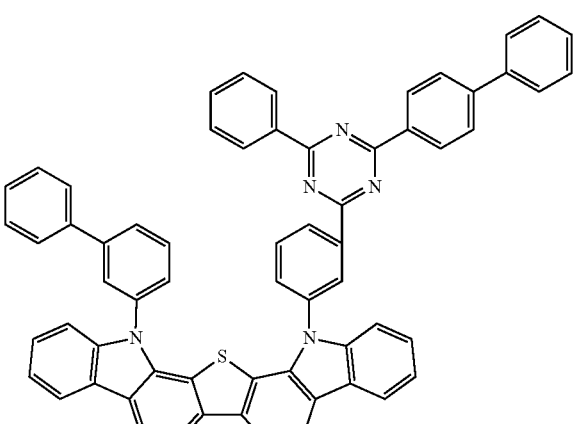
[236]
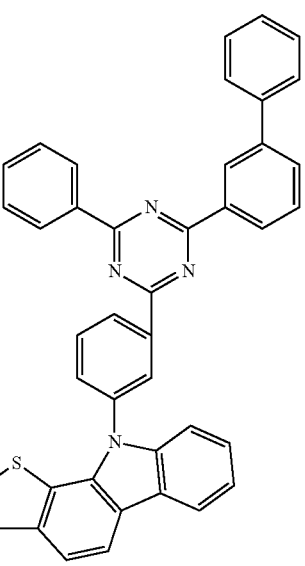
[237]
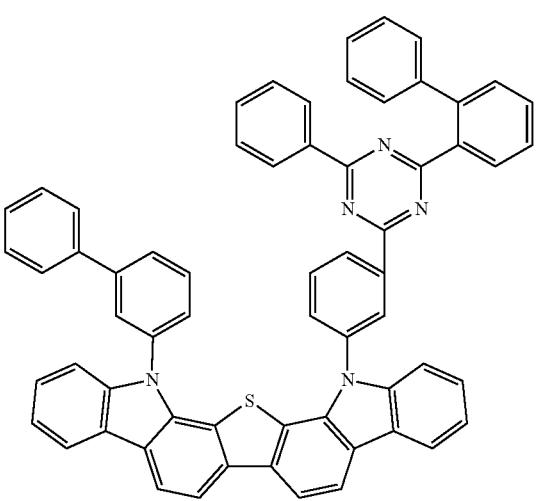

[238]
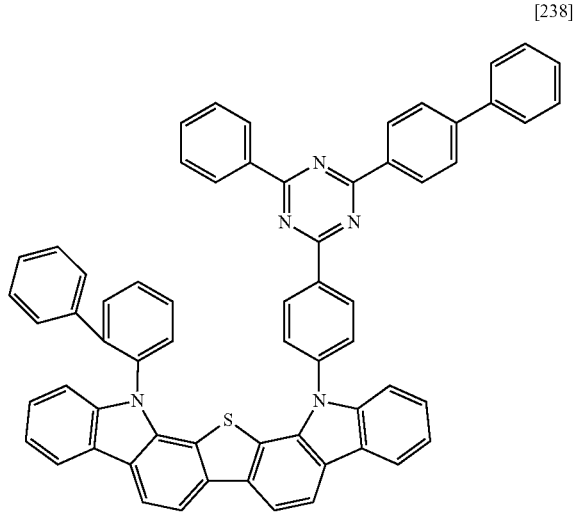
[239]
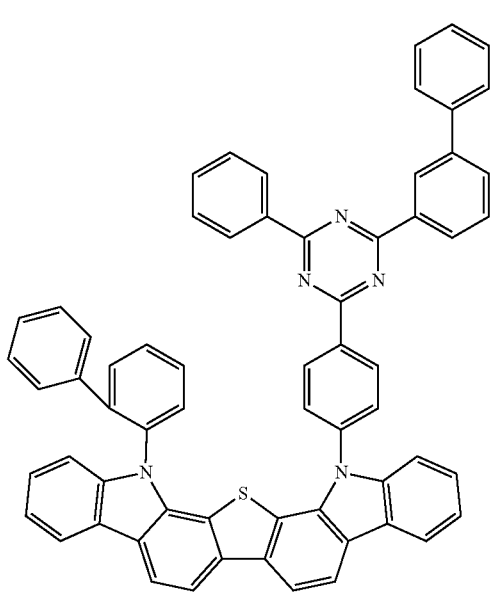
[240]
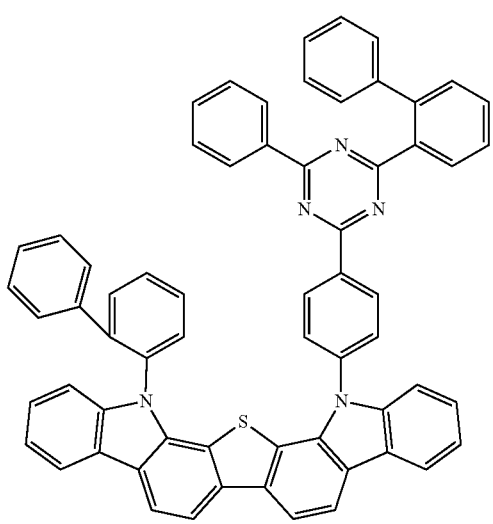
[241]
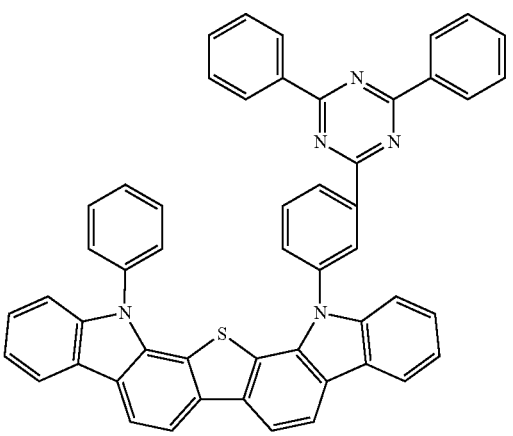
[242]
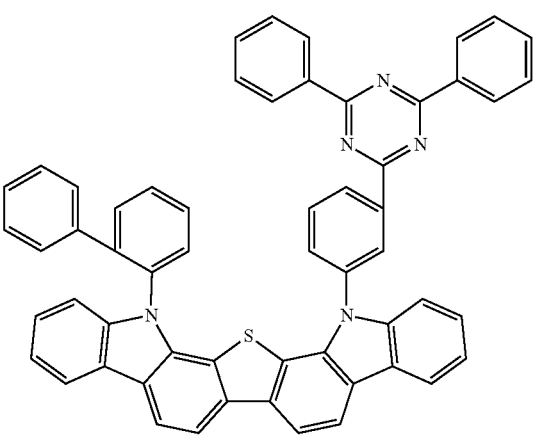
[243]

[244]
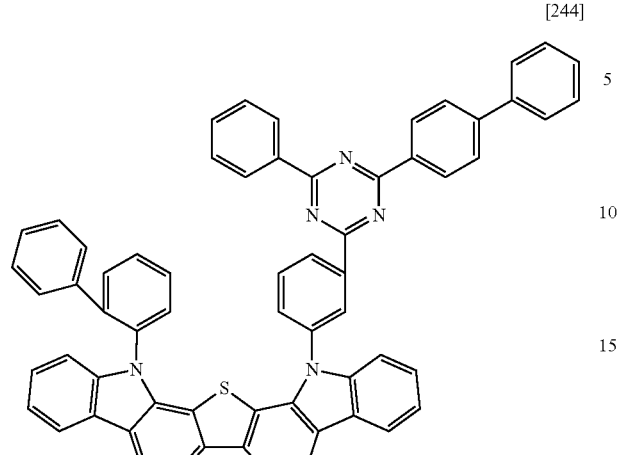
[245]
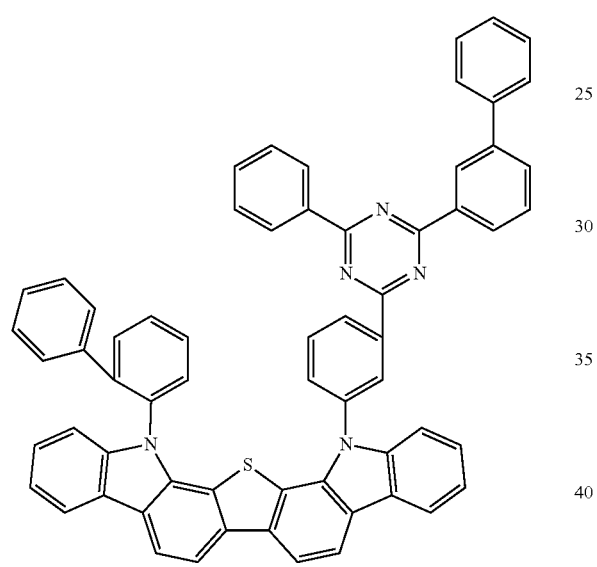
[246]
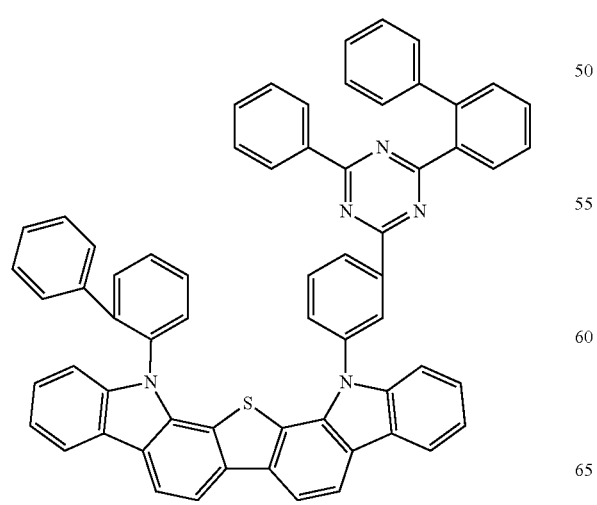
[247]
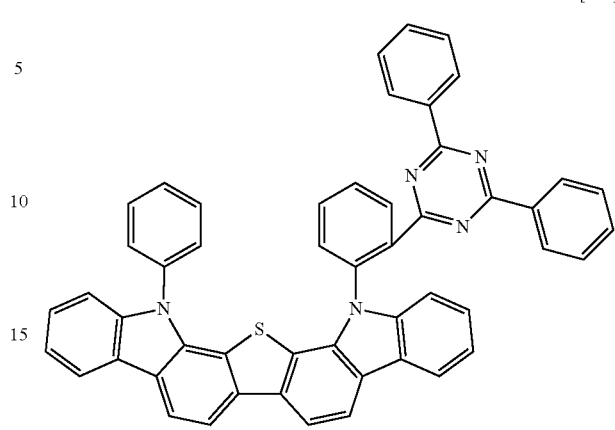
[248]
[249]
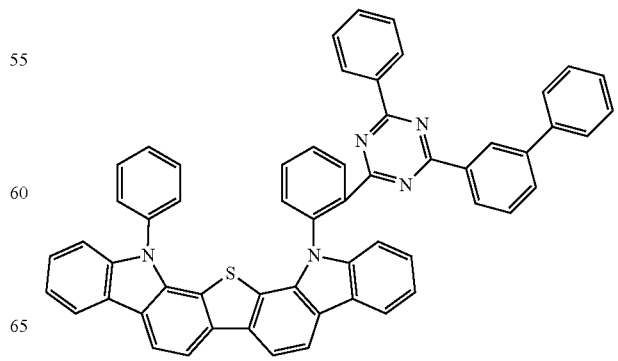

[250]
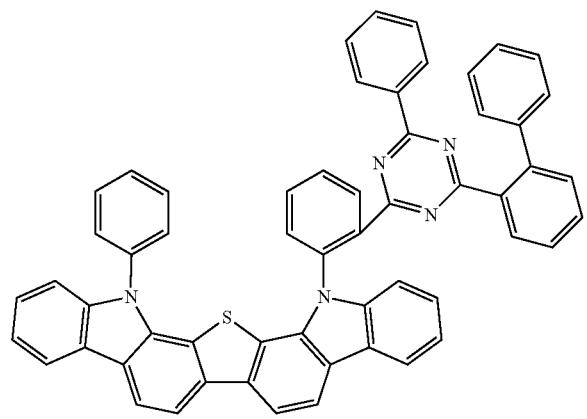
[251]
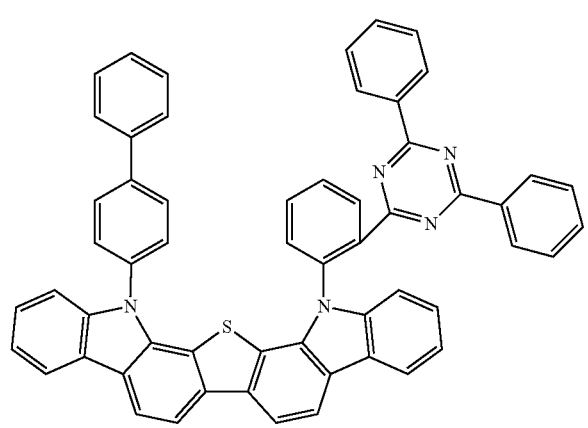
[252]
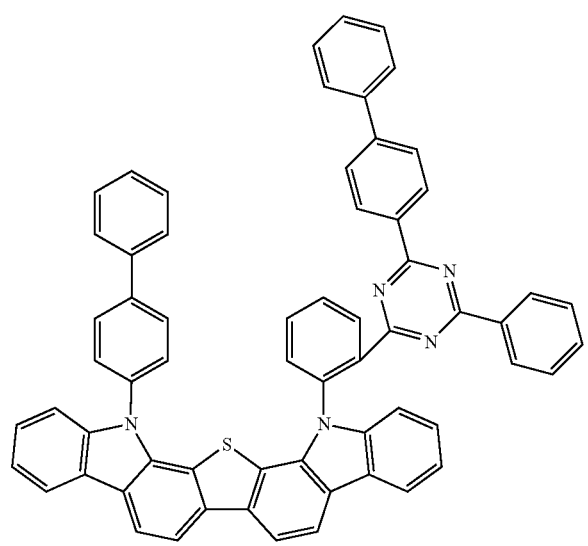
[253]
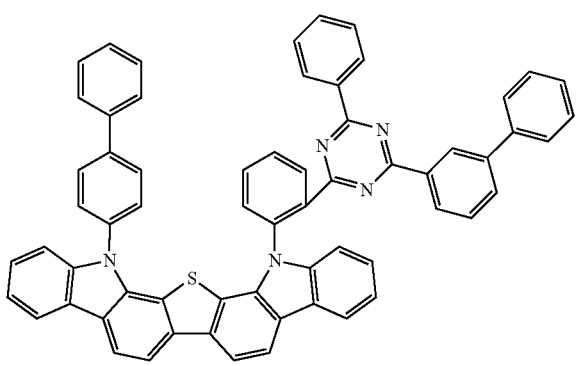
[254]
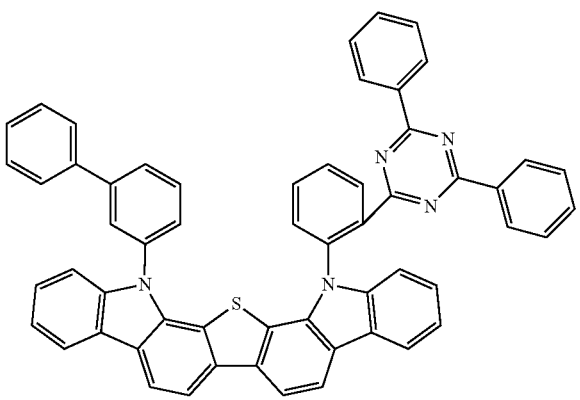
[255]

[256]
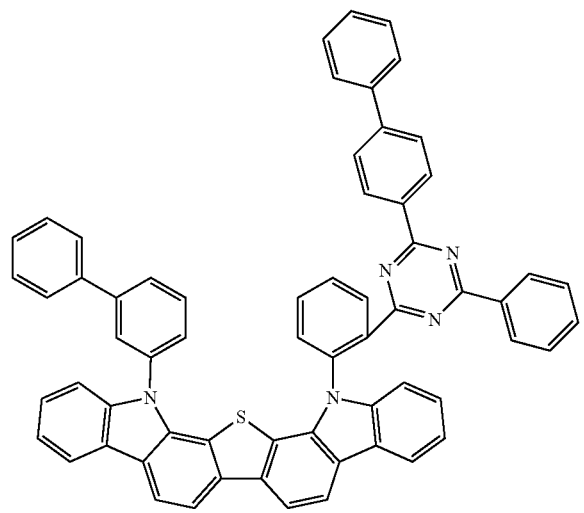
[257]
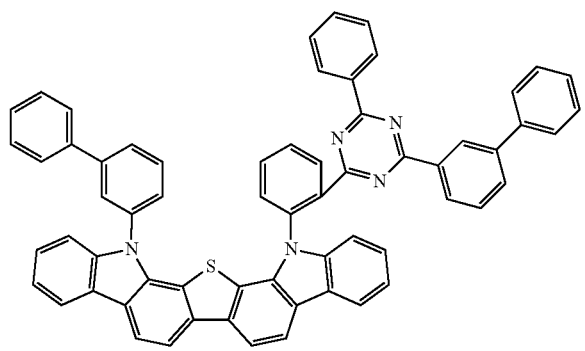
[258]
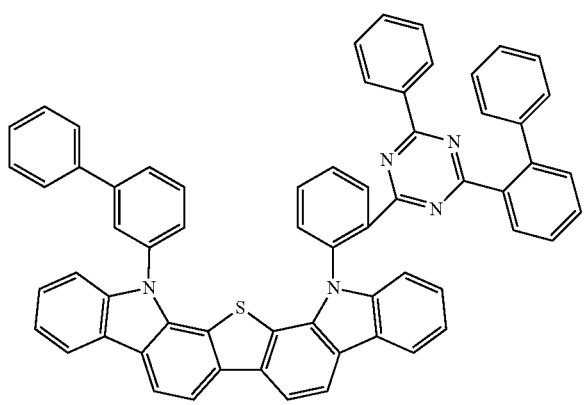
[259]
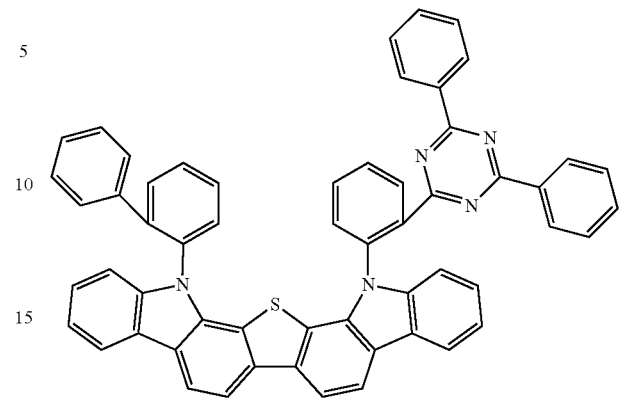
[260]
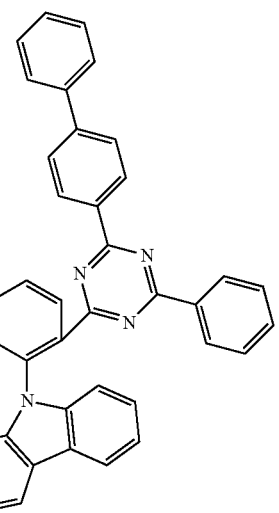
[261]
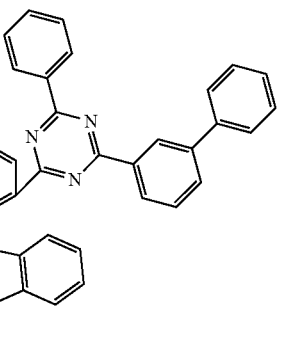

91
-continued
[262]
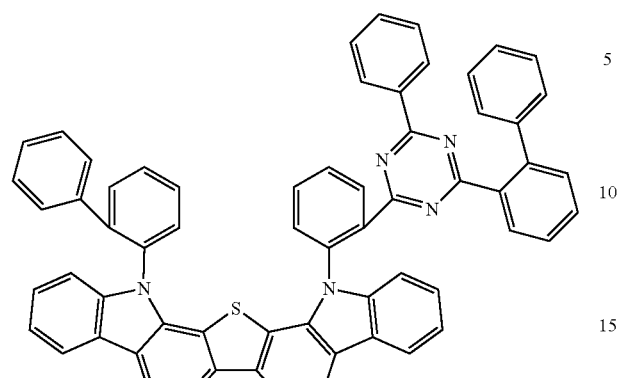
[263]
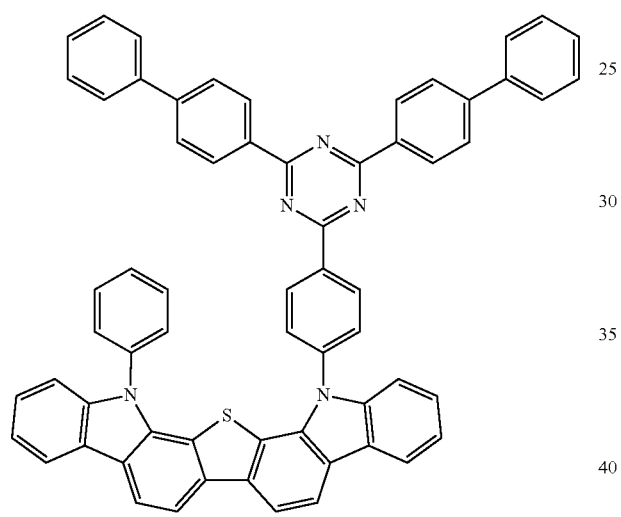
[264]
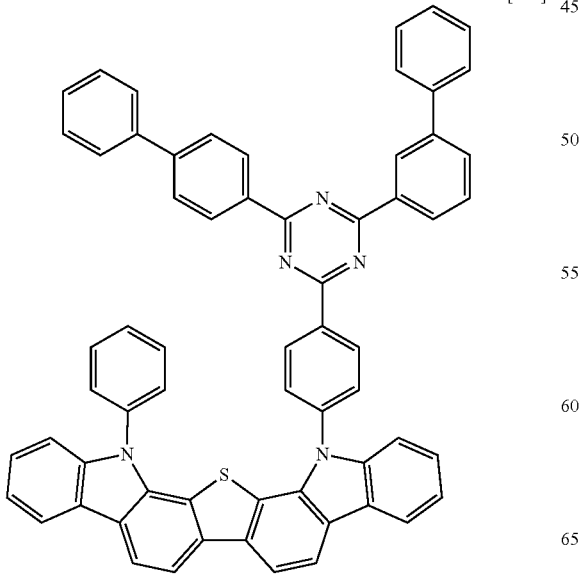
92
-continued
[265]
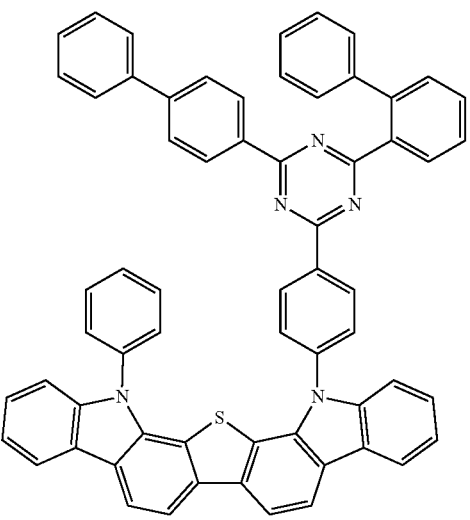
[266]
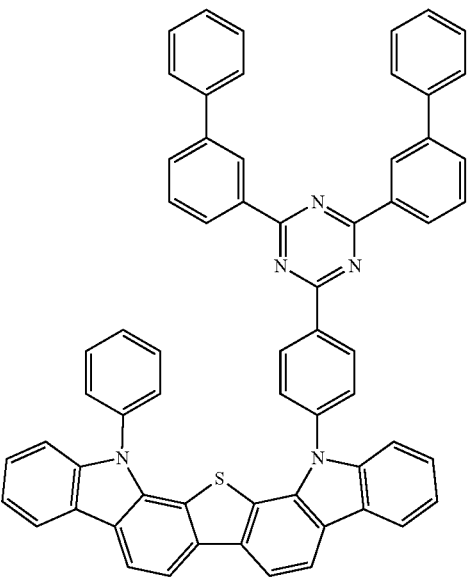
[267]
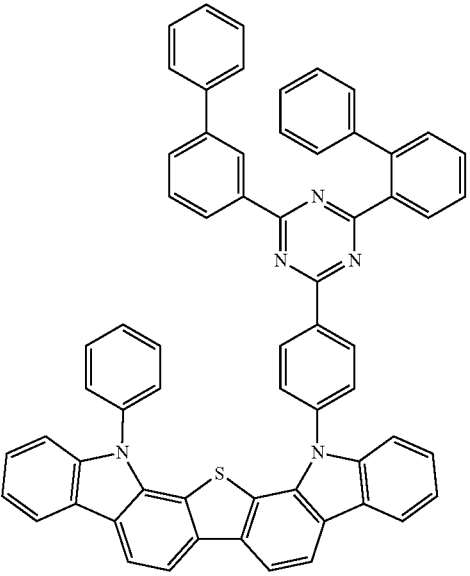

[268]
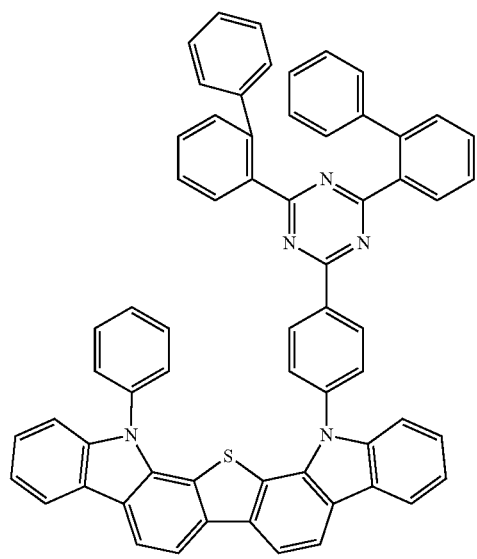
[269]
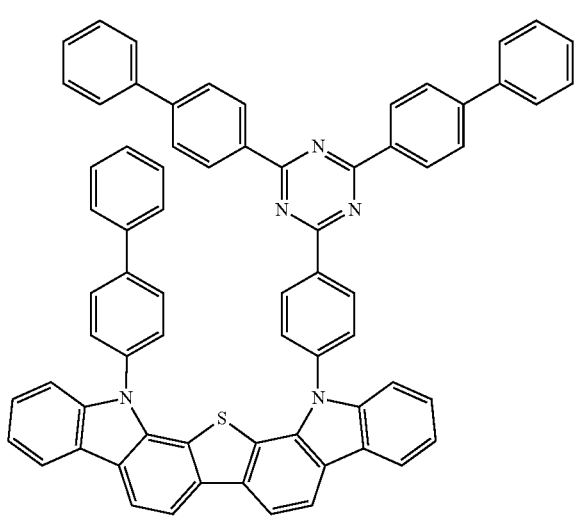
[270]
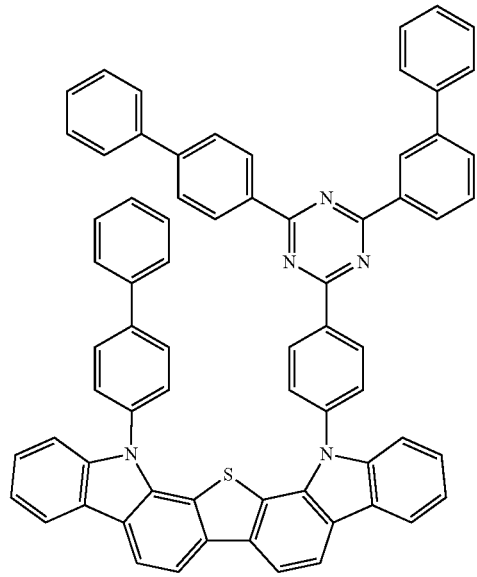
[271]
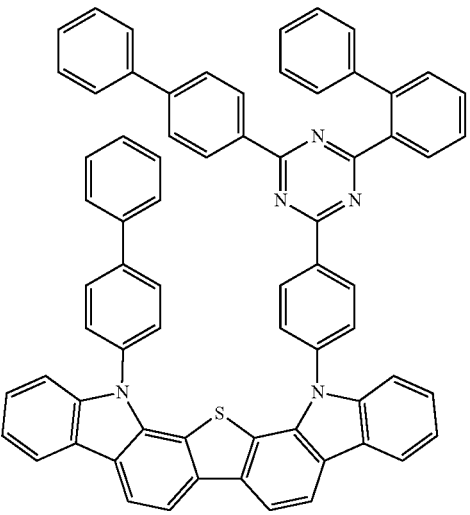
[272]
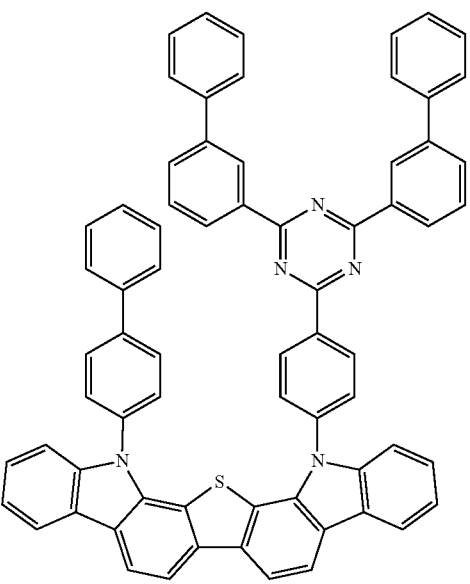
[273]
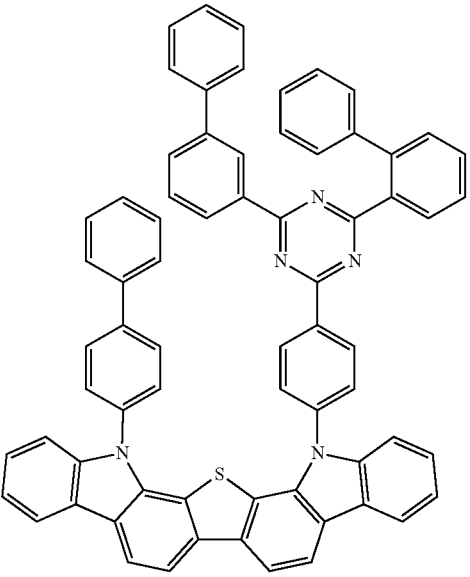

[274]
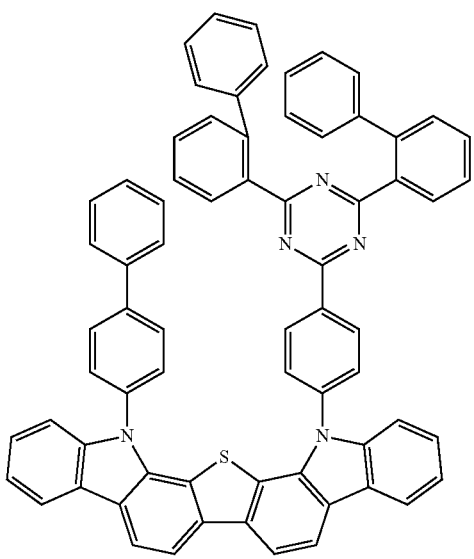
[275]
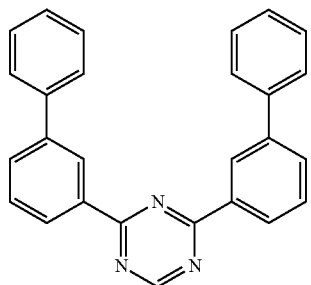
[276]
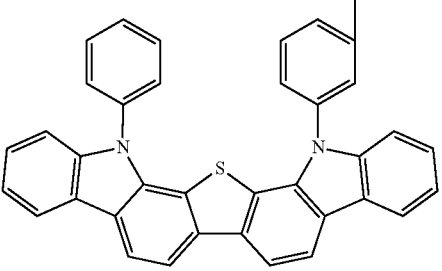
[277]
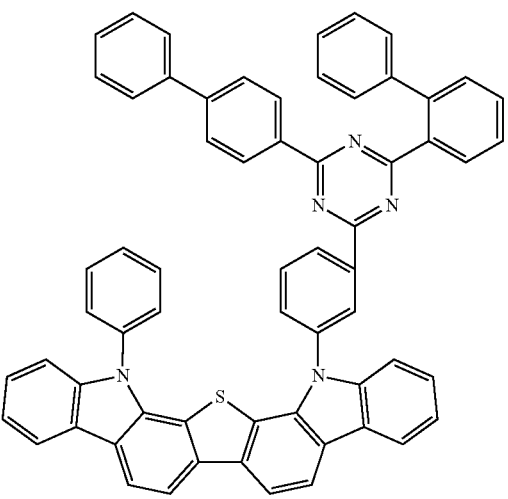
[278]
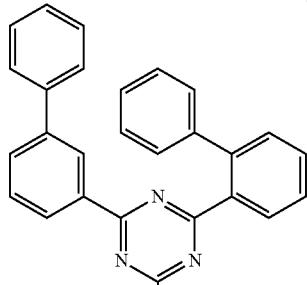
[279]
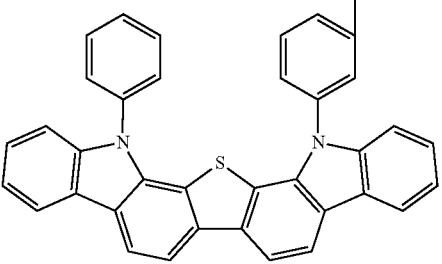

-continued
[280]
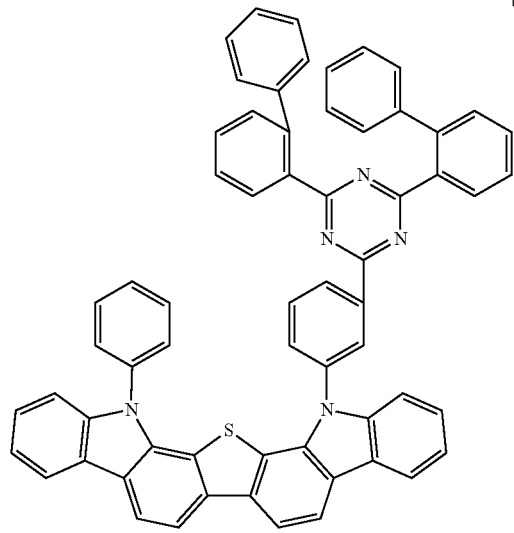
[281]
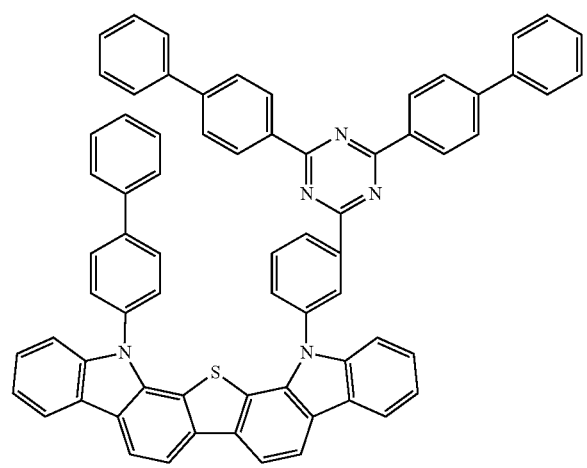
[282]
[283]
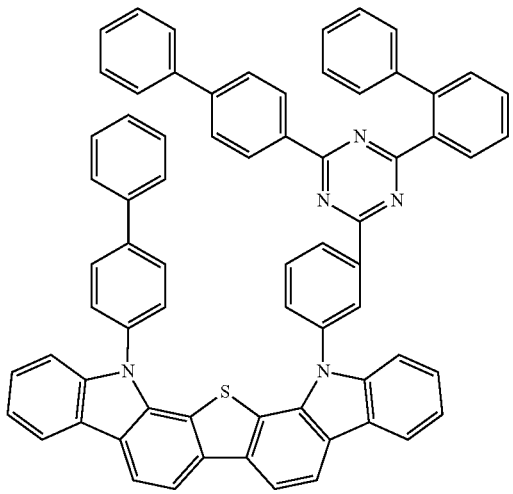
[284]
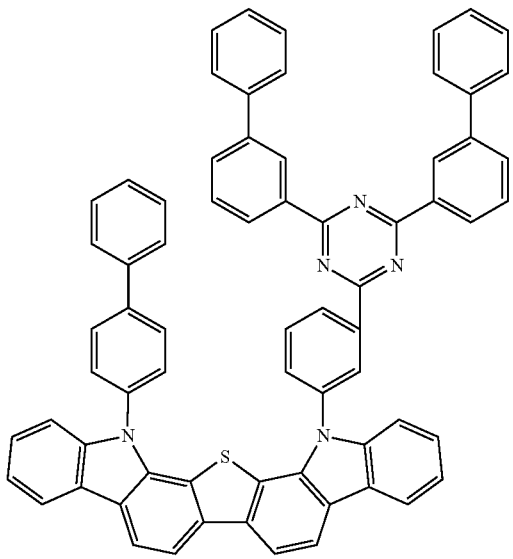
[285]
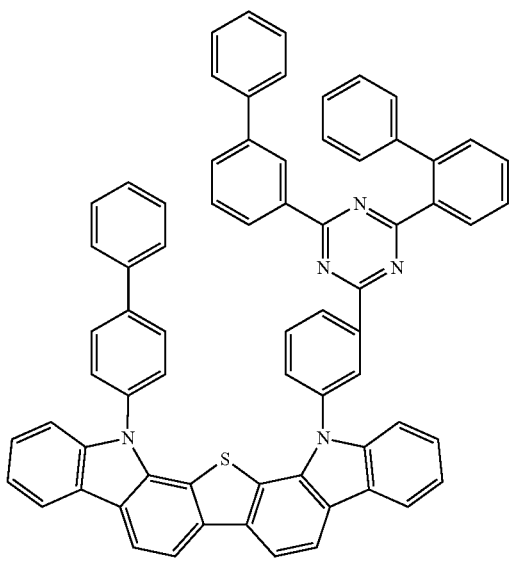

-continued
[286]
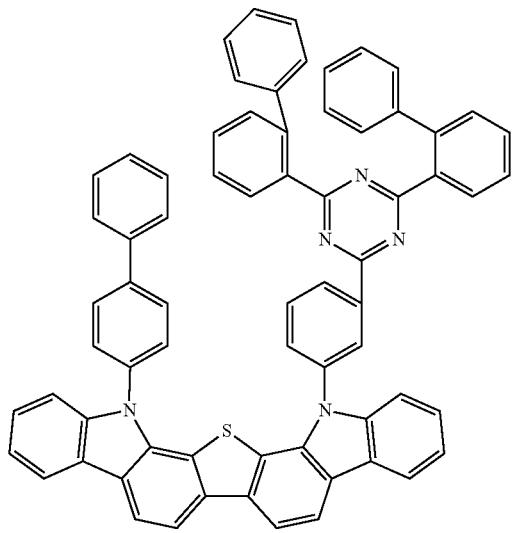
[287]
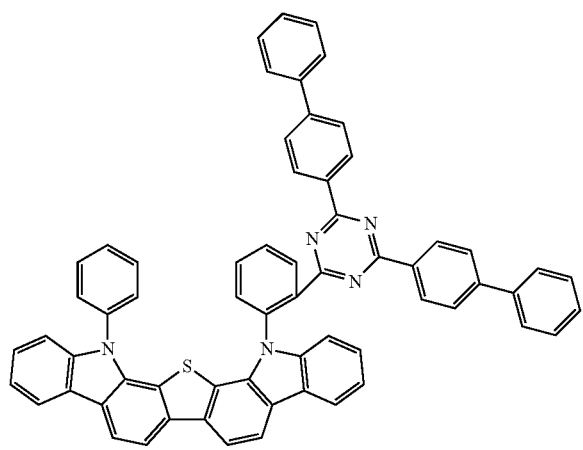
[288]
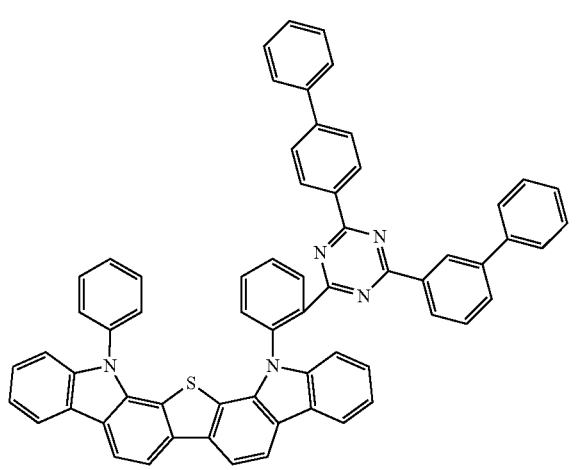
[289]
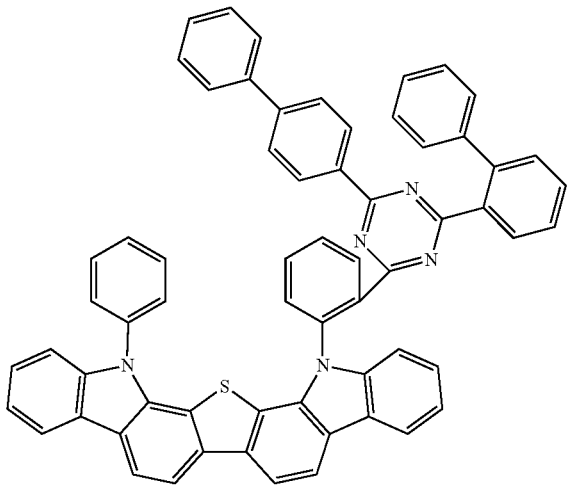
[290]
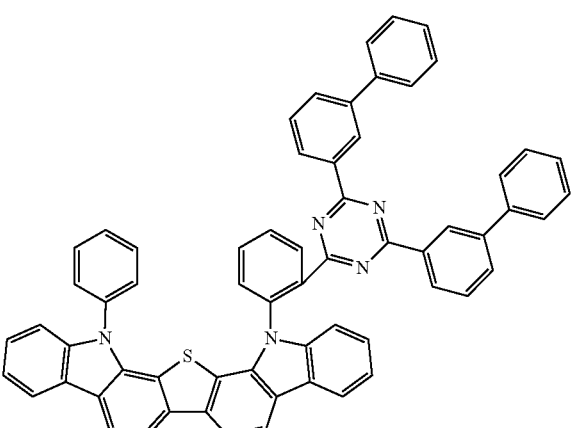
[291]
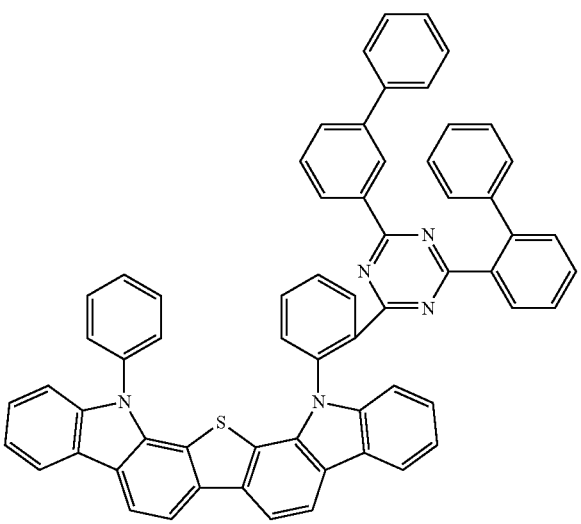

[292]
[295]
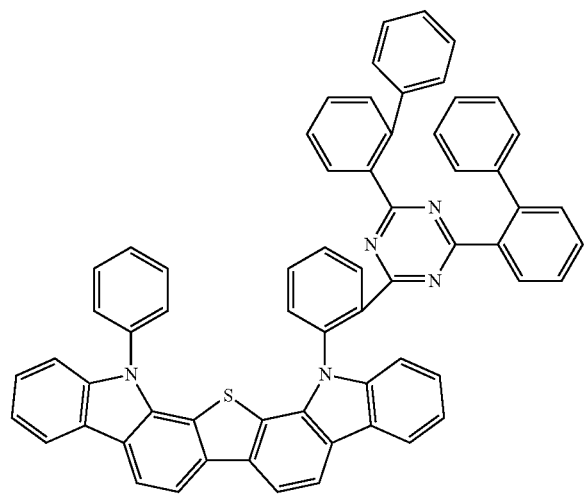
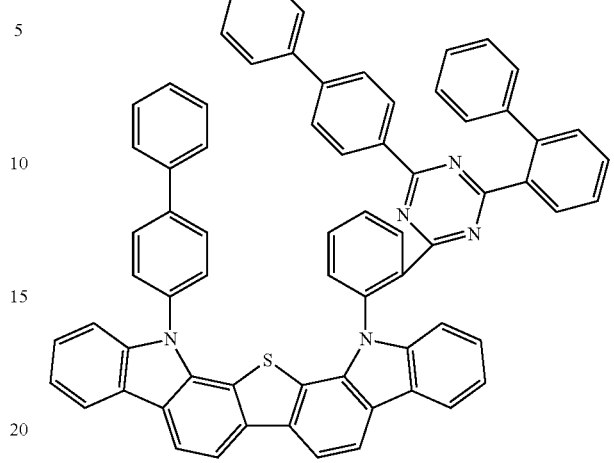
[293]
[296]
[294]
[297]
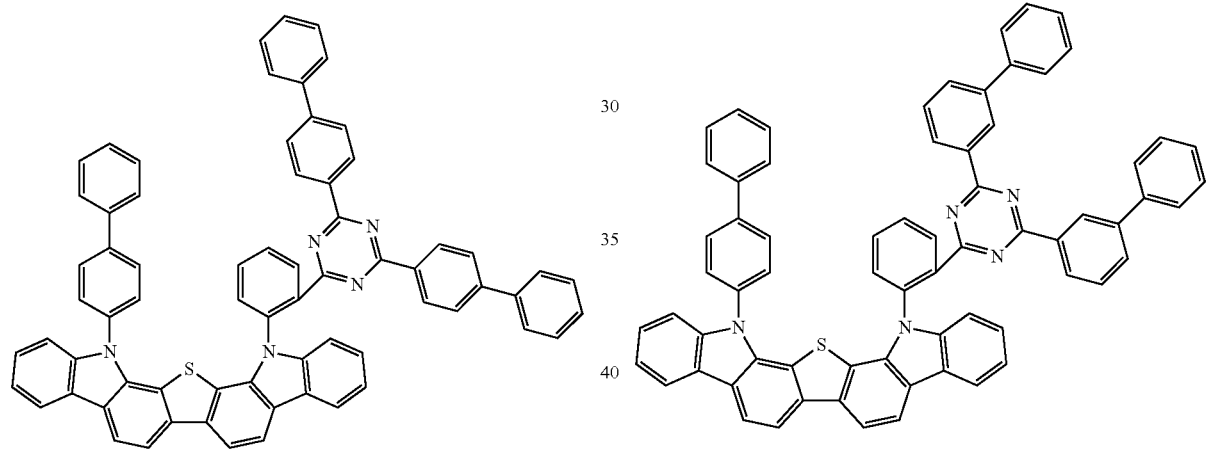
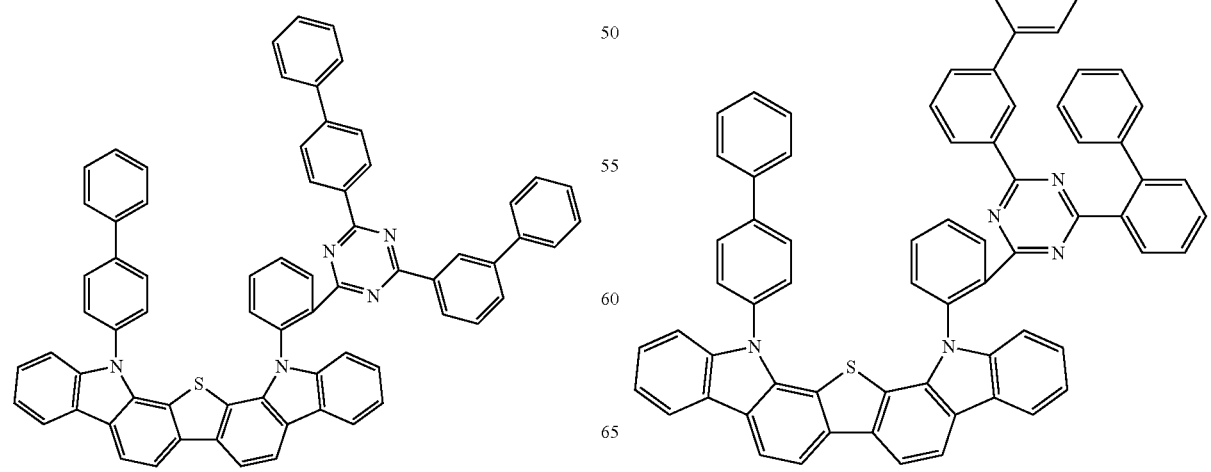

[298]
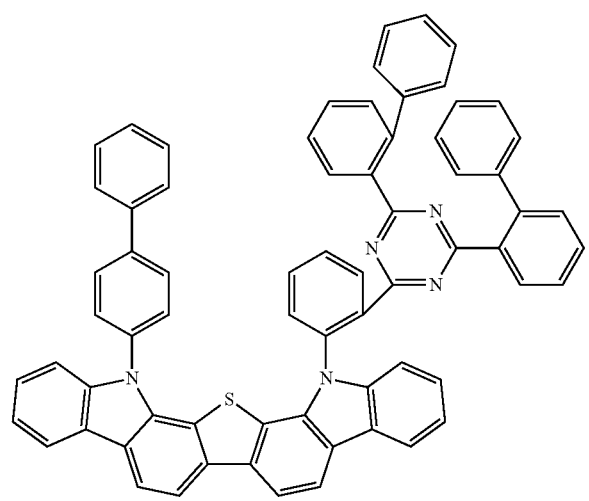
[299]
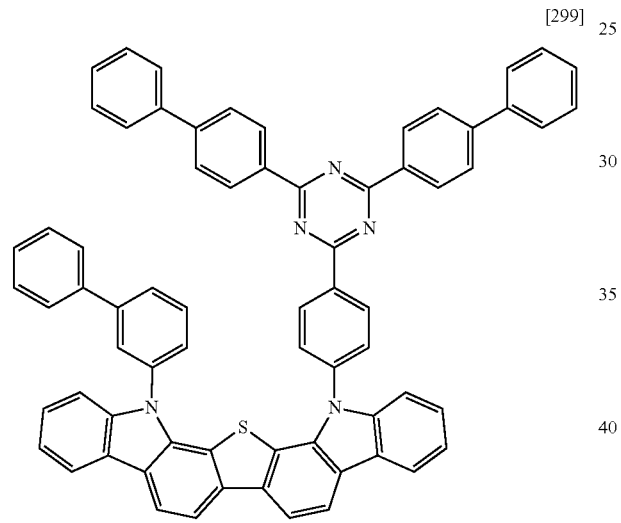
[300]
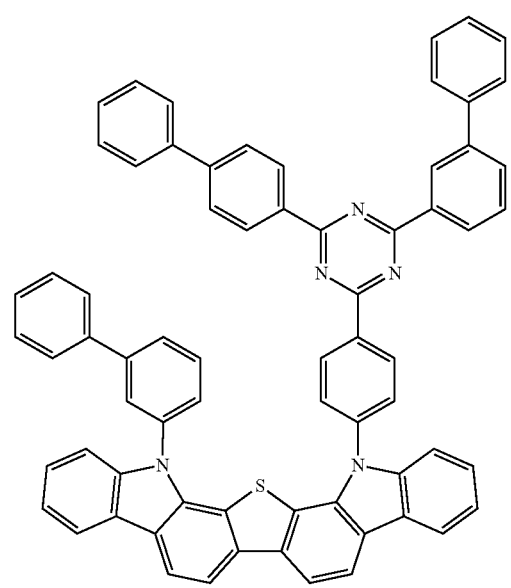
[301]
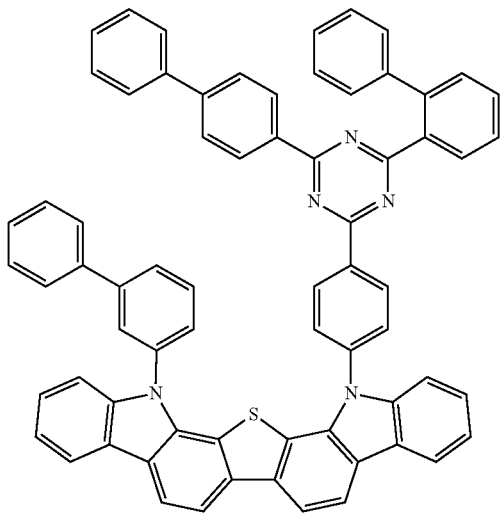
[302]
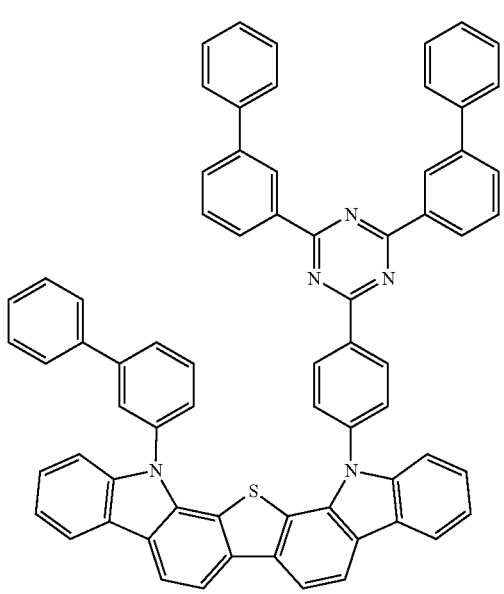
[303]
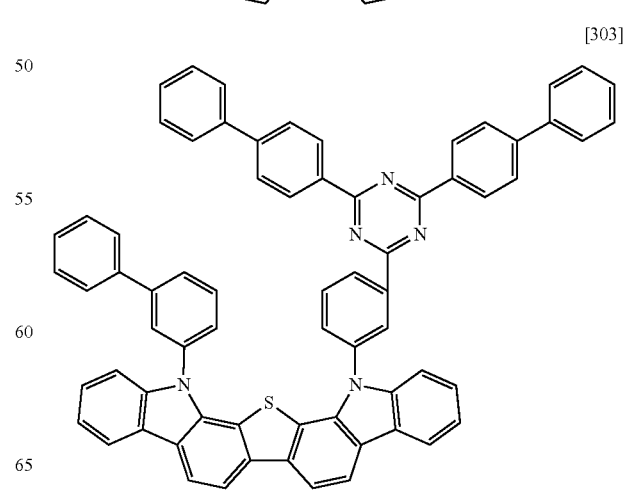

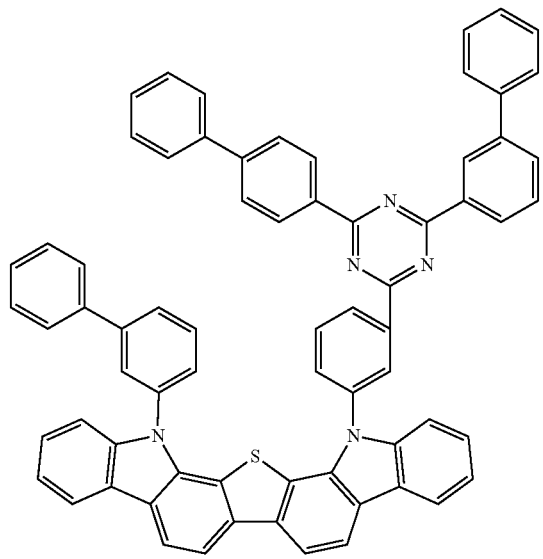
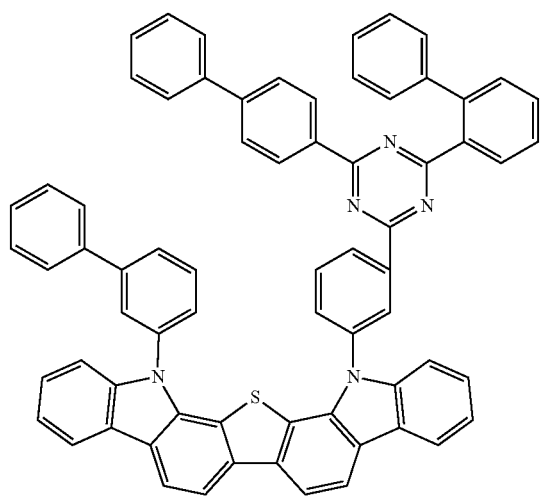
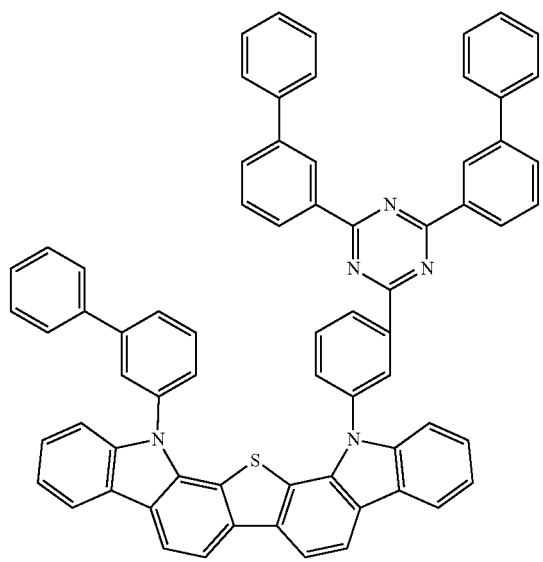
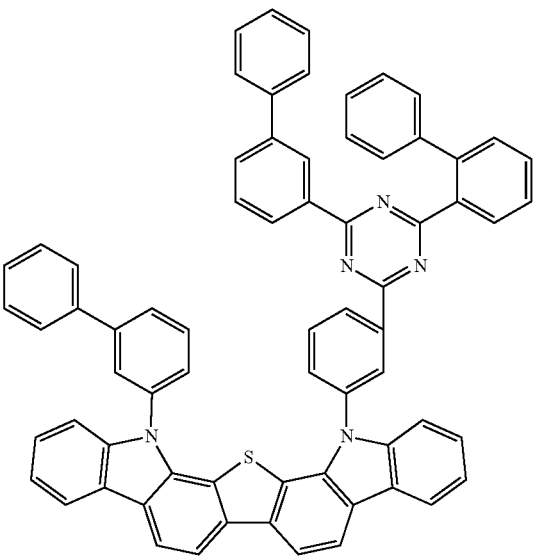
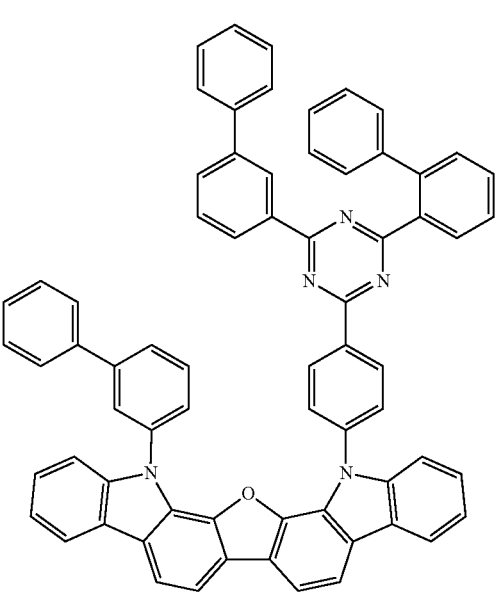

[309]
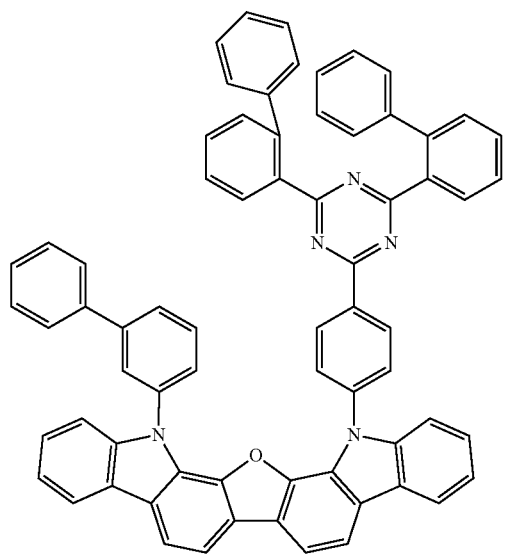
[310]
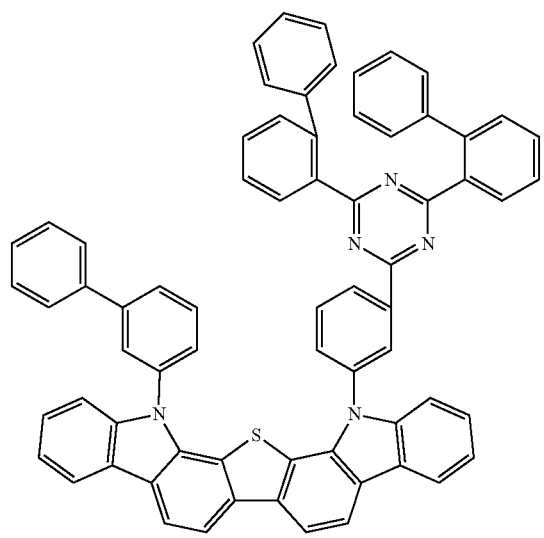
[311]
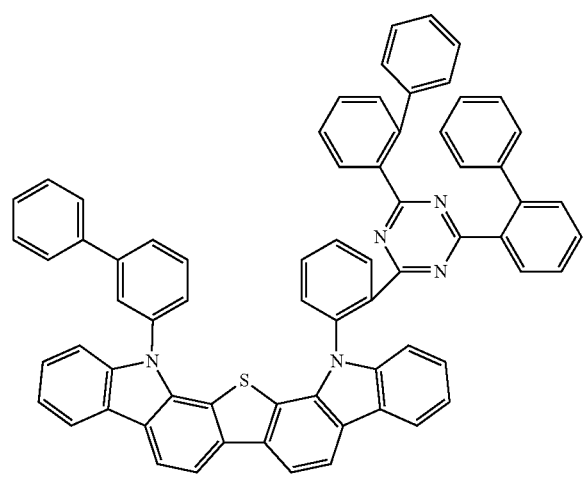
[312]
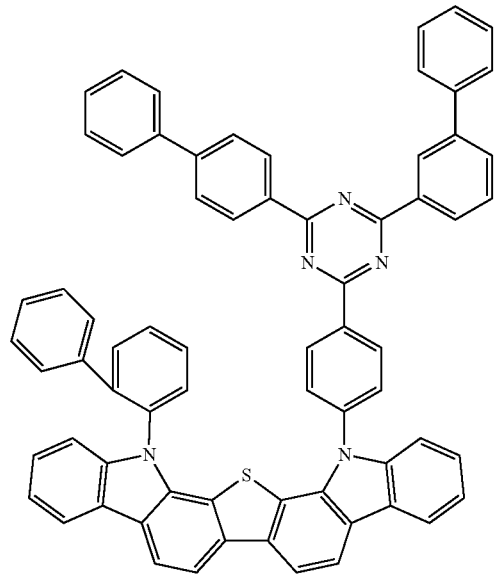
[313]
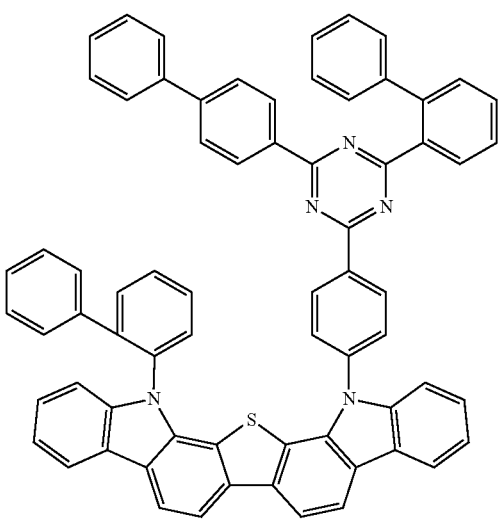

[314]
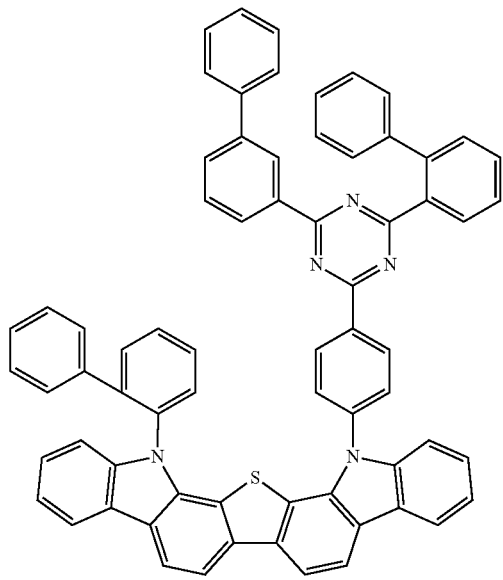
[315]
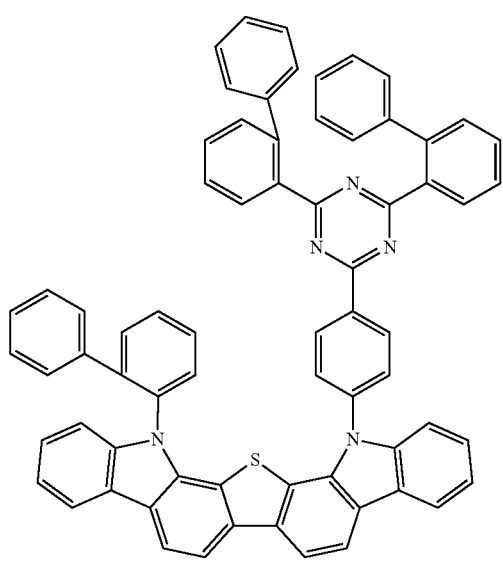
[316]
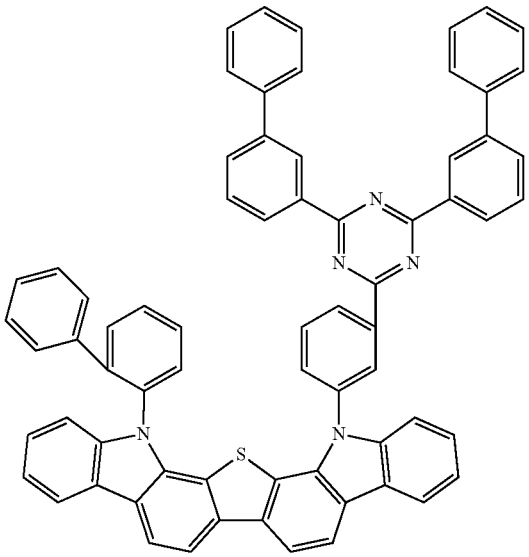
[317]
[318]
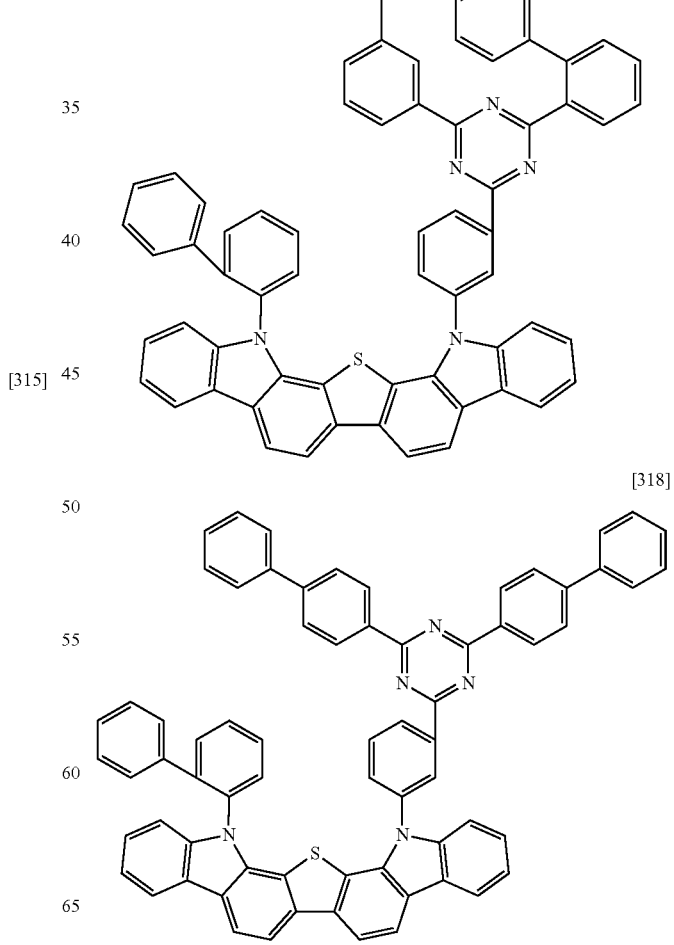

-continued
[319]
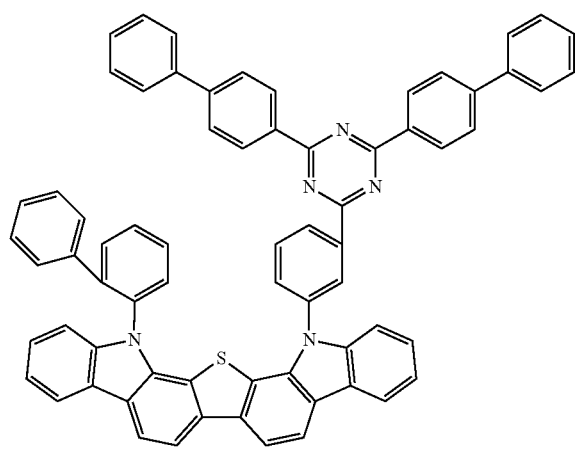
[320]
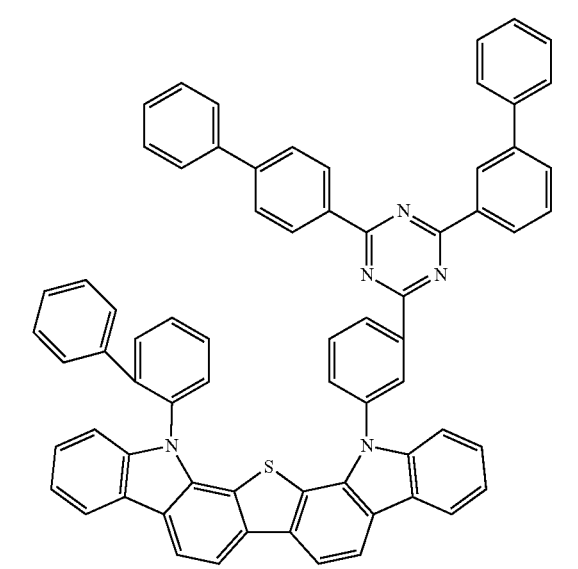
[321]
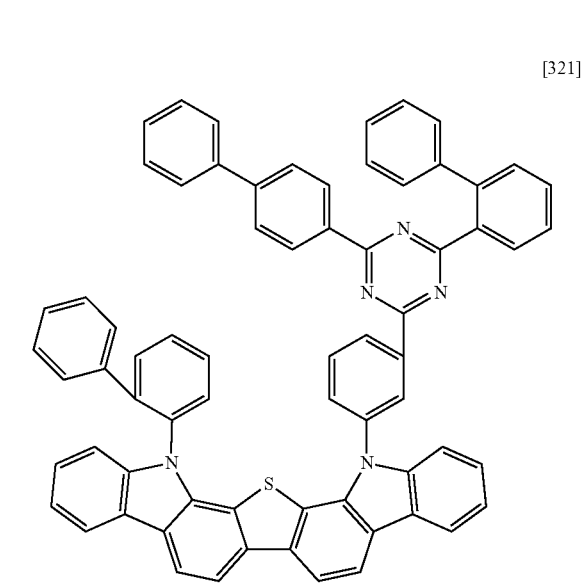
-continued
[322]
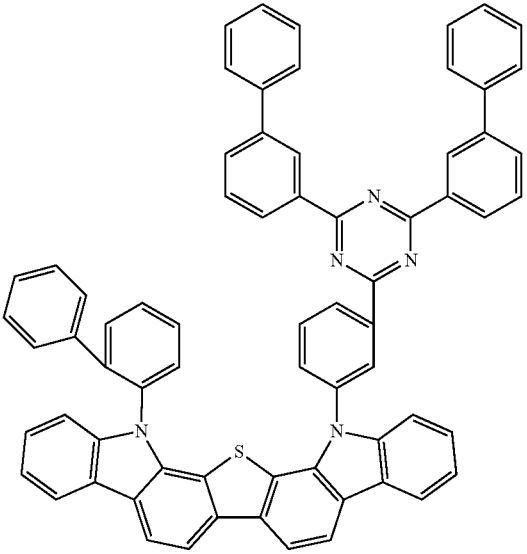
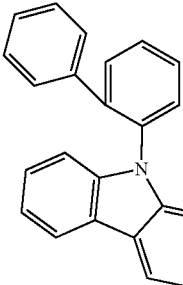
[323]
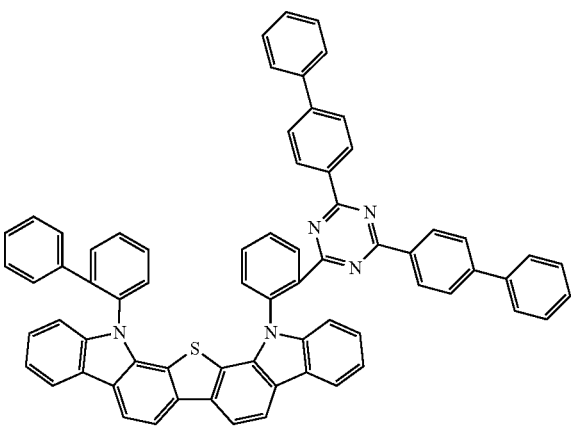
[324]
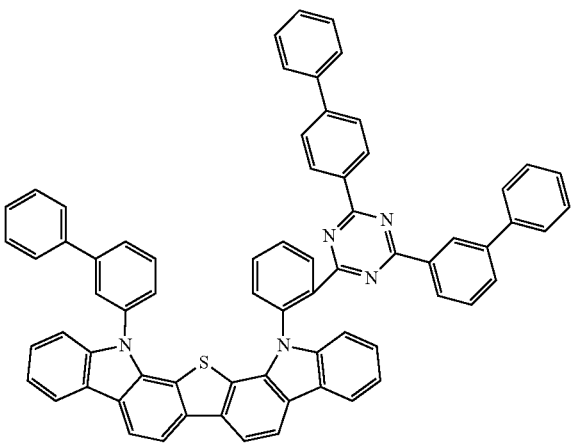

[325]
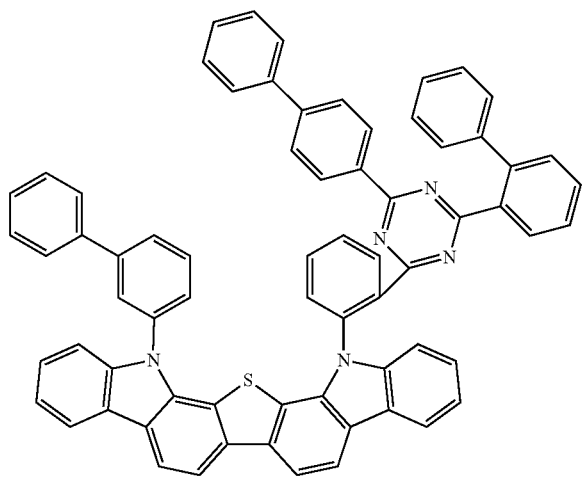
[326]
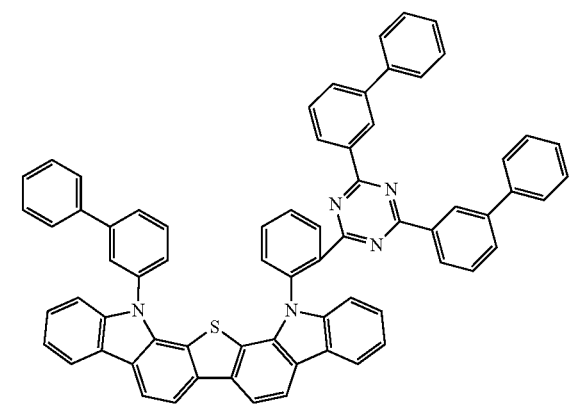
[327]
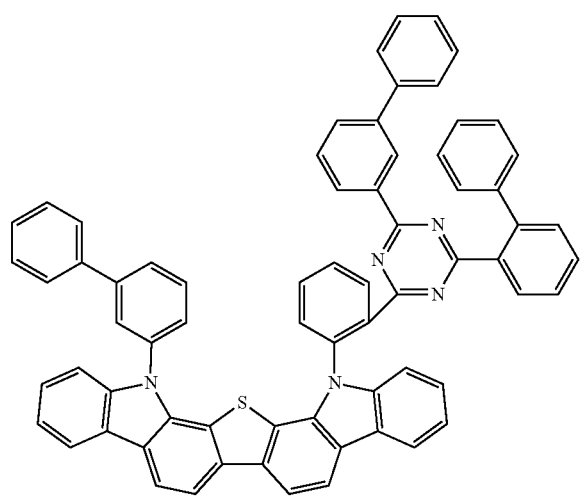
[328]
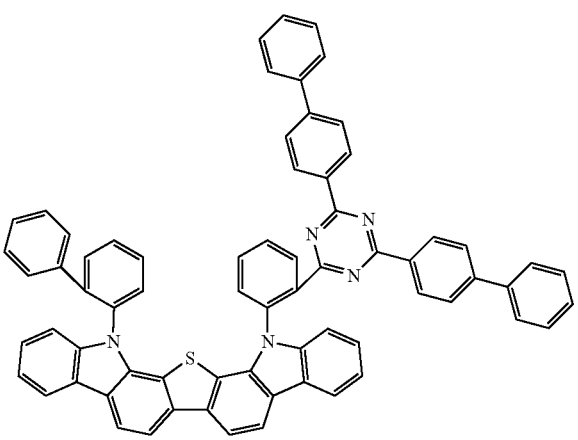
[329]
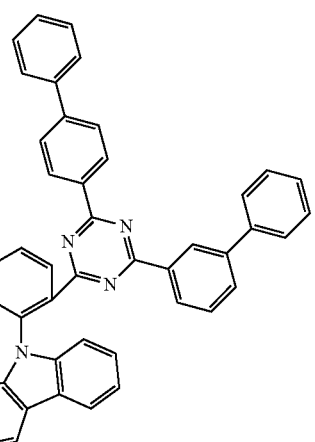
[330]
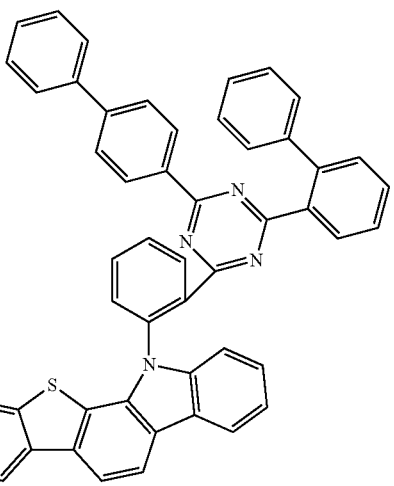

[331]

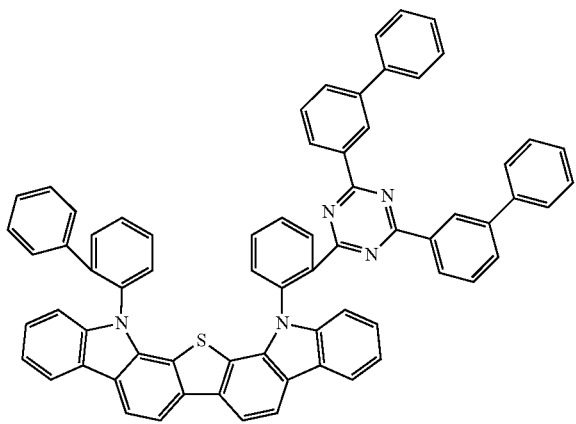

[332]

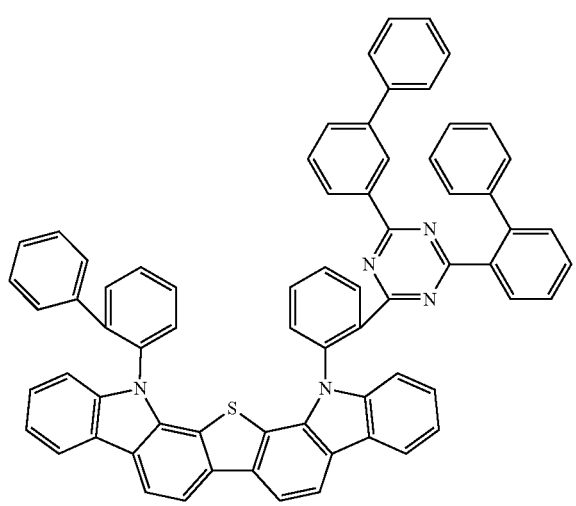

[333]

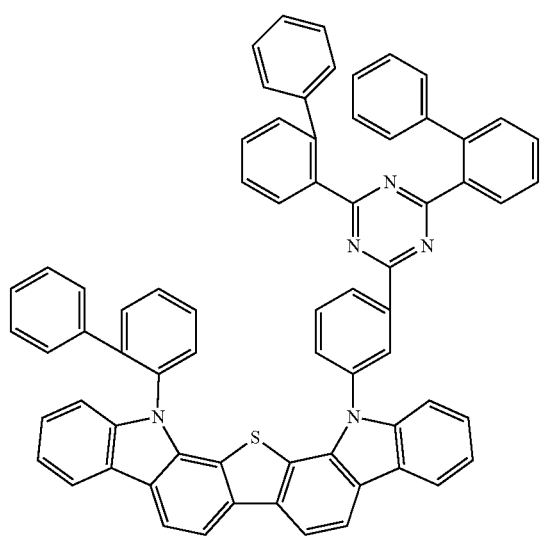

[334]

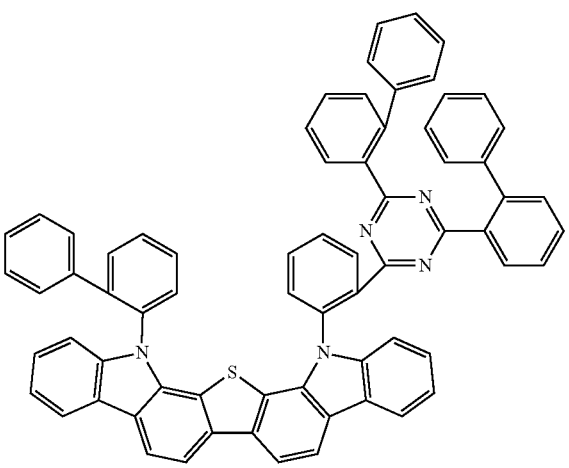

A composition for an organic optoelectronic device according to another embodiment may include, e.g., a first compound for an organic optoelectronic device and a second compound for an organic optoelectronic device (e.g., as a mixture). The first compound for an organic optoelectronic device may be the compound for an organic optoelectronic device described above, and the second compound for an organic optoelectronic device may be represented by, e.g., Chemical Formula 2 or a combination of Chemical Formula 3 and Chemical Formula 4.

[Chemical Formula 2]

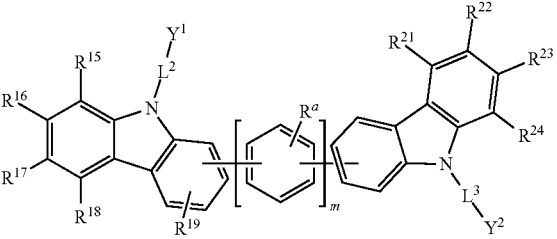

In Chemical Formula 2, $Y^1$ and $Y^2$ may each independently be or include, e.g., a substituted or unsubstituted C6 to C20 aryl group or a substituted or unsubstituted C2 to C30 heterocyclic group.

$L^2$ and $L^3$ may each independently be or include, e.g., a single bond, or a substituted or unsubstituted C6 to C20 arylene group.

$R^a$ and $R^{15}$ to $R^{24}$ may each independently be or include, e.g., hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

m may be, e.g., an integer of 0 to 2;

[Chemical Formula 3]

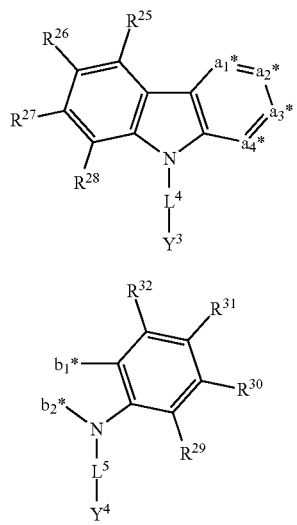

[Chemical Formula 4]

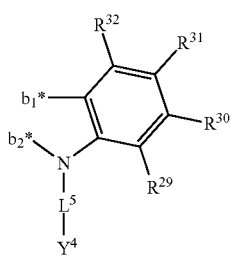

In Chemical Formulas 3 and 4, $Y^3$ and $Y^4$ may each independently be or include, e.g., a substituted or unsubstituted C6 to C20 aryl group or a substituted or unsubstituted C2 to C30 heterocyclic group.

Two adjacent ones of $a_1^*$ to $a_4^*$ of Chemical Formula 3 are linking carbons linked at $b_1^*$ and $b_2^*$ of Chemical Formula 4. The remaining two of $a_1^*$ to $a_4^*$ of Chemical Formula 3, not linked at $b_1^*$ and $b_2^*$ of Chemical Formula 4, are each independently $C-L^a-R^b$. As used herein, the term "linking carbon" refers to a shared carbon at which fused rings are linked.

$L^a$, $L^4$, and $L^5$ may each independently be or include, e.g., a single bond, or a substituted or unsubstituted C6 to C20 arylene group.

$R^b$ and $R^{25}$ to $R^{32}$ may each independently be or include, e.g., hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

The second compound for an organic optoelectronic device may be used in the light emitting layer together with the first compound for an organic optoelectronic device to help increase charge mobility and stability, thereby improving luminous efficiency and life-span characteristics.

In an implementation, $Y^1$ and $Y^2$ in Chemical Formula 2 may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, a substituted or unsubstituted fluorenyl group, or a substituted or unsubstituted pyridinyl group.

In an implementation, $L^2$ and $L^3$ in Chemical Formula 2 may each independently be, e.g., a single bond, a substituted or unsubstituted phenylene group, or a substituted or unsubstituted biphenylene group.

In an implementation, $R^{15}$ to $R^{24}$ in Chemical Formula 2 may each independently be, e.g., hydrogen, deuterium or a substituted or unsubstituted C6 to C12 aryl group.

In an implementation, m may be, e.g., 0 or 1.

In an implementation, "substituted" of Chemical Formula 2 may mean that at least one hydrogen is replaced by deuterium, a C1 to C4 alkyl group, a C6 to C18 aryl group, or a C2 to C30 heteroaryl group.

In an implementation, Chemical Formula 2 may be represented by one of Chemical Formula 2-1 to Chemical Formula 2-15.

[Chemical Formula 2-1]

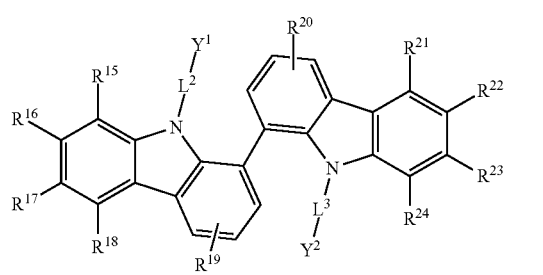

[Chemical Formula 2-2]

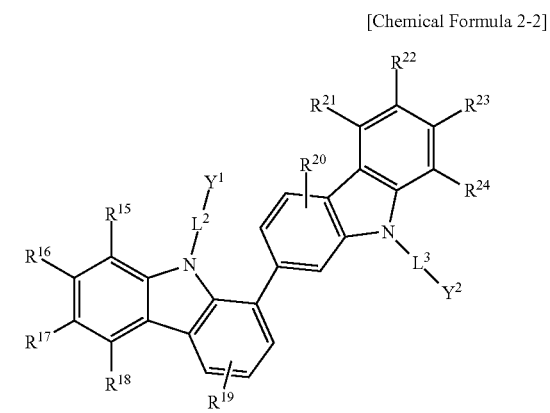

[Chemical Formula 2-3]

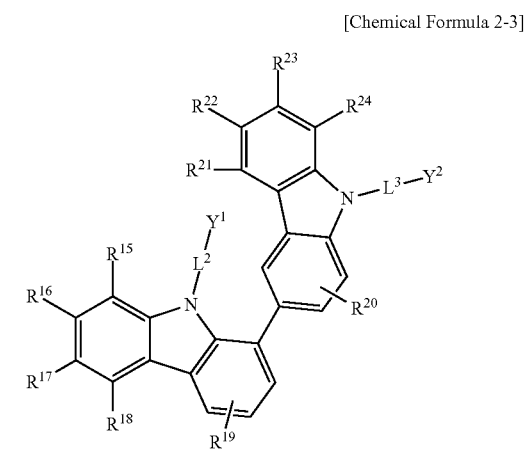

[Chemical Formula 2-4]

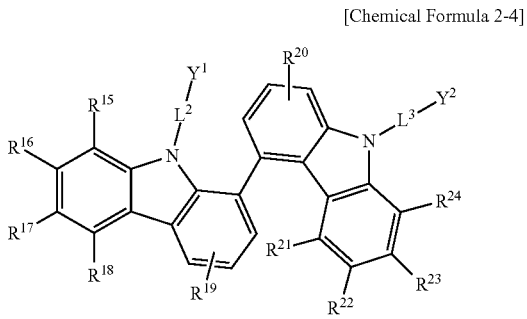

[Chemical Formula 2-5]
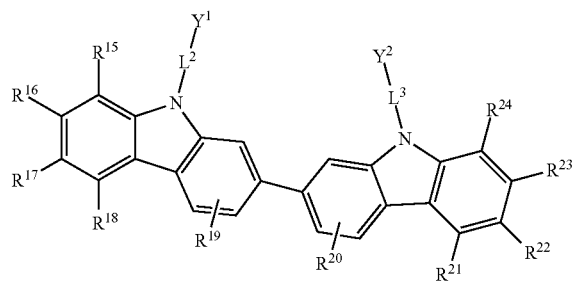
[Chemical Formula 2-6]
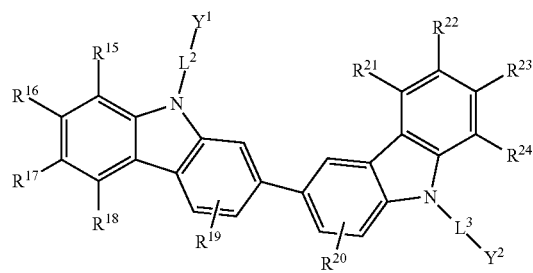
[Chemical Formula 2-7]
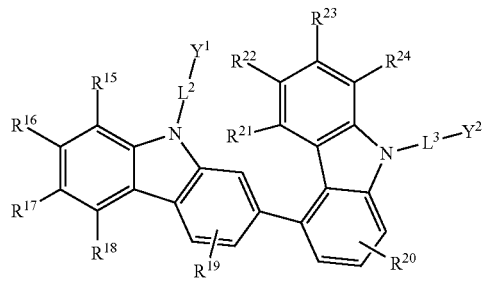
[Chemical Formula 2-8]
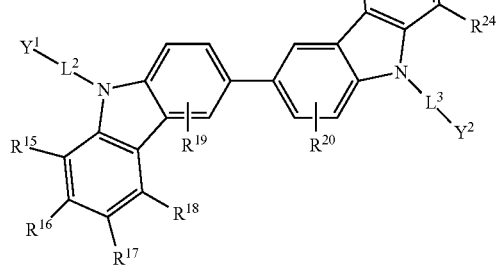
[Chemical Formula 2-9]
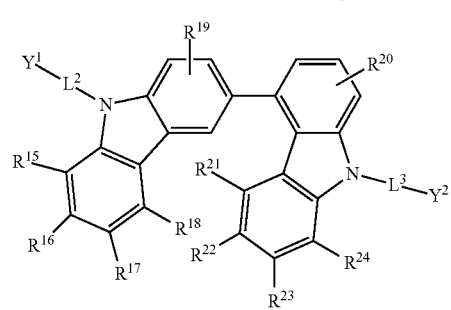
[Chemical Formula 2-10]
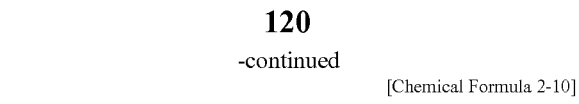
[Chemical Formula 2-11]
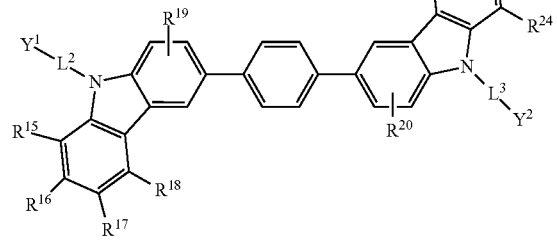
[Chemical Formula 2-12]
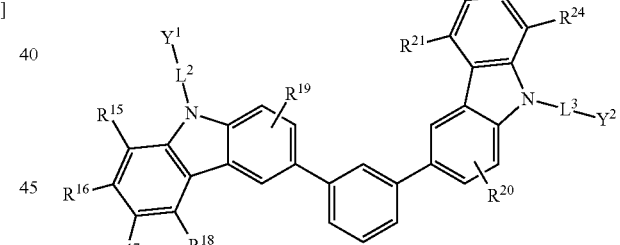
[Chemical Formula 2-13]
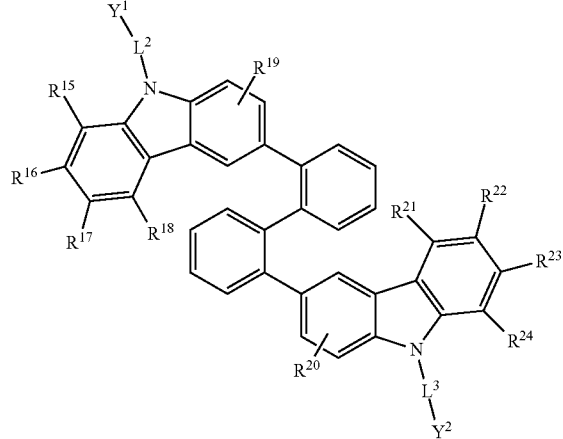

[Chemical Formula 2-14]

[Chemical Formula 2-15]

In Chemical Formula 2-1 to Chemical Formula 2-15, $R^{15}$ to $R^{24}$ may each independently be, e.g., hydrogen or a substituted or unsubstituted C6 to C12 aryl group, and moieties *-$L^2$-$Y^1$ and *-$L^3$-$Y^2$ may each independently be, e.g., a moiety of Group II.

[Group II]

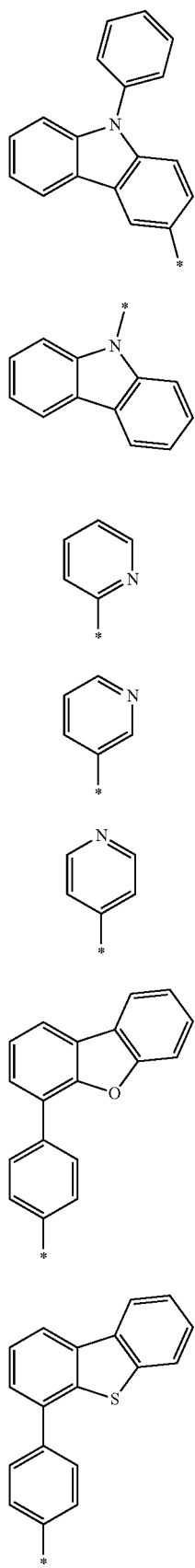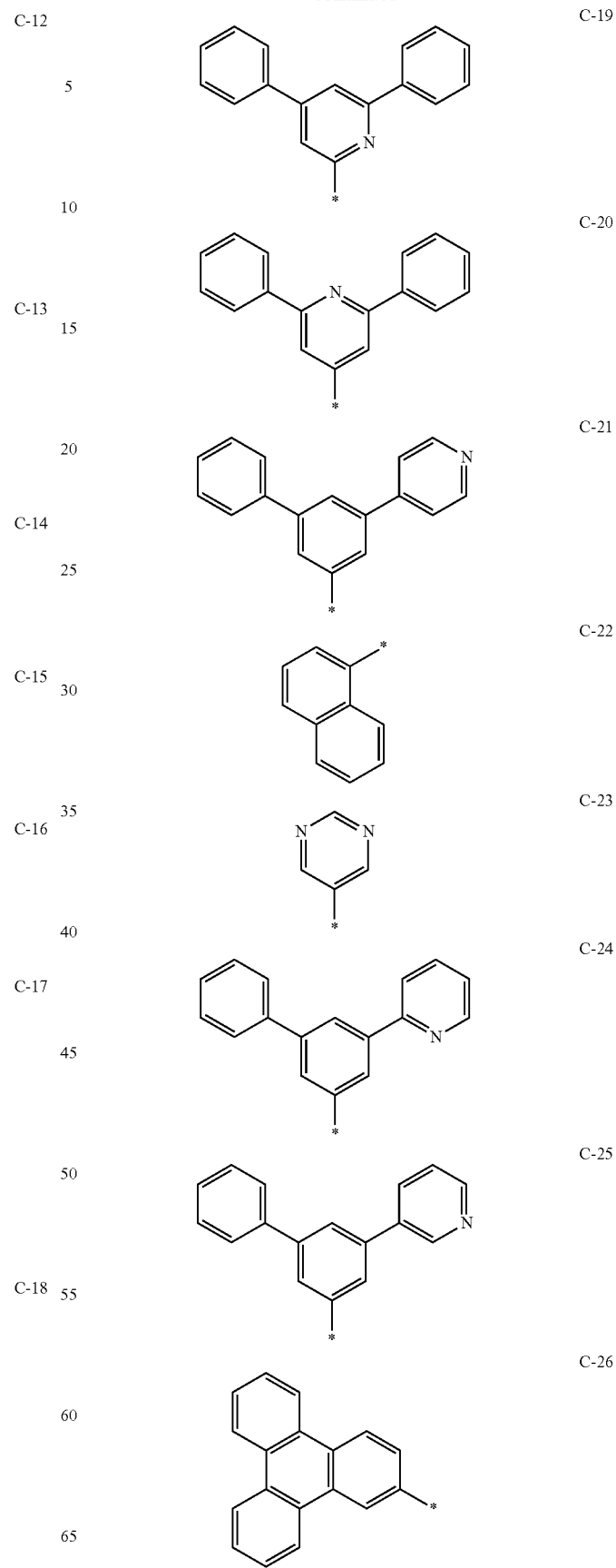

125

-continued

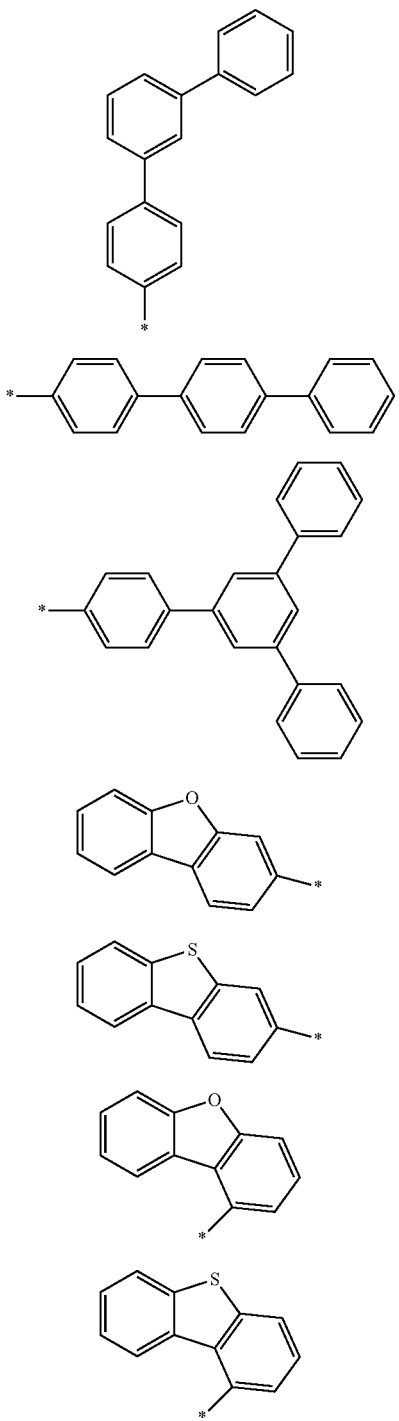

C-27

C-28

C-29

C-30

C-31

C-32

C-33

In Group II, * is a linking point.

In an implementation, Chemical Formula 2 may be represented by Chemical Formula 2-8.

In an implementation, moieties *-$L^2$-$Y^1$ and *-$L^3$-$Y^2$ of Chemical Formula 2-8 may each independently be, e.g., a moiety of Group II. In an implementation, moieties *-$L^2$-$Y^1$ and *-$L^3$-$Y^2$ of Chemical Formula 2-8 may each independently be, e.g., C-1, C-2, or C-3 of Group II.

In an implementation, the second compound for an organic optoelectronic device represented by the combina-

126 tion of Chemical Formula 3 and Chemical Formula 4 may be, e.g., represented by Chemical Formula 3A, Chemical Formula 3B, Chemical Formula 3C, Chemical Formula 3D, or Chemical Formula 3E.

[Chemical Formula 3A]

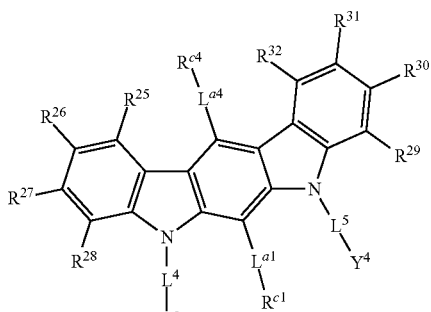

[Chemical Formula 3B]

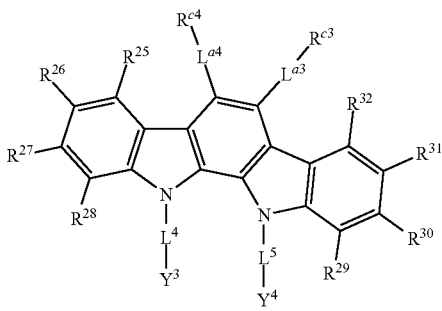

[Chemical Formula 3C]

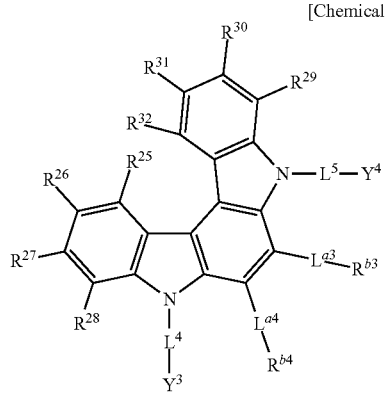

[Chemical Formula 3D]

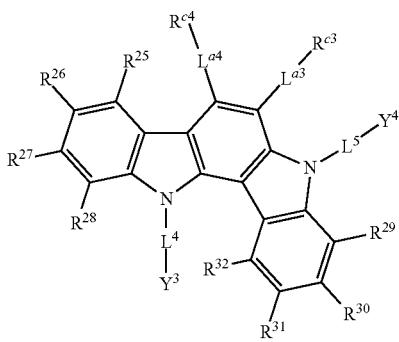

[Chemical Formula 3E]

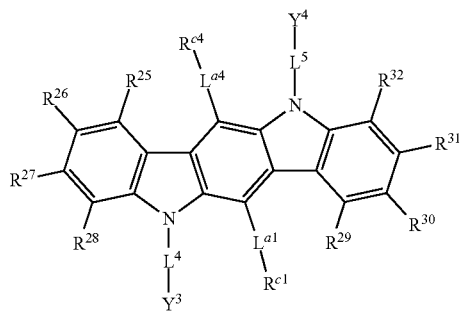

In Chemical Formula 3A to Chemical Formula 3E, $Y^3$, $Y^4$, $L^4$, $L^5$, and $R^{25}$ to $R^{32}$ may be defined the same those as described above.

$L^{a1}$ to $L^{a4}$ may be defined the same as $L^4$ and $L^5$ described above.

$R^{c1}$ to $R^{c4}$ may be defined the same as $R^{25}$ to $R^{32}$ described above.

In an implementation, $Y^3$ and $Y^4$ of Chemical Formulae 3 and 4 may each independently be, e.g., a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $R^{c1}$ to $R^{c4}$ and $R^{25}$ to $R^{32}$ may each independently be, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $Y^3$ and $Y^4$ of Formulae 3 and 4 may each independently be, e.g., a group of Group III.

[Group III]

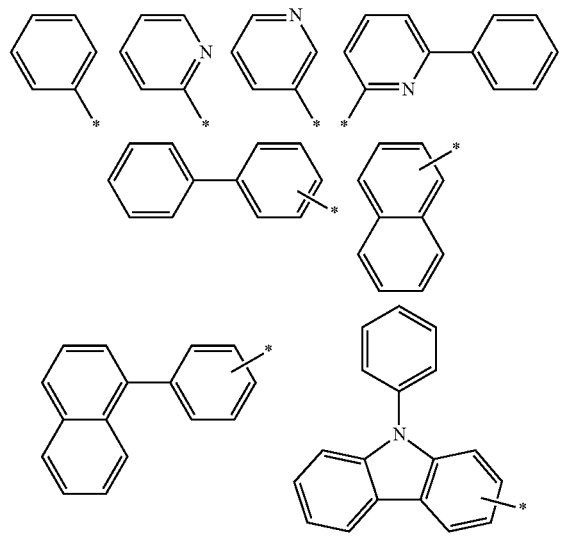

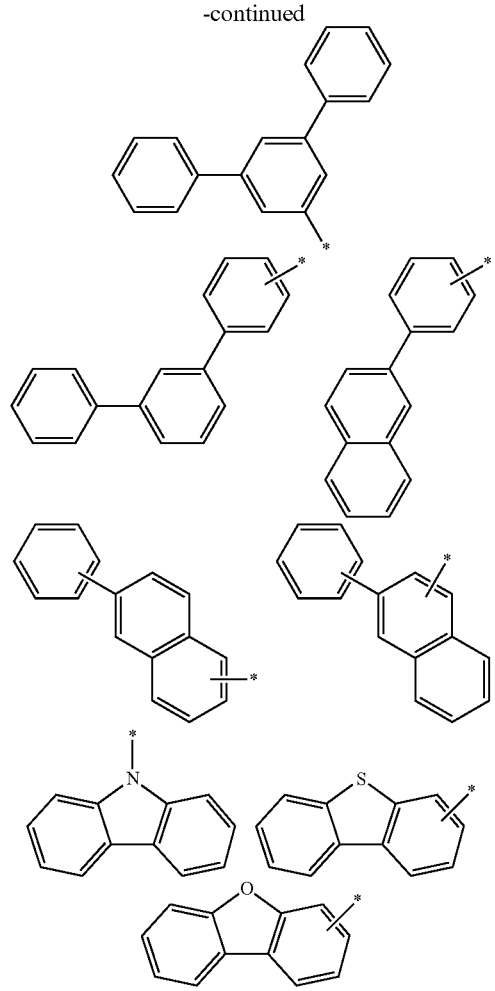

In Group III, * is a linking point with $L^4$ or $L^5$.

In an implementation, $R^{c1}$ to $R^{c4}$ and $R^{25}$ to $R^{32}$ may each independently be, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $R^{c1}$ to $R^{c4}$ and $R^{25}$ to $R^{32}$ may each independently be, e.g., hydrogen, deuterium, a cyano group, or a substituted or unsubstituted phenyl group.

In an implementation, $R^{c1}$ to $R^{c4}$ may each be hydrogen, and $R^{25}$ to $R^{32}$ may each independently be, e.g., hydrogen or a substituted or unsubstituted phenyl group.

In an implementation, the second compound for an organic optoelectronic device may be represented by Chemical Formula 2-8. In an implementation, $Y^1$ and $Y^2$ of Chemical Formula 2-8 may each independently be, e.g., a substituted or unsubstituted phenyl group or a substituted or unsubstituted biphenyl group, $L^2$ and $L^3$ may each independently be, e.g., a single bond or a substituted or unsubstituted phenylene group, and $R^{15}$ to $R^{24}$ may each independently be, e.g., hydrogen or a substituted or unsubstituted phenyl group.

In an implementation, the second compound for an organic optoelectronic device may be represented by Chemical Formula 3C. In an implementation, $L^{a1}$ and $L^{a2}$ in Chemical Formula 3C may be a single bond, $L^4$ and $L^5$ may each independently be, e.g., a single bond or a substituted or unsubstituted C6 to C12 arylene group, $R^{25}$ to $R^{32}$, $R^{c1}$, and $R^{c2}$ may each be hydrogen, and $Y^3$ and $Y^4$ may each independently be, e.g., a substituted or unsubstituted phenyl group, a substituted or unsubstituted naphthyl group, or a substituted or unsubstituted biphenyl group.

In an implementation, the second compound for an organic optoelectronic device may be, e.g., a compound of Group 2.

[Group 2]

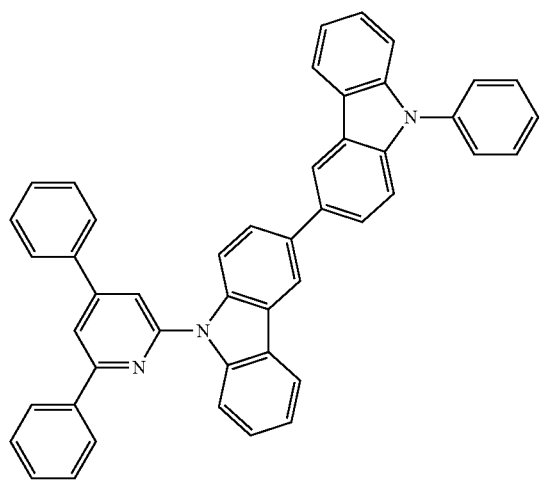

[A-1]

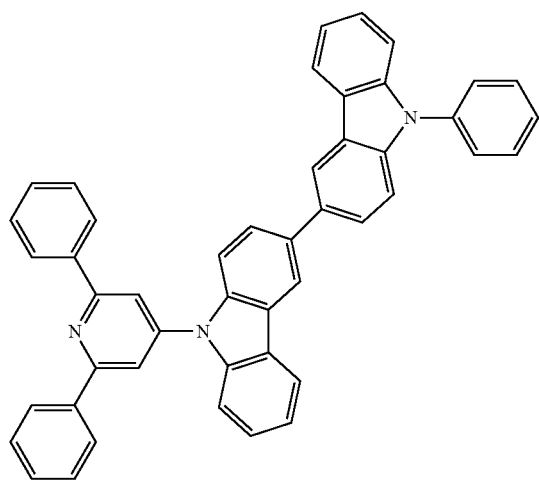

[A-2]

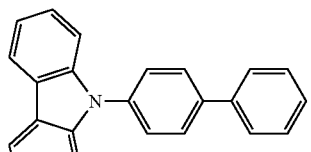

[A-3]

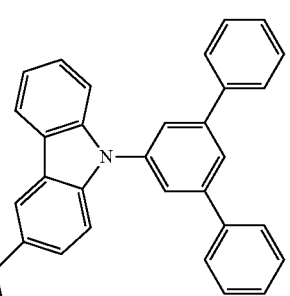

[A-4]

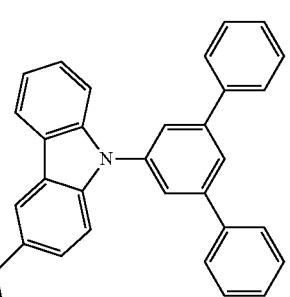

[A-5]

[A-6]
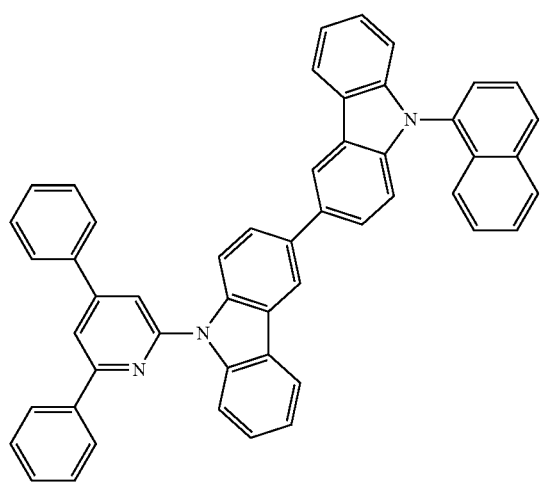
[A-7]
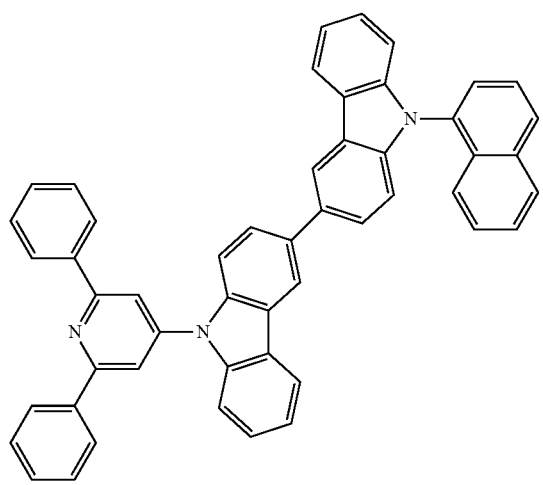
[A-8]
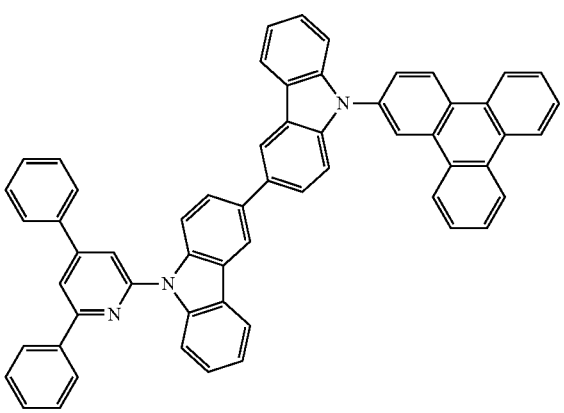
[A-9]
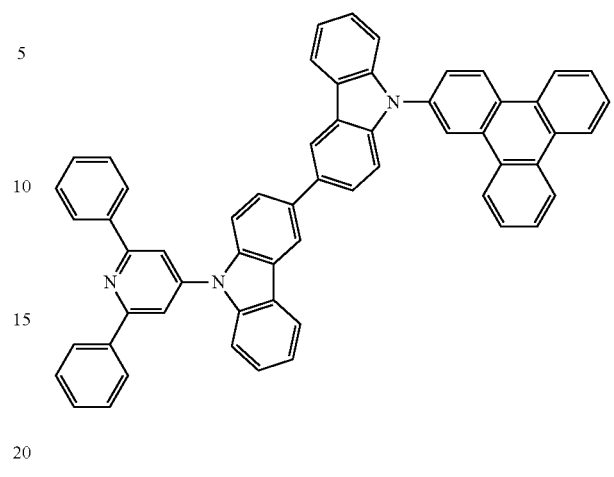
[A-10]
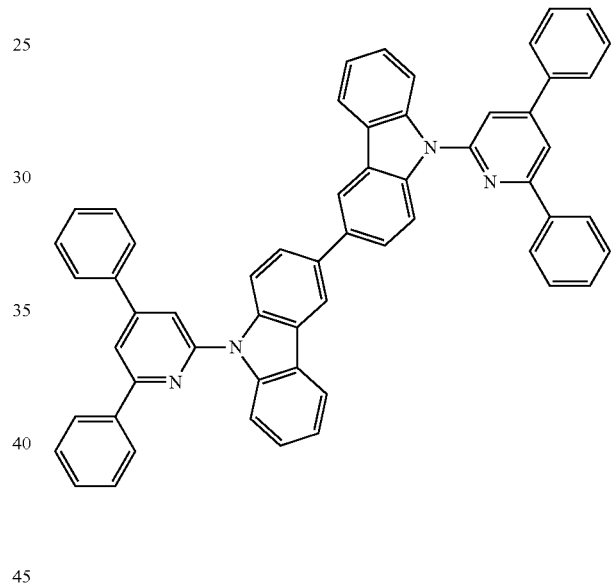
[A-11]
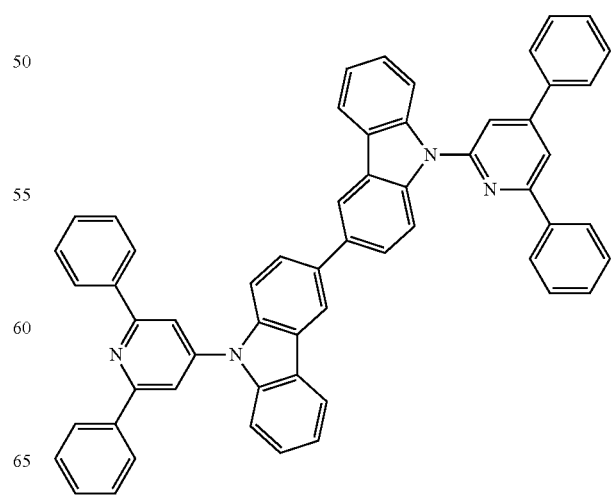

[A-12]
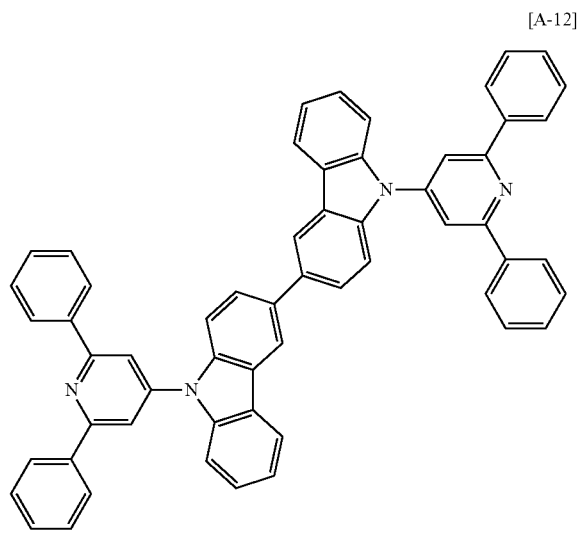
[A-13]
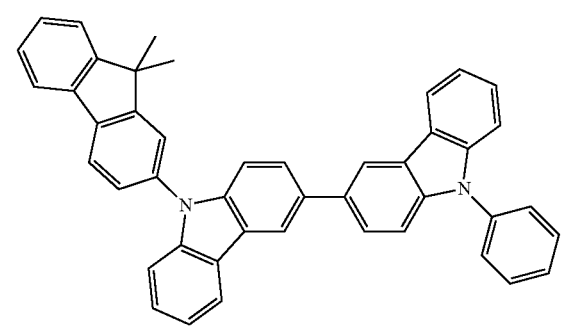
[A-14]
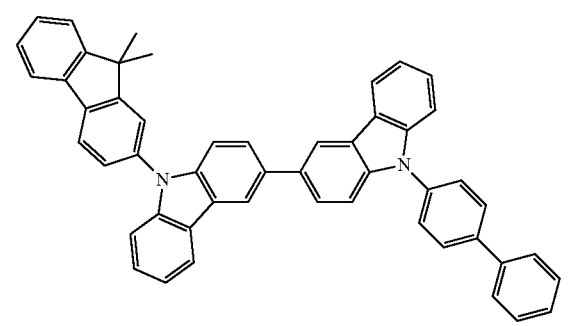
[A-15]
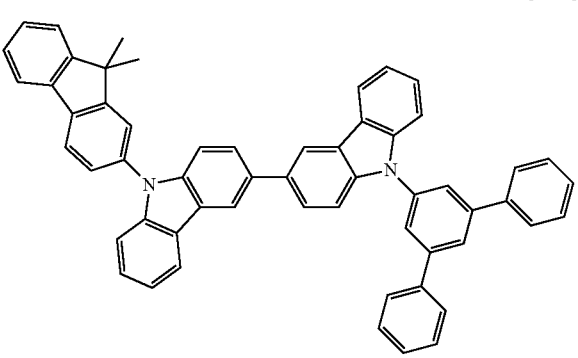
[A-16]
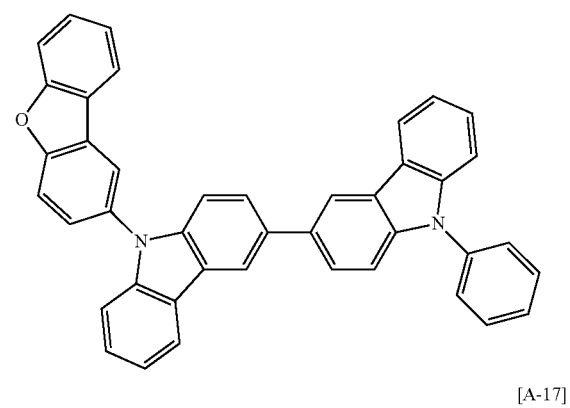
[A-17]
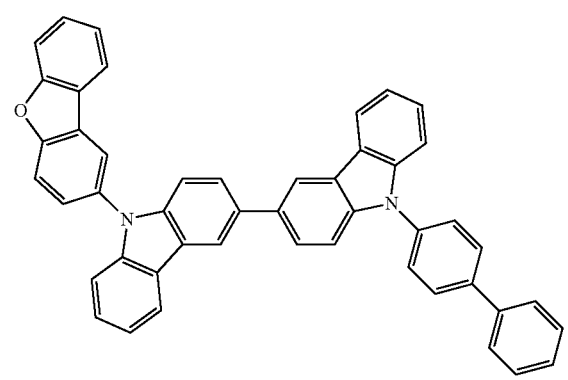
[A-18]
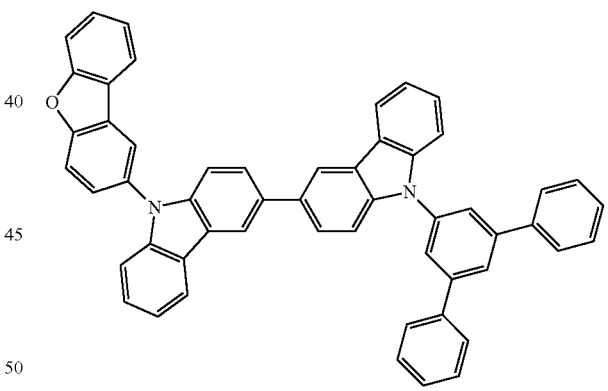
[A-19]
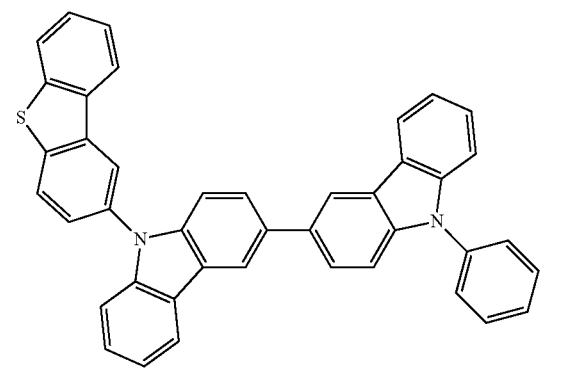

-continued
[A-20]
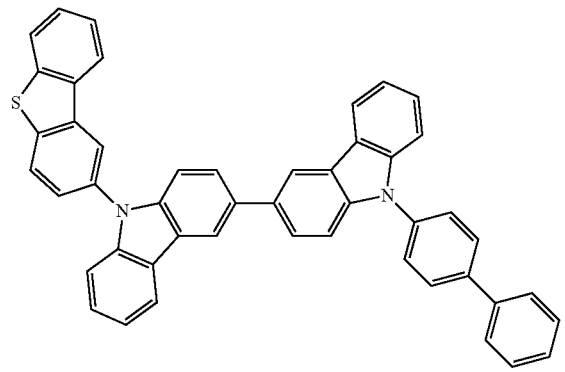
[A-21]
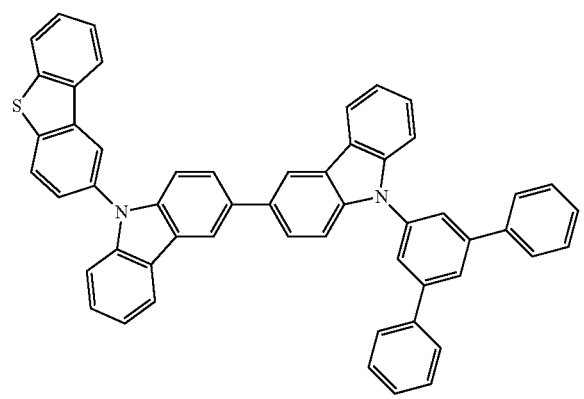
[A-22]
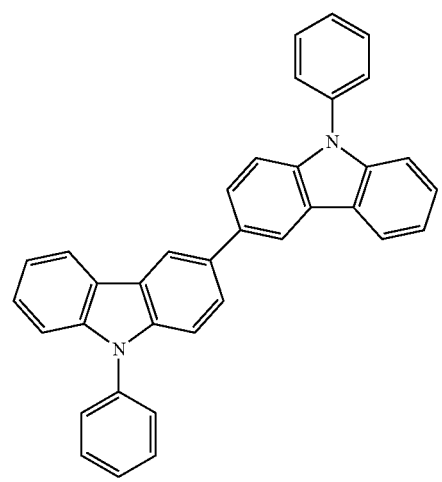
-continued
[A-23]
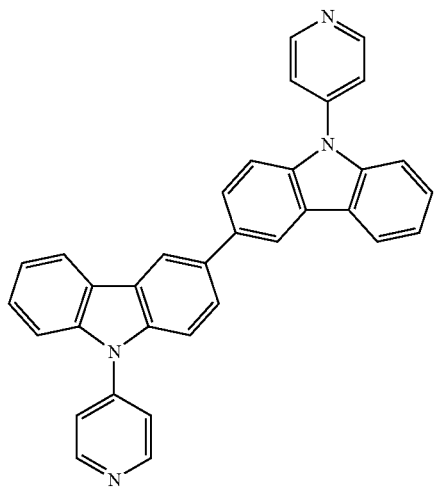
[A-24]
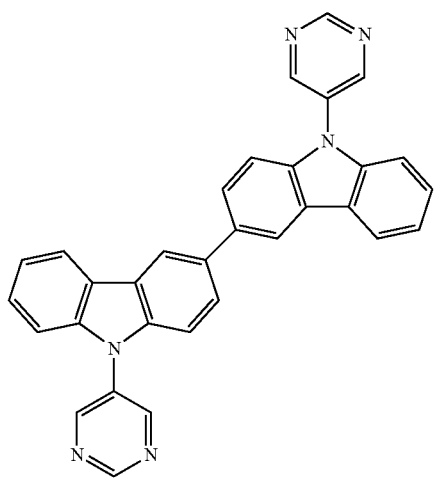
[A-25]
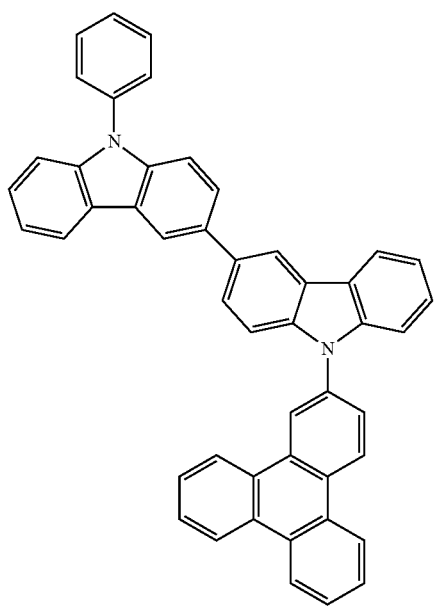

[A-26]
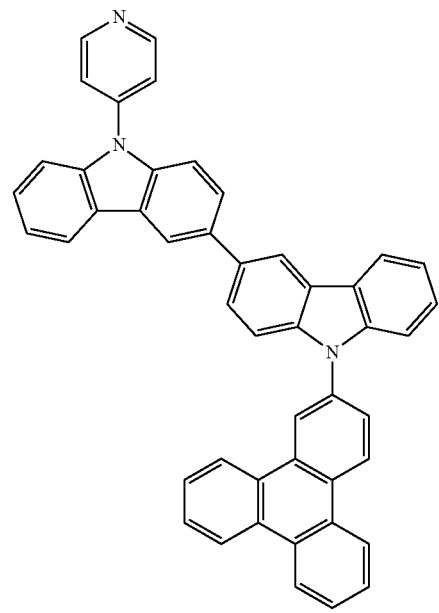
[A-27]
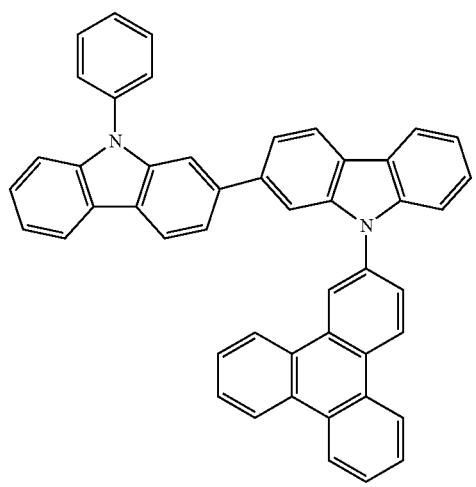
[A-28]
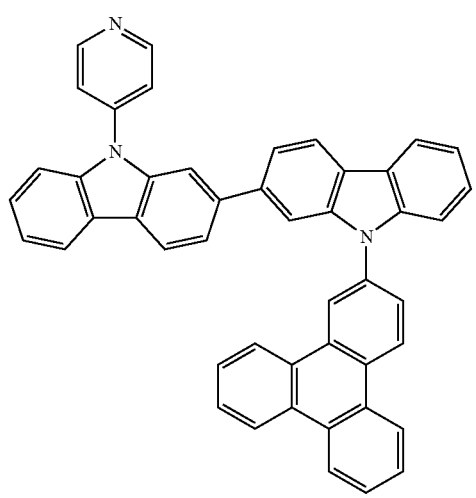
[A-29]
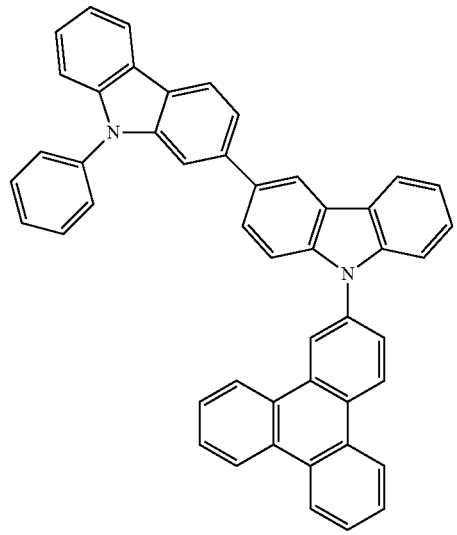
[A-30]
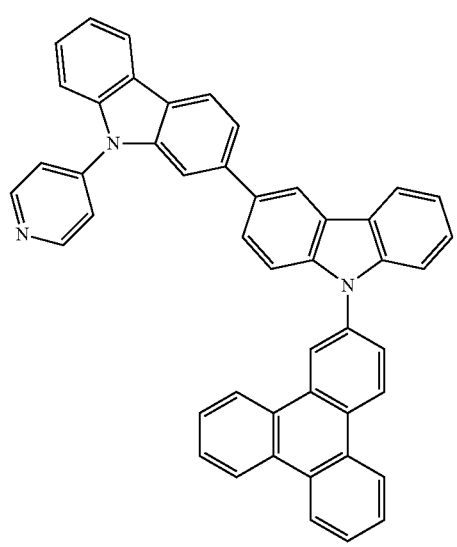
[A-31]
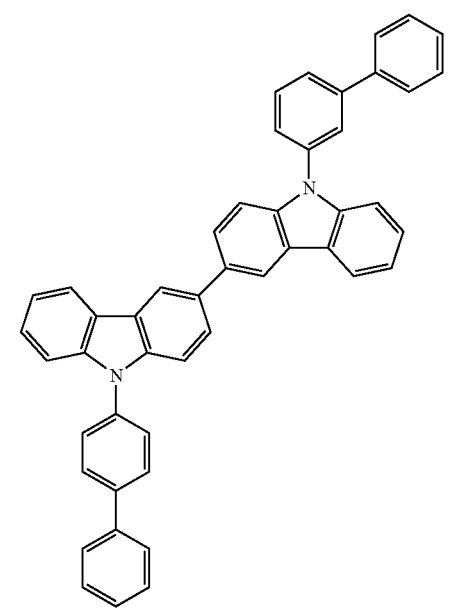

[A-32]
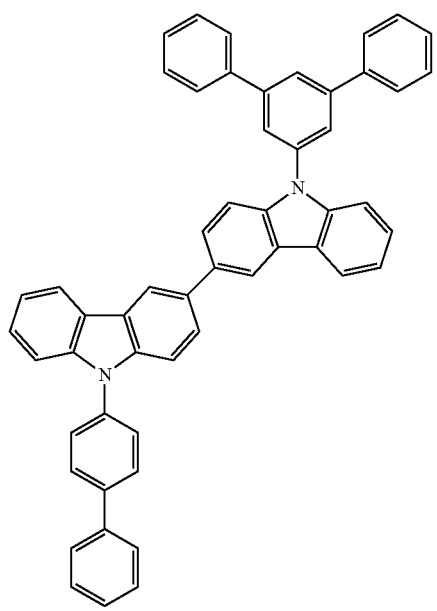
[A-34]
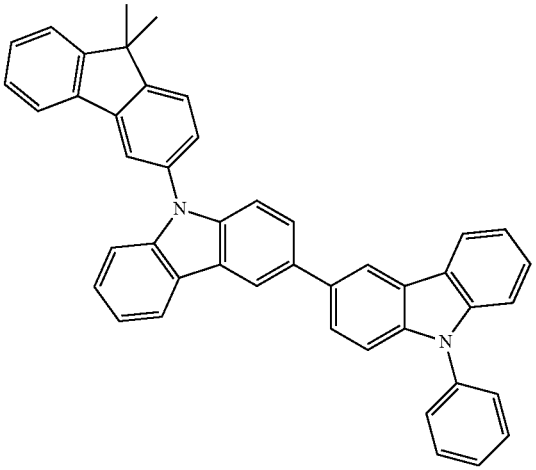
[A-35]
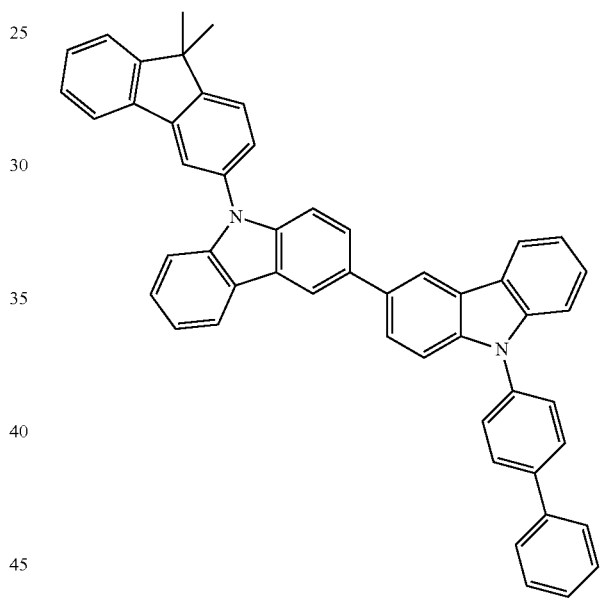
[A-33]
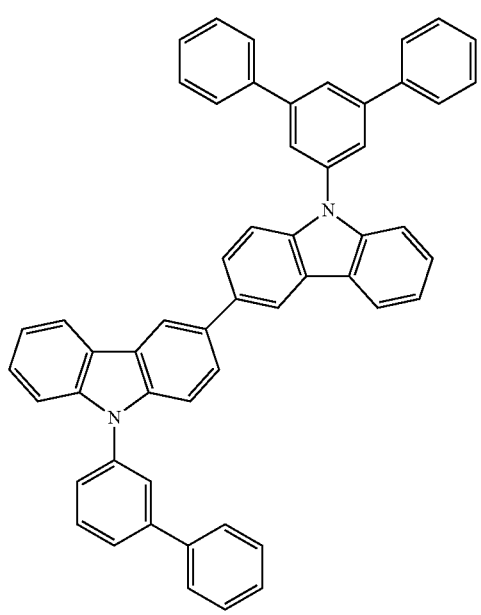
[A-36]
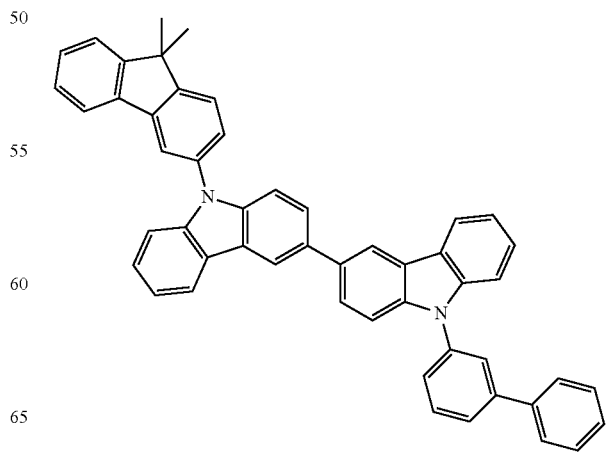

[A-37]
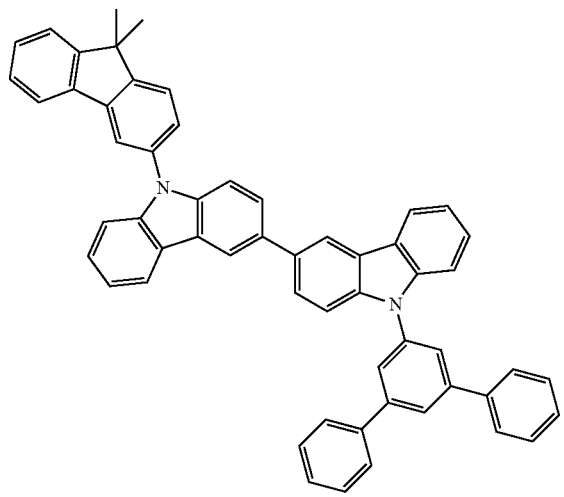
[A-38]
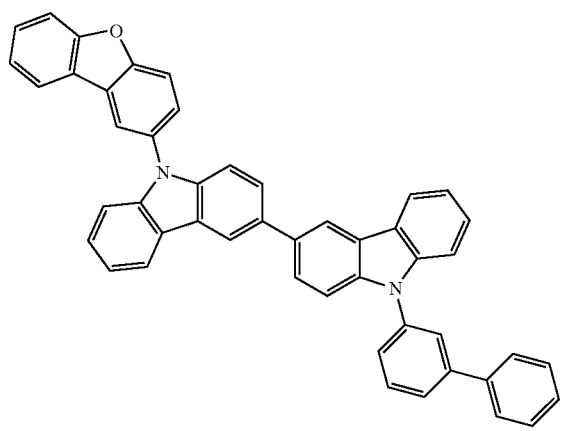
[A-39]
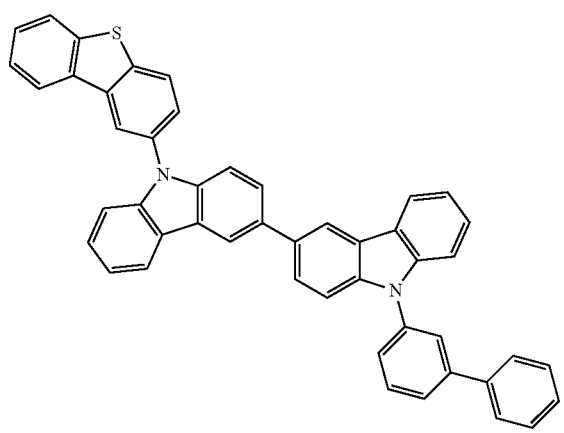
[A-40]
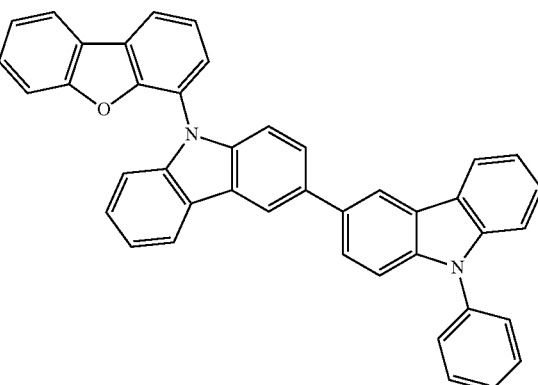
[A-41]
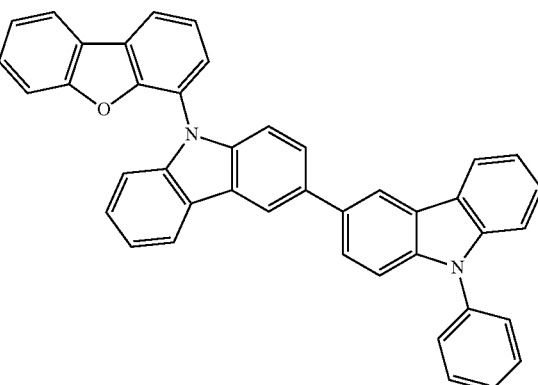
[A-42]
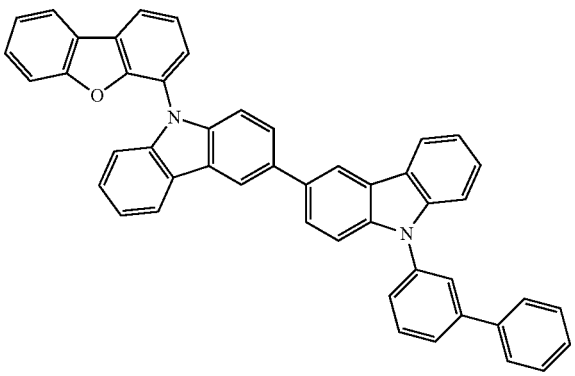

-continued
[A-43]
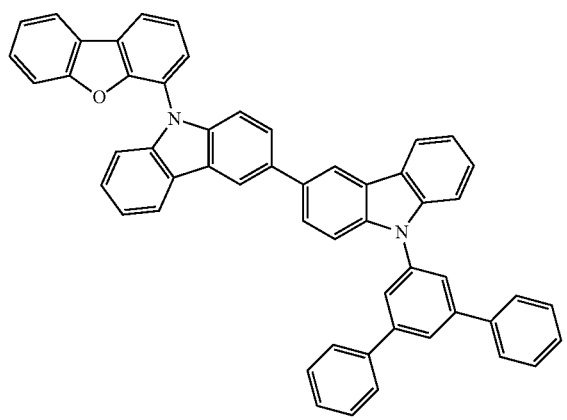
[A-44]
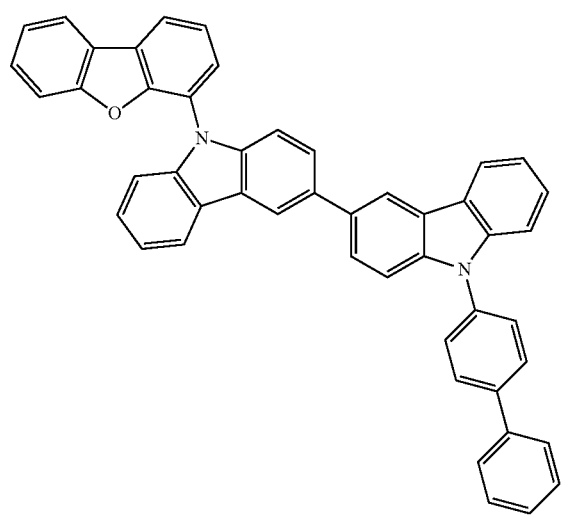
[A-45]
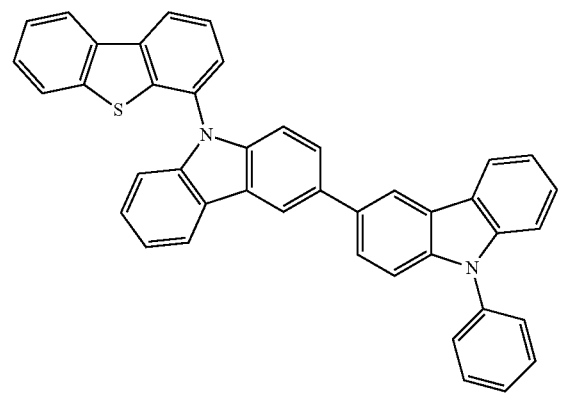
-continued
[A-46]
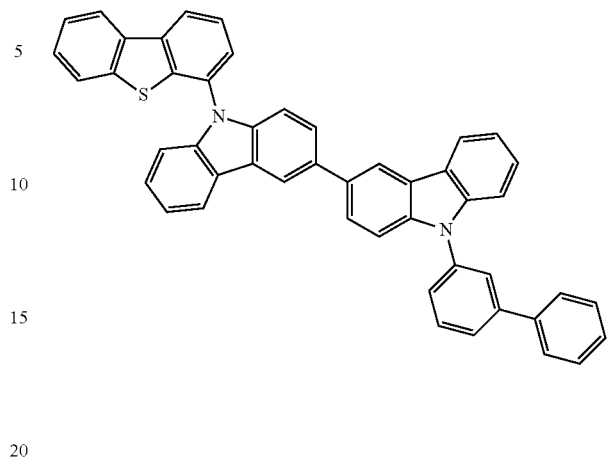
[A-47]
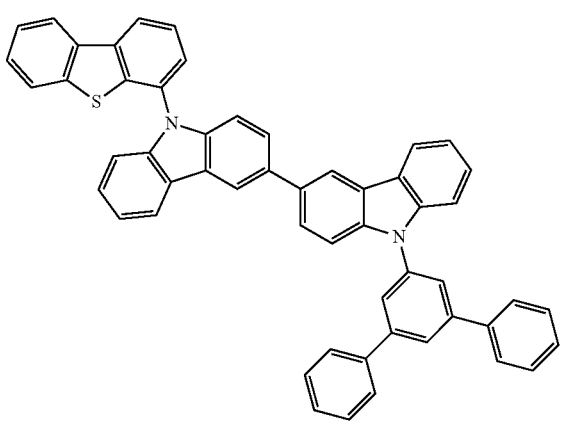
[A-48]
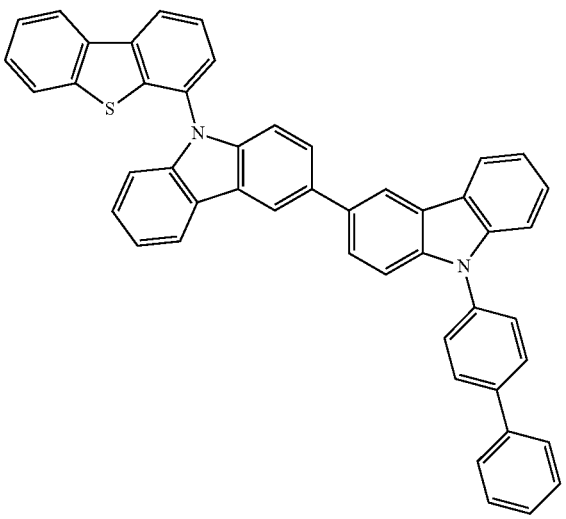

[A-49]
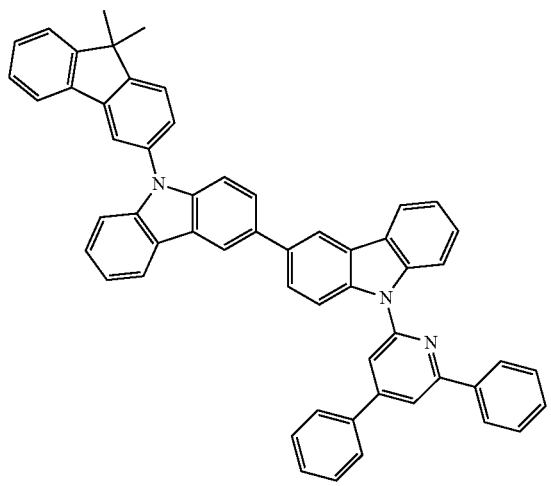
[A-50]
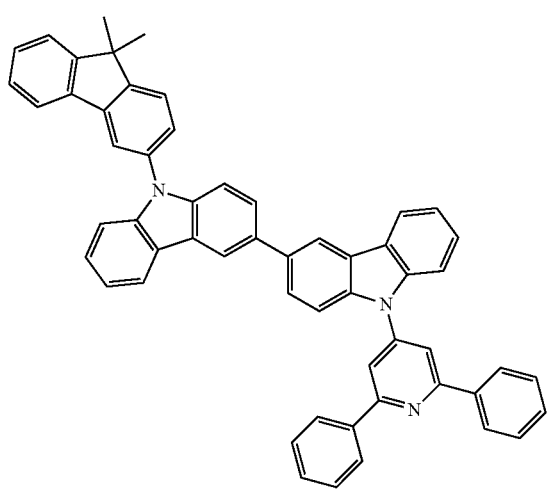
[A-51]
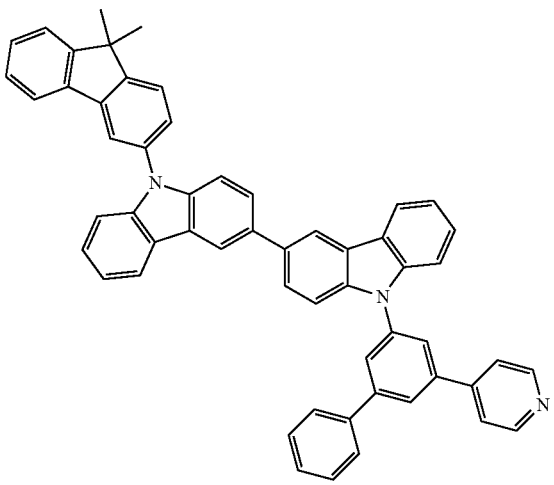
[A-52]
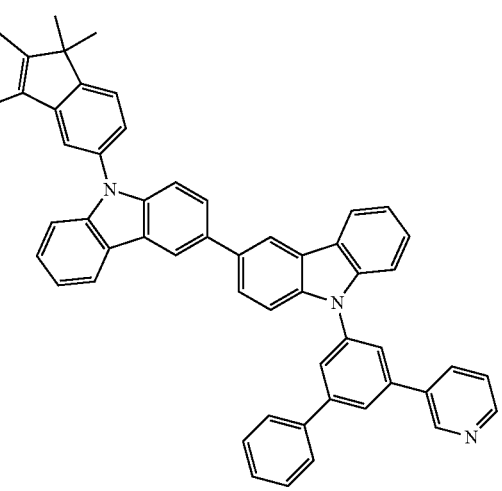
[A-53]
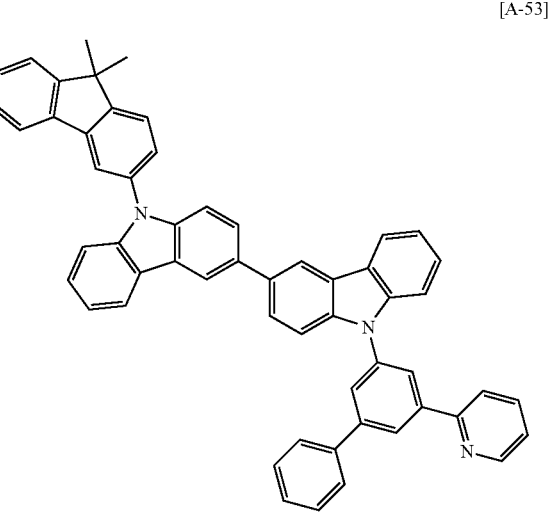
[A-54]
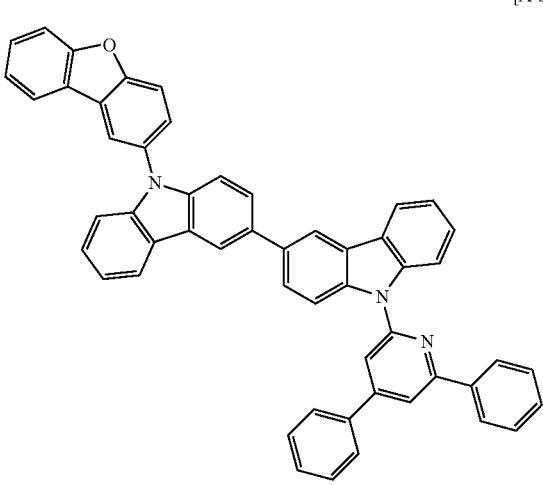

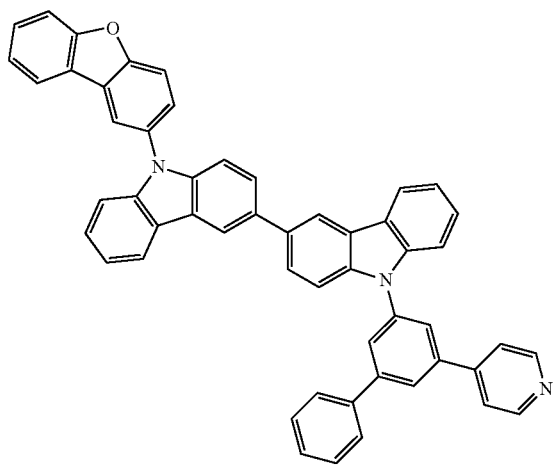
[A-55]
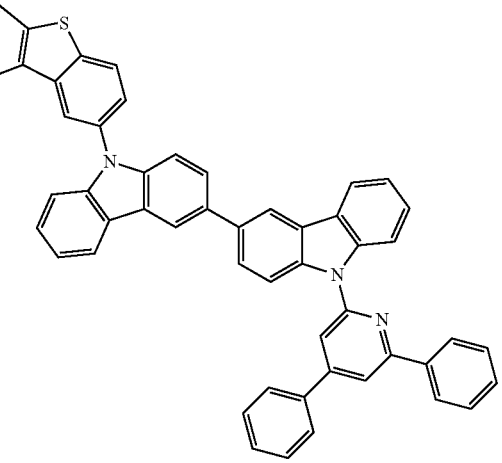
[A-58]
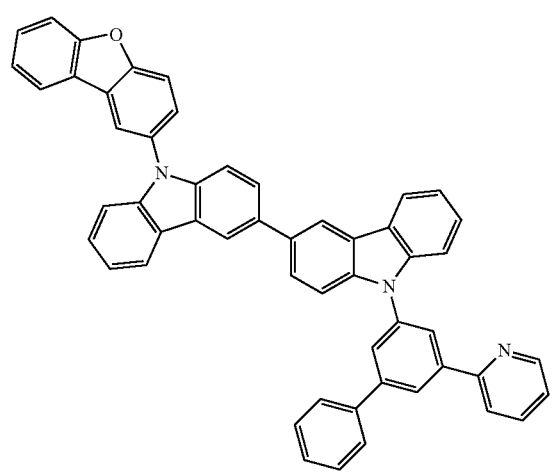
[A-56]
[A-59]
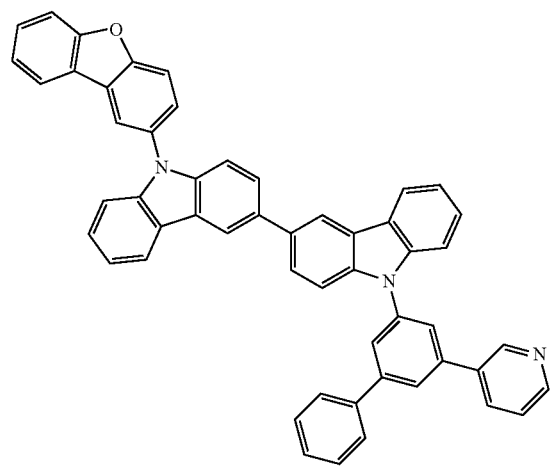
[A-57]
[A-60]

[A-61]
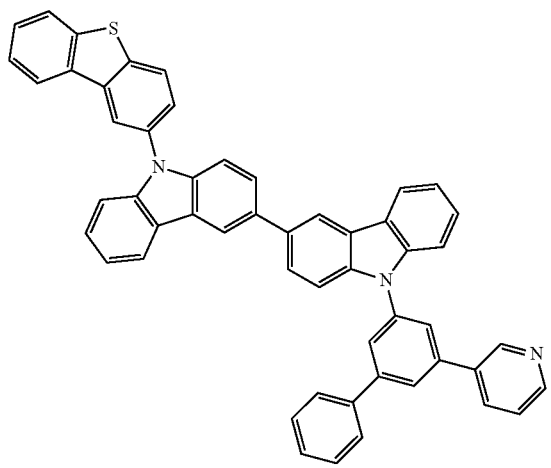
[A-62]
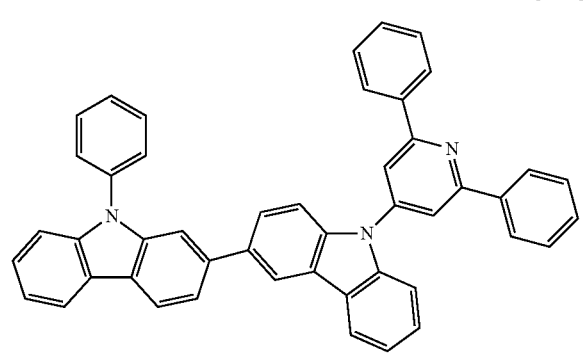
[A-63]
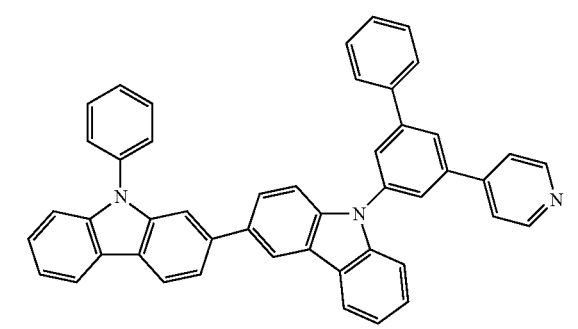
[A-64]
[A-65]
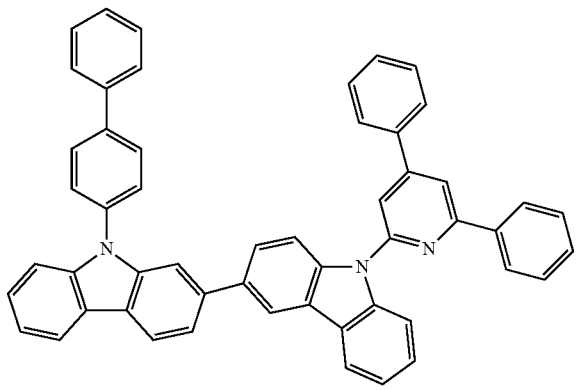
[A-66]
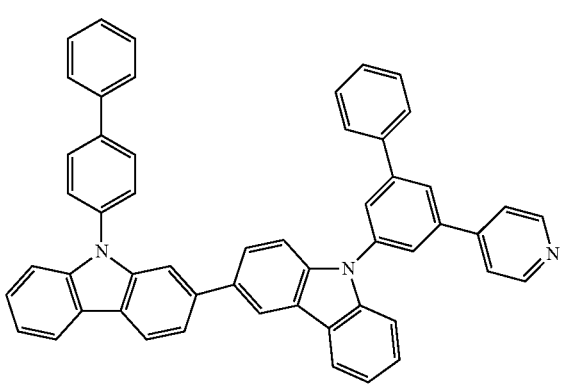
[A-67]
[A-68]
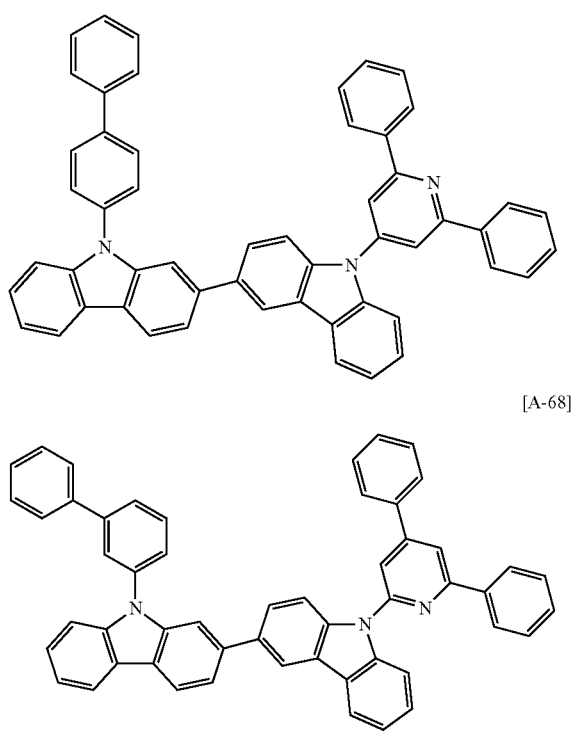

[A-69]
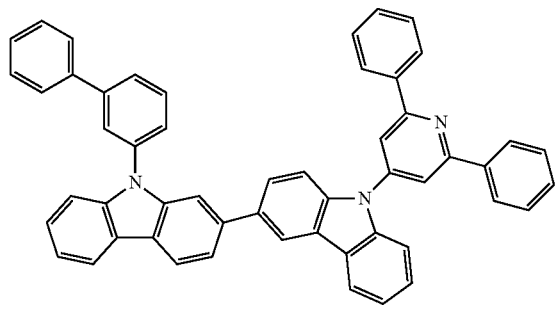
[A-70]
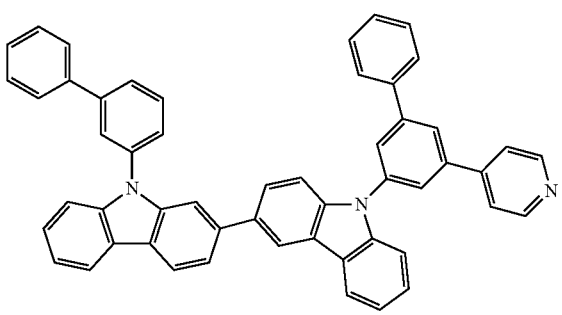
[A-71]
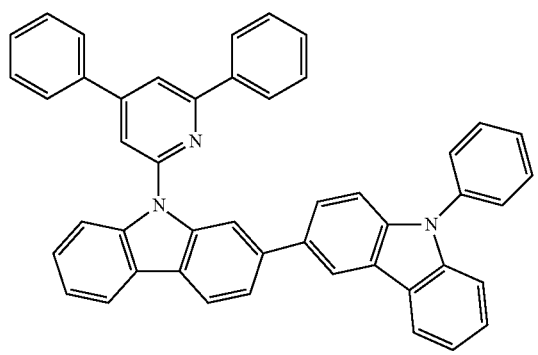
[A-72]
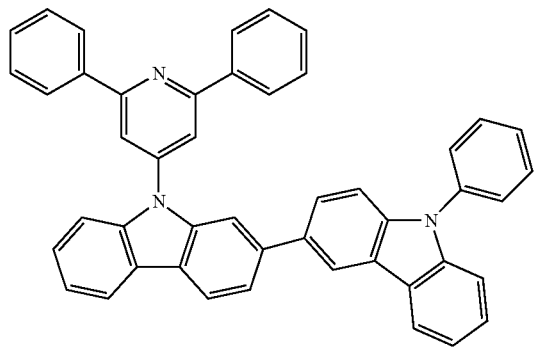
[A-73]
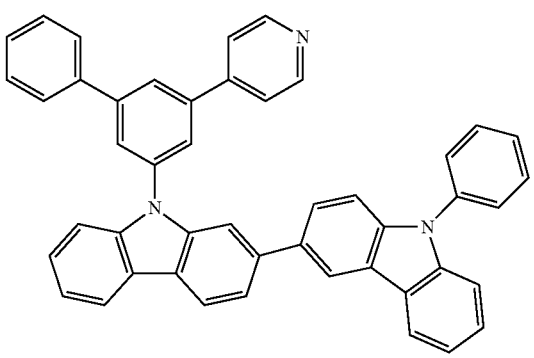
[A-74]
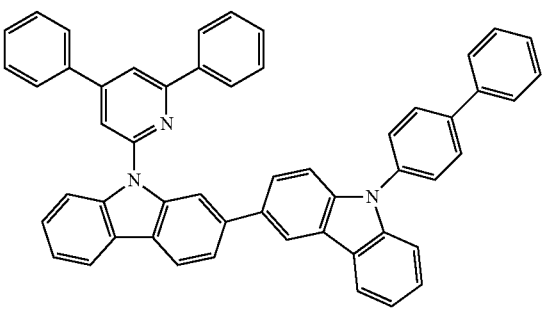
[A-75]
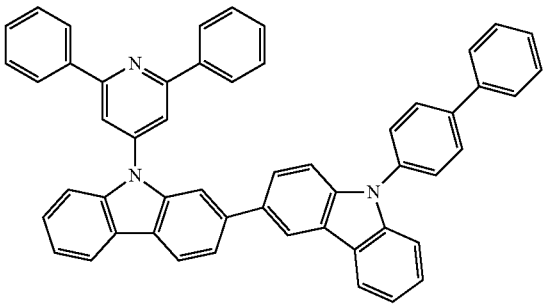
[A-76]
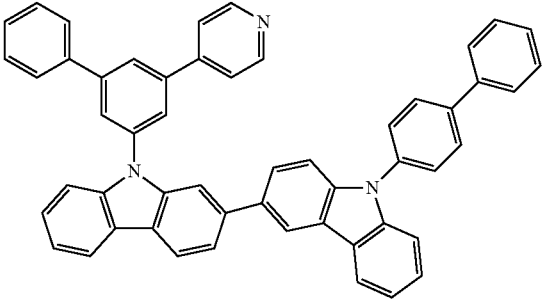

[A-77]
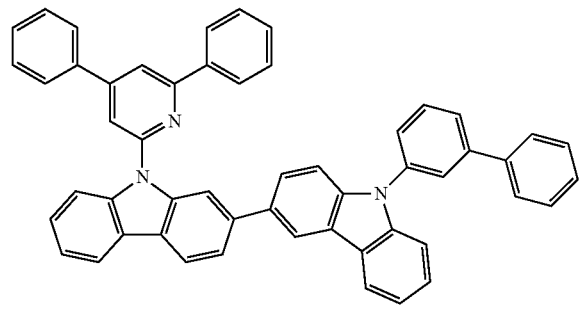
[A-81]
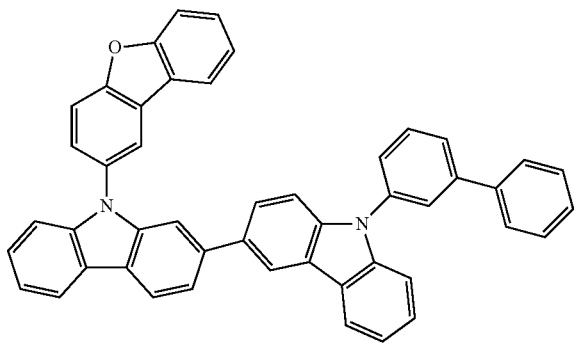
[A-78]
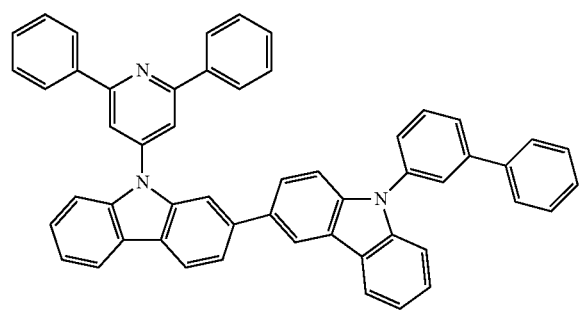
[A-82]
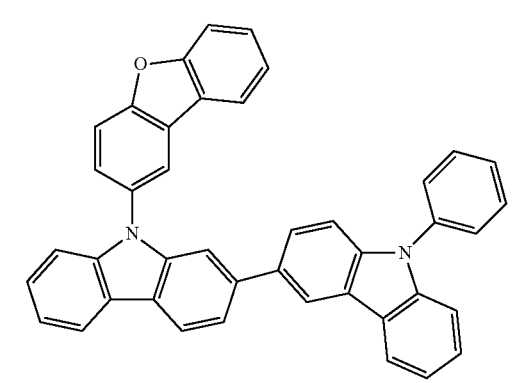
[A-79]
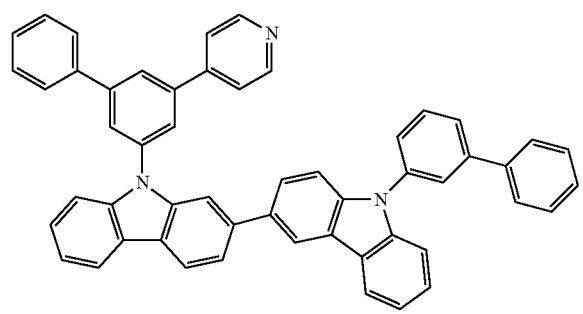
[A-83]
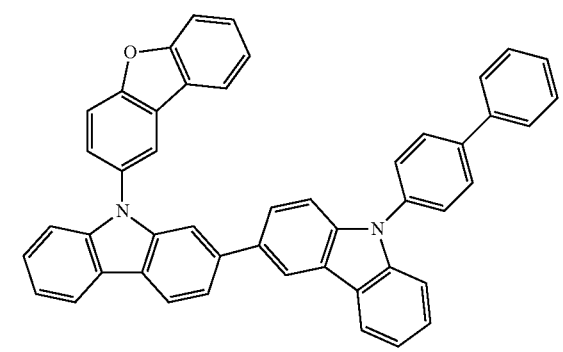
[A-80]
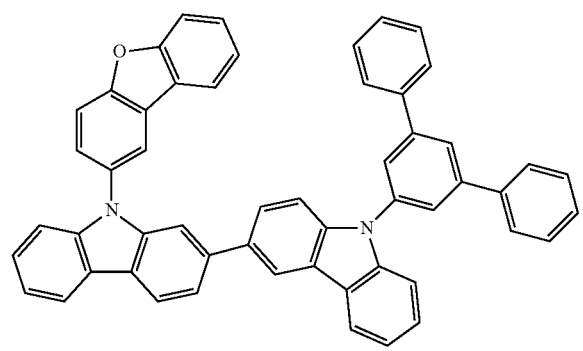
[A-84]
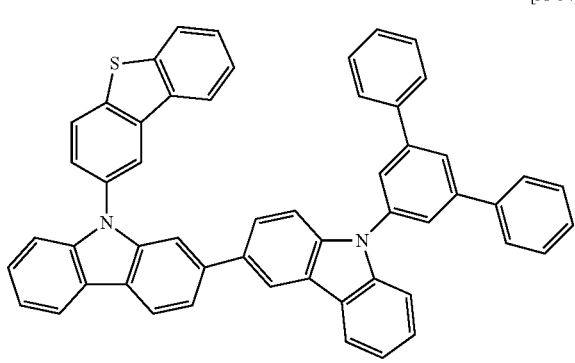

[A-85]
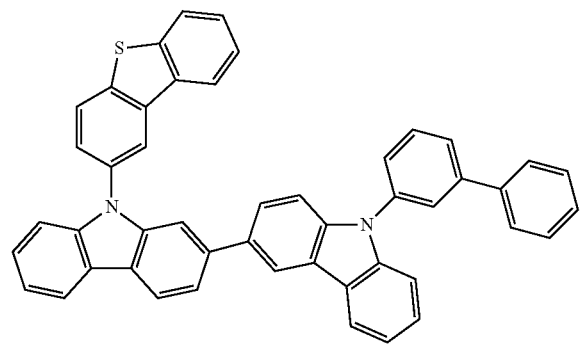
[A-89]
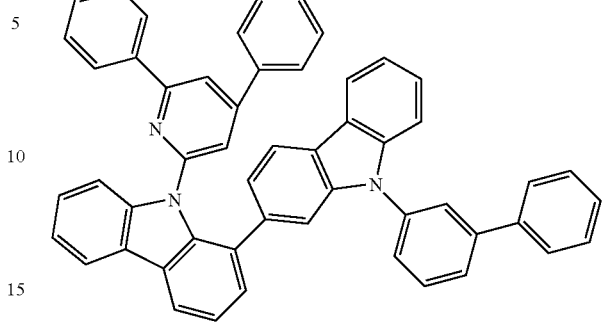
[A-86]
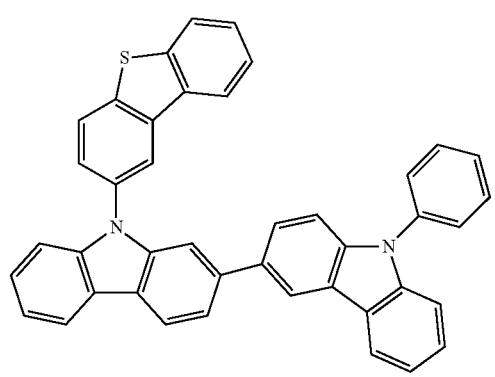
[A-90]
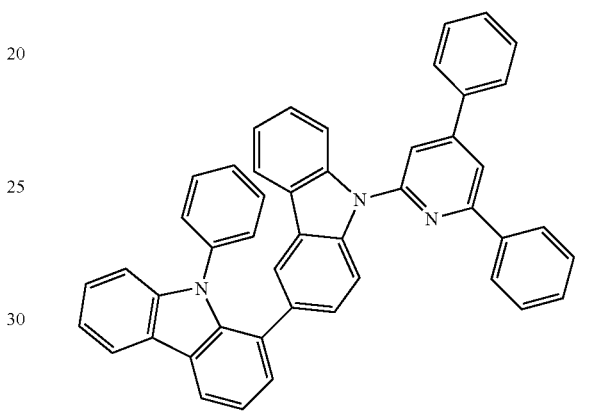
[A-87]
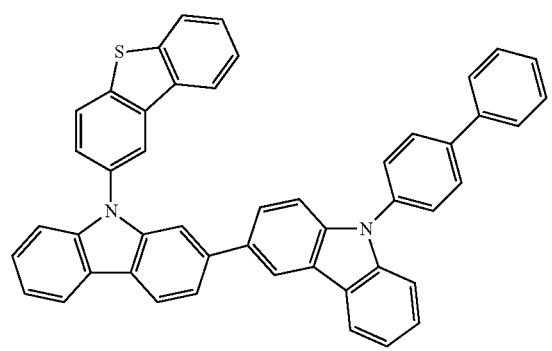
[A-91]
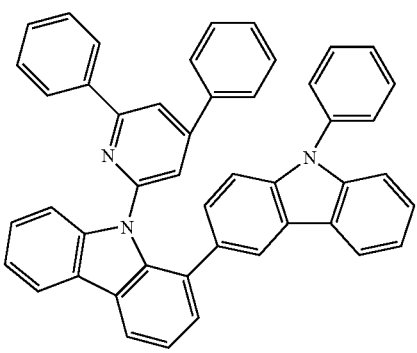
[A-88]
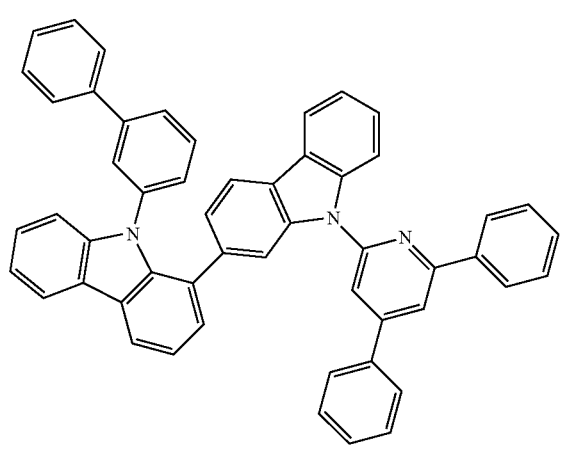
[A-92]
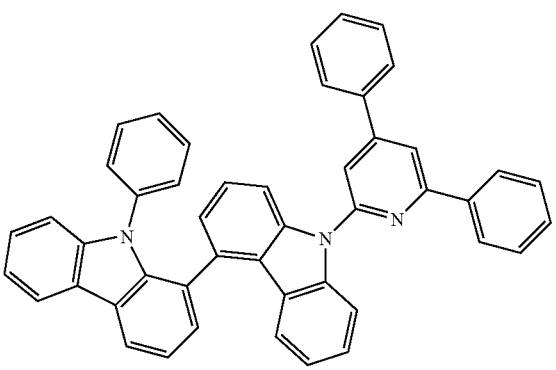

[A-93]
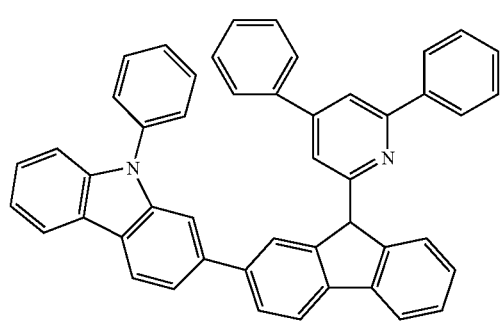
[A-94]
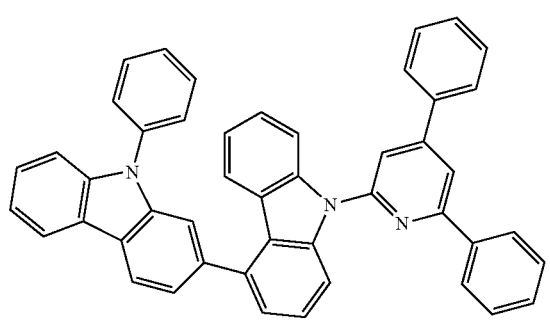
[A-95]
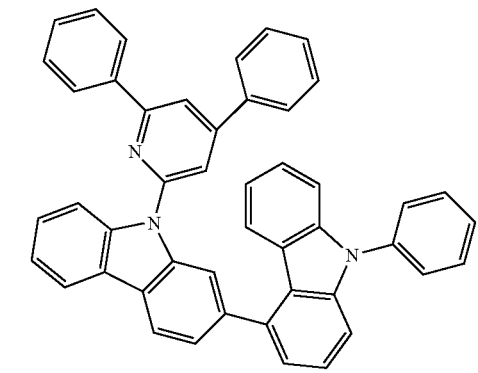
[A-96]
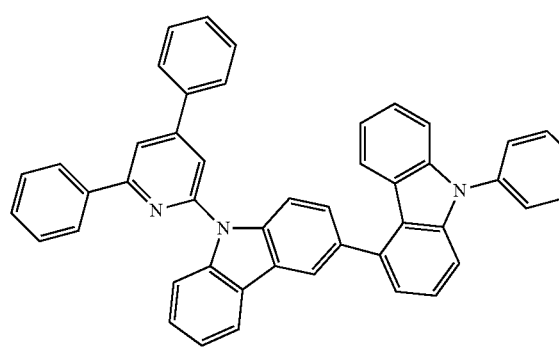
[A-97]
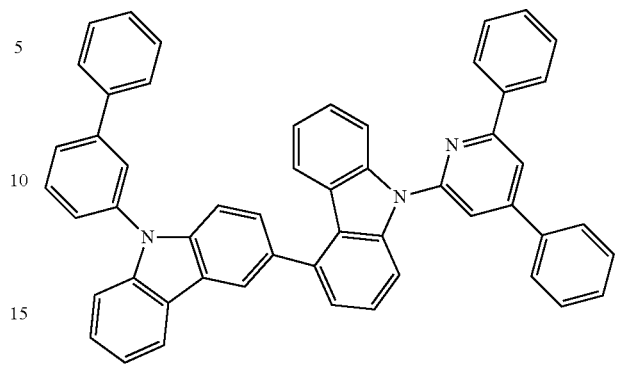
[A-98]
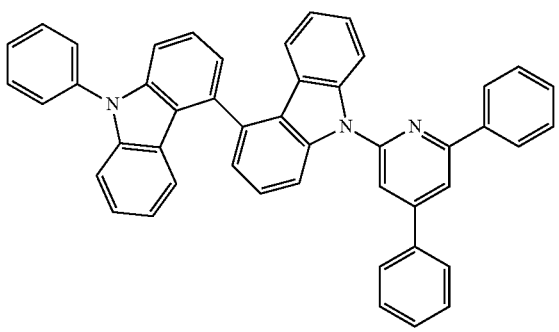
[A-99]
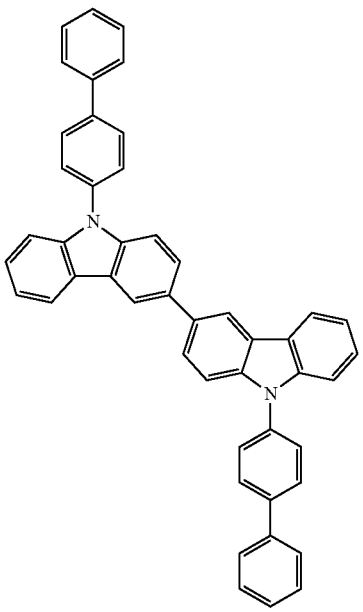

[A-100]
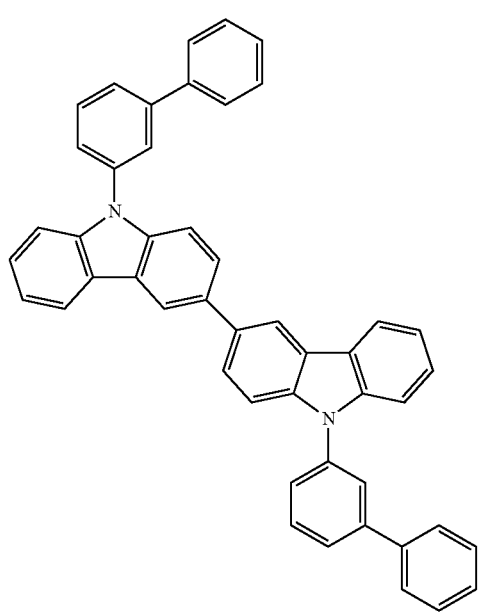
[A-101]
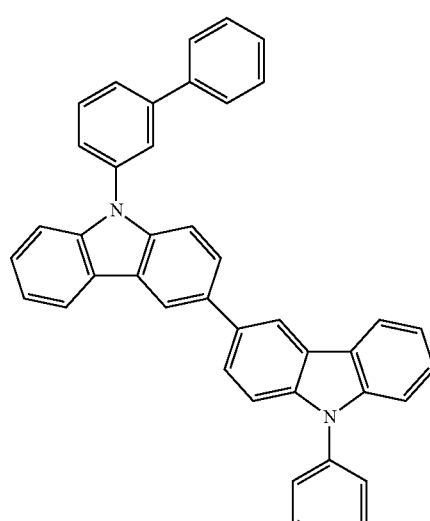
[A-102]
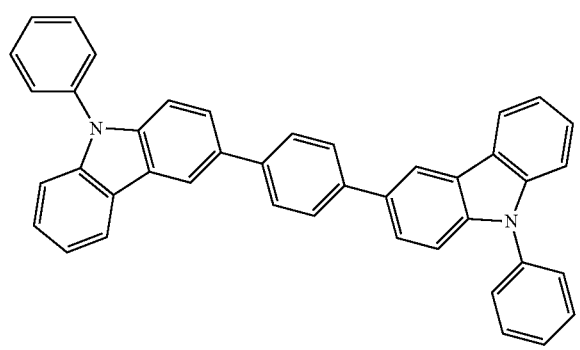
[A-103]
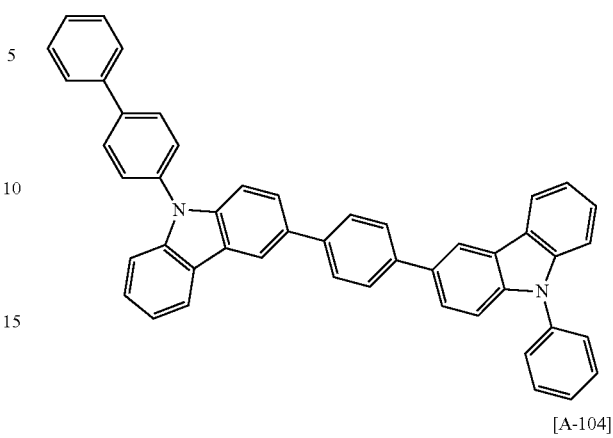
[A-104]
[A-105]
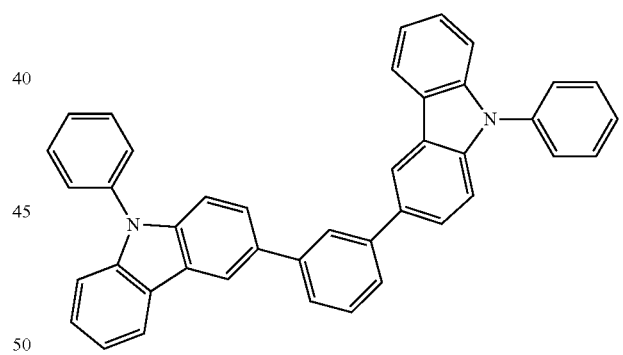
[A-106]
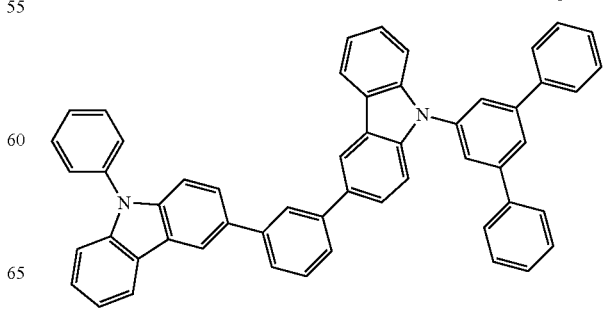

[A-107]
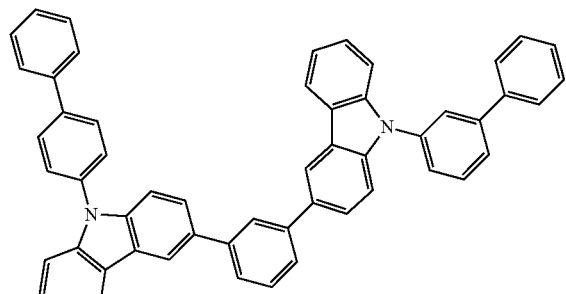
[A-108]
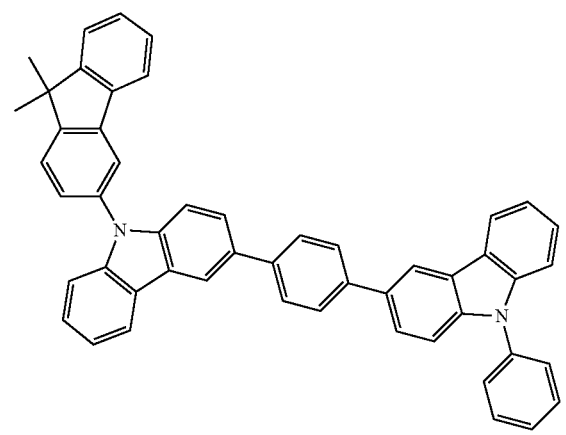
[A-109]
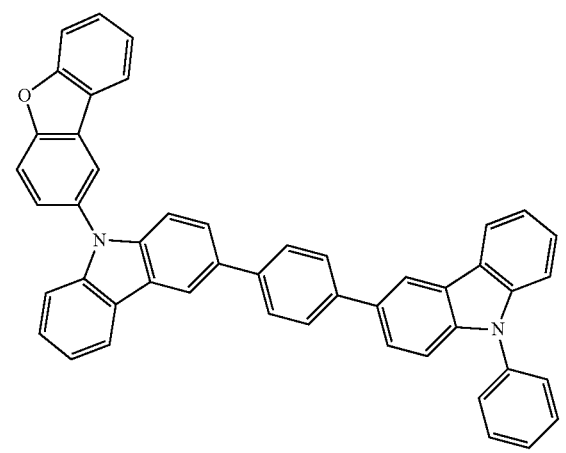
[A-110]
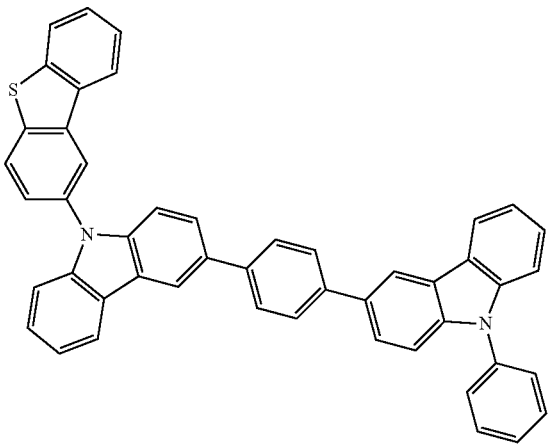
[A-111]
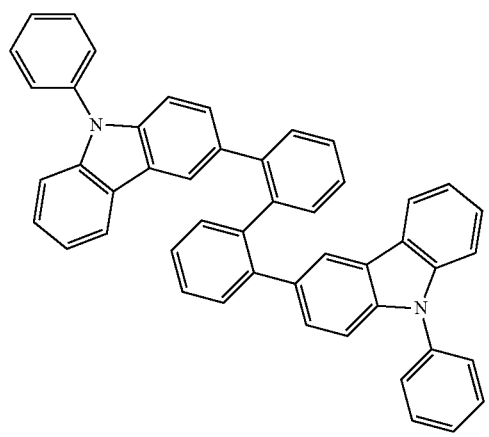
[A-112]
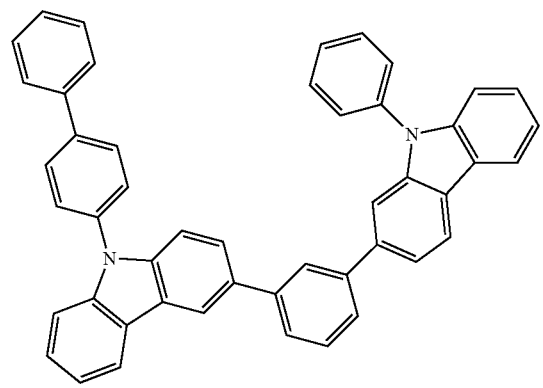

-continued
[A-113]
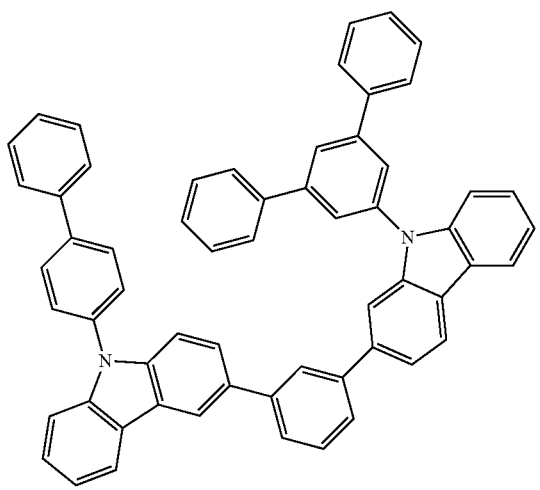
[A-114]
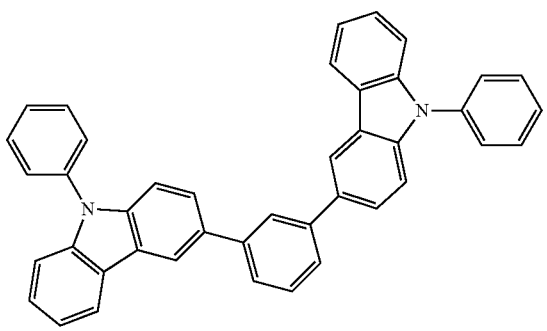
[A-115]
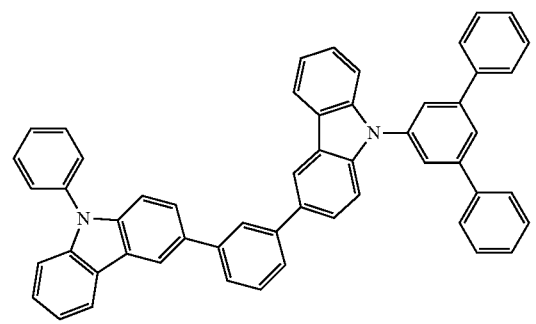
-continued
[A-116]
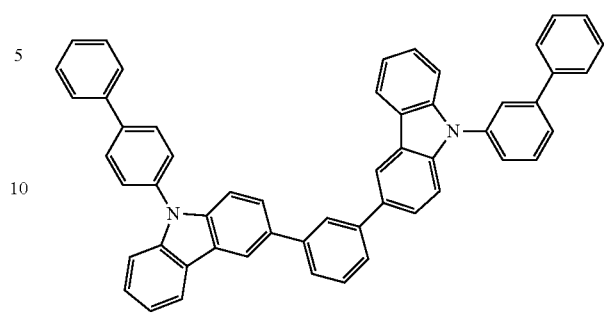
[A-117]
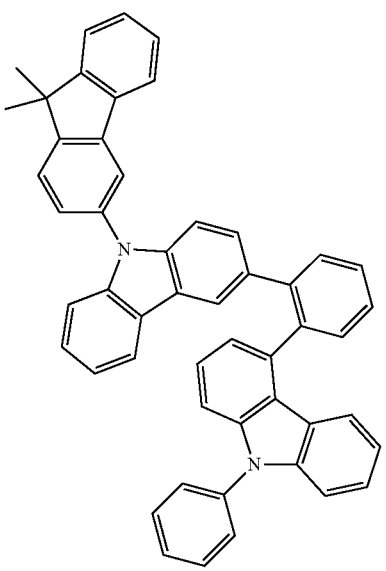
[A-118]
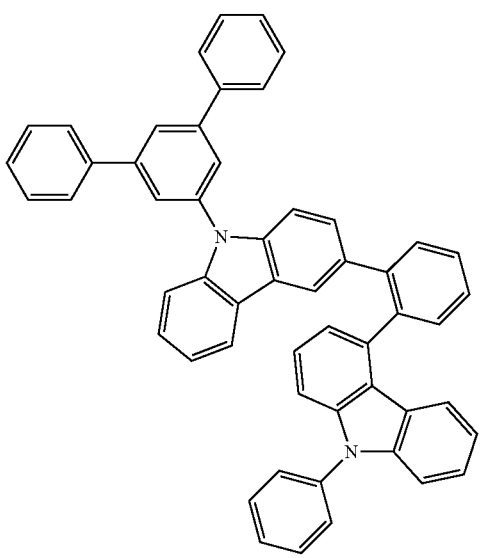

[A-119]
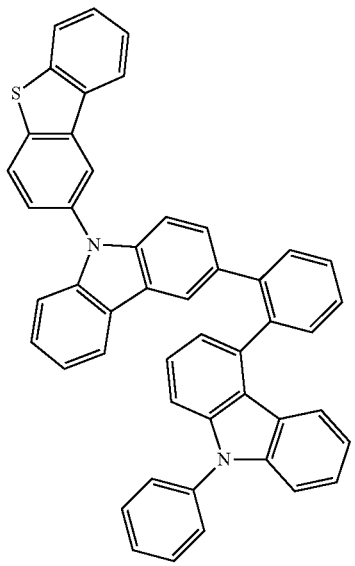
[A-122]
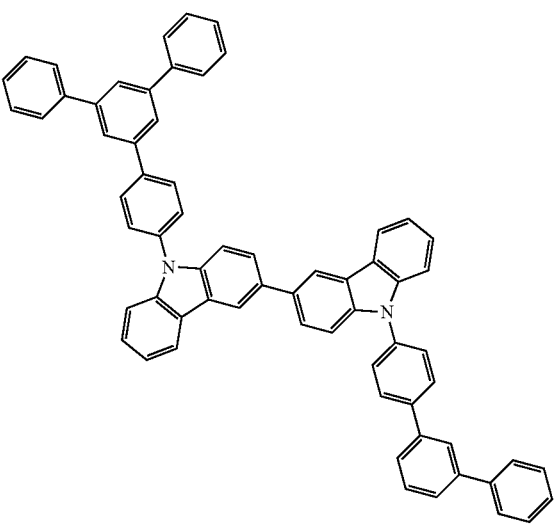
[A-120]
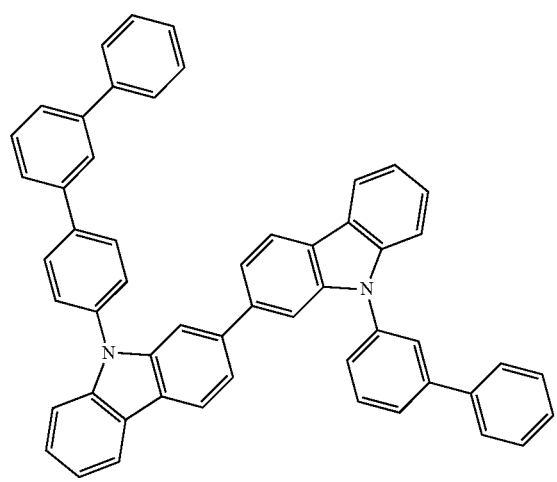
[A-123]
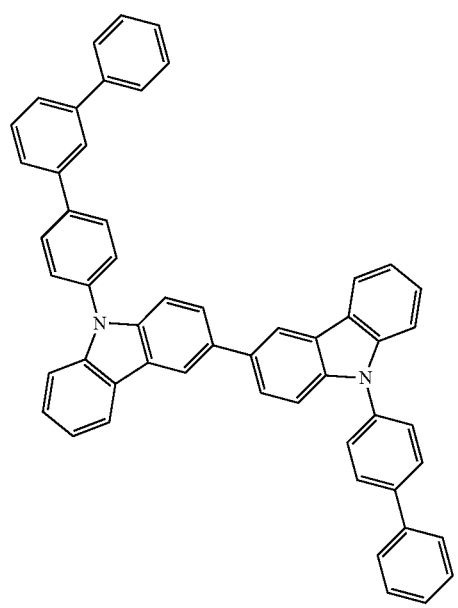
[A-121]
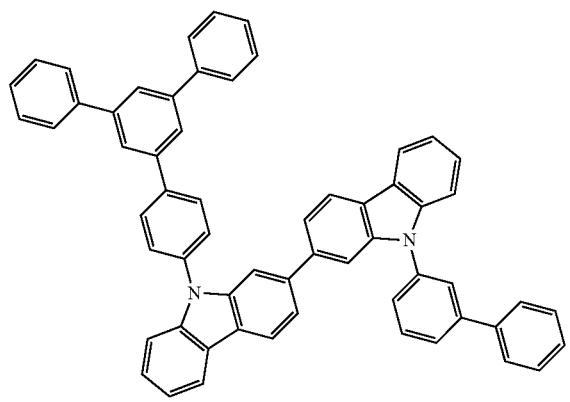
[A-124]
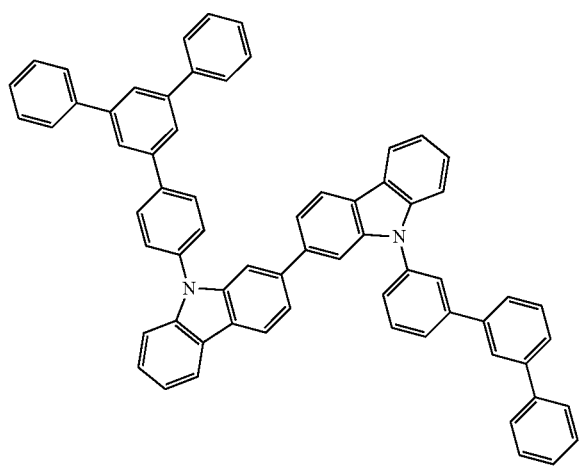

[A-125]
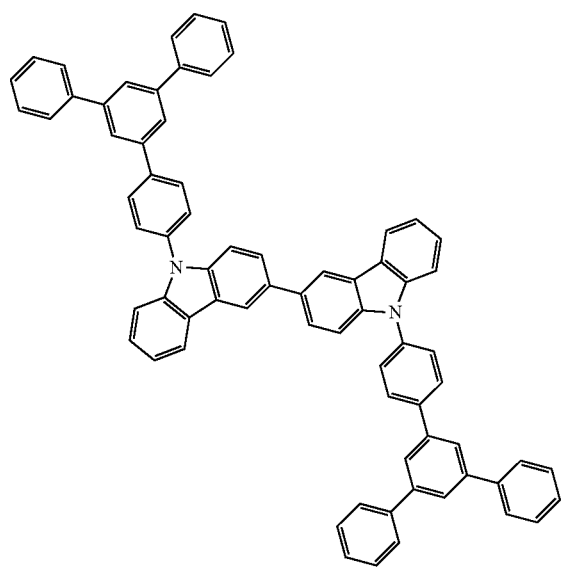
[A-126]
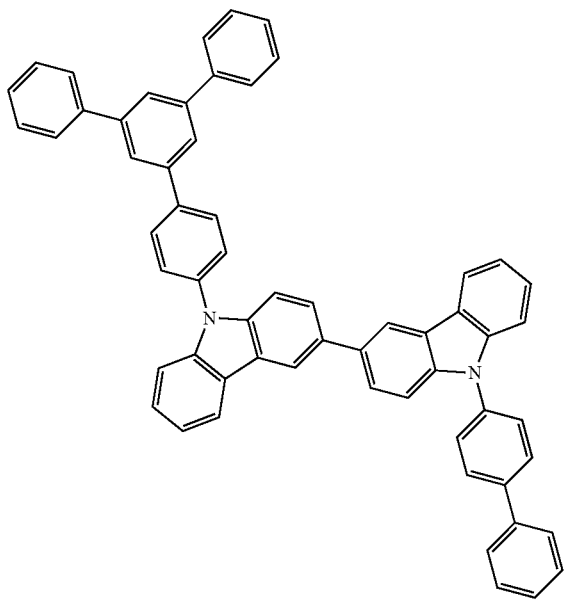
[A-127]
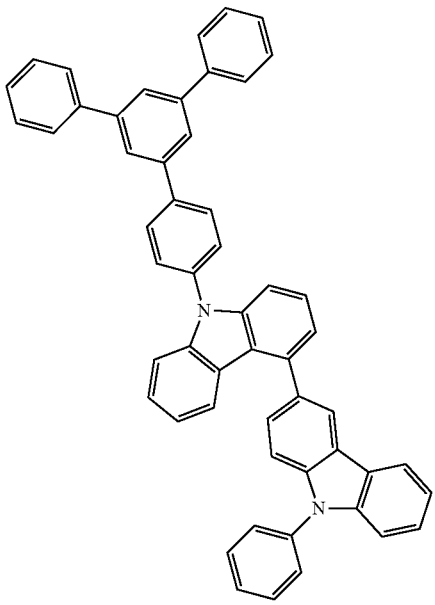
[A-128]

[A-129]
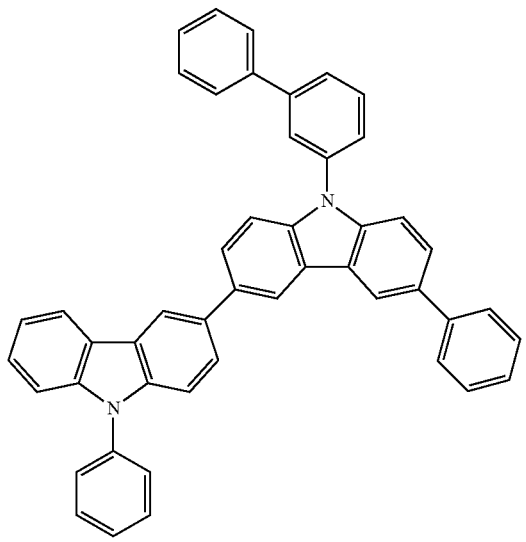
[A-130]
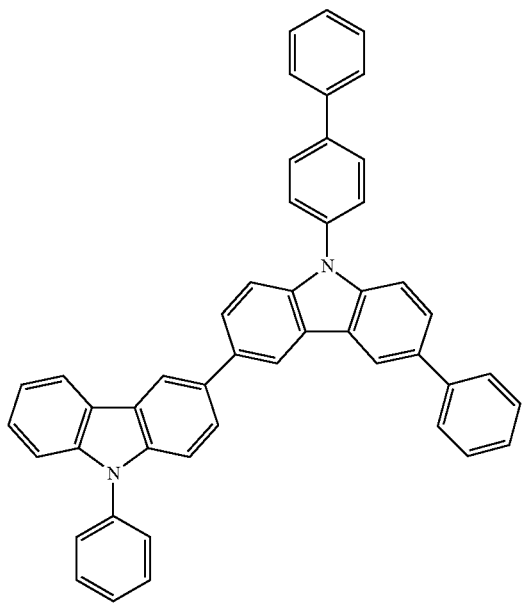
[A-131]
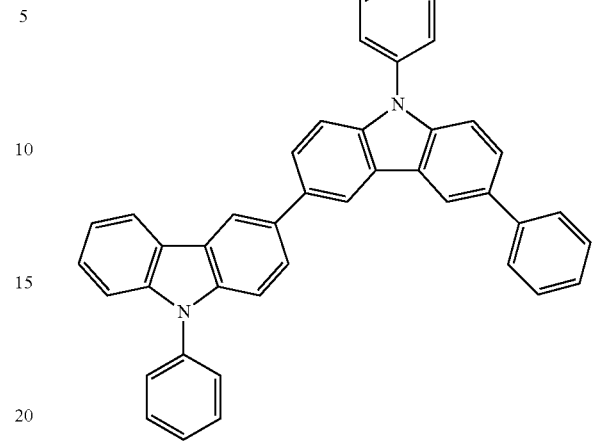
[A-132]
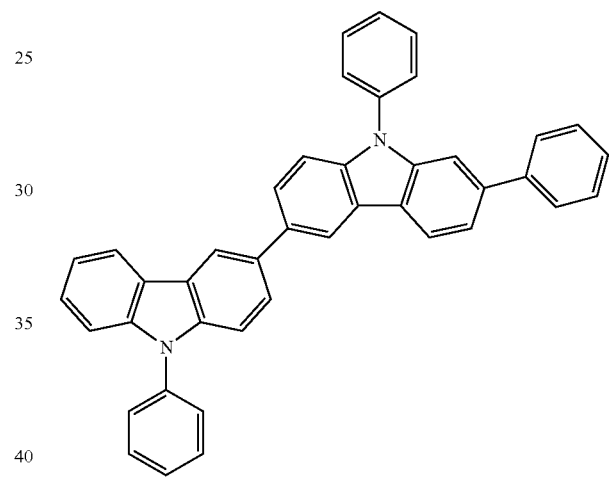
[A-133]
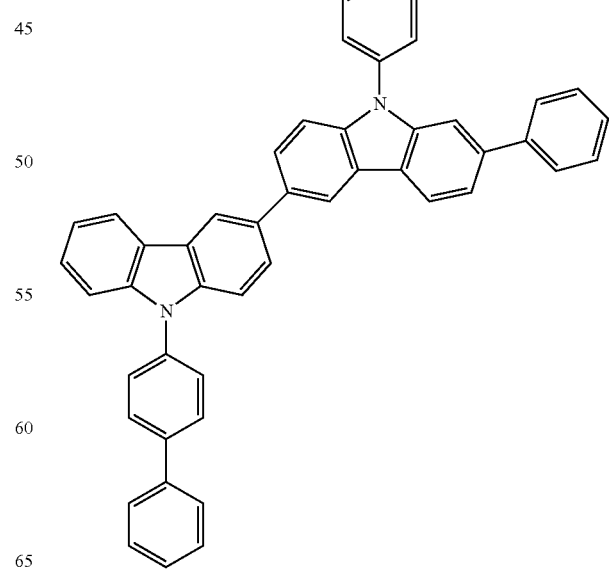

-continued
[A-134]
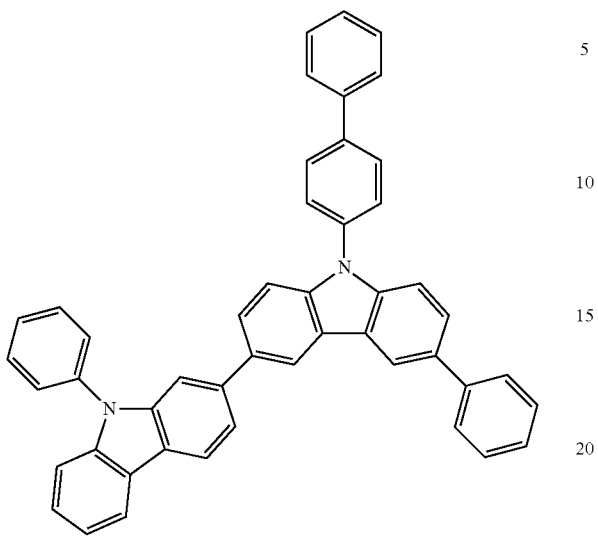
[A-135]
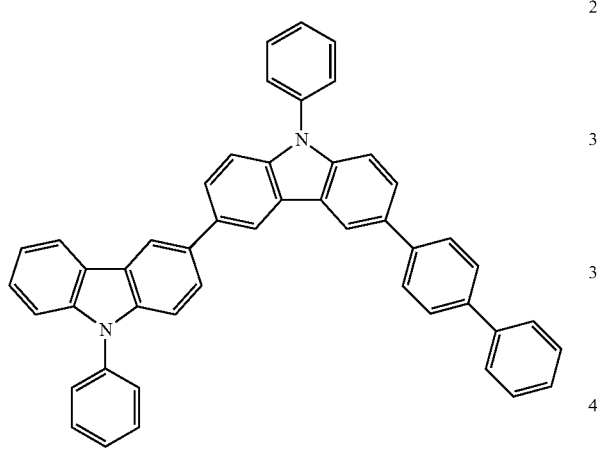
[A-136]
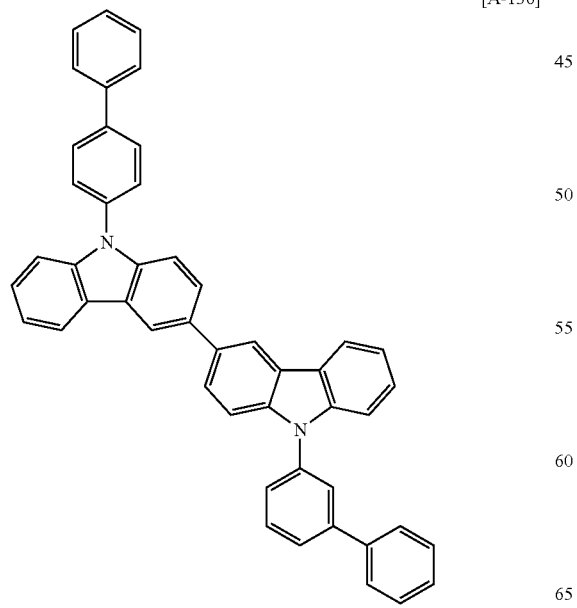
[A-137]
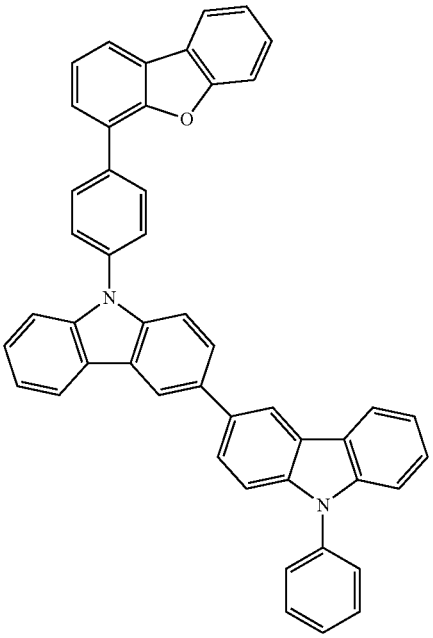
[A-138]
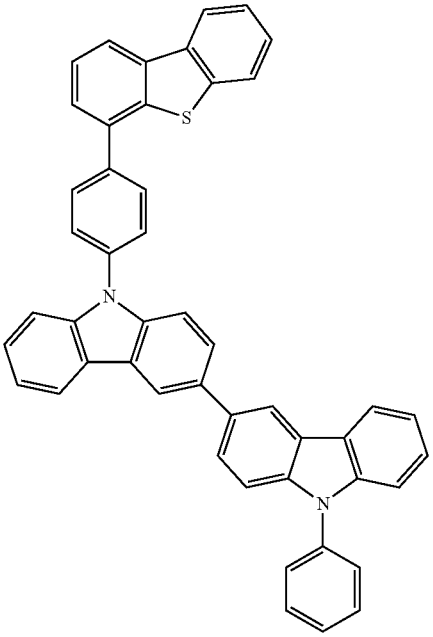

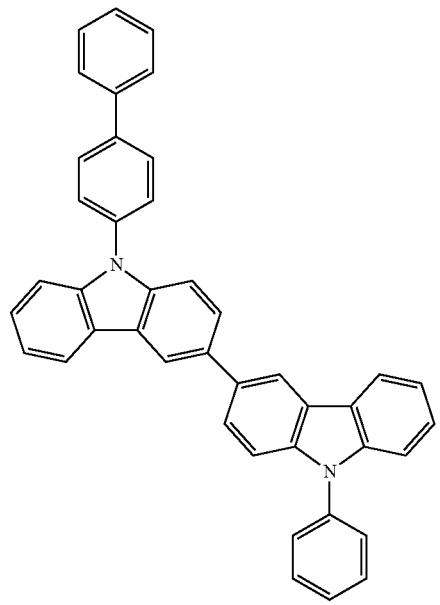
[A-139]
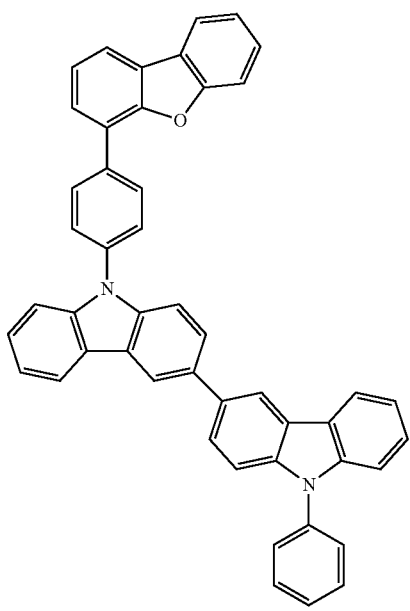
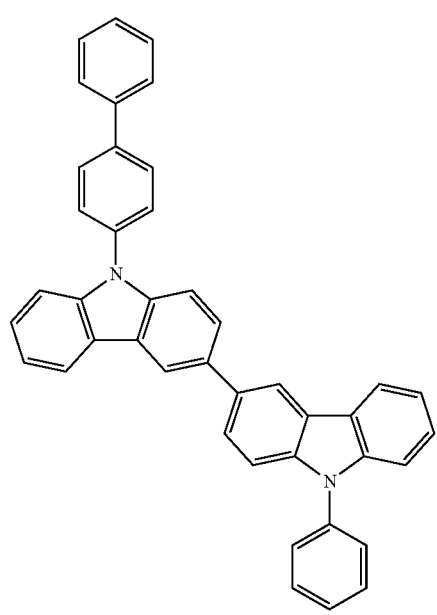
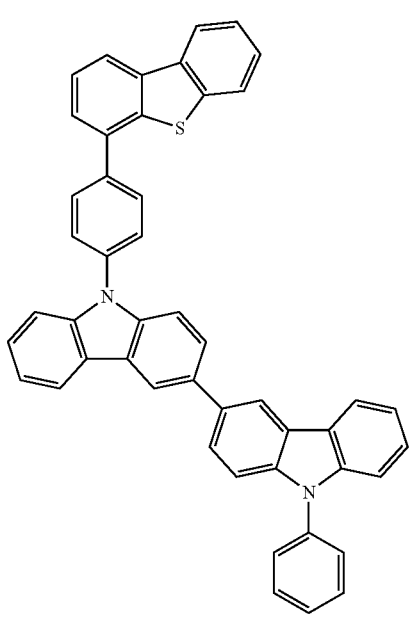

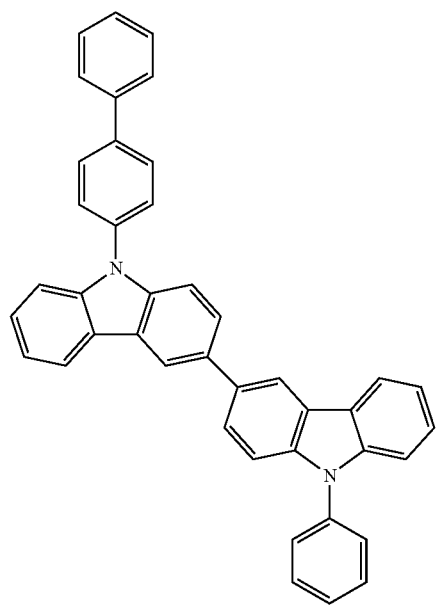
[B-1]
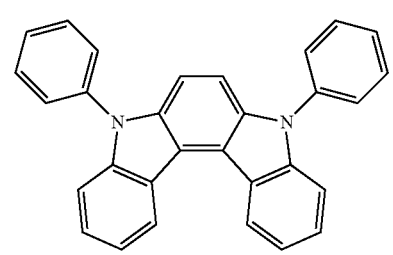
[B-2]
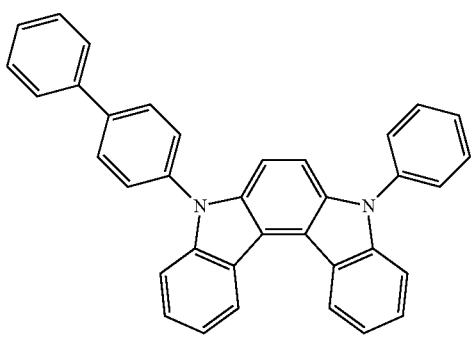
[B-3]
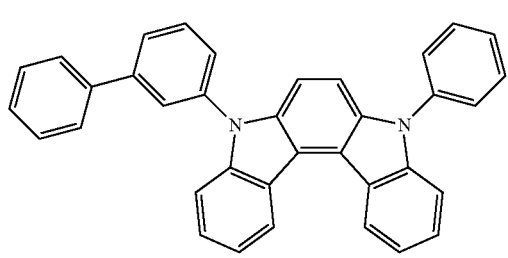
[B-4]
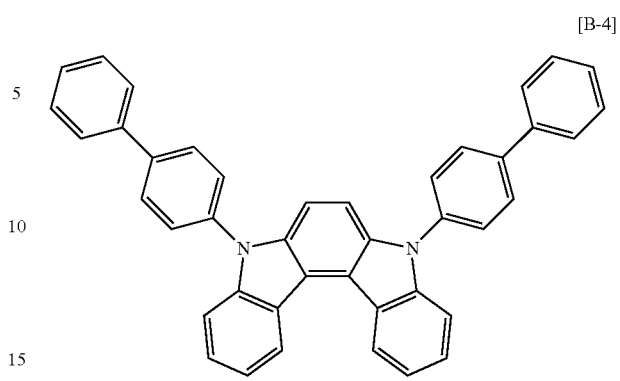
[B-5]
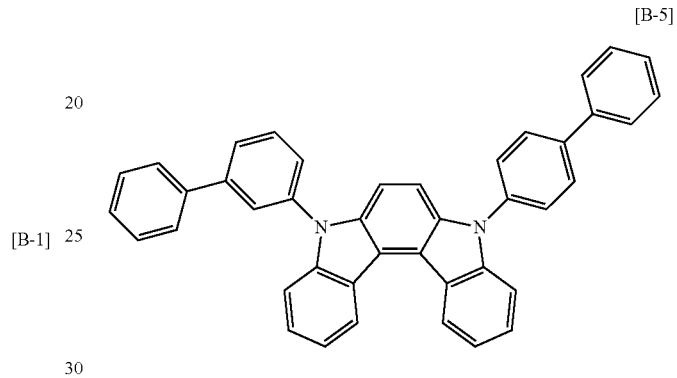
[B-6]
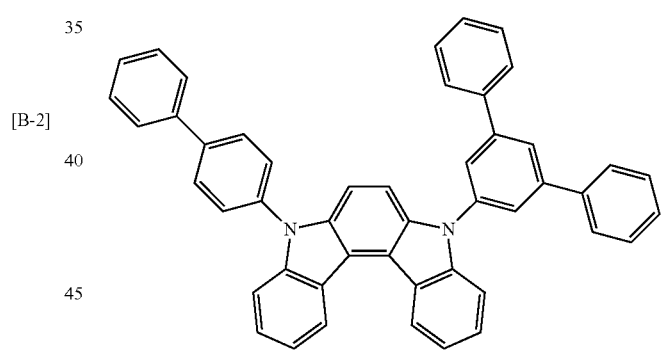
[B-7]
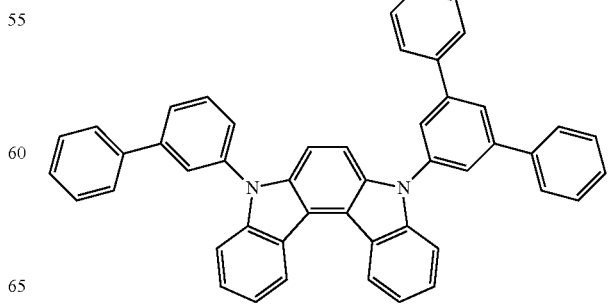

[B-8]
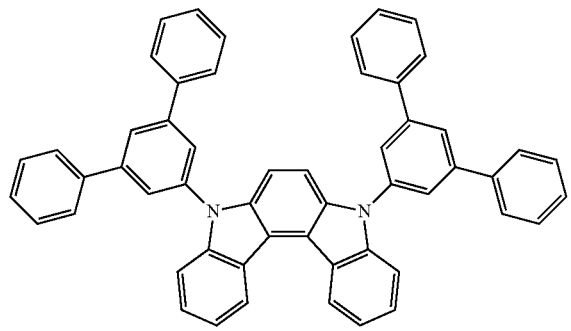
[B-9]
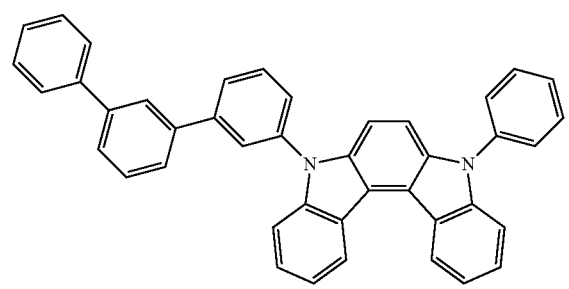
[B-10]
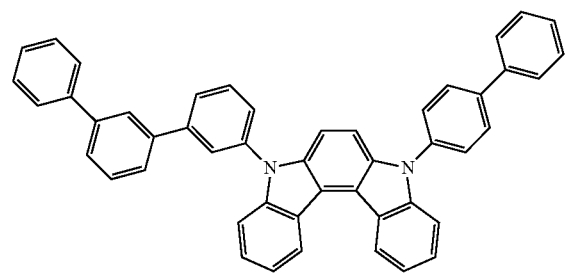
[B-11]
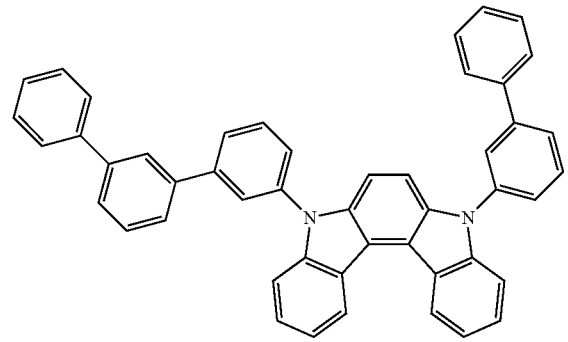
[B-12]
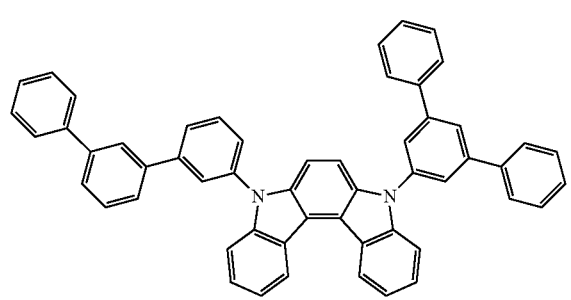
[B-13]
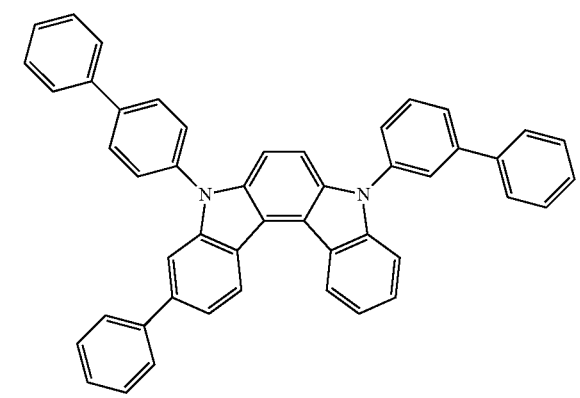
[B-14]
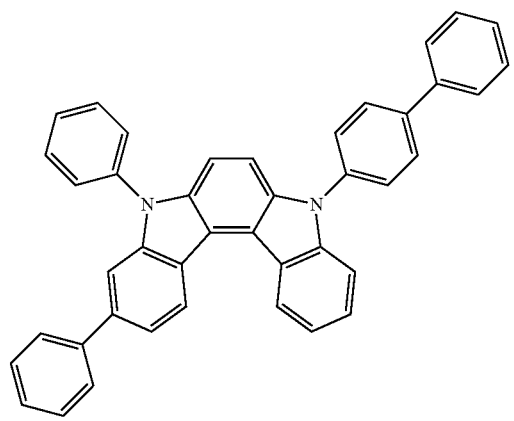
[B-15]
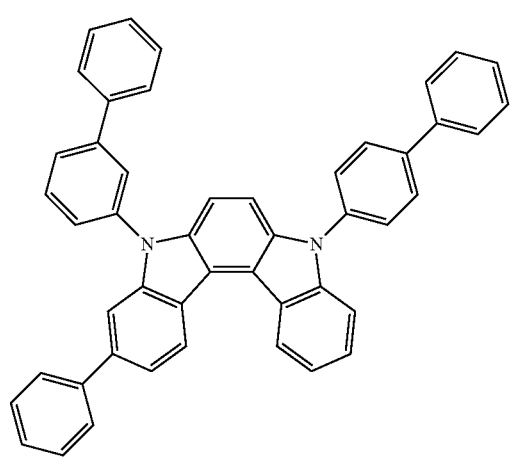

[B-16]
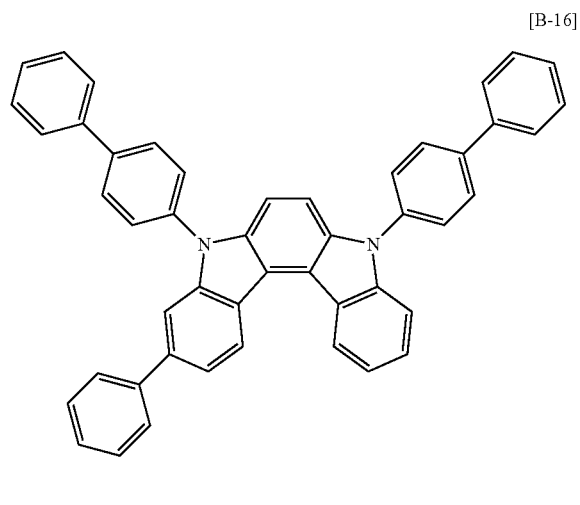
[B-17]
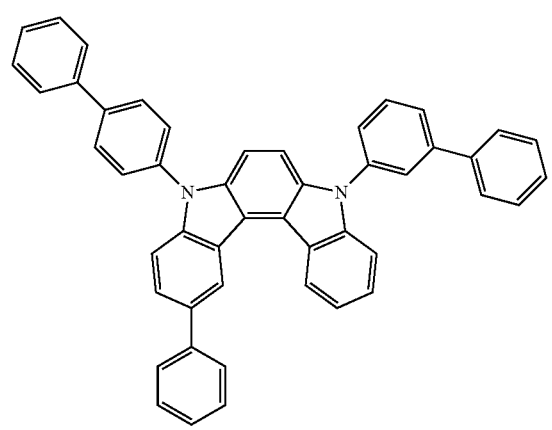
[B-18]
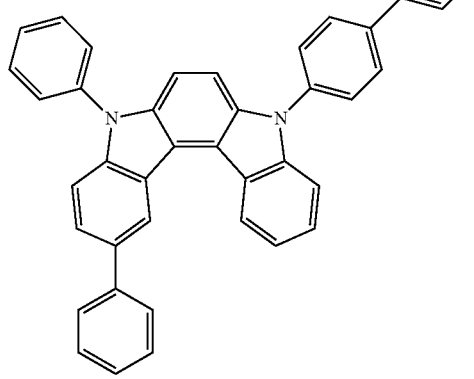
[B-19]
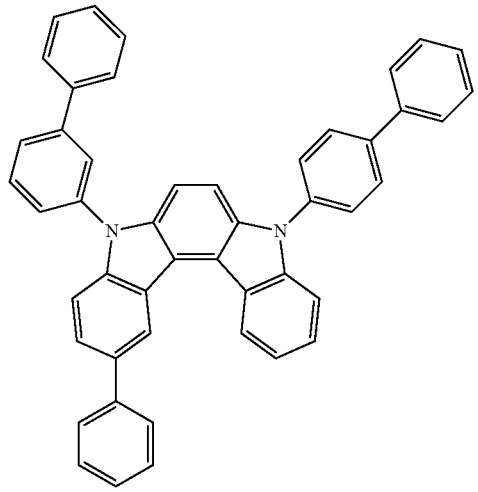
[B-20]
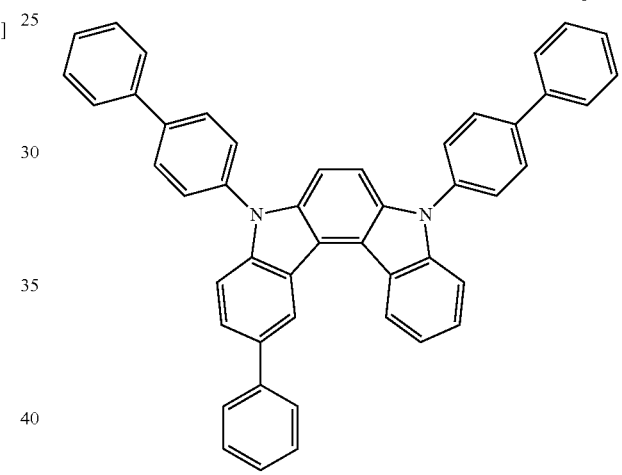
[B-21]
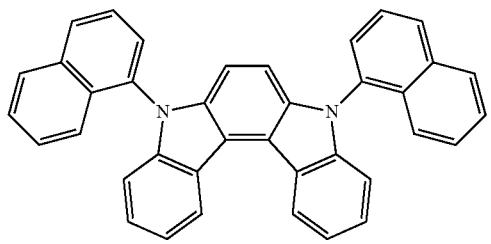
[B-22]
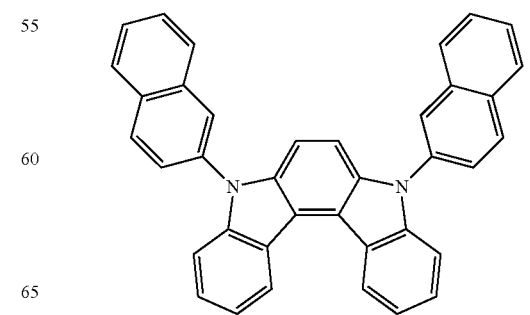

[B-23]
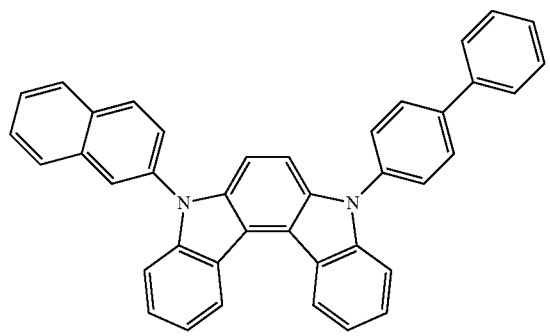
[B-24]
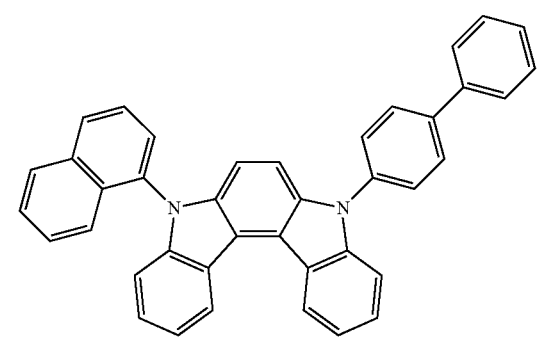
[B-25]
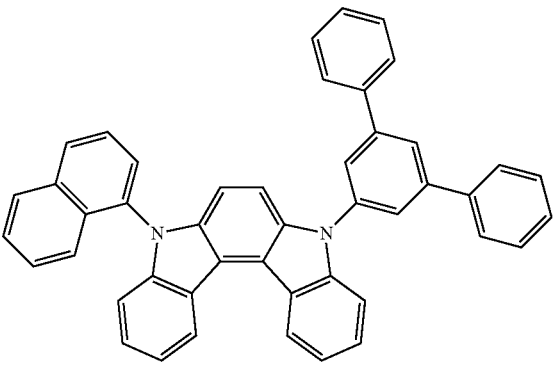
[B-26]
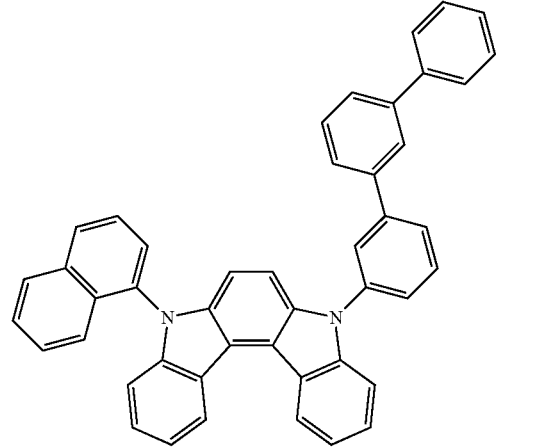
[B-27]
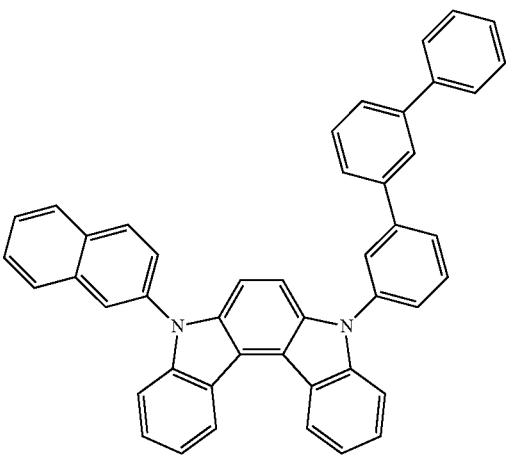
[B-28]
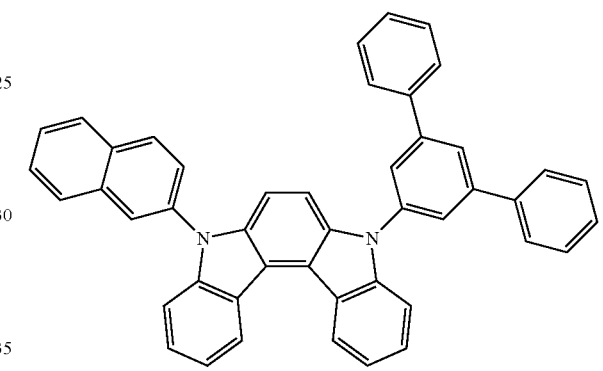
[B-29]
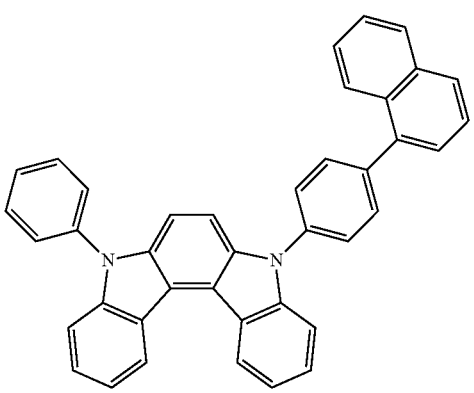
[B-30]
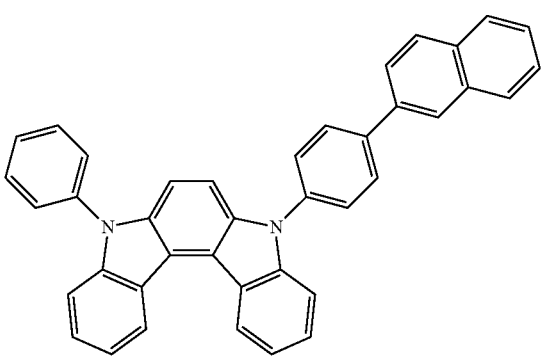

[B-31] 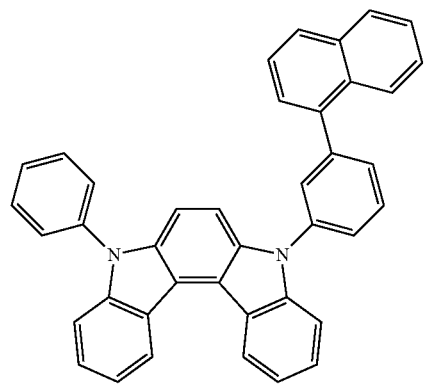
[B-32] 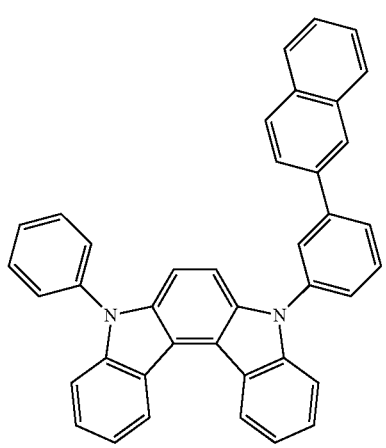
[B-33] 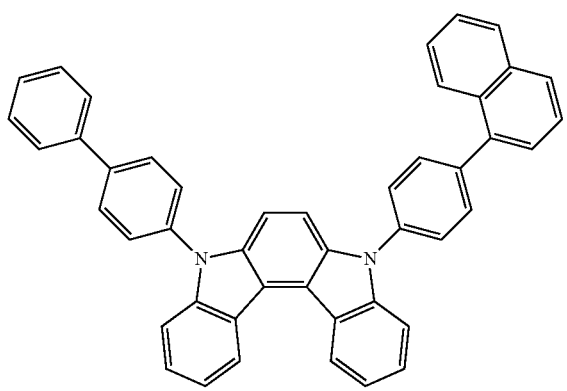
[B-34] 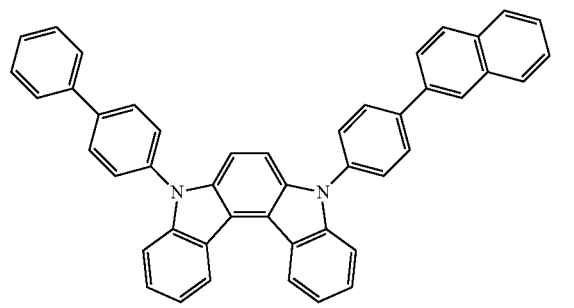
[B-35] 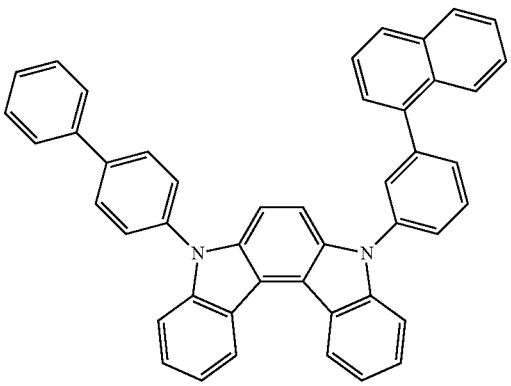
[B-36] 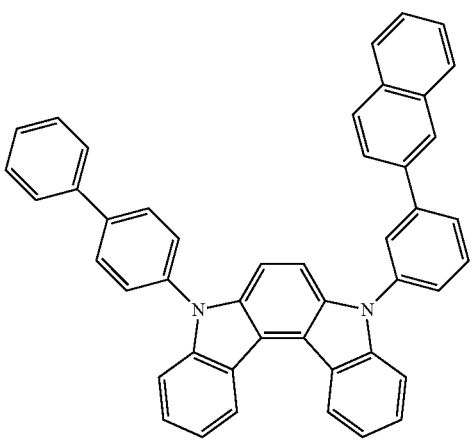
[B-37] 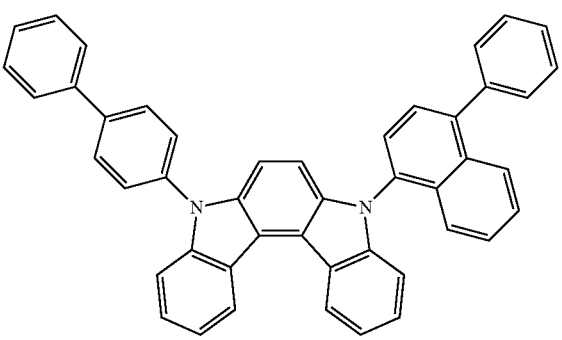
[B-38] 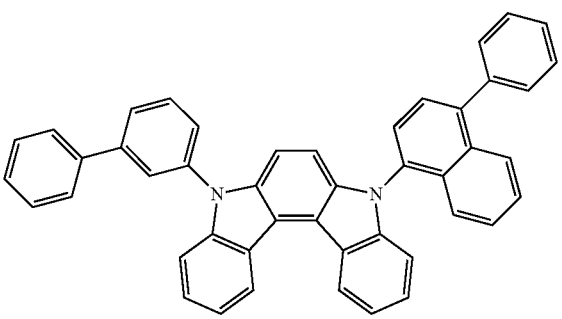

[B-39]
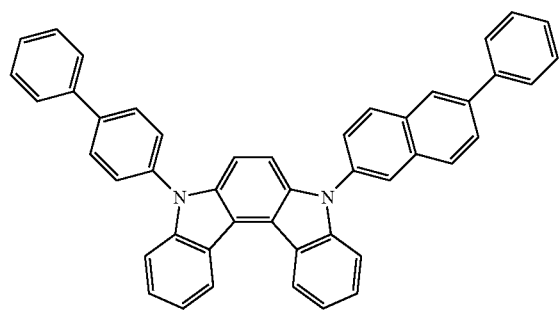
[B-40]
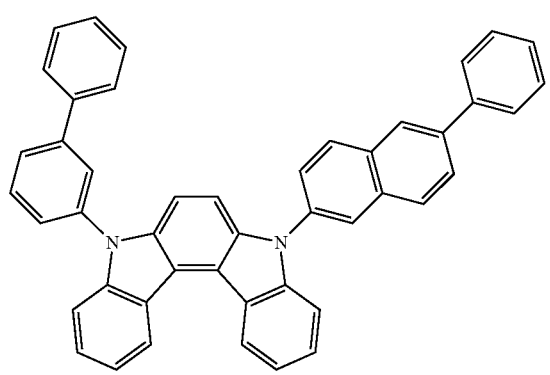
[B-41]
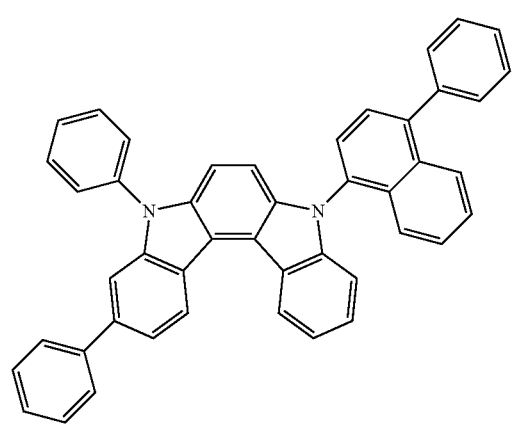
[B-42]
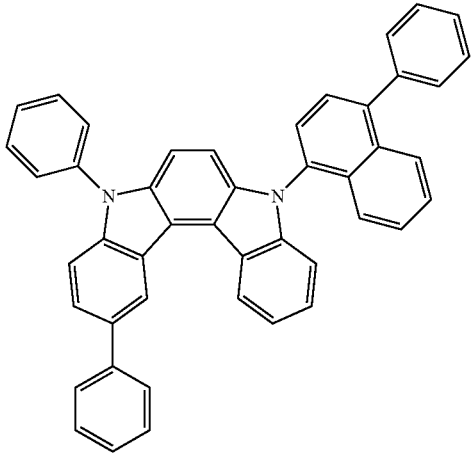
[B-43]
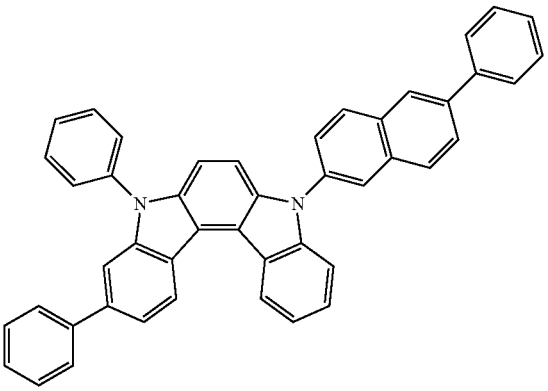
[B-44]
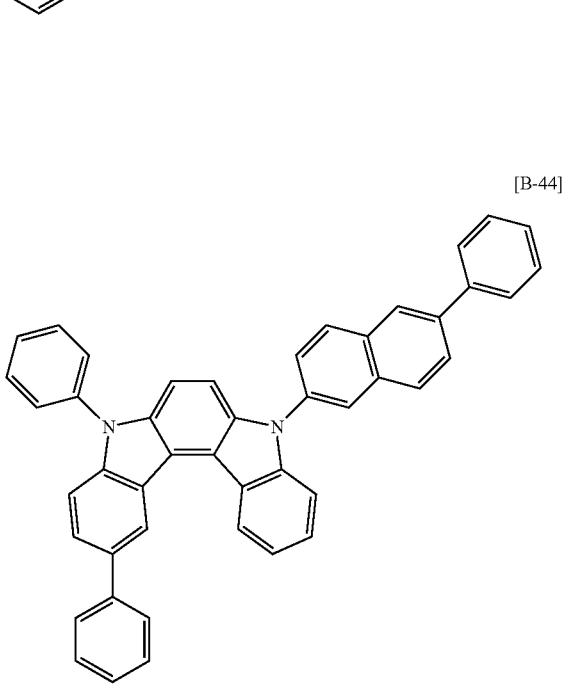
[B-45]
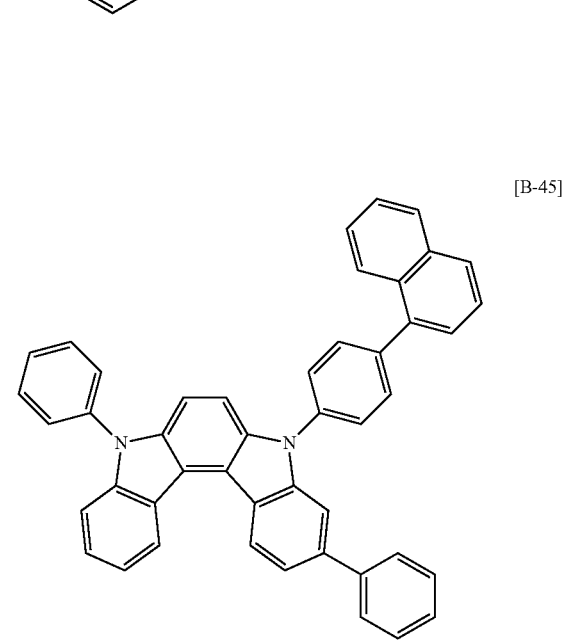

[B-46]
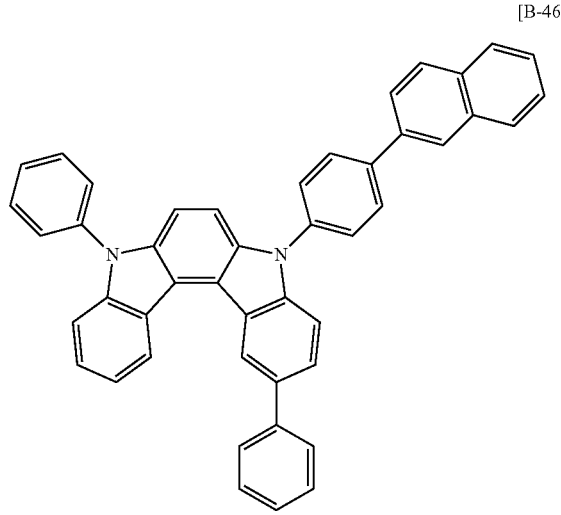
[B-47]
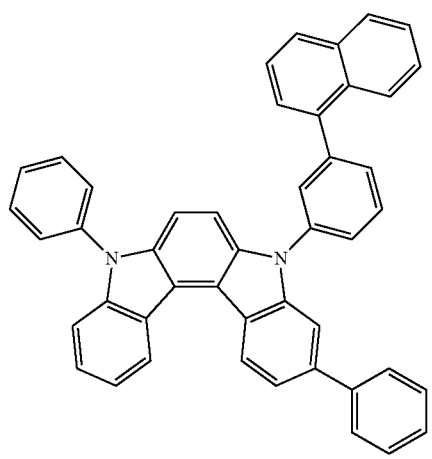
[B-48]
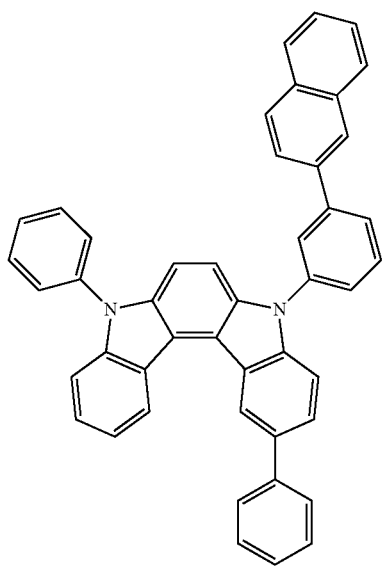
[B-49]
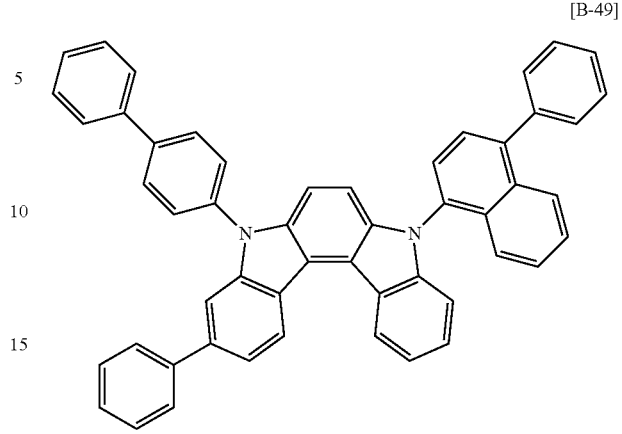
[B-50]
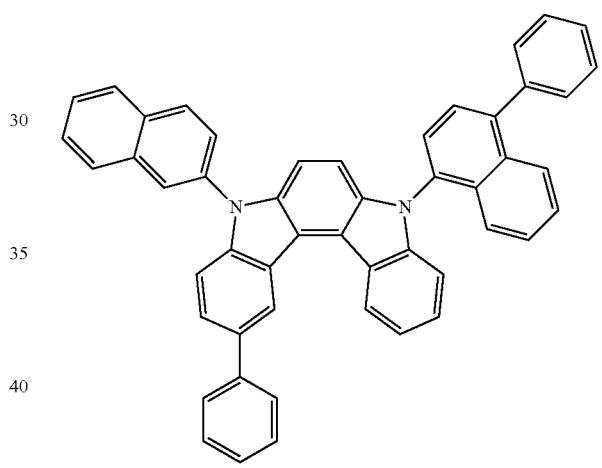
[B-51]
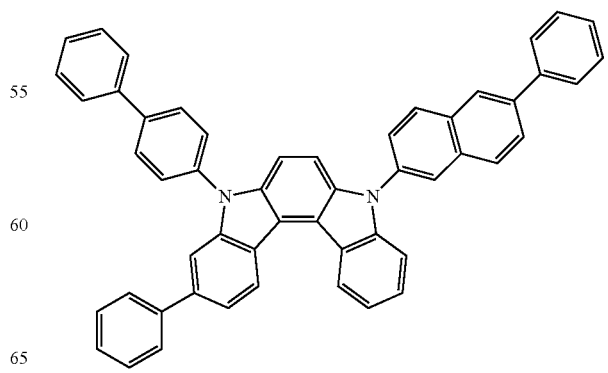

189
-continued

[B-52]
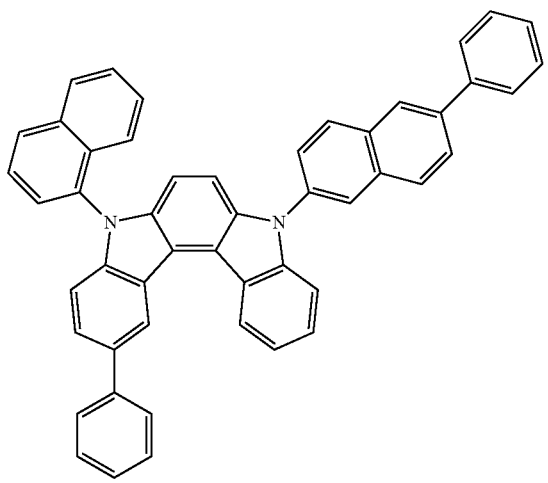

[B-53]
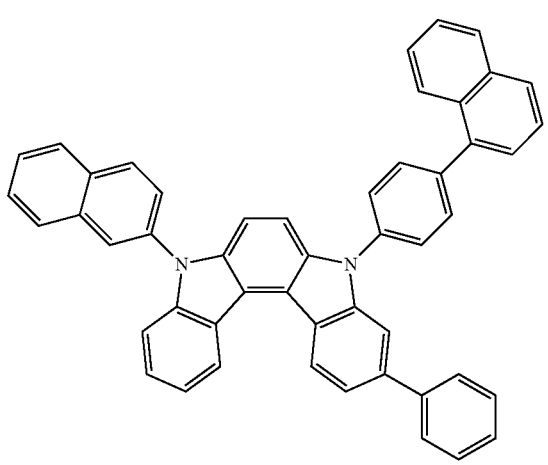

[B-54]
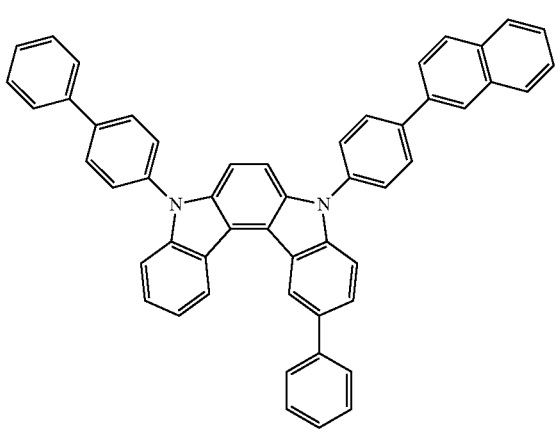

190
-continued

[B-55]
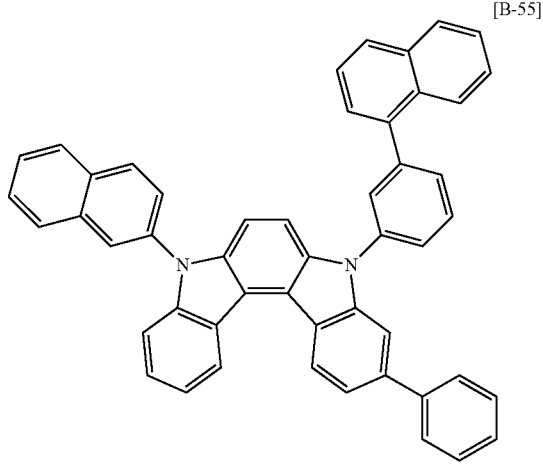

[B-56]
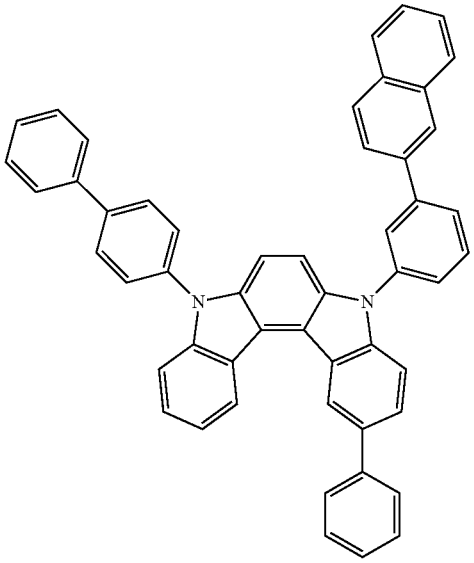

The first compound for an organic optoelectronic device and the second compound for an organic optoelectronic device may be, e.g., included in a weight ratio of about 1:99 to about 99:1. Within the above range, a weight ratio using the electron transport capability of the first compound for an organic optoelectronic device and the hole transport capability of the second compound for an organic optoelectronic device may be suitably adjusted to implement bipolar characteristics and improve efficiency and life-span. Within the above range, e.g., they may be included in a weight ratio of about 10:90 to about 90:10, about 10:90 to about 80:20, e.g., about 10:90 to about 70:30, about 10:90 to about 60:40, or about 20:80 to about 60:40. In an implementation, they may be included in a weight ratio of about 20:80 to about 50:50.

In addition to the aforementioned first compound for an organic optoelectronic device and second compound for an organic optoelectronic device, one or more additional compounds may be further included.

The aforementioned compound for an organic optoelectronic device or composition for an organic optoelectronic device may be a composition further including a dopant (e.g., the compound or the composition may be a host).

The dopant may be, e.g., a phosphorescent dopant. The dopant may be, e.g., a red, green or blue phosphorescent dopant. The dopant may be, e.g., a red or green phosphorescent dopant.

A dopant is a material that emits light by being mixed in a small amount with a compound or composition for an organic optoelectronic device. In an implementation, the dopant may be a material such as a metal complex that emits light by multiple excitation into a triplet or more. The dopant may be, e.g., an inorganic, organic, or organic-inorganic compound, and may include one or two or more different compounds.

An example of the dopant may be a phosphorescent dopant, and examples of the phosphorescent dopant may include an organometallic compound including Ir, Pt, Os, Ti, Zr, Hf, Eu, Tb, Tm, Fe, Co, Ni, Ru, Rh, Pd, or a combination thereof. The phosphorescent dopant may be, e.g., a compound represented by Chemical Formula Z.

$$L^6MX^3$$ [Chemical Formula Z]

In Chemical Formula Z, M may be, e.g., a metal, and $L^6$ and $X^3$ may each independently be, e.g., ligands forming a complex compound with M.

The M may be, e.g., Ir, Pt, Os, Ti, Zr, Hf, Eu, Tb, Tm, Fe, Co, Ni, Ru, Rh, Pd, or a combination thereof and $L^6$ and $X^3$ may be, e.g., a bidendate ligand.

The aforementioned compound for an organic optoelectronic device or composition for an organic optoelectronic device may be formed into a film by a dry film forming method such as chemical vapor deposition.

Hereinafter, an organic optoelectronic device including the aforementioned compound for an organic optoelectronic device or composition for an organic optoelectronic device is described.

The organic optoelectronic device may be a suitable device to convert electrical energy into photoenergy and vice versa without particular limitation, and may be, e.g., an organic photoelectric device, an organic light emitting diode, an organic solar cell, or an organic photoconductor drum.

Herein, an organic light emitting diode as one example of an organic optoelectronic device is described referring to drawings.

Figure 2:
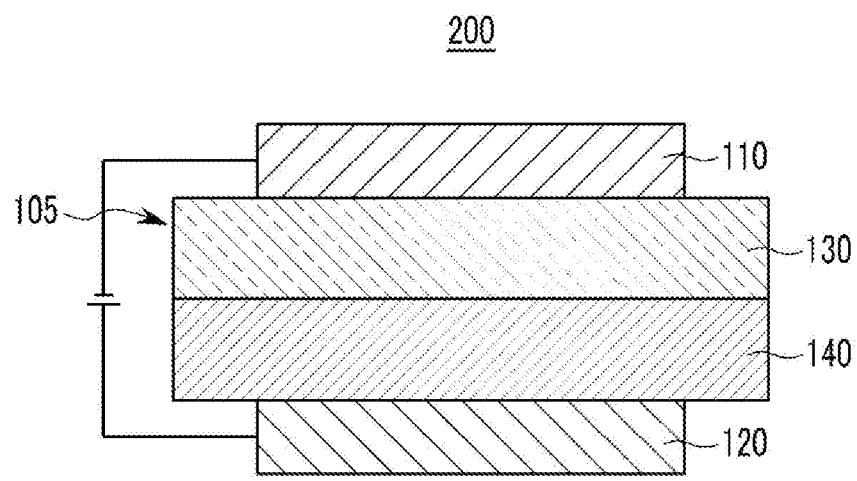

FIGS. 1 and 2 are cross-sectional views showing organic light emitting diodes according to embodiments.

Referring to FIG. 1, an organic light emitting diode 100 according to an embodiment may include an anode 120 and a cathode 110 facing each other and an organic layer 105 disposed between the anode 120 and cathode 110.

The anode 120 may be made of a conductor having a large work function to help hole injection, and may be, e.g., a metal, a metal oxide, or a conductive polymer. The anode 120 may be, e.g., a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; or a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to help electron injection, and may be, e.g., a metal, a metal oxide, or a conductive polymer. The cathode 110 may be, e.g., a metal such as magnesium, calcium, sodium, potassium, titanium, indium, yttrium, lithium, gadolinium, aluminum silver, tin, lead, cesium, barium, or the like, or an alloy thereof; or a multi-layer structure material such as LiF/Al, $LiO_2$/Al, LiF/Ca, or $BaF_2$/Ca.

The organic layer 105 may include the aforementioned compound for an organic optoelectronic device or composition for an organic optoelectronic device.

The organic layer 105 may include a light emitting layer 130 and the a light emitting layer 130 may include the aforementioned compound for an organic optoelectronic device or composition for an organic optoelectronic device.

The composition for an organic optoelectronic device further including a dopant may be, e.g., a red light emitting composition.

The light emitting layer 130 may include, e.g., the first compound for an organic optoelectronic device and the second compound for an organic optoelectronic device, respectively, as a phosphorescent host.

The organic layer may further include an auxiliary layer in addition to the light emitting layer.

The auxiliary layer may be, e.g., a hole auxiliary layer 140.

Referring to FIG. 2, an organic light emitting diode 200 may further include a hole auxiliary layer 140 in addition to the light emitting layer 130. The hole auxiliary layer 140 may further increase hole injection or hole mobility and blocks electrons between the anode 120 and the light emitting layer 130.

The hole auxiliary layer 140 may include, e.g., a compound of Group E.

In an implementation, the hole auxiliary layer 140 may include a hole transport layer between the anode 120 and the light emitting layer 130 and a hole transport auxiliary layer between the light emitting layer 130 and the hole transport layer, and a compound of Group E may be included in the hole transport auxiliary layer.

[Group E]

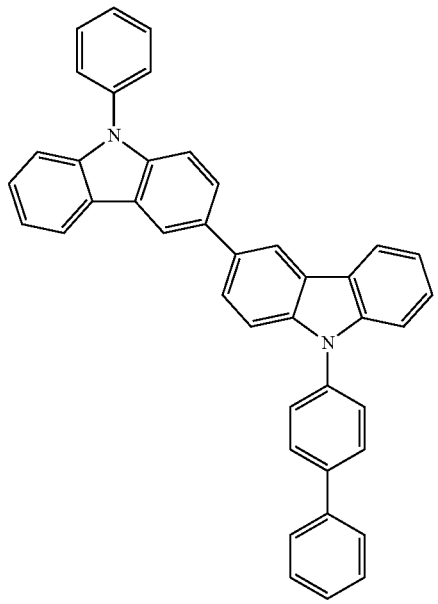

193
-continued
194
-continued
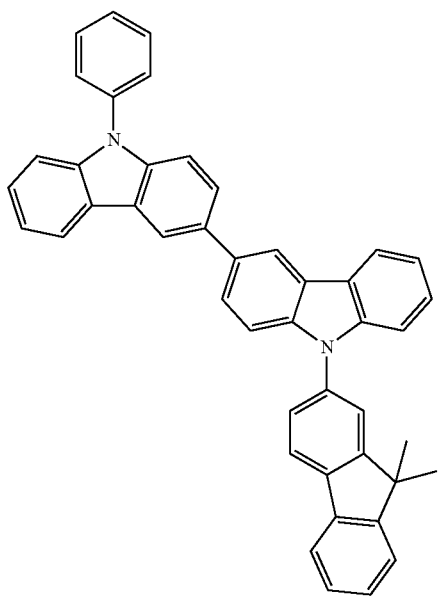
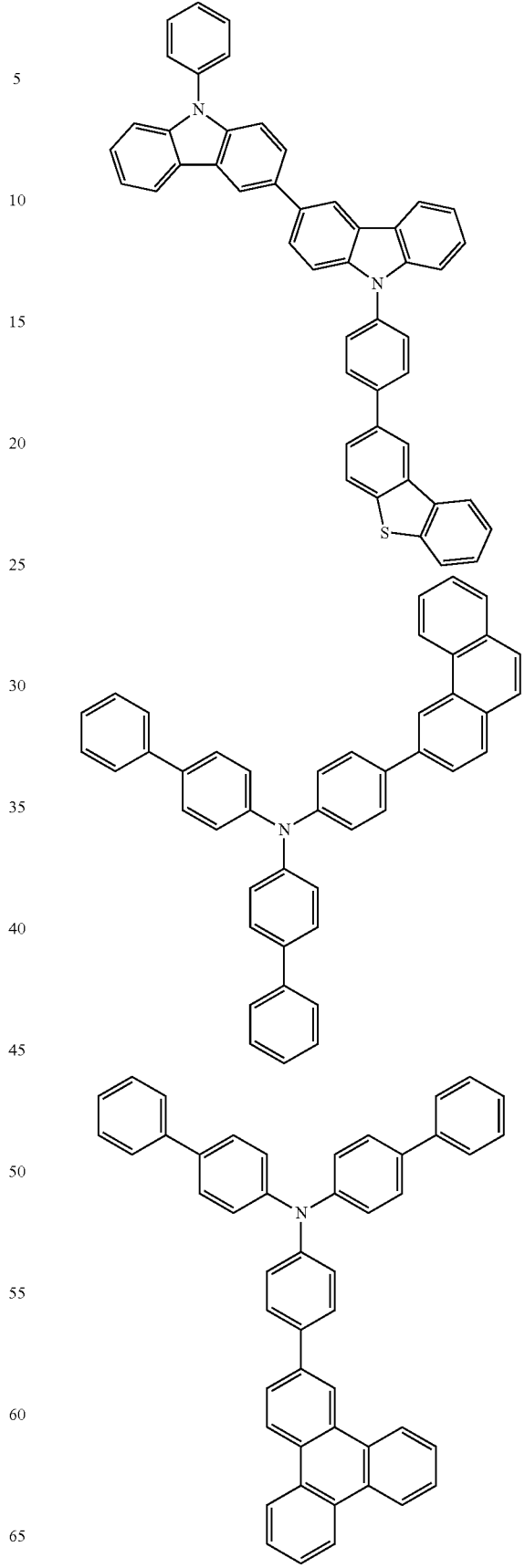
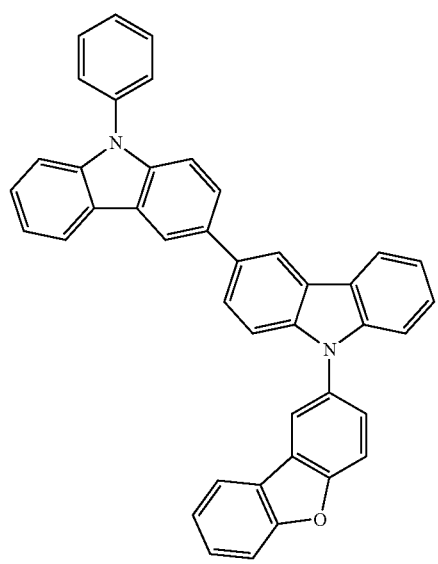

195
-continued
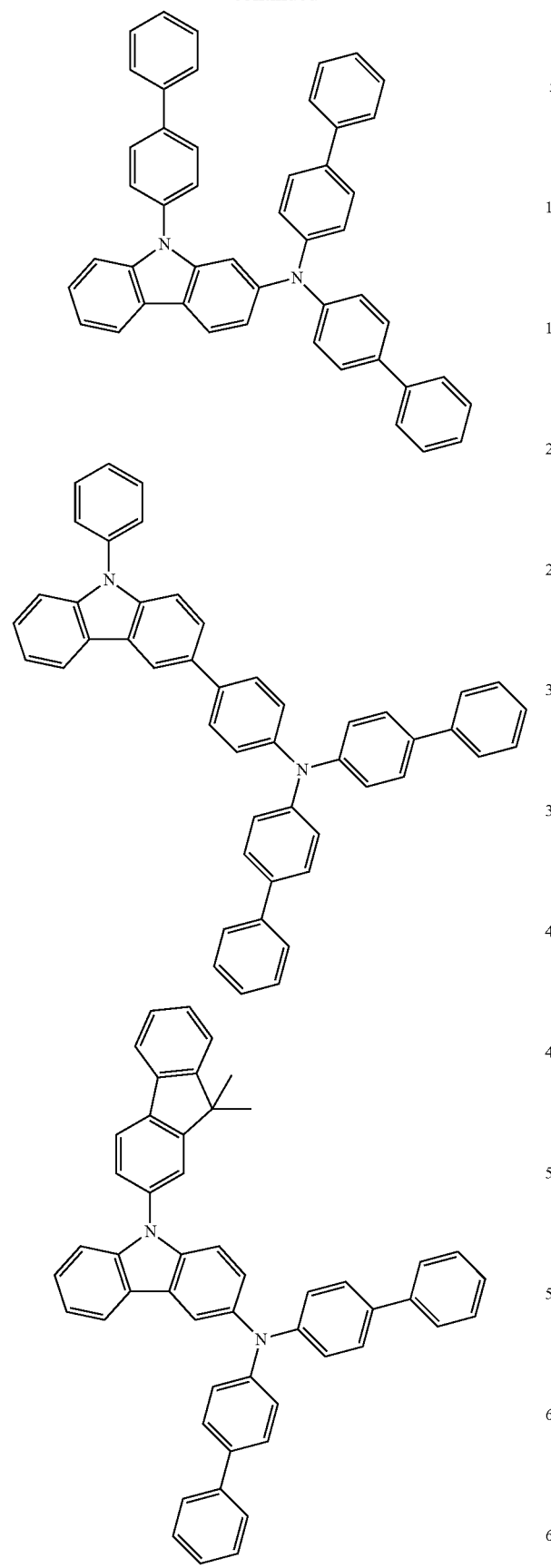
196
-continued
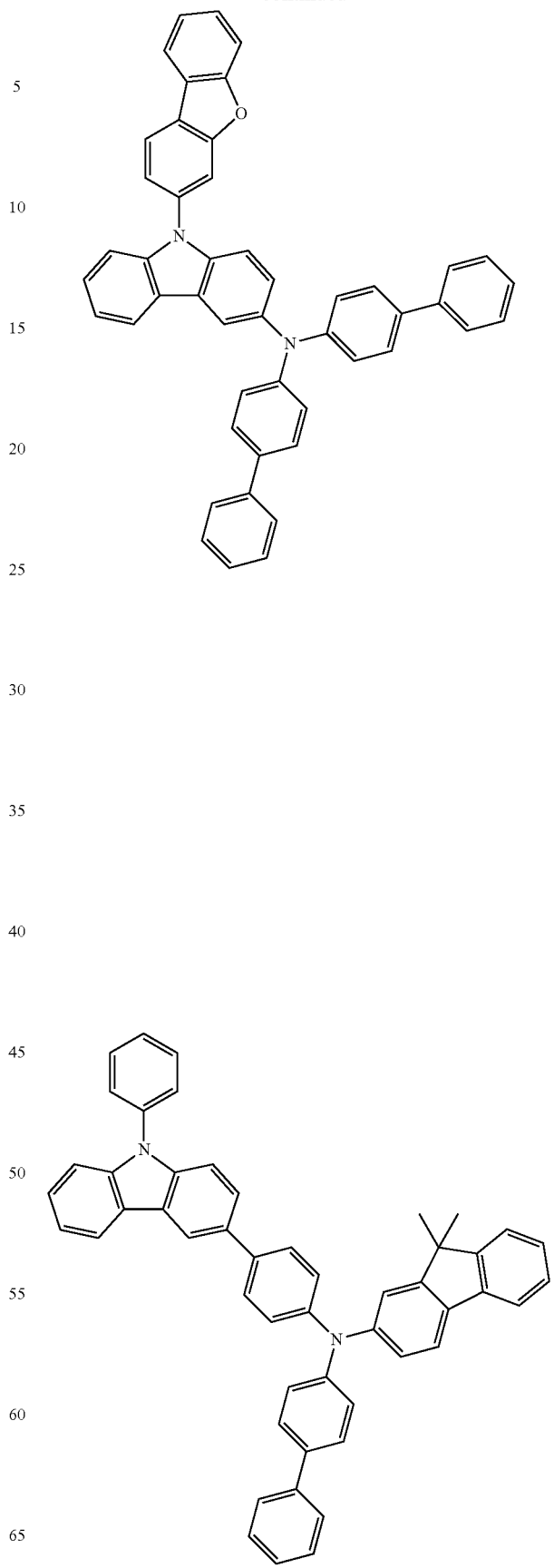

197
-continued
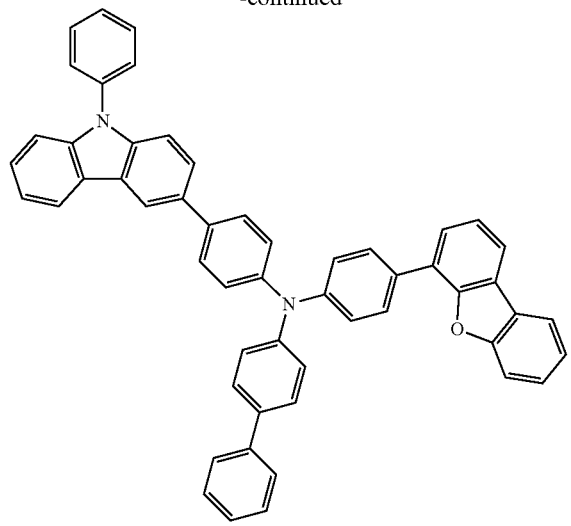
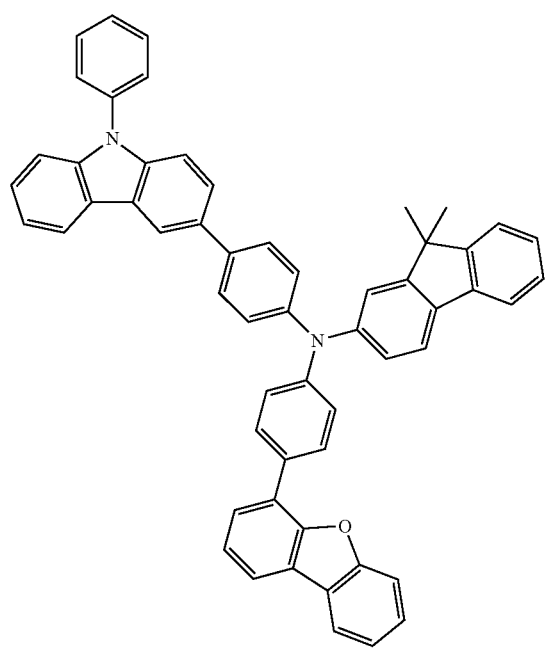
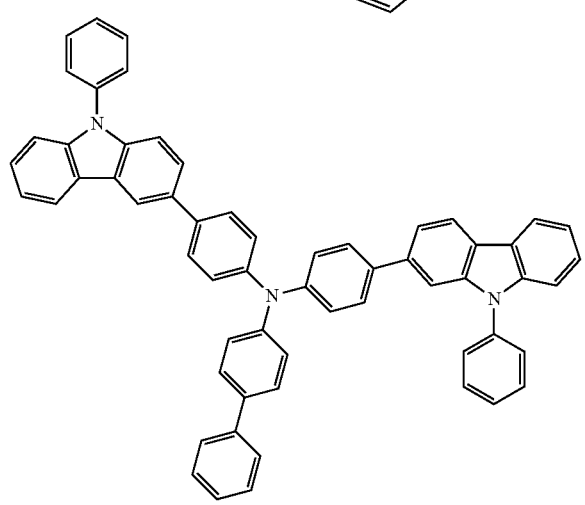
198
-continued
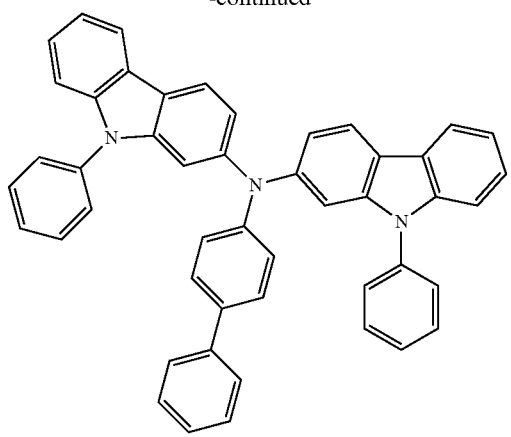
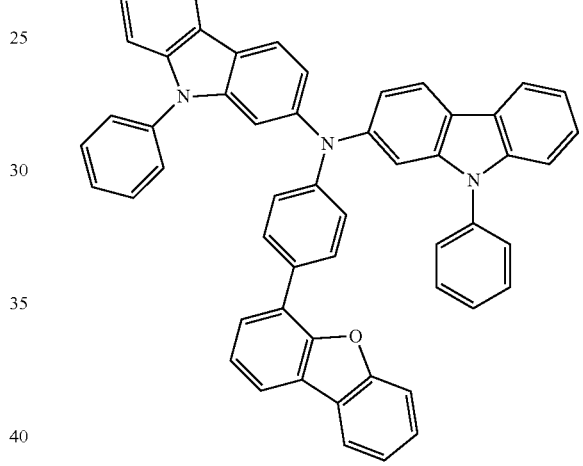
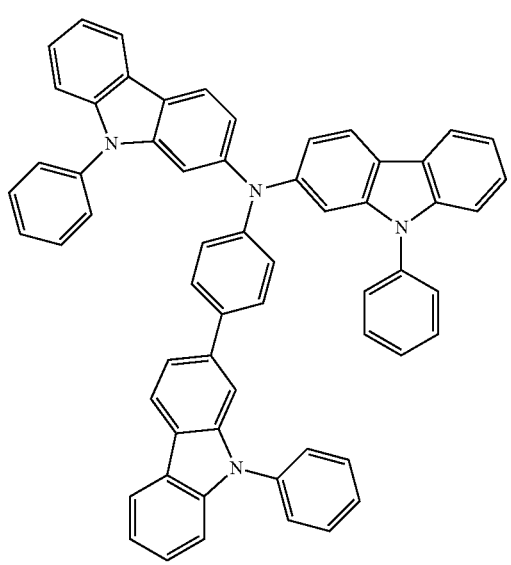

199
-continued
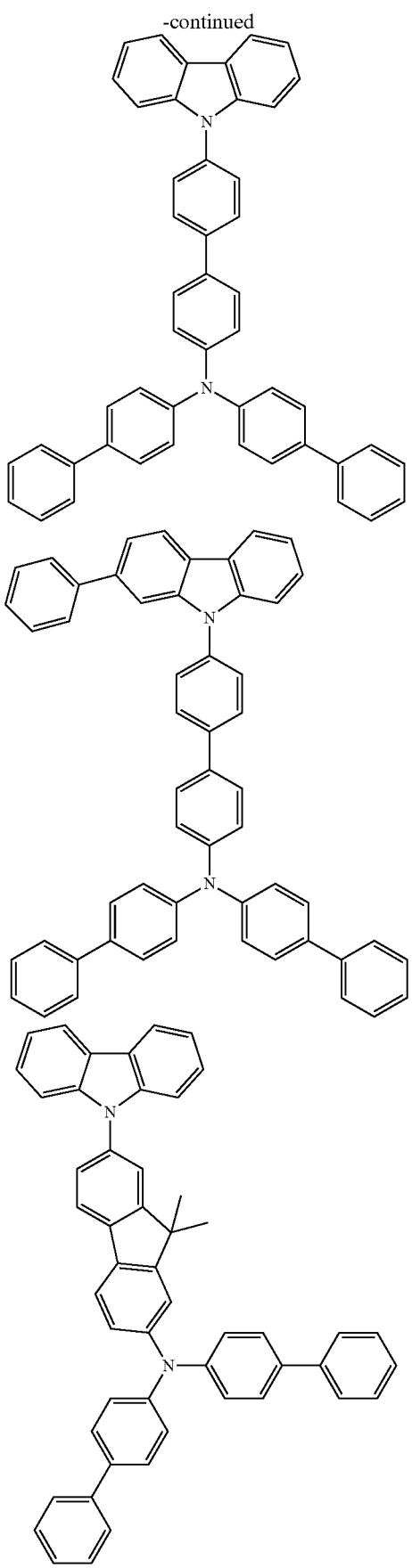
200
-continued
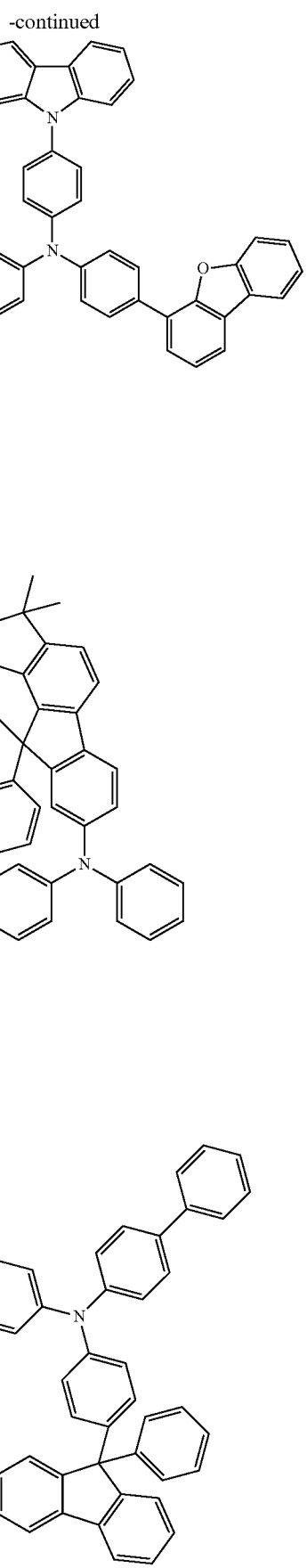

201
-continued
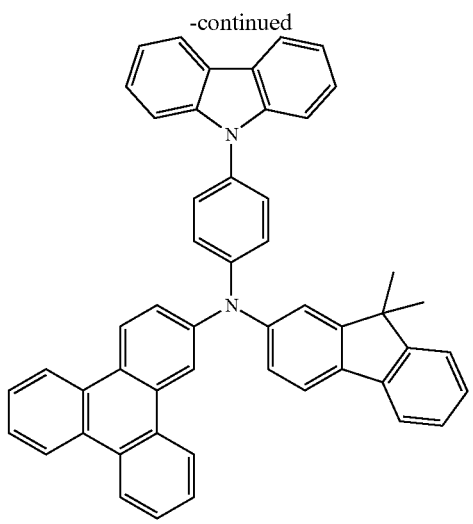
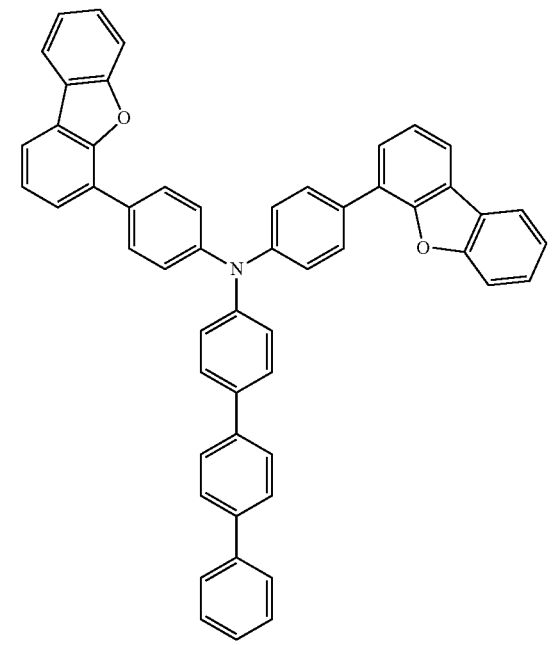
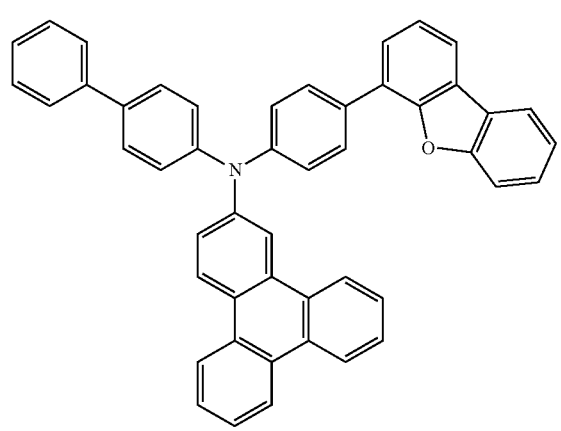
202
-continued
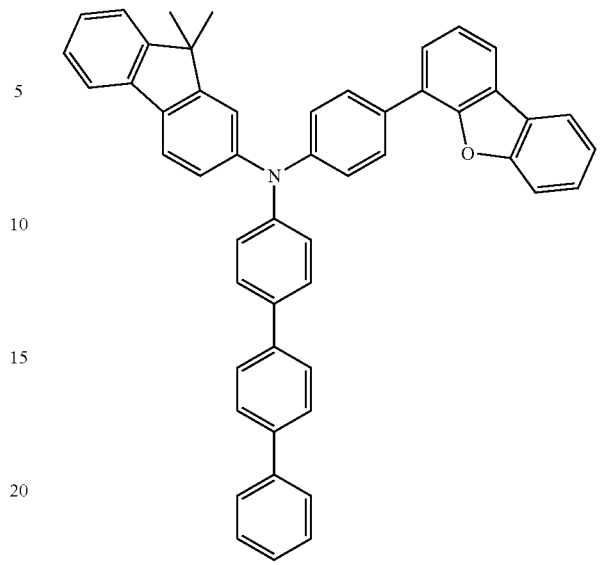
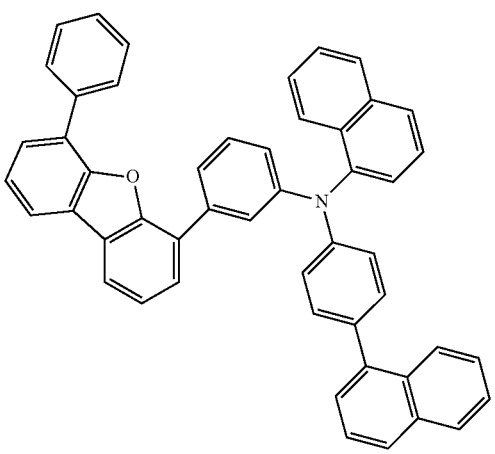
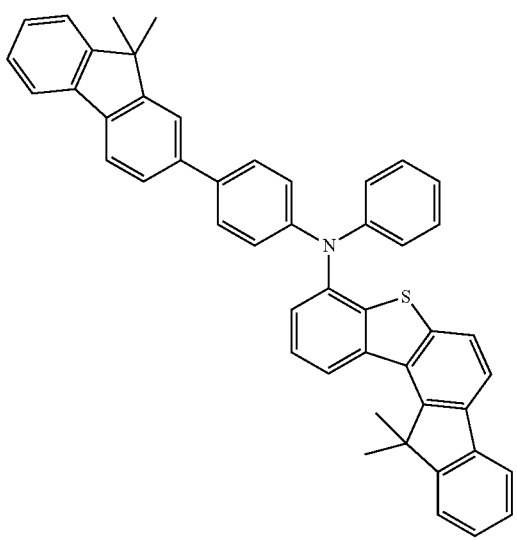

203
-continued
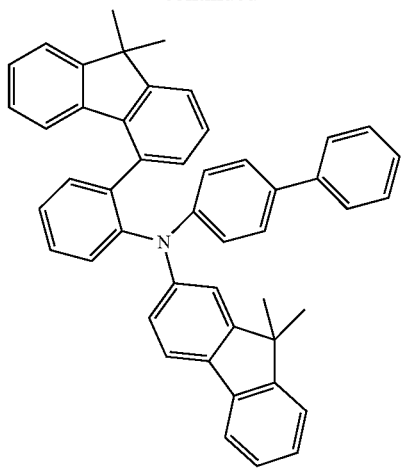
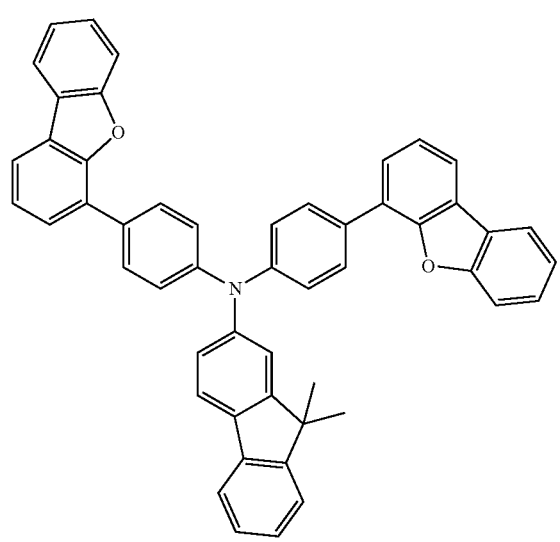
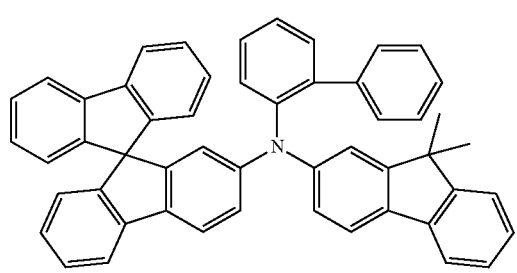
204
-continued
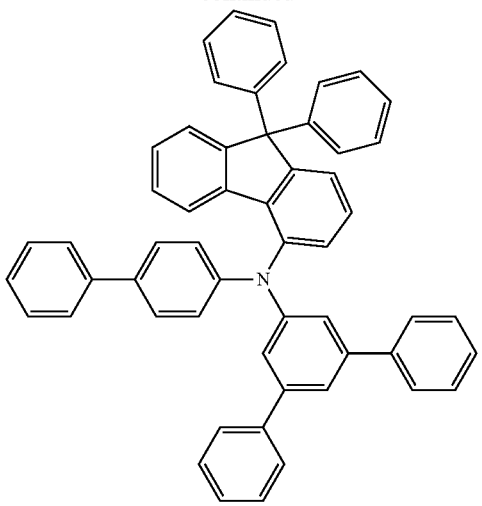
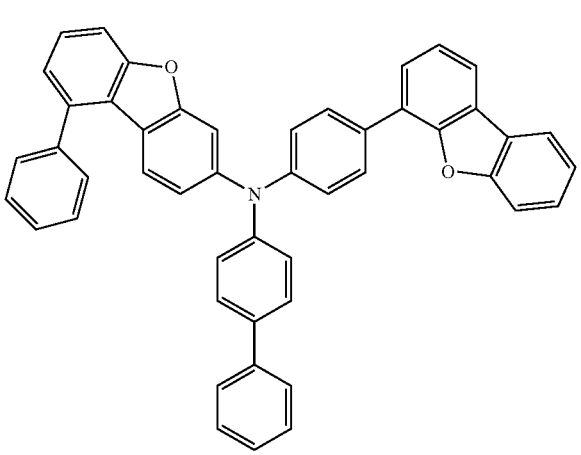
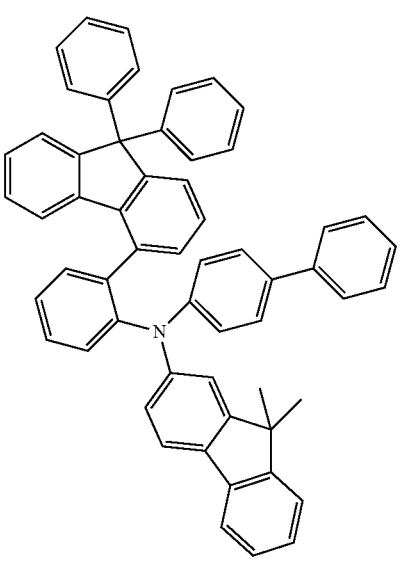

205
-continued
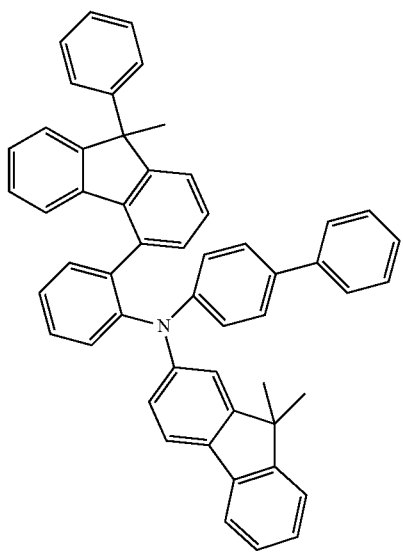
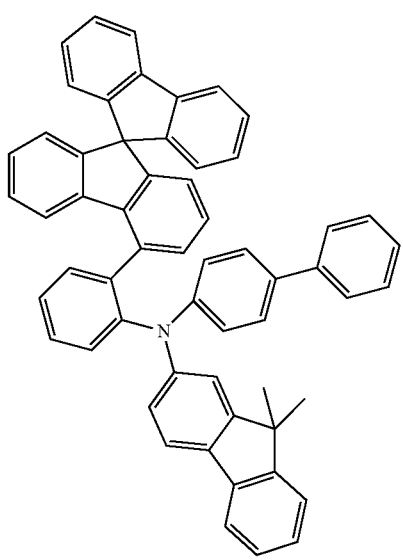
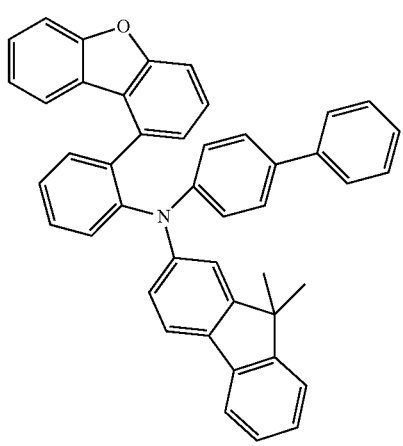
206
-continued
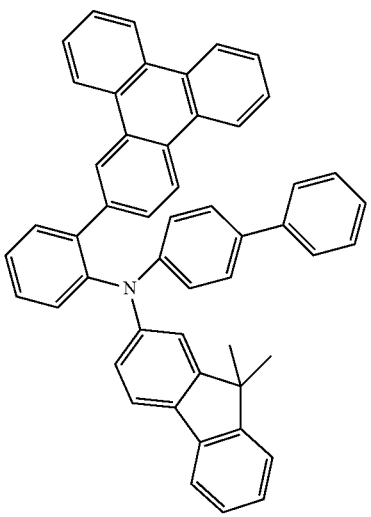
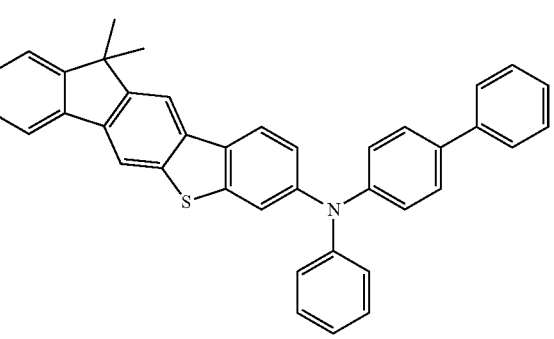

207
-continued
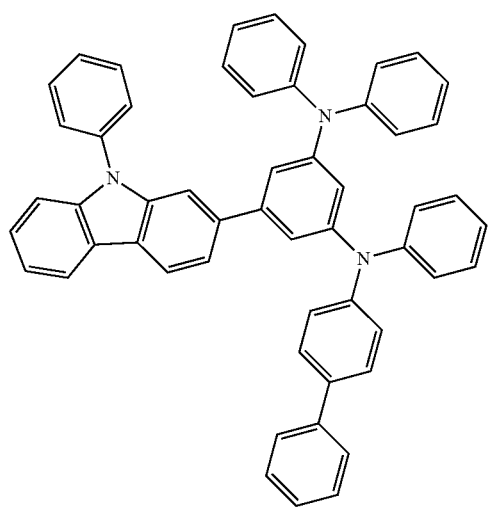
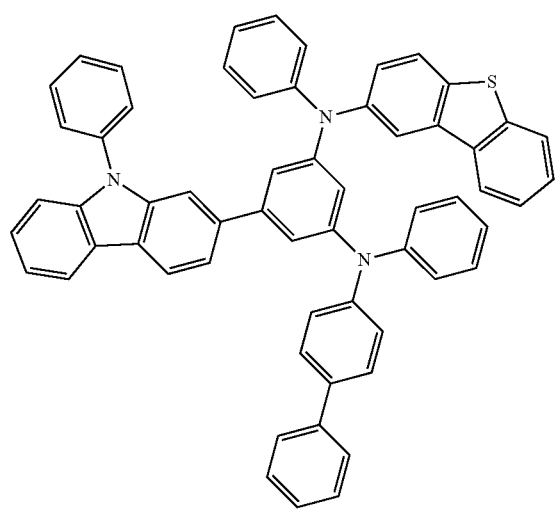
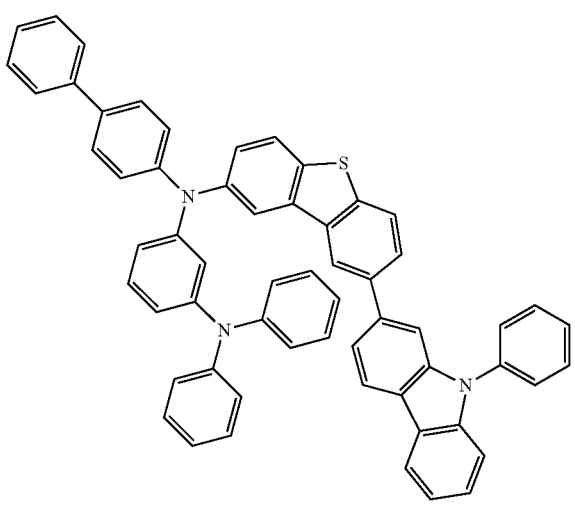
208
-continued
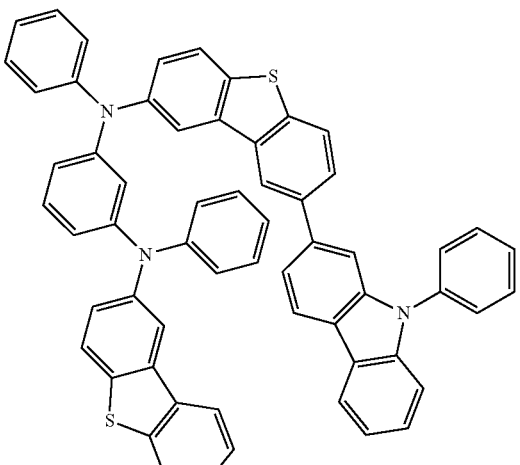
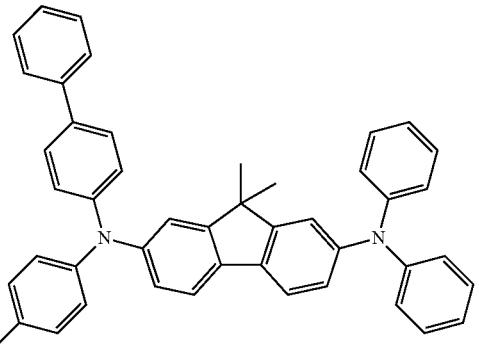

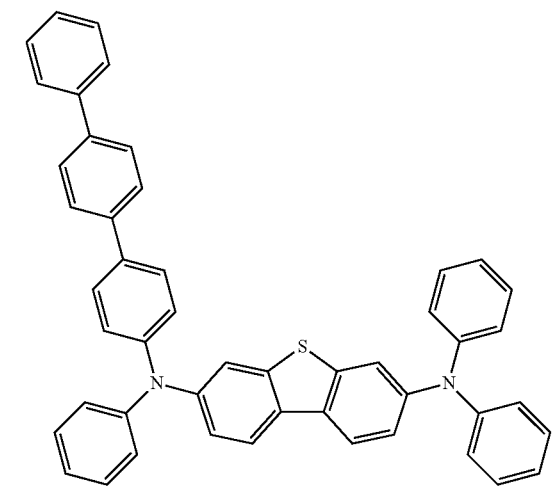
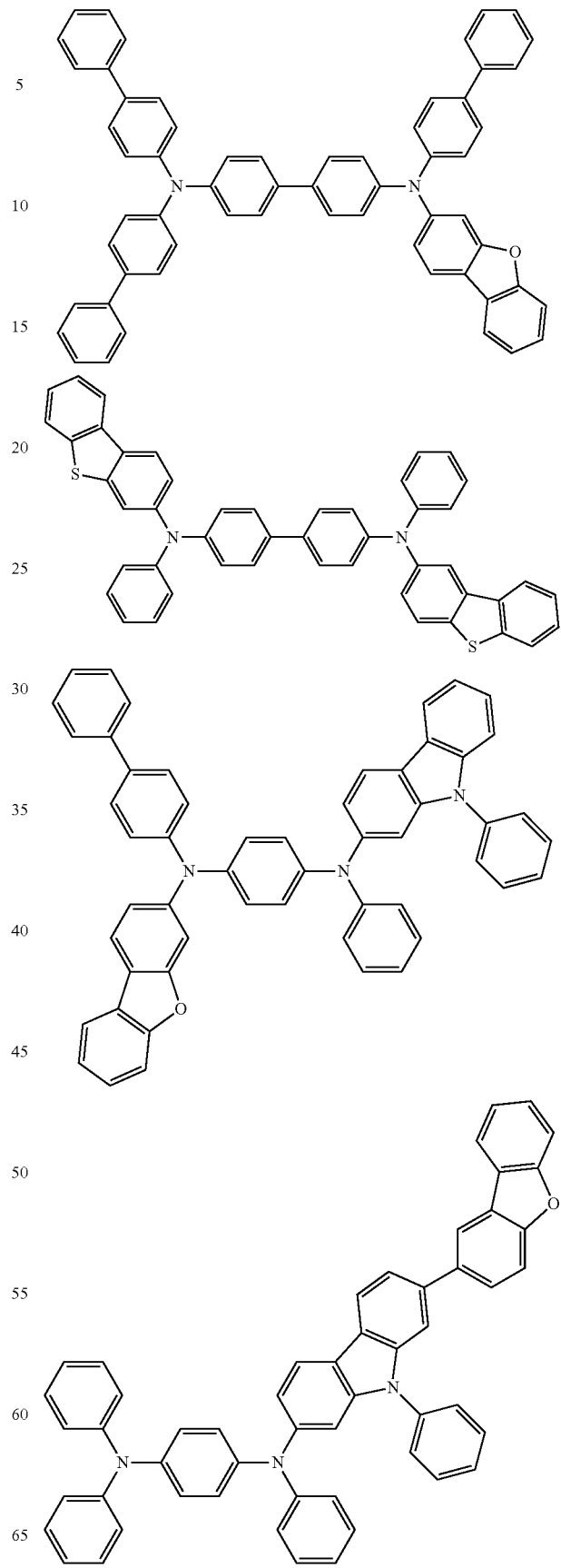

211
-continued
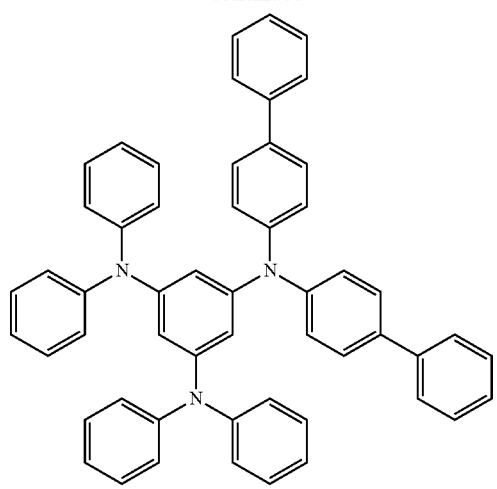
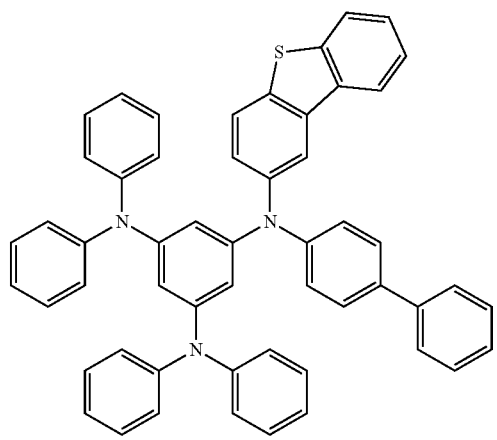
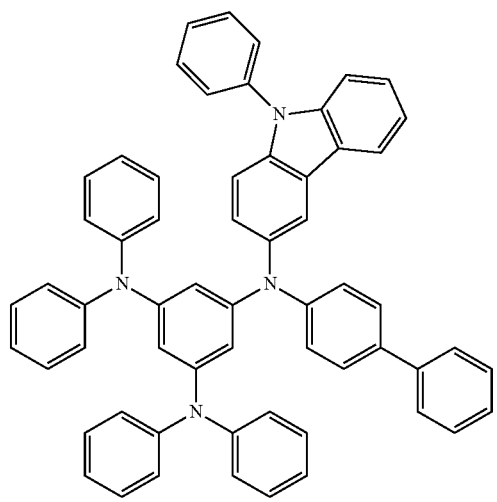
212
-continued
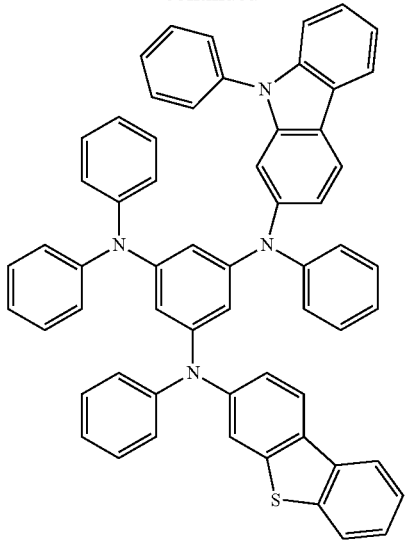
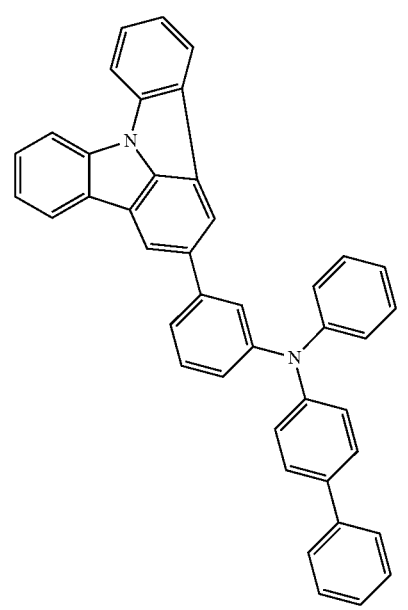
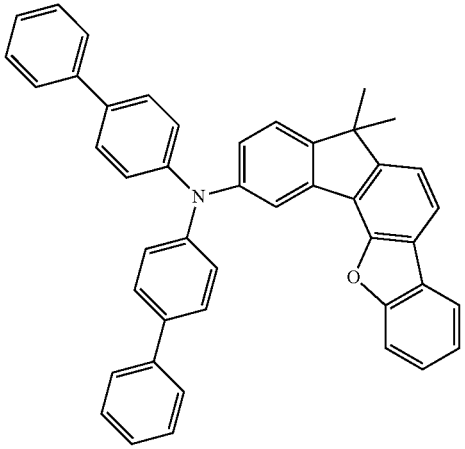

213
-continued
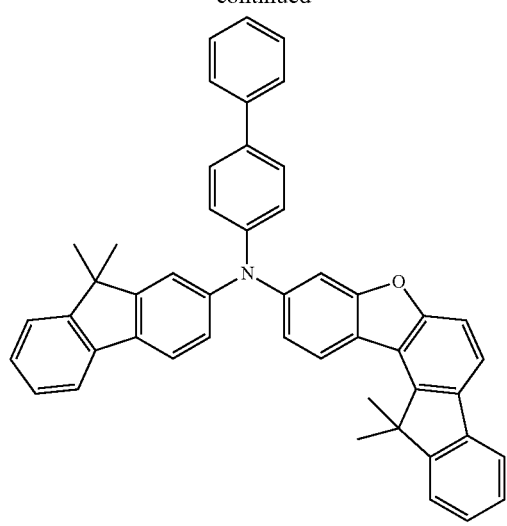
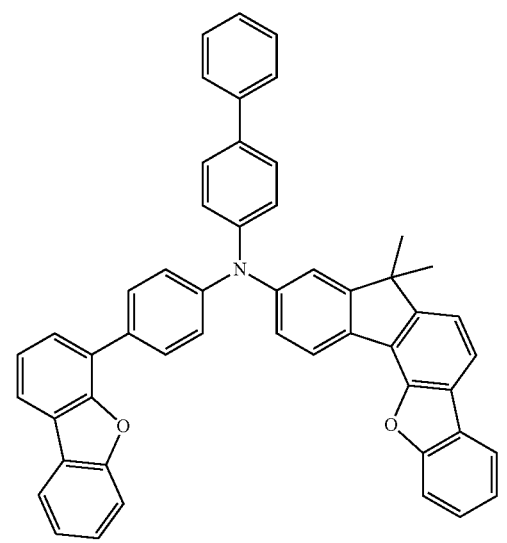
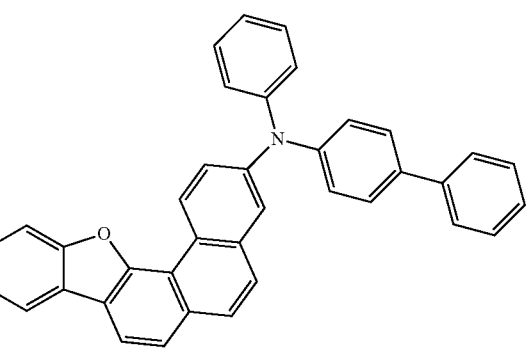
214
-continued
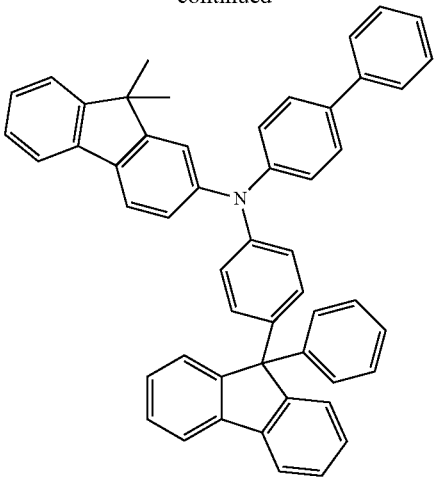
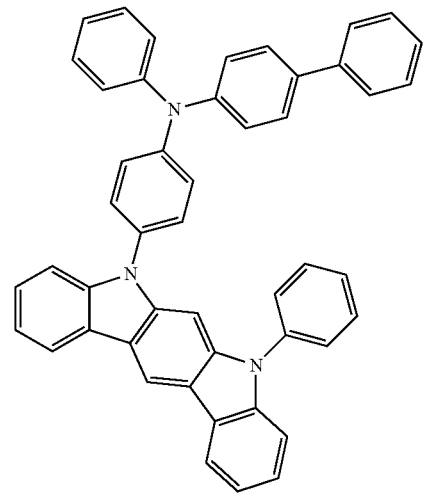
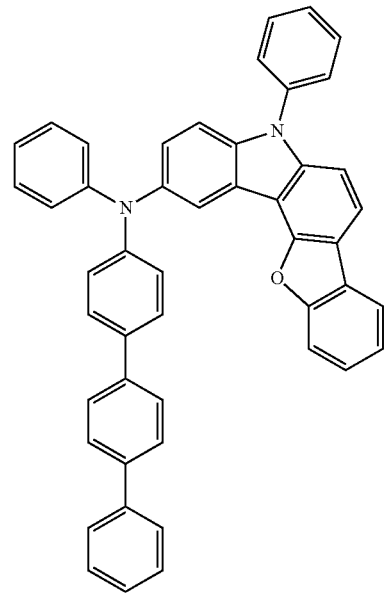

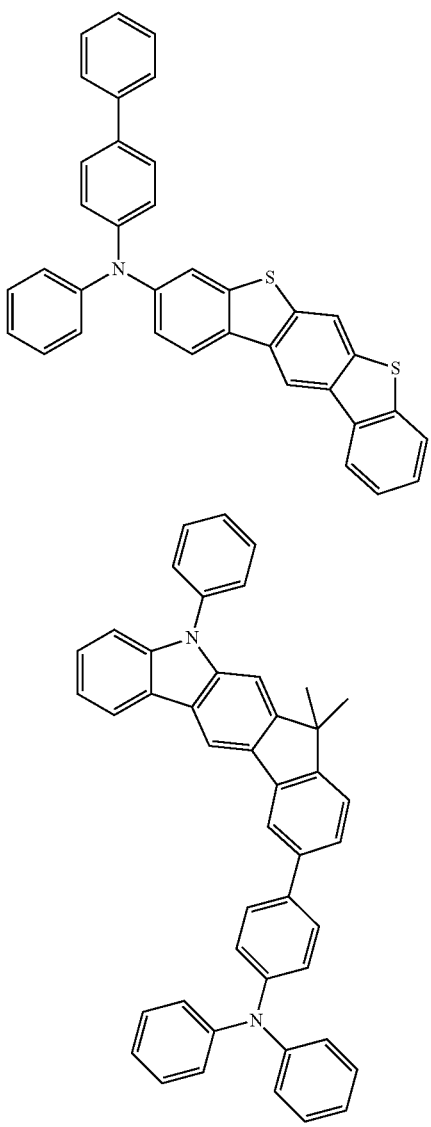

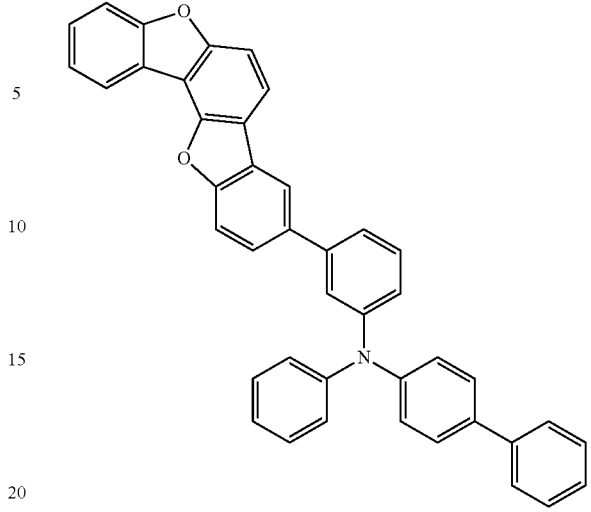

In the hole transport auxiliary layer, other suitable compounds may be used in addition to the above compounds.

In an implementation, an organic light emitting diode may further include an electron transport layer, an electron injection layer, or a hole injection layer as the organic layer 105.

The organic light emitting diodes 100 and 200 may be produced by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

Hereinafter, the embodiments are illustrated in more detail with reference to examples. However, these examples are exemplary, and the scope as claimed in claims is not limited thereto.

Hereinafter, starting materials and reactants used in examples and synthesis examples were purchased from Sigma-Aldrich Co. Ltd., TCI Inc., Tokyo chemical industry or P&H tech as far as there is no particular comment or were synthesized by suitable methods.

(Preparation of Compound for Organic Optoelectronic Device)

Compounds were synthesized through the following steps.

Synthesis Example 1: Synthesis of Intermediate M-1

[Reaction Scheme 1]

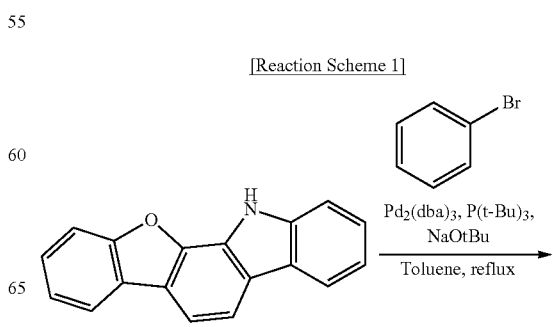

-continued

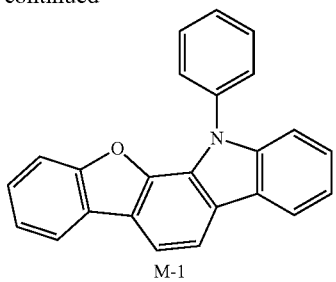

M-1

12H-benzofuro[2,3-a]carbazole (20 g, 77.73 mmol), bromobenzene (30.5 g, 194.33 mmol), NaOtBu (11.21 g, 116.6 mmol), and Pd$_2$(dba)$_3$ (3.56 g, 3.89 mmol) were added to 130 ml of toluene and suspended therein, and P(t-Bu)$_3$ (4.72 ml, 11.66 mmol) were added thereto and then, stirred under reflux for 12 hours under a nitrogen atmosphere. Subsequently, distilled water was added to the reaction solution, and a solid produced therein was filtered and separated under a reduced pressure. The solid was recrystallized with toluene to obtain Intermediate M-1 (29.8 g, Yield: 80%).

LC-MS M+H: 334.12 g/mol,

Synthesis Example 2: Synthesis of Intermediate M-2

[Reaction Scheme 2]

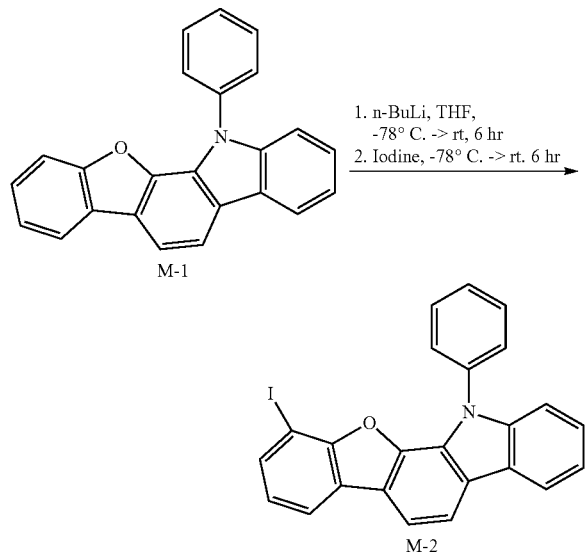

29.8 g (89.39 mmol) of Intermediate M-1 was added to 224 ml of tetrahydrofuran and dissolved therein and then, cooled down to −78° C. and stirred under a nitrogen atmosphere, while heated up to ambient temperature. Subsequently, 42.9 ml (107.26 mmol) of a 2.5 M n-BuLi solution (in n-hexane) was slowly added thereto and then, stirred at ambient temperature under a nitrogen atmosphere for 6 hours. The reaction solution was cooled down to −78° C., and a solution prepared by dissolving 26.09 g (102.80 mmol) of iodine in 199 ml of tetrahydrofuran was slowly added thereto and then, stirred under a nitrogen atmosphere for 6 hours, while heated up to ambient temperature. A solid produced therein was filtered under a reduced pressure, dissolved in 600 ml of xylene, and silica gel-filtered. After all distilling the xylene under a reduced pressure, the residue was stirred in 600 ml of n-hexane and then, filtered under a reduced pressure to separate a solid and thus obtain Intermediate M-2 (24.63 g, Yield: 60%).

LC-MS M+H: 459.02 g/mol

Synthesis Example 3: Synthesis of Intermediate M-3

[Reaction Scheme 3]

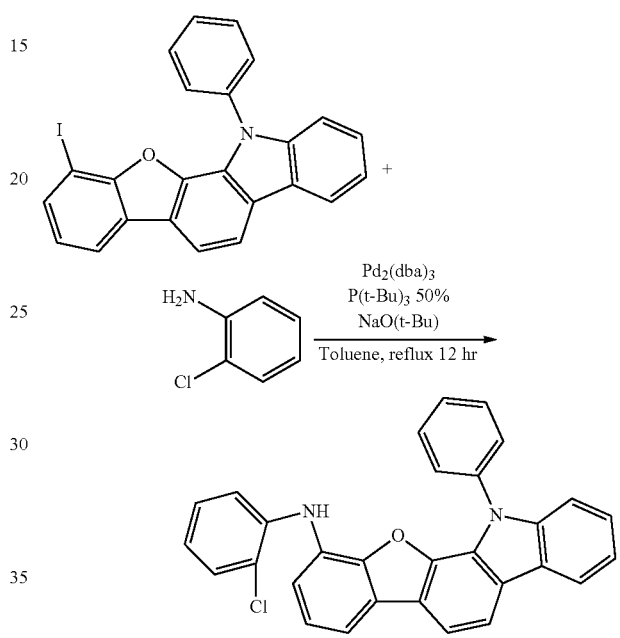

Intermediate M-2 (24.63 g, 53.63 mmol), 2-chloroaniline (8.21 g, 64.36 mmol), NaOtBu (6.18 g, 64.36 mmol), and Pd$_2$(dba)$_3$ (0.98 g, 1.07 mmol) were added to 299 ml of toluene and suspended therein, and P(t-Bu)$_3$ (3.26 g, 8.04 mmol) was added thereto and then, stirred under reflux for 12 hours under a nitrogen atmosphere. Subsequently, distilled water was added to the reaction solution, and a solid produced therein was filtered and separated under a reduced pressure. The solid was recrystallized with toluene to obtain Intermediate M-3 (21.66 g, Yield: 88%).

LC-MS M+H: 459.12 g/mol

Synthesis Example 4: Synthesis of Intermediate M-4

[Reaction Scheme 4]

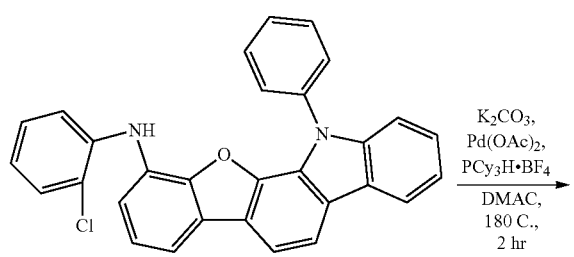

-continued

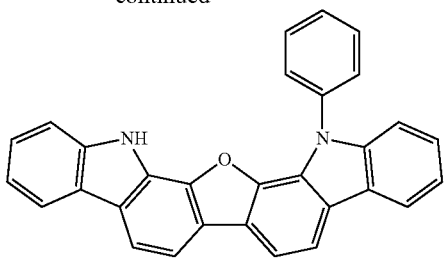

Intermediate M-3 (21.66 g, 47.20 mmol), potassium carbonate (19.57 g, 141.59 mmol), palladium(II) acetate (1.06 g, 4.72 mmol), and tricyclohexylphosphine-tetrafluoroborate (3.48 g, 9.44 mmol) were added to 251 ml of dimethylacetamide and suspended therein and then, stirred under reflux for 2 hours under a nitrogen atmosphere. Subsequently, distilled water was added to the reaction solution, and a solid produced therein was filtered and separated under a reduced pressure. The solid was dissolved in 500 ml of xylene and silica gel-filtered, and a filtrate therefrom was recrystallized to obtain Intermediate M-4 (6.58 g, Yield: 33%).

LC-MS M+H: 423.14 g/mol

Synthesis Example 5: Synthesis of Compound 1

[Reaction Scheme 5]

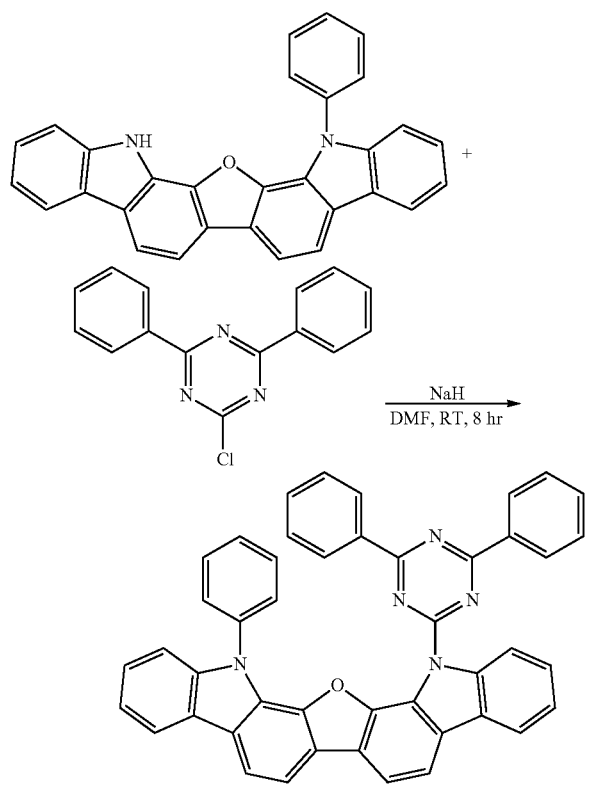

Intermediate M-4 (6.58 g, 14.95 mmol), 2-chloro-4,6-diphenyl-1,3,5-triazine (4.60 g, 17.19 mmol), and sodium hydride anhydrous (0.84 g, 20.93 mmol) were added to 60 ml of dimethylformamide and suspended therein and then, stirred under reflux for 6 hours under a nitrogen atmosphere. Subsequently, distilled water was added to the reaction solution, and a solid produced therein was filtered and separated under a reduced pressure. The solid was dissolved in 500 ml of toluene and silica gel-filtered, and a solid obtained by recrystallizing a filtrate therefrom was purified by sublimation to obtain Compound 1 (4.69 g, Yield: 48%).

LC-MS M+H: 654.22 g/mol

Synthesis Example 6: Synthesis of Compound 2

[Reaction Scheme 6]

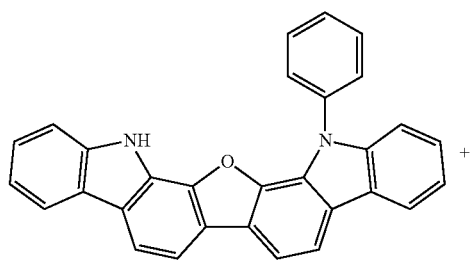

Intermediate M-4 (6.58 g, 14.95 mmol), 2-chloro-4-(biphenyl-4-yl)-6-phenyl-1,3,5-triazine (5.65 g, 16.45 mmol), and sodium hydride anhydrous (0.84 g, 20.93 mmol) were added to 117 ml of dimethylformamide and suspended therein and then, stirred under reflux for 6 hours under a nitrogen atmosphere. Subsequently, distilled water was added to the reaction solution, and a solid produced therein was filtered and separated under a reduced pressure. The solid was dissolved in 500 ml of xylene and silica gel-filtered, and then, a solid obtained by recrystallizing a filtrate therefrom was purified by sublimation to obtain Compound 2 (5.46 g, Yield: 50%).

LC-MS M+H: 730.25 g/mol

Synthesis Example 7: Synthesis of Intermediate M-5

[Reaction Scheme 7]

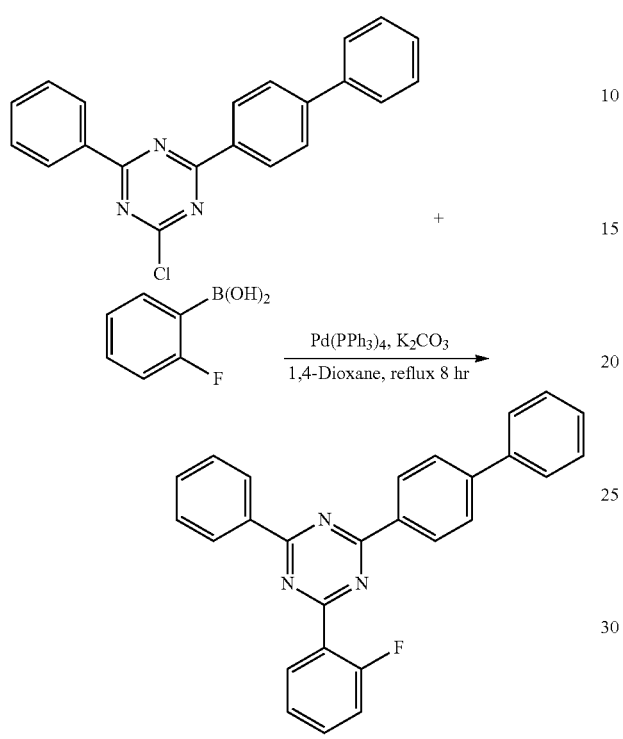

2-chloro-4-(biphenyl-4-yl)-6-phenyl-1,3,5-triazine (6.4 g, 18.62 mmol), 2-fluorophenylboronic acid (2.87 g, 20.48 mmol), potassium carbonate (6.43 g, 46.54 mmol), and tetrakis(triphenylphosphine) palladium (0) (1.08 g, 0.93 mmol) were added to 20 ml of distilled water and 60 ml of 1,4-dioxane and suspended therein and then, stirred under reflux for 8 hours under a nitrogen atmosphere. Subsequently, distilled water was added to the reaction solution, and a solid produced therein was filtered and separated under a reduced pressure. The solid was dissolved in 100 ml of toluene and silica gel-filtered, and a filtrate therefrom was all distilled under a reduced pressure. Herein, the obtained solid was stirred in 100 ml of n-hexane for 1 hour and filtered under a reduced pressure to obtain Intermediate M-5 (6.01 g, Yield: 80%).

LC-MS M+H: 404.15 g/mol

Synthesis Example 8: Synthesis of Compound 81

[Reaction Scheme 8]

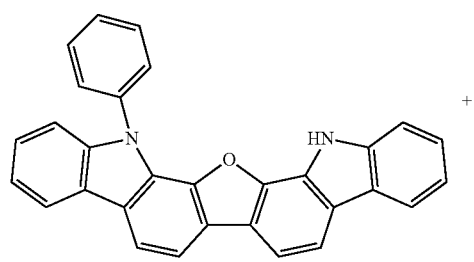

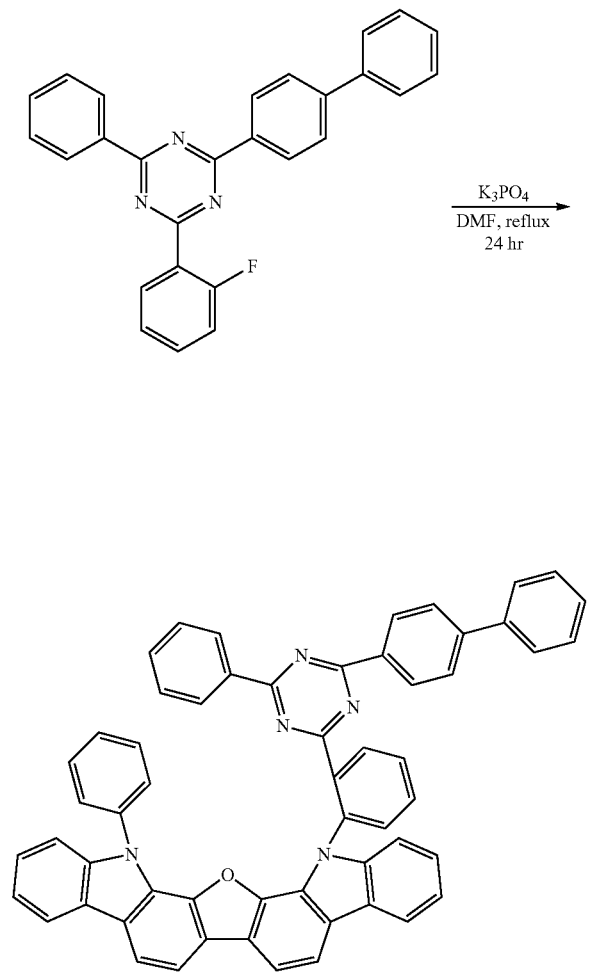

Intermediate M-4 (5.2 g, 12.3 mmol), Intermediate M-5 (5.96 g, 14.77 mmol), and tripotassium phosphate (3.92 g, 18.46 mmol) were suspended in 246 ml of dimethylformamide and then, stirred under reflux for 24 hours under a nitrogen atmosphere. Subsequently, distilled water was added to the reaction solution, and a solid produced therein was filtered and separated under a reduced pressure. The solid was dissolved in 100 ml of toluene and then, silica gel-filtered under a reduced pressure, and a filtrate therefrom was recrystallized by using methanol and then, filtered under a reduced pressure to obtain a solid. Herein, the obtained solid was stirred in 100 ml of acetone for 5 hours and filtered under a reduced pressure, which was equally twice performed, followed by sublimation purification. Through the aforementioned process, Compound 81 (4.46 g, Yield: 45%) was obtained.

LC-MS M+H: 806.28 g/mol

Synthesis Example 9: Synthesis of Compound A-139

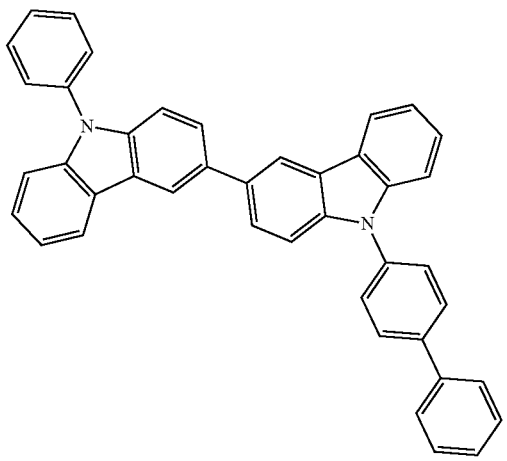 [SMILES: c1ccc(-c2ccc(-n3c4ccccc4c4cc(-c5ccc6c(c5)c5ccccc5n6-c5ccccc5)ccc43)cc2)cc1]

Compound A-139 was synthesized as described in KR10-2019-0007968A.

Comparative Synthesis Example 1: Synthesis of Intermediate M-6

[Reaction Scheme 9]

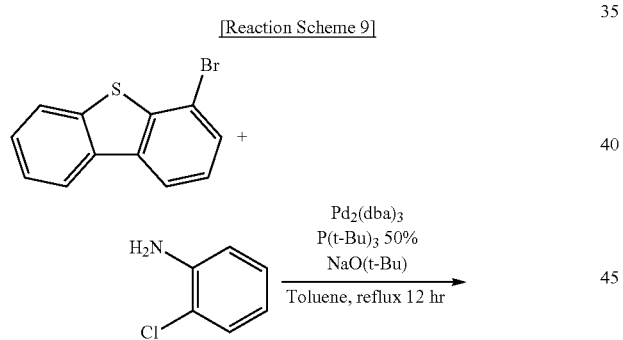

4-bromodibenzothiophene (20 g, 76 mmol), 2-chloroaniline (22.3 g, 174.81 mmol), sodium tert-butoxide (16.8 g, 174.81 mmol), and $Pd_2(dba)_3$ (3.48 g, 3.80 mmol) were added to 253 ml of toluene and suspended therein, and $P(t-Bu)_3$ (9.23 g, 22.8 mmol) was added thereto and then, stirred under reflux for 12 hours under a nitrogen atmosphere. Subsequently, distilled water was added to the reaction solution, and a solid produced therein was filtered and separated under a reduced pressure. Then, the solid was recrystallized in toluene to obtain Intermediate M-6 (18.84 g, Yield: 80%).

LC-MS M+H: 310.04 g/mol

Comparative Synthesis Example 2: Synthesis of Intermediate M-7

[Reaction Scheme 10]

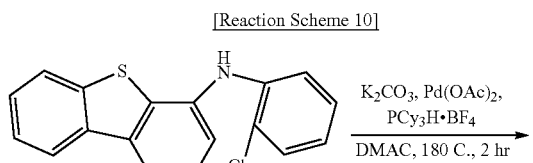

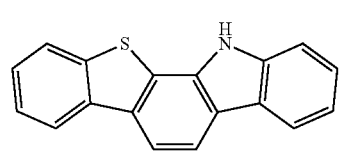

Intermediate M-6 (18.83 g, 60.78 mmol), potassium carbonate (25.20 g, 182.34 mmol), palladium(II) acetate (1.36 g, 6.08 mmol), and tricyclohexylphosphine-tetrafluoroborate (4.48 g, 12.16 mmol) were added to 276 ml of dimethylacetamide and suspended therein and then, stirred under reflux for 2 hours under a nitrogen atmosphere. Subsequently, distilled water was added to the reaction solution, and a solid produced therein was filtered and separated under a reduced pressure. Then, the solid was dissolved in 500 ml of xylene and silica gel-filtered, and a filtrate therefrom was recrystallized to obtain Intermediate M-7 (5.73 g, Yield: 34.5%).

LC-MS M+H: 274.06 g/mol

Comparative Synthesis Example 3: Synthesis of Compound P1

[Reaction Scheme 11]

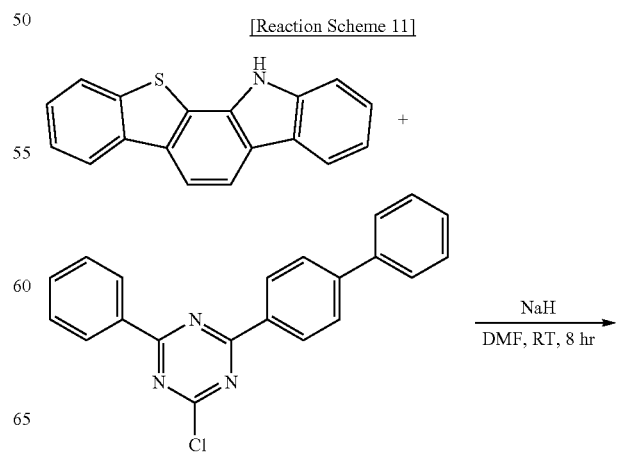

-continued

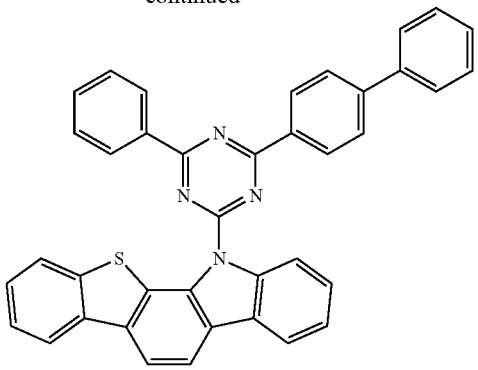

Intermediate M-7 (5.73 g, 20.12 mmol), 2-chloro-4-(biphenyl-4-yl)-6-phenyl-1,3,5-triazine (7.61 g, 22.14 mmol), and sodium hydride anhydrous (1.13 g, 28.17 mmol) were put in 159 ml of dimethylformamide and suspended therein and then, stirred under a nitrogen atmosphere for 8 hours at ambient temperature. Subsequently, distilled water was added to the reaction solution, and a solid produced therein was filtered and separated under a reduced pressure. Then, the solid was dissolved in 500 ml of xylene and silica gel-filtered, and then, a solid obtained by recrystallizing a filtrate therefrom was purified by sublimation to obtain Compound P1 (5.99 g, Yield: 51.3%).

LC-MS M+H: 581.17 g/mol (Manufacture of Organic Light Emitting Diode)

Example 1

A glass substrate coated with ITO (indium tin oxide) as a 1,500 Å-thick thin film was washed with distilled water. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 700 Å thick to form a hole transport layer. On the hole transport layer, a 400 Å-thick light emitting layer was formed by vacuum-depositing Compound 1 of Synthesis Example 5 as a host and doping 2 wt % of [Ir(piq)$_2$acac] as a dopant. Subsequently, on the light emitting layer, a 300 Å-thick electron transport layer was formed by simultaneously vacuum-depositing Compound D and Liq in a weight ratio of 1:1, and on the electron transport layer, Liq and Al were sequentially vacuum-deposited to be 15 Å thick and 1,200 Å thick, manufacturing an organic light emitting diode.

The organic light emitting diode included a five-layered organic thin layer, and specifically the following structure.

ITO/Compound A (700 Å)/Compound B (50 Å)/Compound C (1,020 Å)/EML[Compound 1: [Ir(piq)$_2$acac]=98 wt %:2 wt %] (400 Å)/Compound D:Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Examples 2 to 6 and Comparative Examples 1 and 2

Devices of Examples 2 to 6 and Comparative Examples 1 and 2 were manufactured in the same manner as in Example 1, except that the host and its weight ratio were changed as described in Tables 1 to 4.

Evaluation

Driving voltage, luminous efficiency, and life-span characteristics of the organic light emitting diodes according to Examples 1 to 6 and Comparative Examples 1 and 2 were evaluated. Specific measurement methods are as follows, and the results are shown in Tables 1 to 4.

(1) Measurement of Current Density Change Depending on Voltage Change

The obtained organic light emitting diodes were measured regarding a current value flowing in the unit diode, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

The luminous efficiency (cd/A) of the same current density (10 mA/cm$^2$) was calculated using the luminance, current density, and voltage measured from the (1) and (2).

(4) Measurement of Life-Span

T95 life-spans of the organic light emitting diodes according to Examples 1 to 6 and Comparative Examples 1 and 2 were measured as a time when their luminance decreased down to 95% relative to the initial luminance (cd/m$^2$) after emitting light with 6,000 cd/m$^2$ as the initial luminance (cd/m$^2$) and measuring their luminance decreases depending on a time with a Polanonix life-span measurement system.

(5) Measurement of Driving Voltage

The driving voltage of each diode at 15 mA/cm$^2$ using a current-voltmeter (Keithley 2400) was measured to obtain the results.

(6) Calculation of T95 Life-Span Ratio (%)

Relative values were calculated relative to the T95 life-span of Comparative Example 1 or Comparative Example 2.

(7) Calculation of Luminous Efficiency Ratio (%)

Relative values were calculated relative to the luminous efficiency of Comparative Example 1 or Comparative Example 2.

(8) Calculation of Driving Voltage Ratio (%)

Relative values were calculated relative to the driving voltage of Comparative Example 1 or Comparative Example 2.

TABLE 1

| | Host alone | Luminous efficiency ratio (%) | Driving voltage ratio (%) |
|---|---|---|---|
| Example 1 | Compound 1 | 101% | 87% |
| Example 2 | Compound 2 | 105% | 88% |

TABLE 1-continued

|  | Host alone | Luminous efficiency ratio (%) | Driving voltage ratio (%) |
|---|---|---|---|
| Example 3 | Compound 81 | 102% | 89% |
| Comparative Example 1 | Compound P1 | 100% | 100% |

TABLE 2

|  | Host alone | T95 life-span ratio (%) |
|---|---|---|
| Example 2 | Compound 2 | 120% |
| Comparative Example 1 | Compound P1 | 100% |

TABLE 3

|  | Host | | | Luminous efficiency ratio (%) | Driving voltage ratio (%) |
|---|---|---|---|---|---|
|  | First host | Second host | First, second host weight ratio | | |
| Example 4 | Compound 1 | Compound A-139 | 30:70 | 101% | 90% |
| Example 5 | Compound 2 | Compound A-139 | 30:70 | 107% | 91% |
| Example 6 | Compound 81 | Compound A-139 | 30:70 | 106% | 92% |
| Comparative Example 2 | Compound P1 | Compound A-139 | 30:70 | 100% | 100% |

TABLE 4

|  | Host | | | T95 life-span ratio (%) |
|---|---|---|---|---|
|  | First host | Second host | First, second host weight ratio | |
| Example 4 | Compound 1 | Compound A-139 | 30:70 | 117% |
| Example 5 | Compound 2 | Compound A-139 | 30:70 | 173% |
| Comparative Example 2 | Compound P1 | Compound A-139 | 30:70 | 100% |

Referring to Tables 1 to 4, the compounds according to the Examples exhibited improved life-span, luminous efficiency, and driving compared to the Comparative Examples.

One or more embodiments may provide a compound for an organic optoelectronic device capable of implementing an organic optoelectronic device having high efficiency and a long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound being represented by Chemical Formula 1:

[Chemical Formula 1]

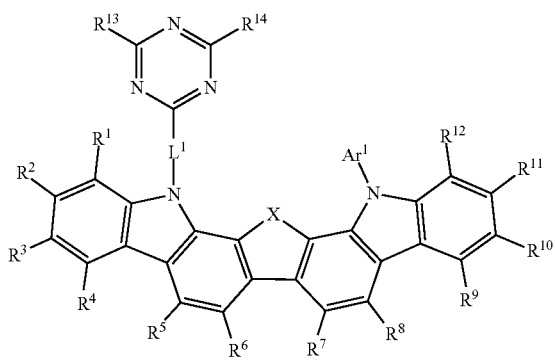

wherein, in Chemical Formula 1,

X is O or S, $L^1$ is a single bond or a substituted or unsubstituted C6 to C20 arylene group, $R^1$ to $R^{12}$ are each independently hydrogen, deuterium, a substituted or unsubstituted C1 to C30 alkyl group, or a substituted or unsubstituted C6 to C20 aryl group, R[13] and R[14] are each independently a substituted or unsubstituted C6 to C30 aryl group, a substituted or unsubstituted dibenzofuranyl group, or a substituted or unsubstituted dibenzothiophenyl group, Ar[1] is a substituted or unsubstituted C6 to C30 aryl group, and 'substituted' refers to replacement of a hydrogen of a substituent or a compound by deuterium, a C1 to C5 alkyl group, or a C6 to C18 aryl group.

2. The compound as claimed in claim 1, wherein L[1] is a single bond or a substituted or unsubstituted phenylene group, provided that the substituted phenylene group is substituted with deuterium, a C1 to C5 alkyl group, or a C6 to C18 aryl group.

3. The compound as claimed in claim 1, wherein R[13] and R[14] are each independently a substituted or unsubstituted phenyl group or a substituted or unsubstituted biphenyl group.

4. The compound as claimed in claim 1, wherein R[13] and R[14] are each independently a substituent of Group I:

[Group I]

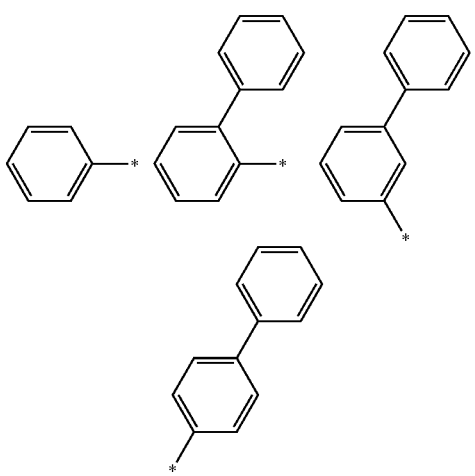

wherein, in Group I, * is a linking point.

5. The compound as claimed in claim 1, wherein Ar[1] is a substituted or unsubstituted phenyl group, a substituted or unsubstituted biphenyl group, or a substituted or unsubstituted naphthyl group.

6. The compound as claimed in claim 1, wherein the compound is a compound of Group 1:

[Group 1]

[1]
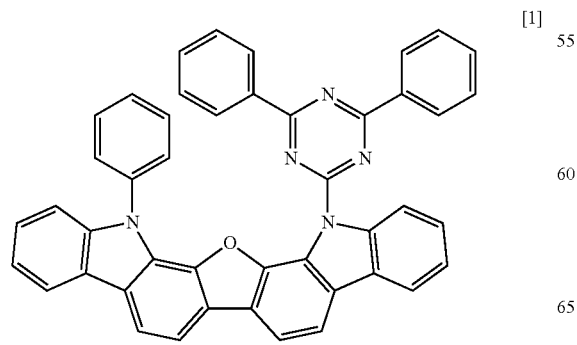

[2]
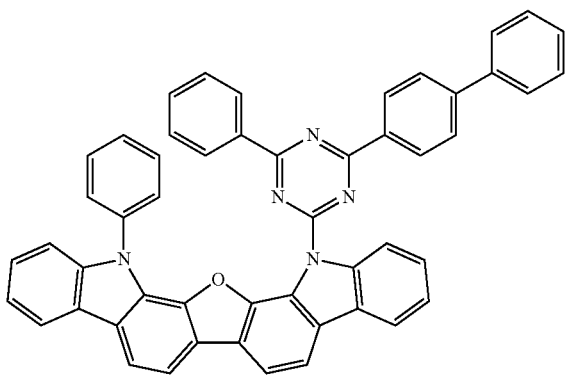

[3]
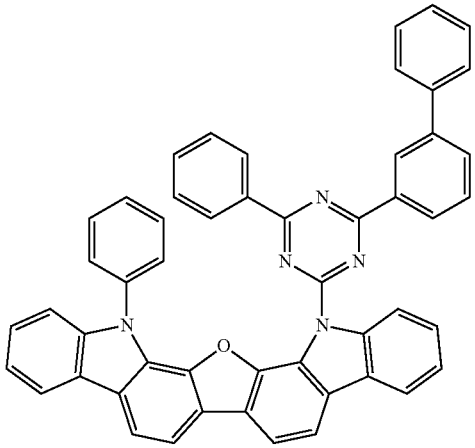

[4]
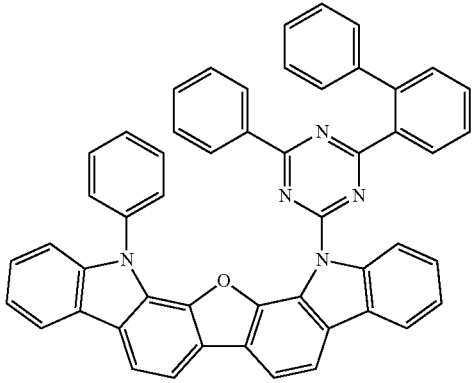

[5]
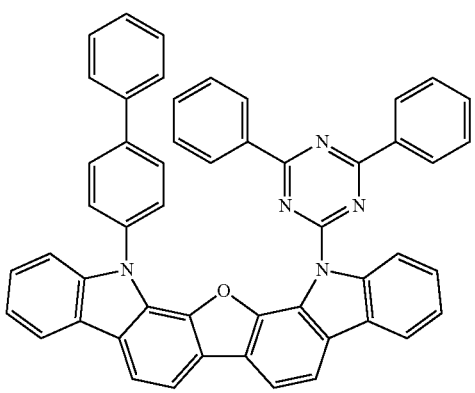

[6]
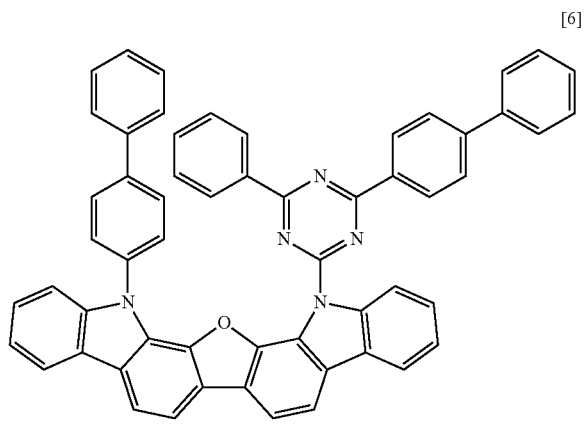
[7]
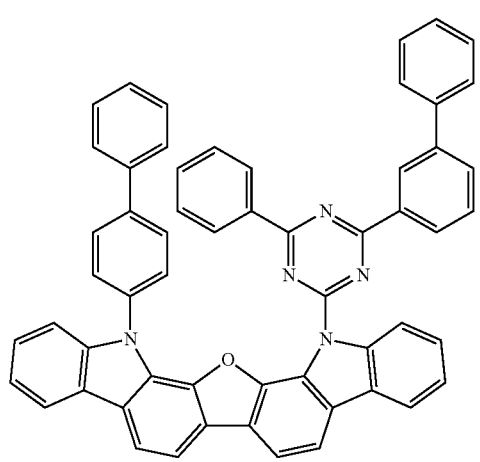
[8]
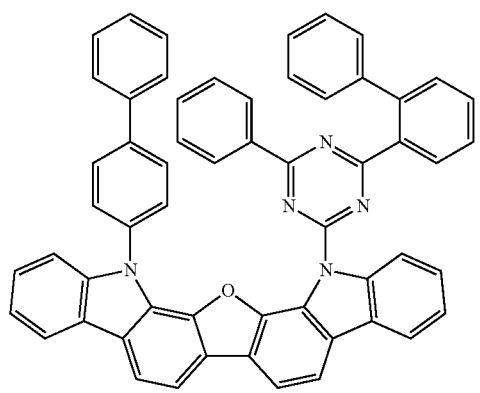
[9]
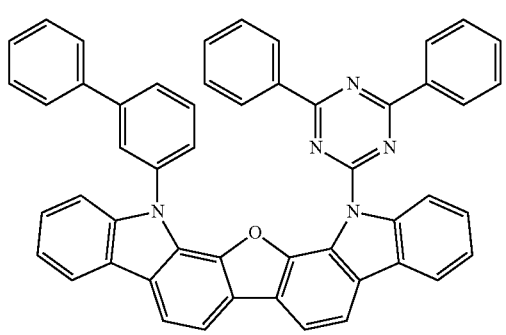
[10]
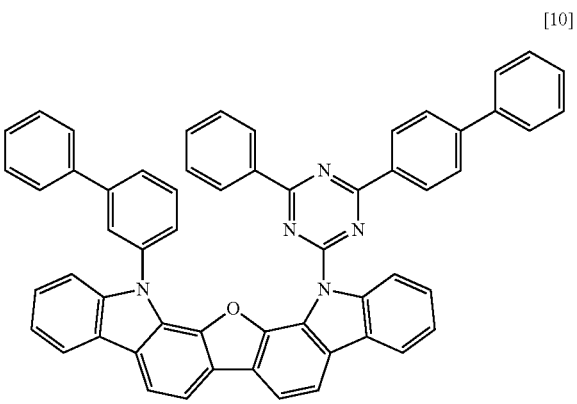
[11]
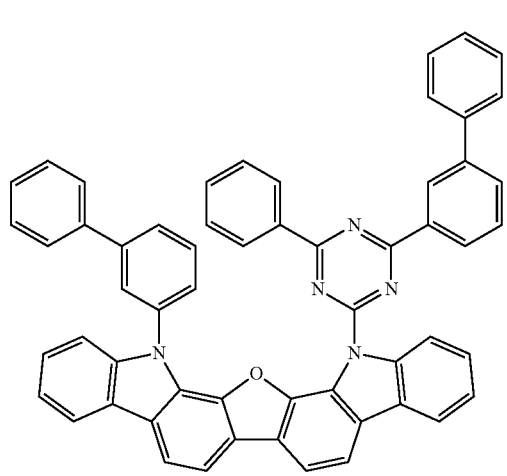
[12]
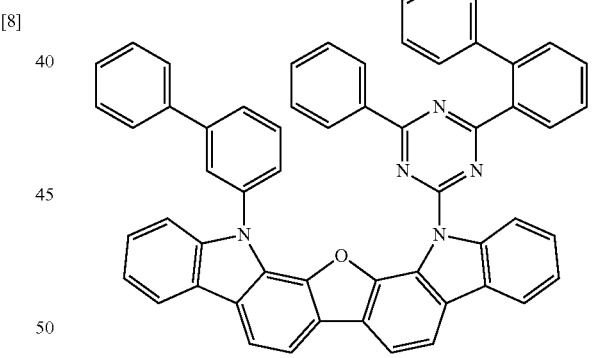
[13]
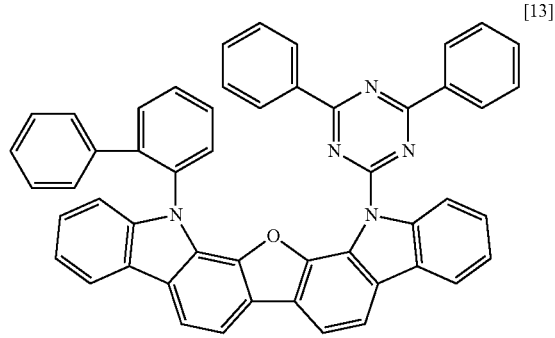

233
-continued
[14]
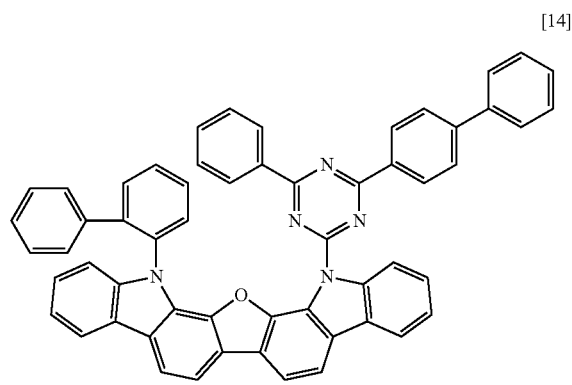
[15]
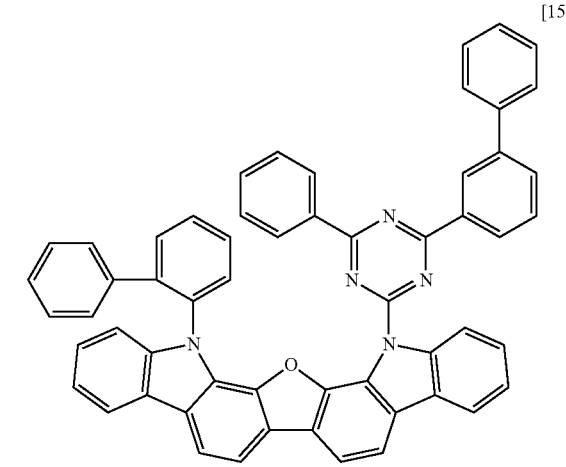
[16]
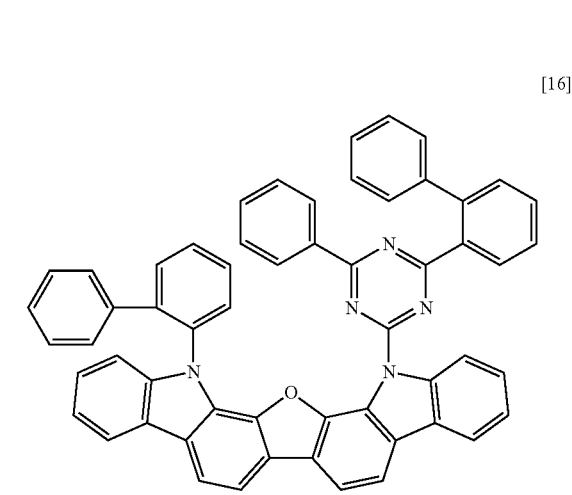
[17]
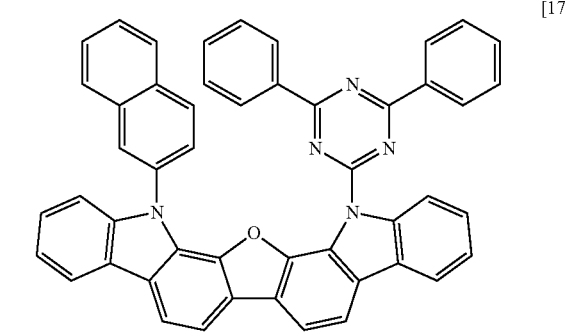
234
-continued
[18]
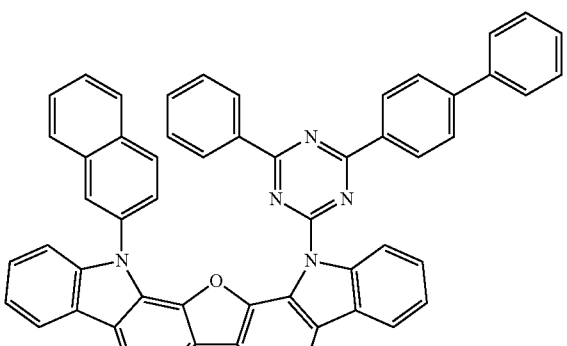
[19]
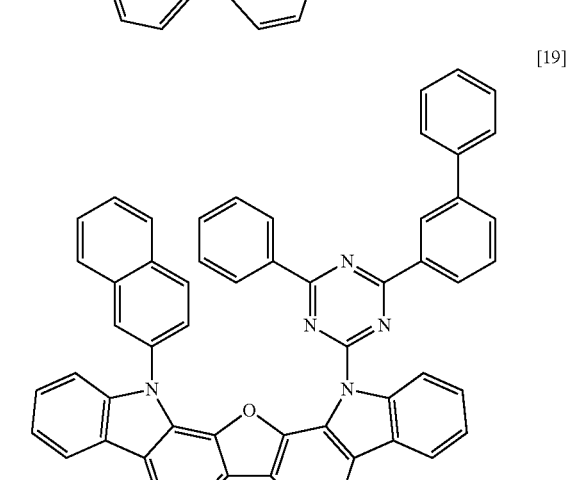
[20]
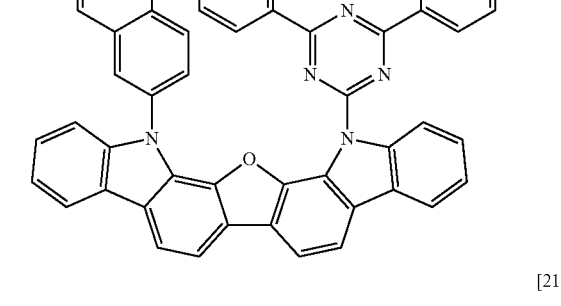
[21]
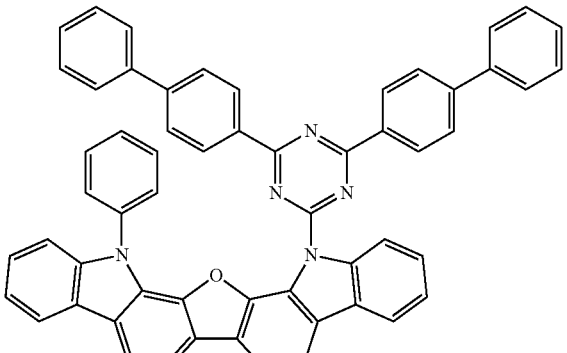

-continued
[22]
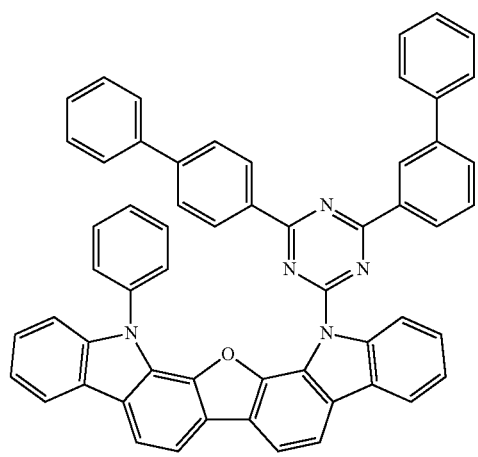
[23]
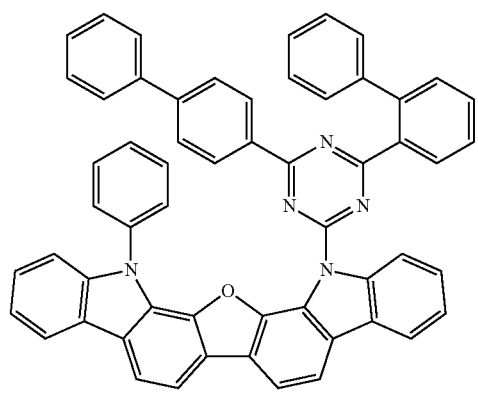
[24]
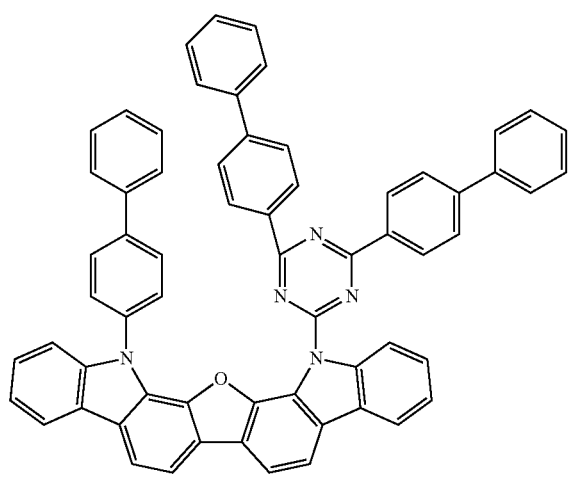
-continued
[25]
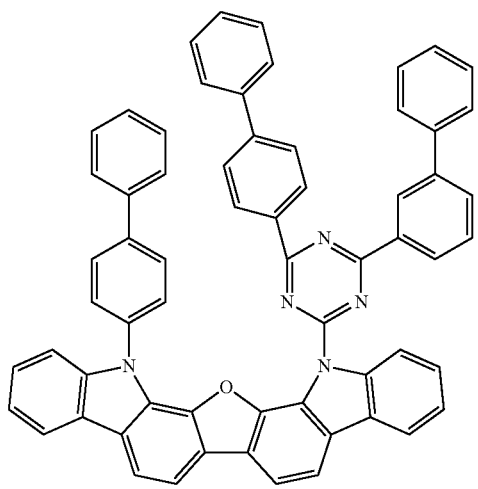
[26]
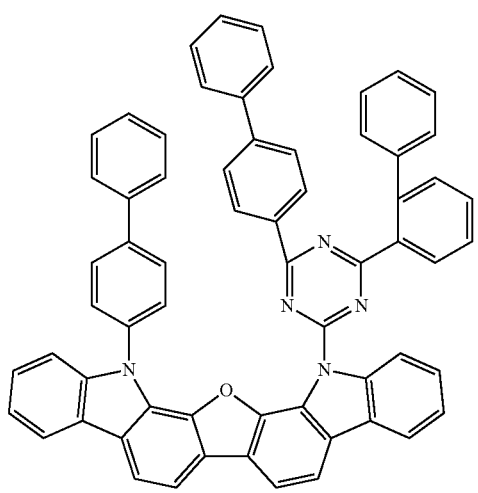
[27]
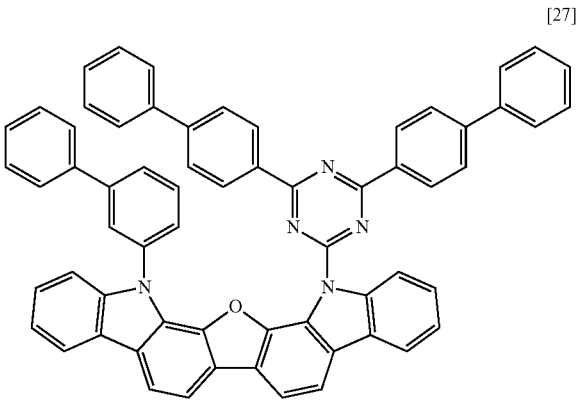

[28]
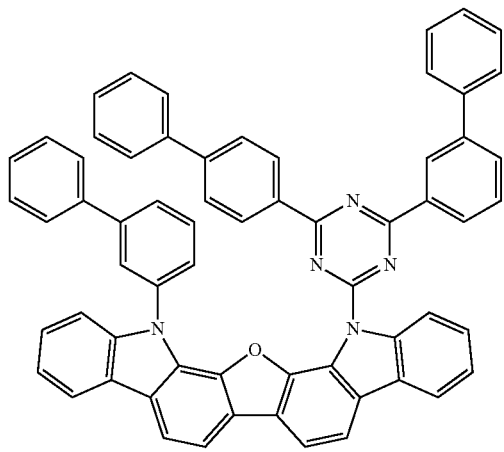
[29]
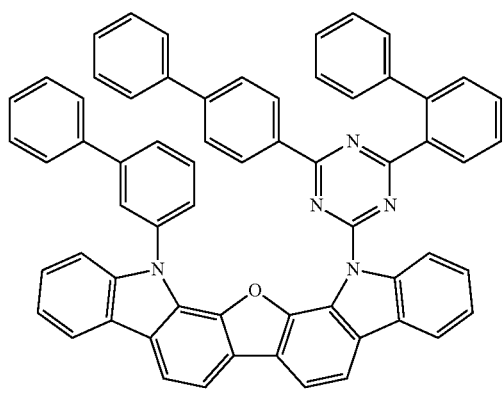
[30]
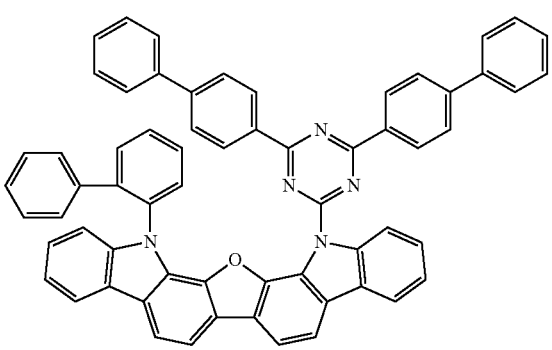
[31]
[32]
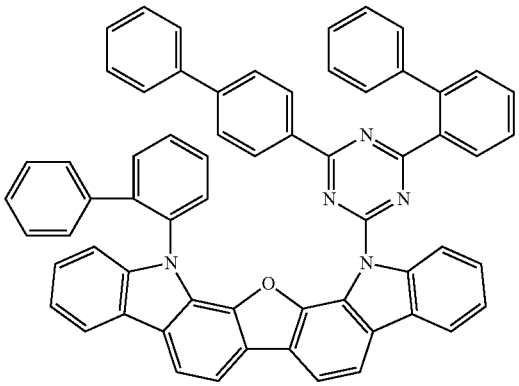
[33]
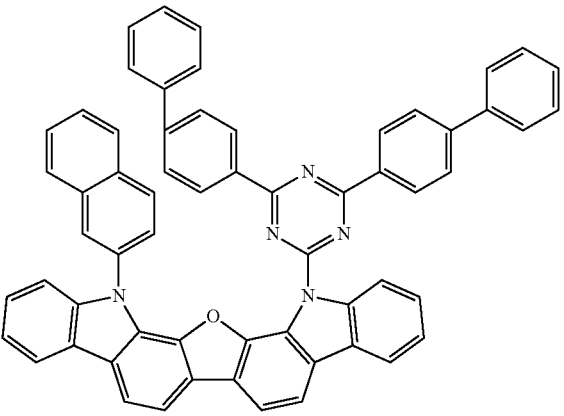
[34]
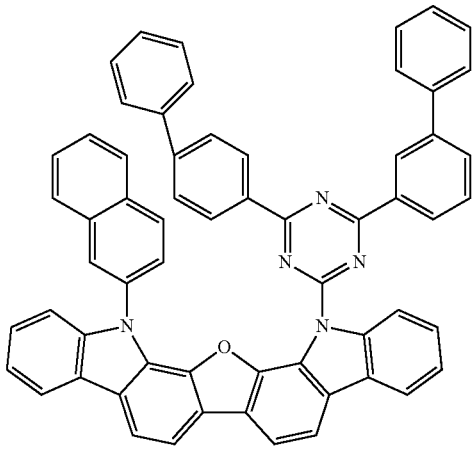

| | |
|---|---|
| [35] 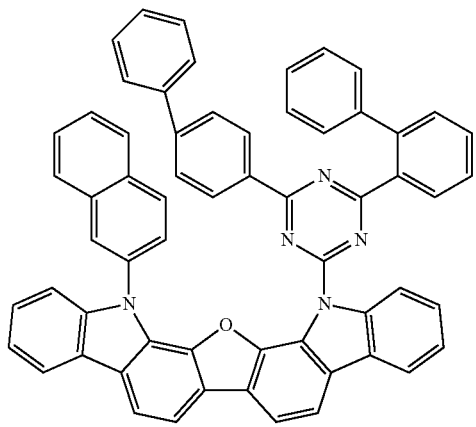 | [38] 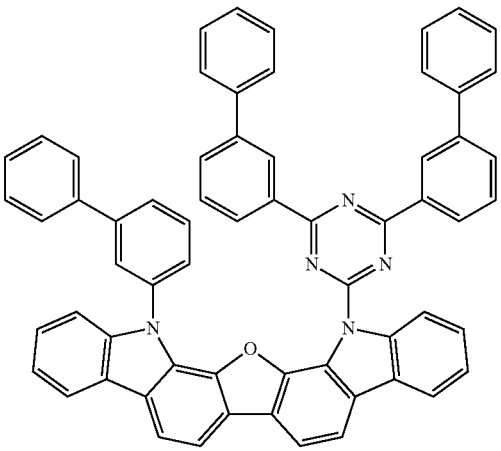 |
| [36] 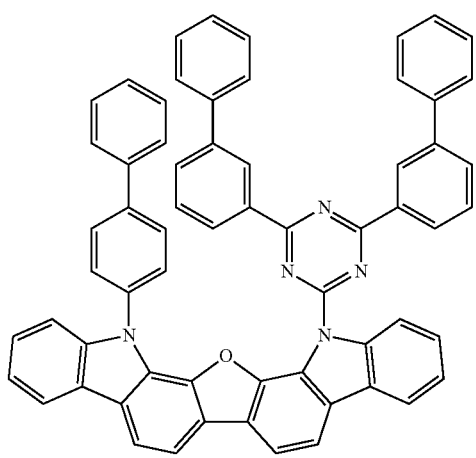 | [39] 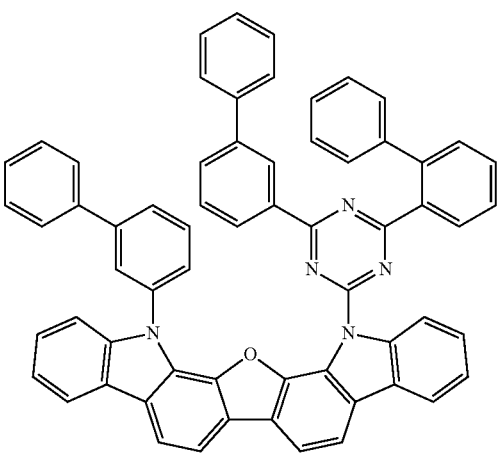 |
| [37] 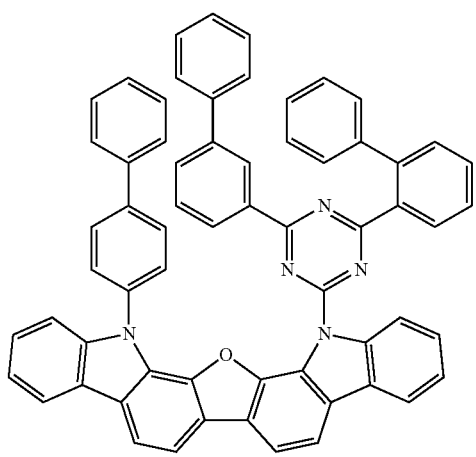 | [40] 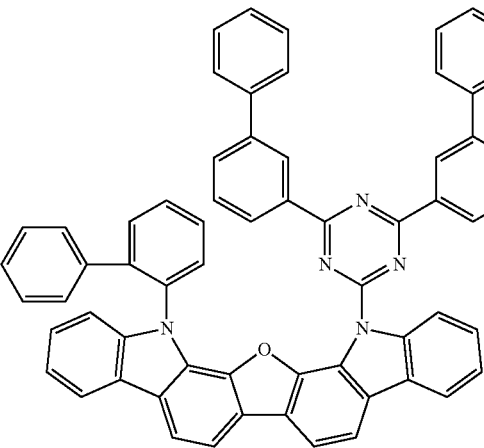 |

[41]
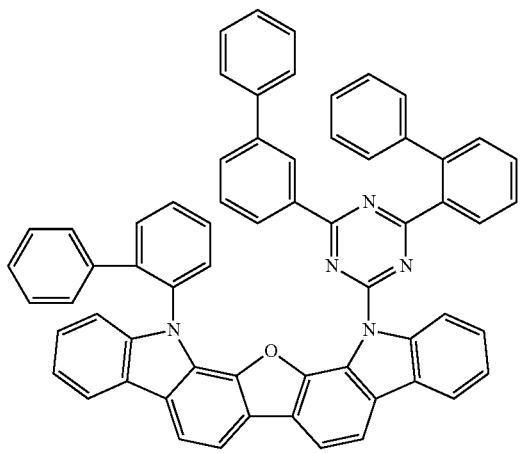
[42]
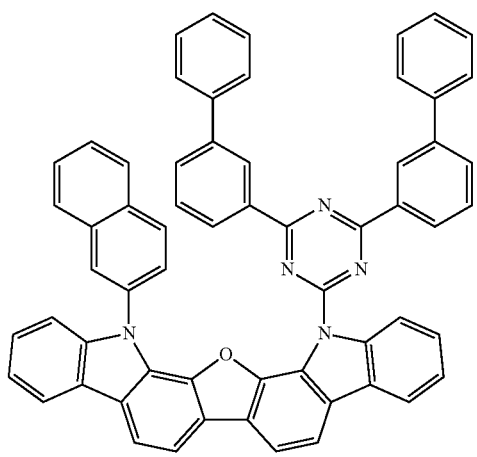
[43]
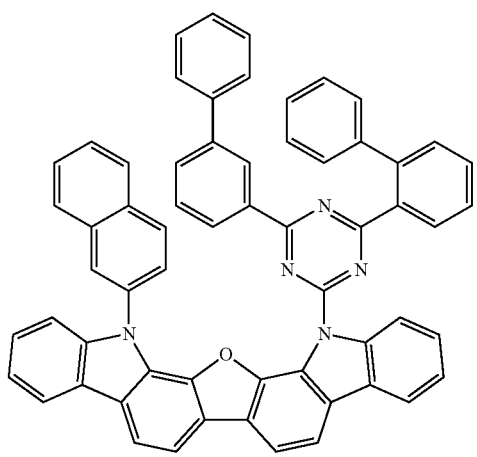
[44]
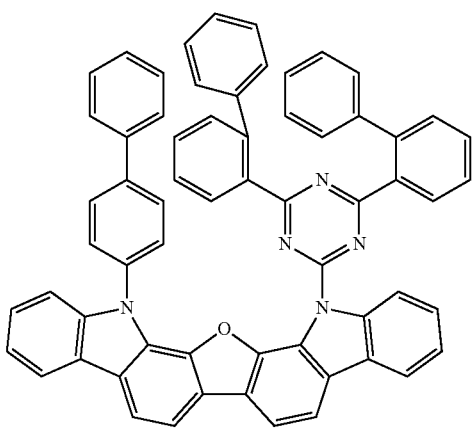
[45]
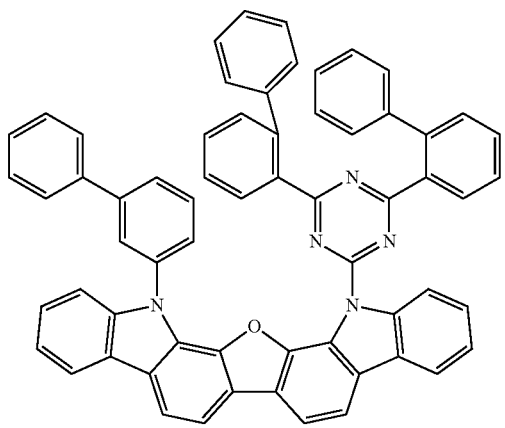
[46]
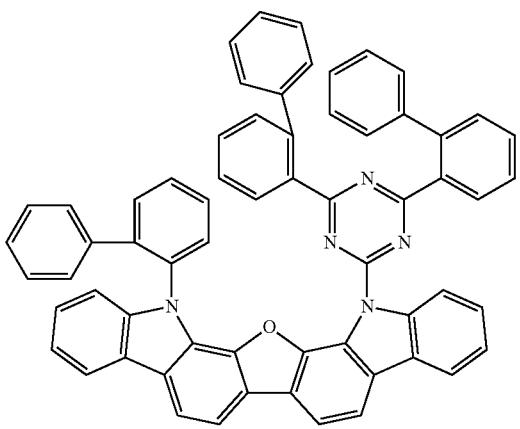

243
-continued
[47]
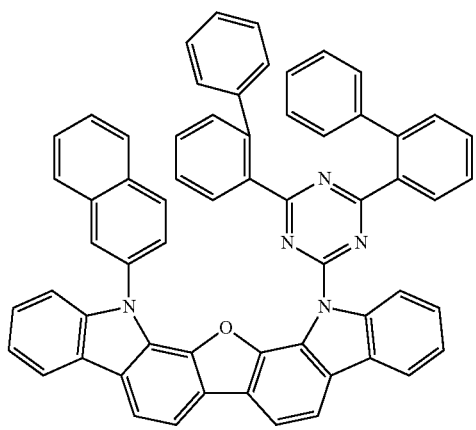
[48]
244
-continued
[50]
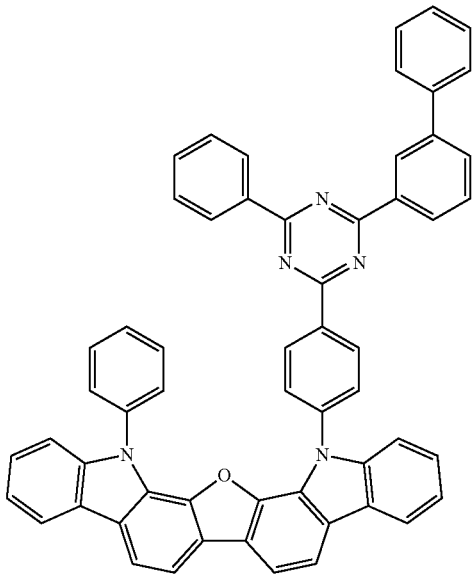
[51]
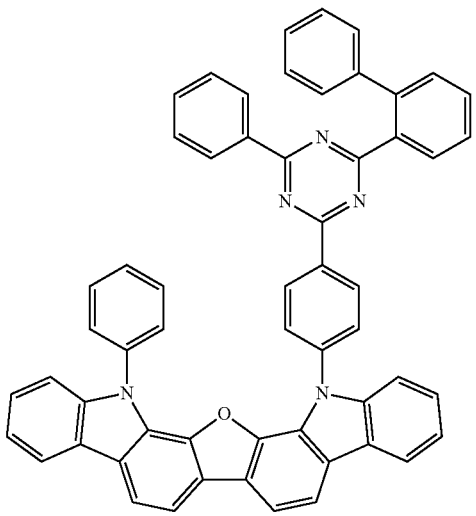
[49]
[52]
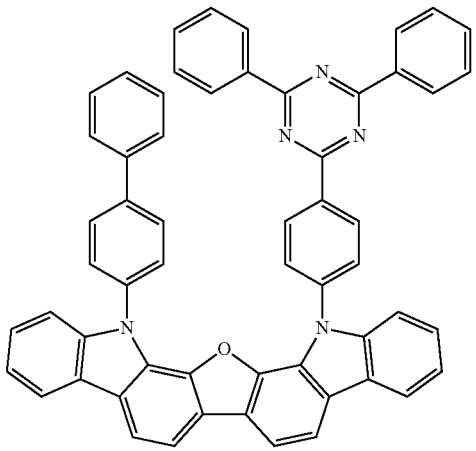

-continued
[53]
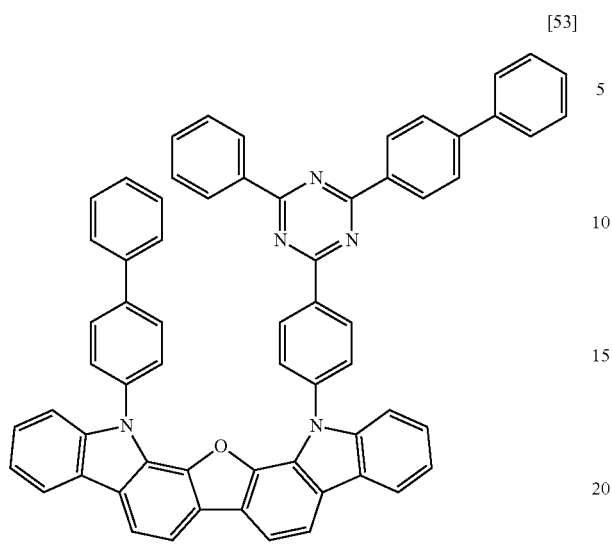
[54]
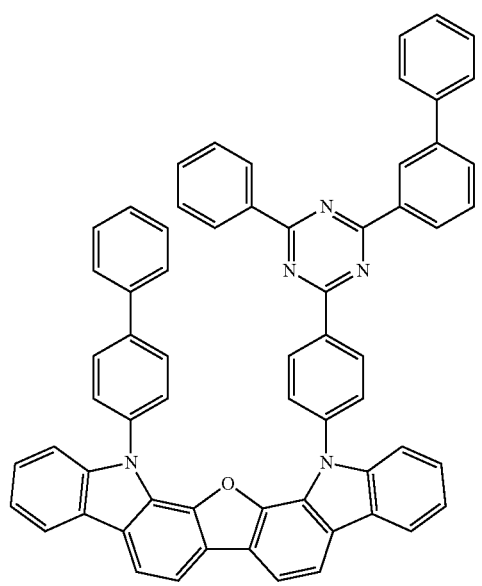
[55]
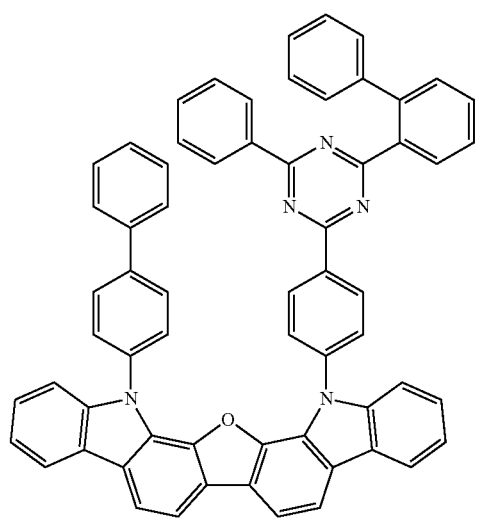
-continued
[56]
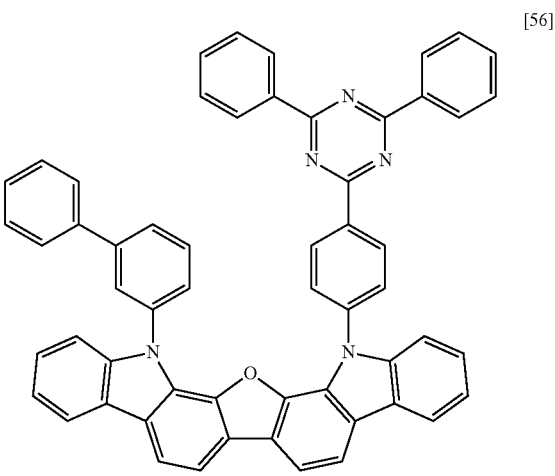
[57]
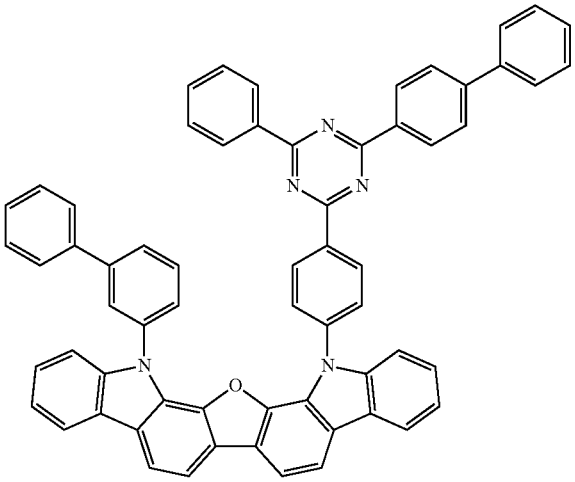
[58]
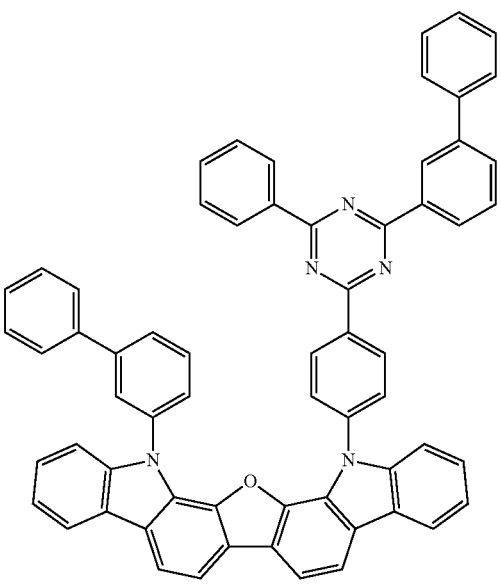

[59]
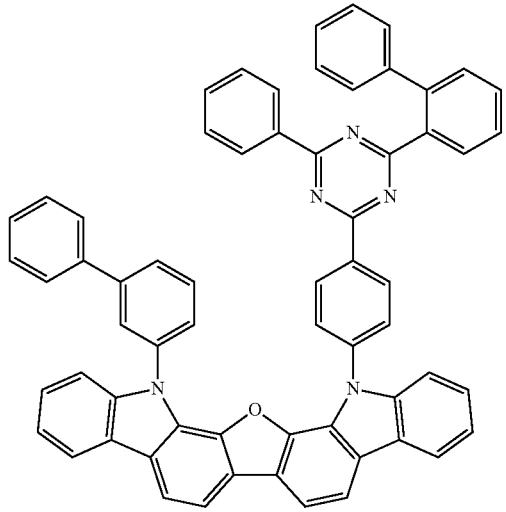
[60]
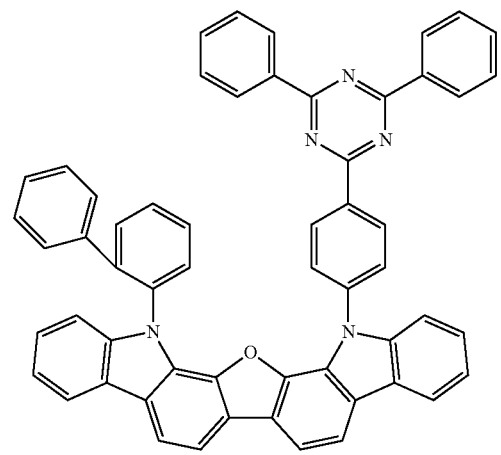
[61]
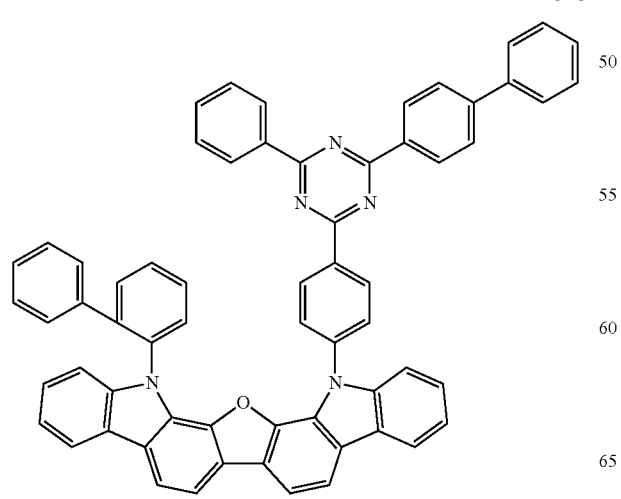
[62]
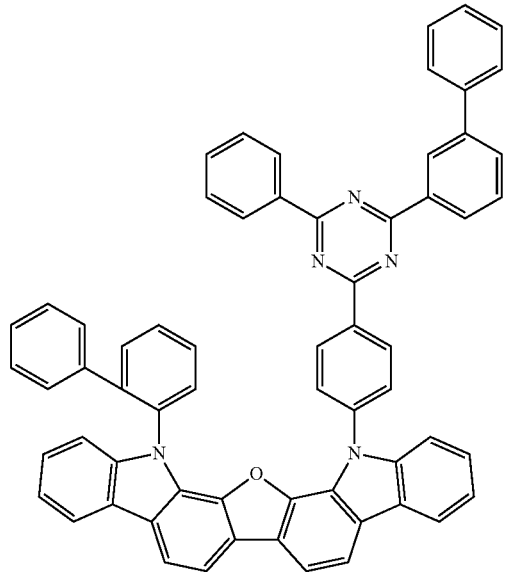
[63]
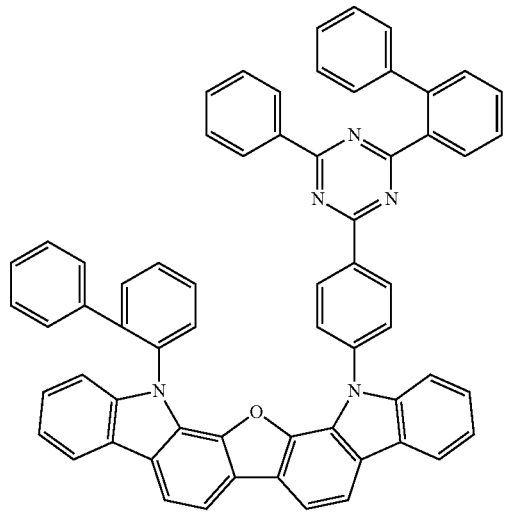
[64]
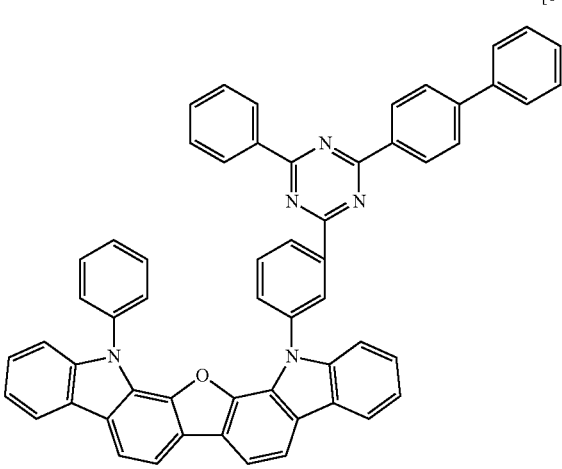

-continued
[65]
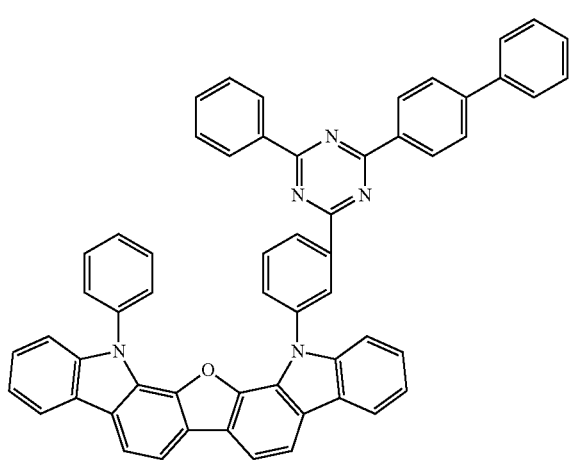
[66]
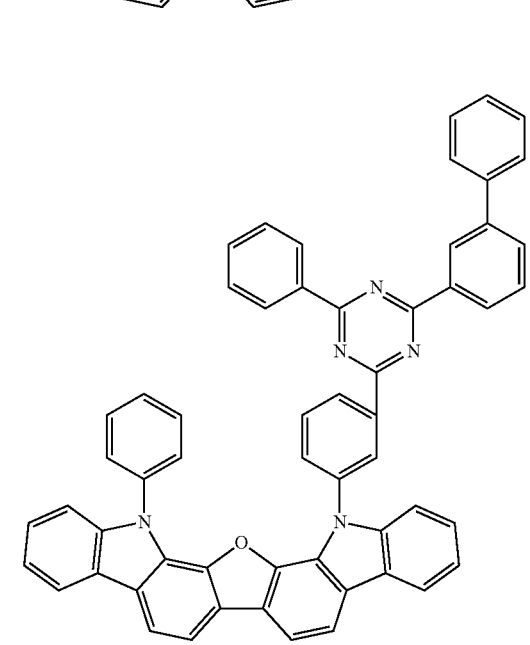
[67]
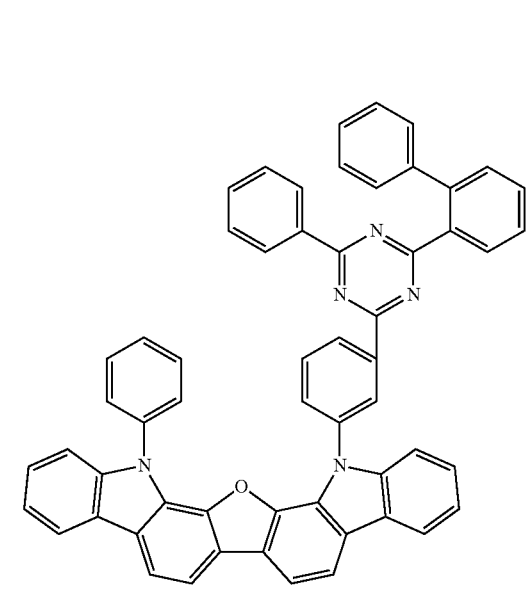
-continued
[68]
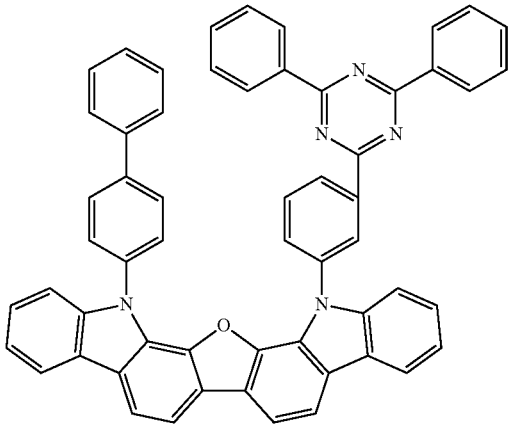
[69]
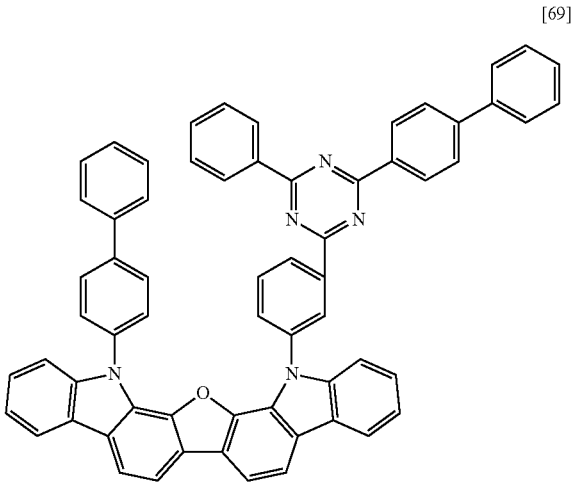
[70]
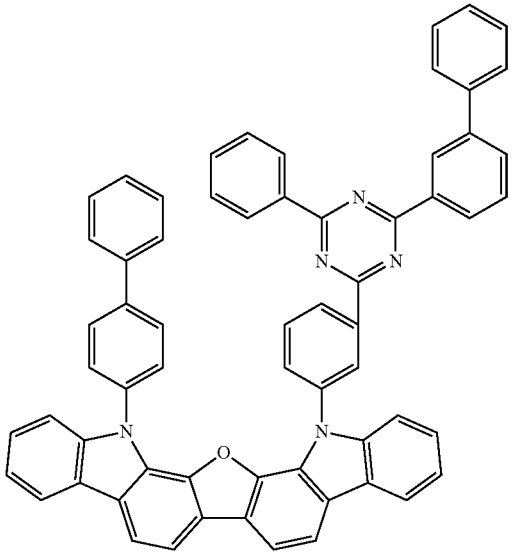

-continued
[71]
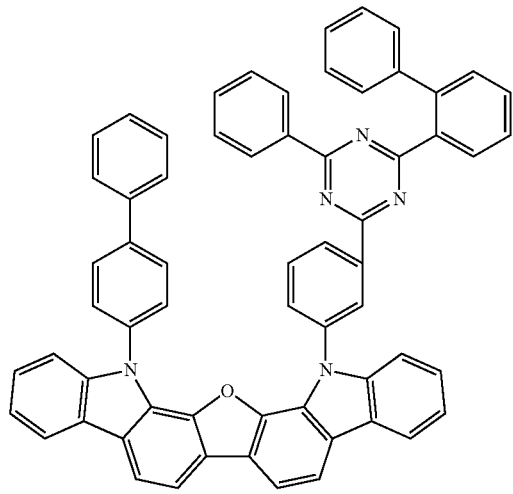
[72]
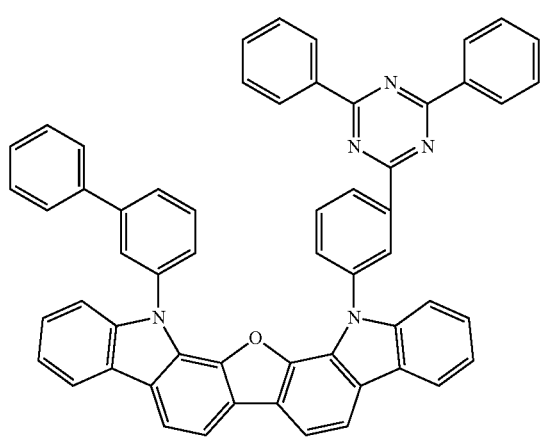
[73]
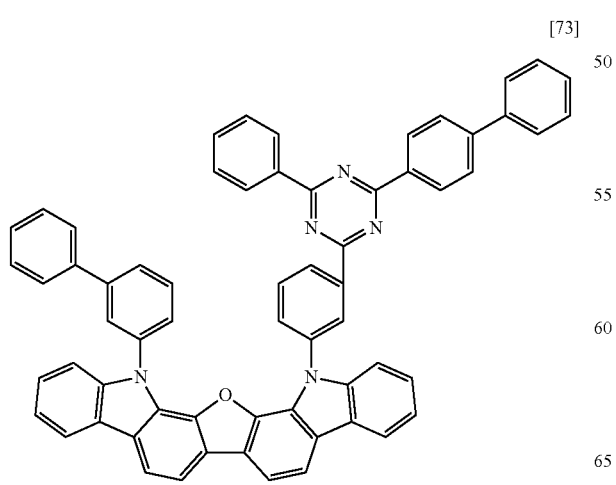
-continued
[74]
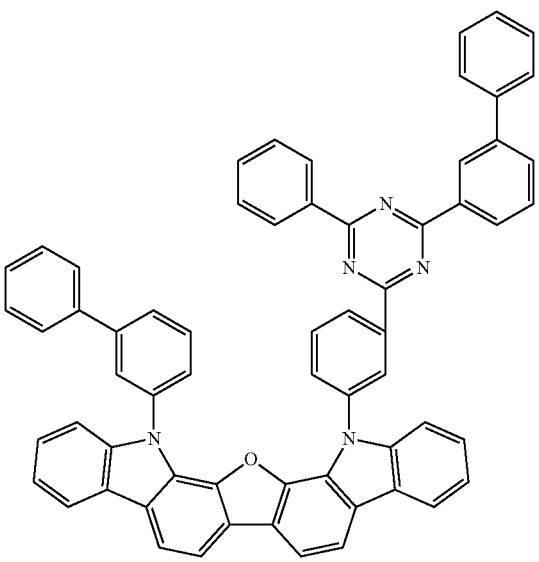
[75]
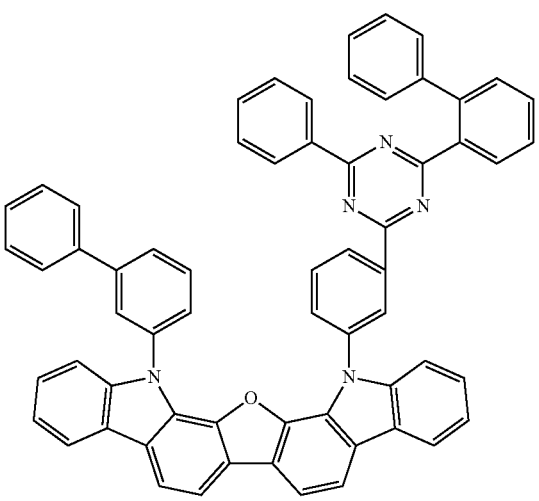
[76]
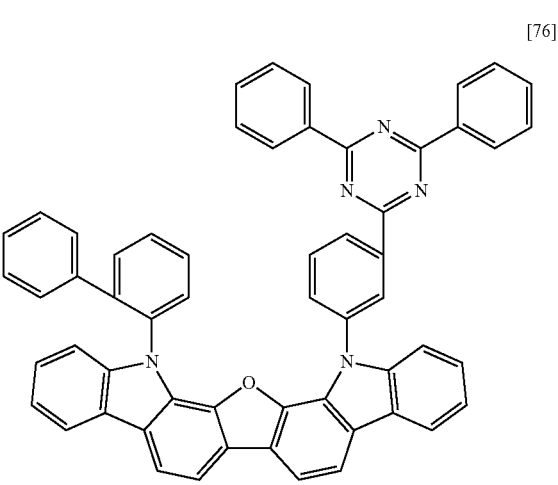

[77]
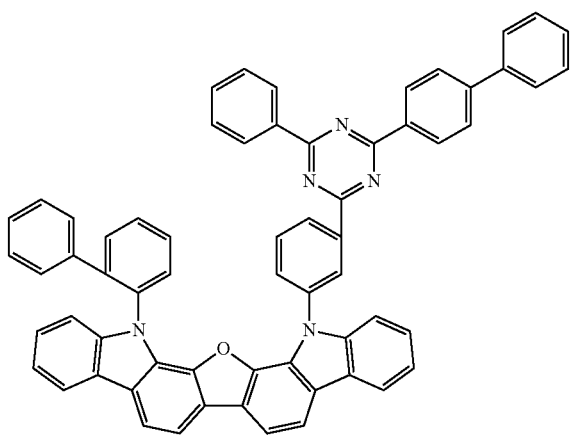
[78]
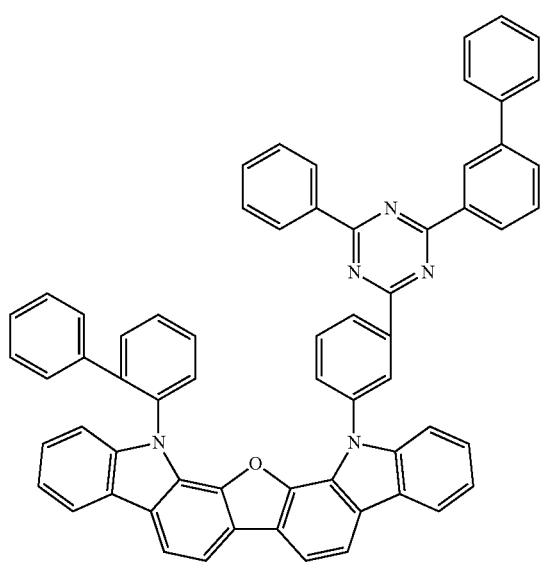
[79]
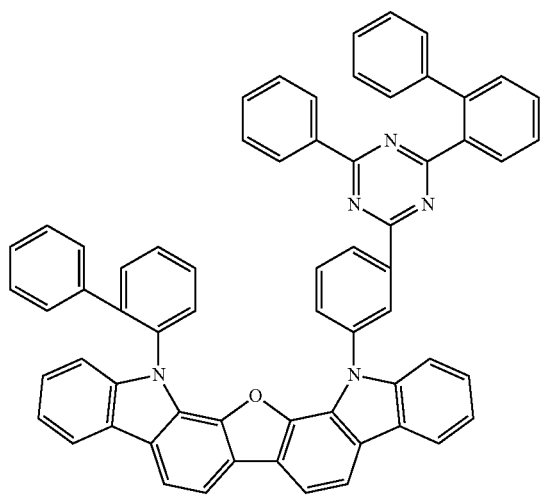
[80]
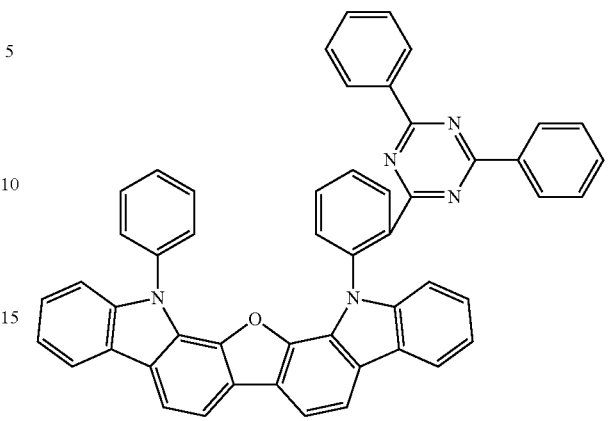
[81]
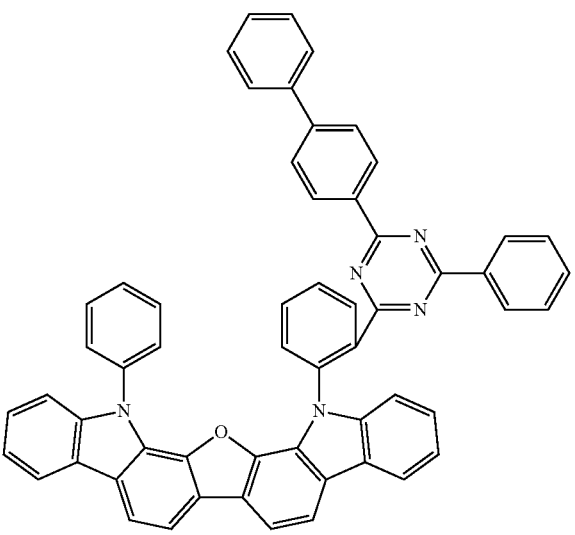
[82]
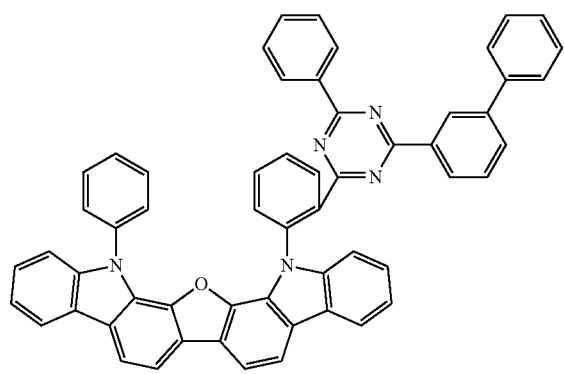

[83]
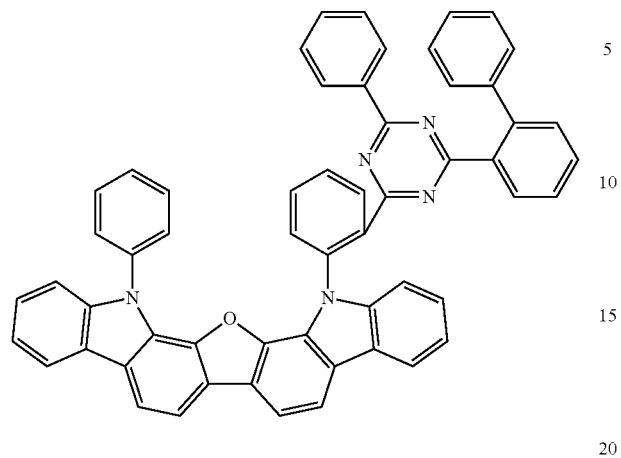
[84]
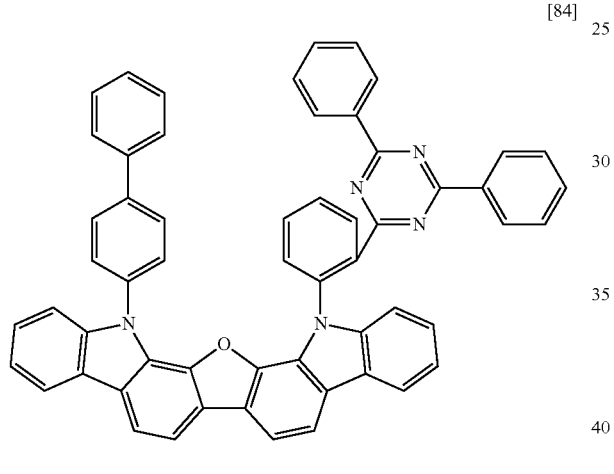
[85]
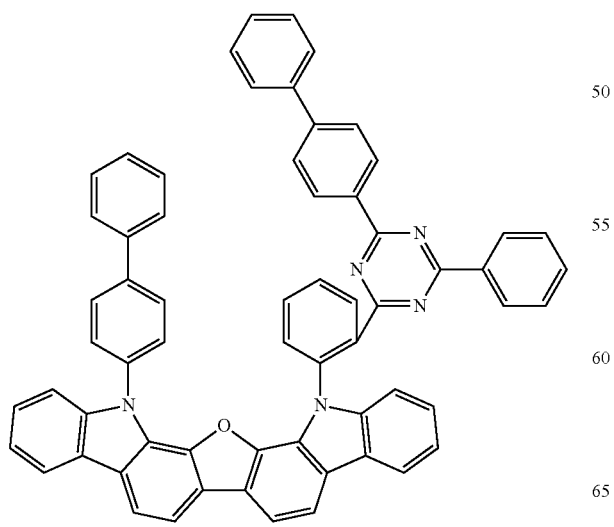
[86]
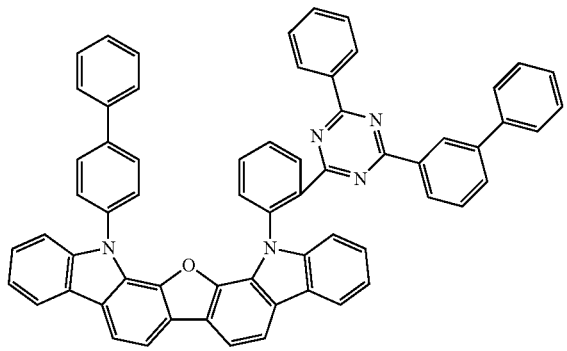
[87]
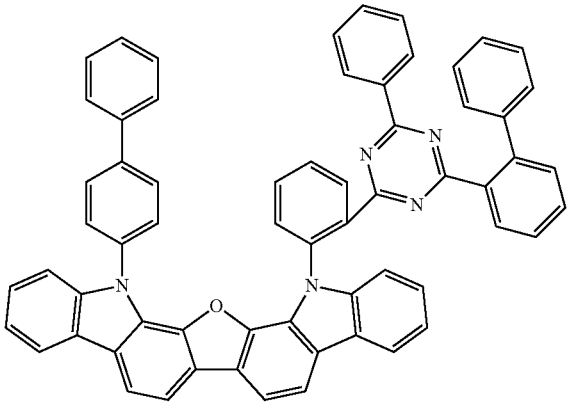
[88]
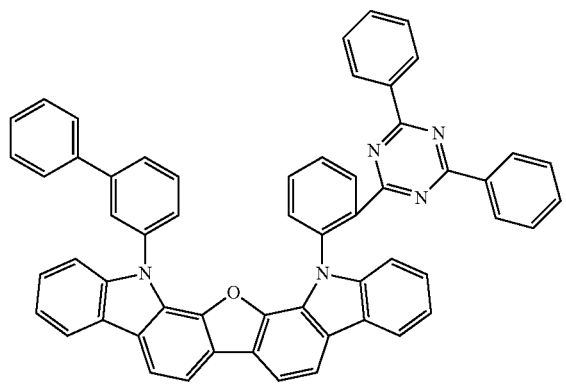

257
-continued
[88]
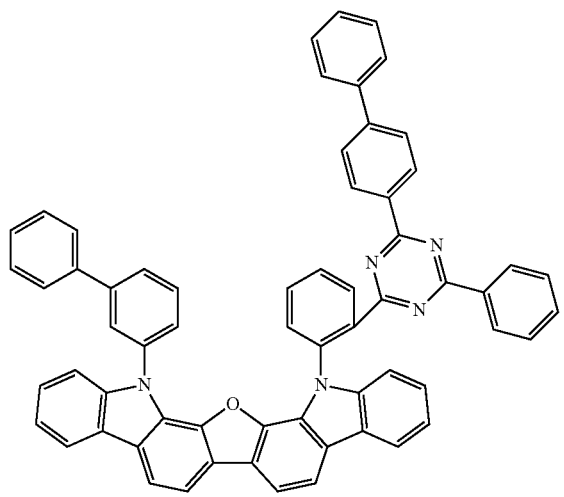
[90]
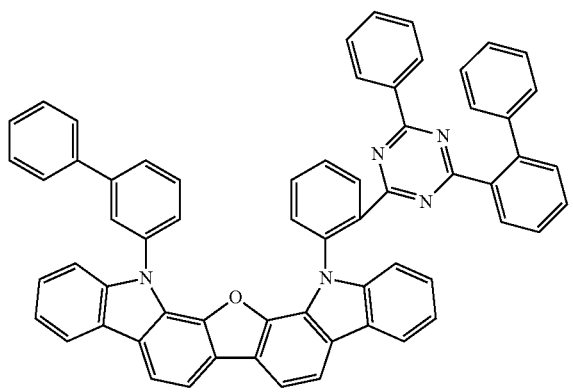
[91]
258
-continued
[92]
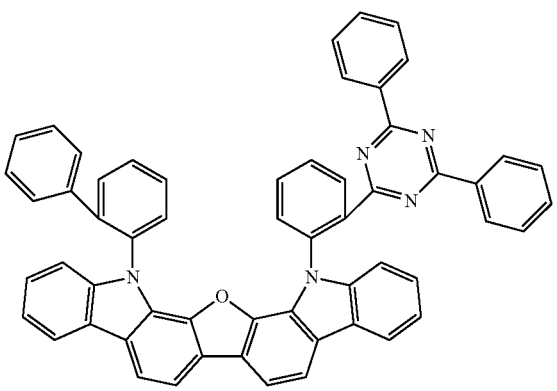
[93]
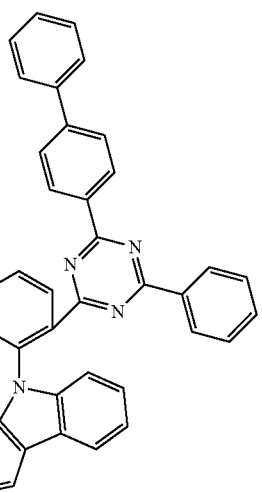
[94]
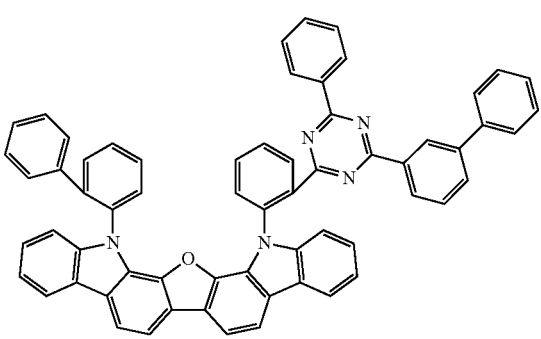

259
-continued
[95]
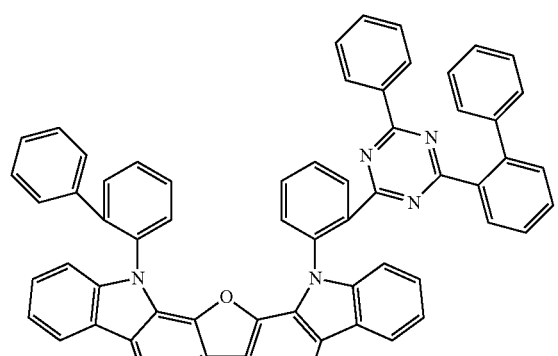
[96]
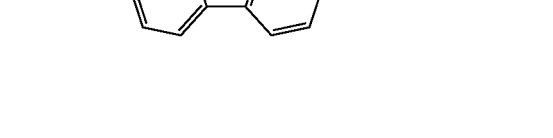
[97]
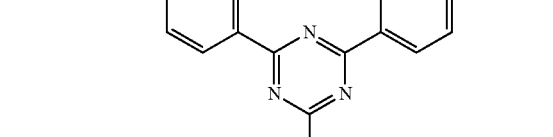
260
-continued
[98]
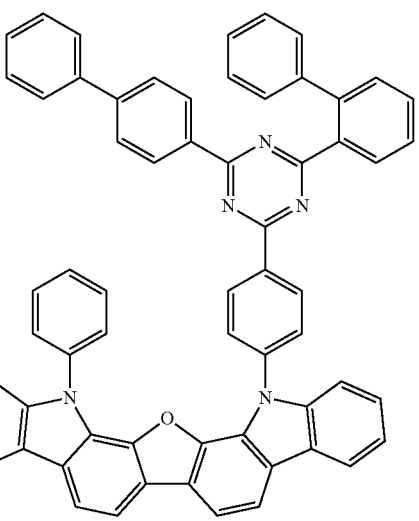
[99]
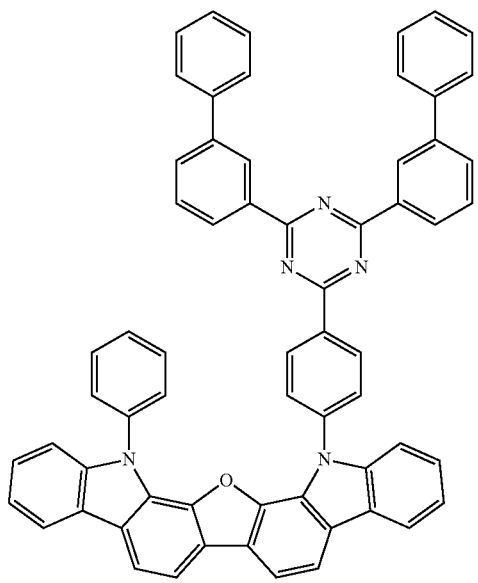
[100]
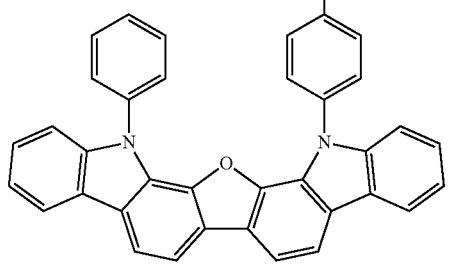

[101]
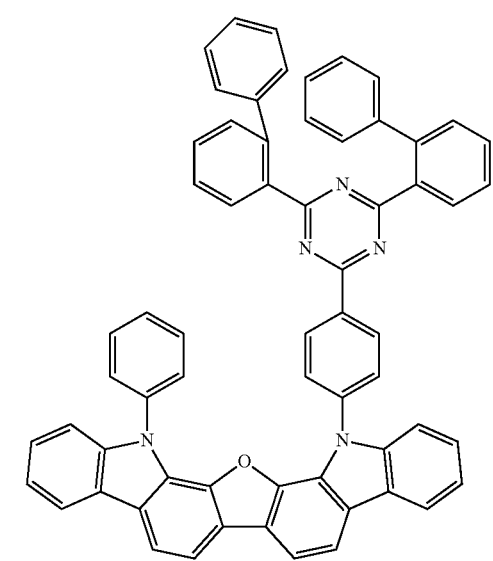
[102]
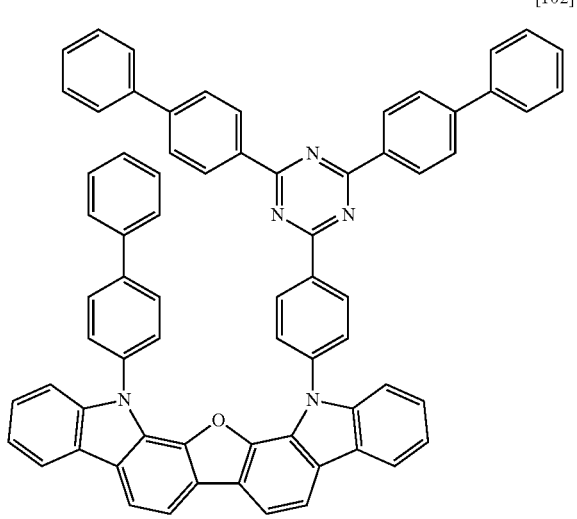
[103]
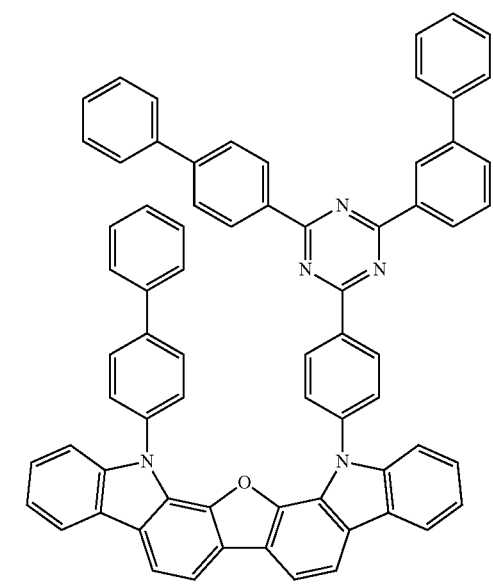
[104]
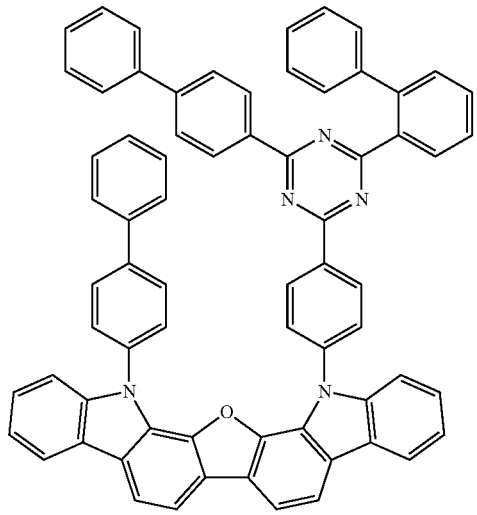
[105]
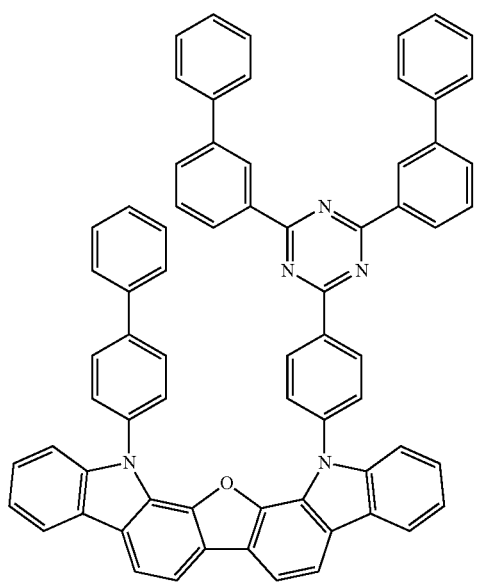
[106]
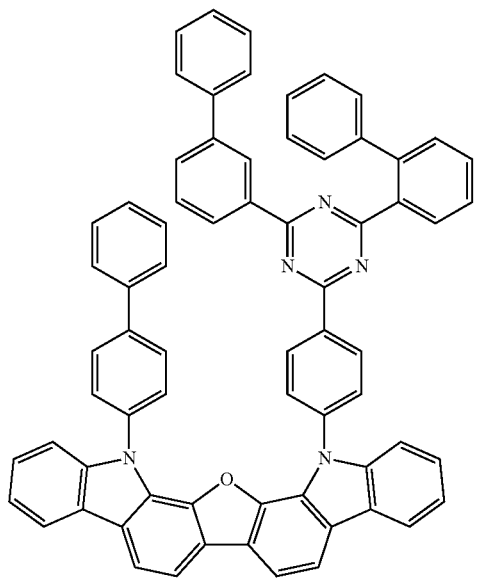

[107]
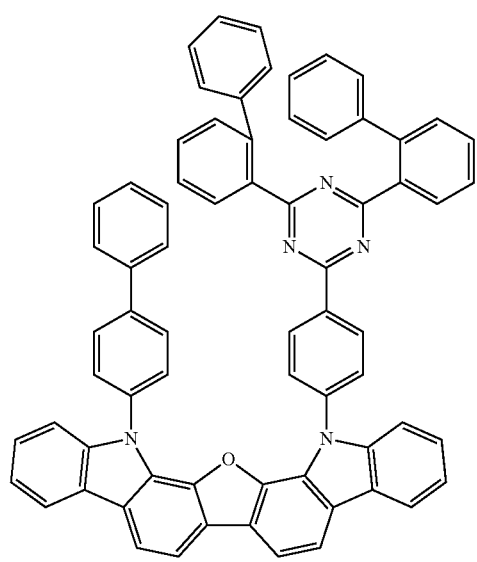
[108]
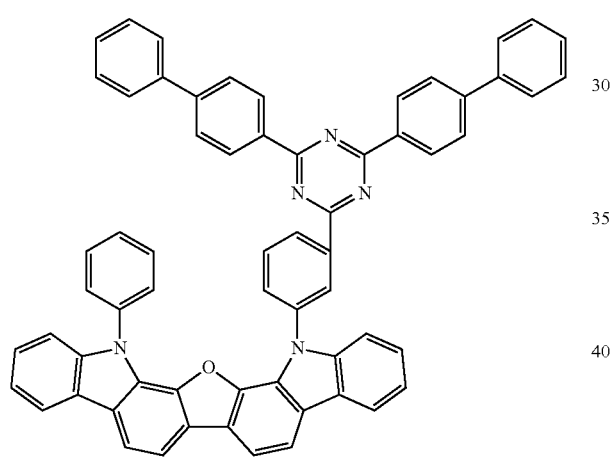
[109]
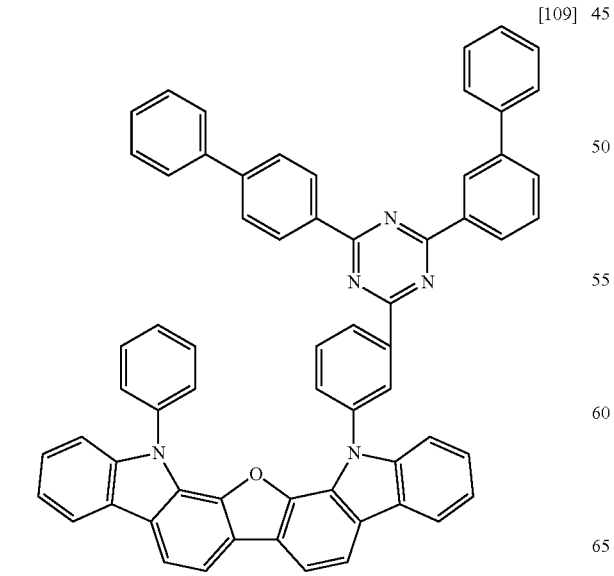
[110]
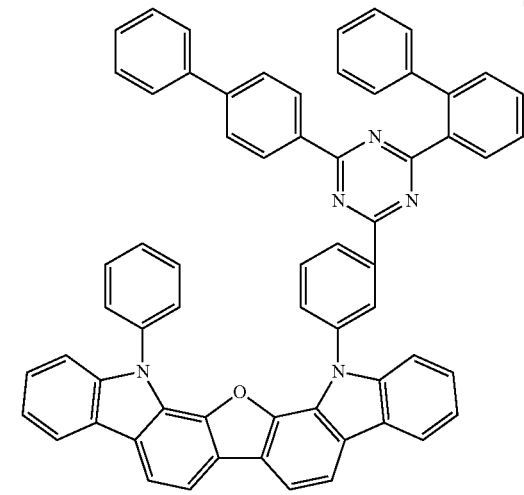
[111]
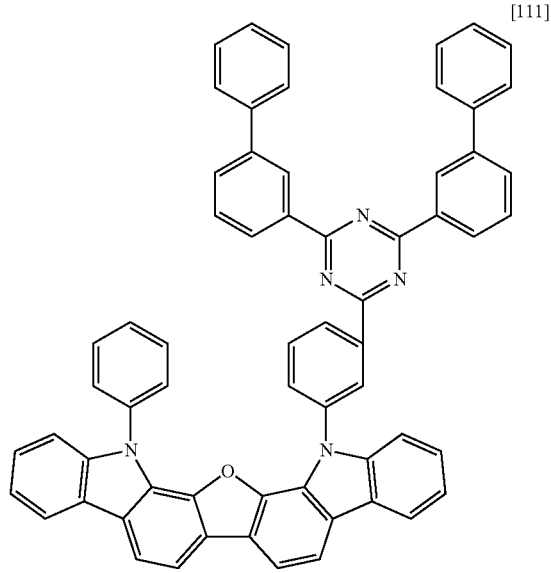
[112]
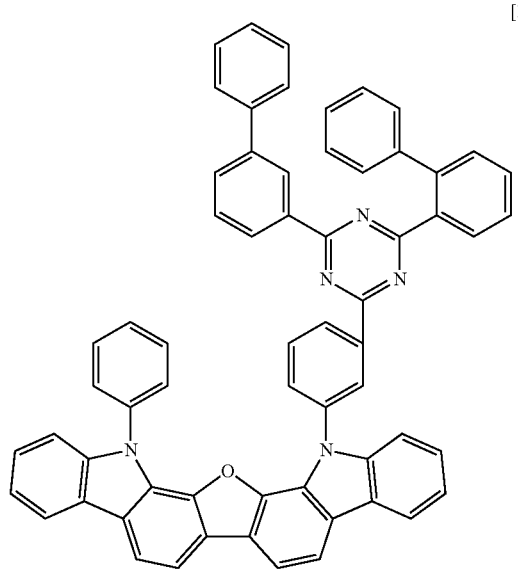

[113]
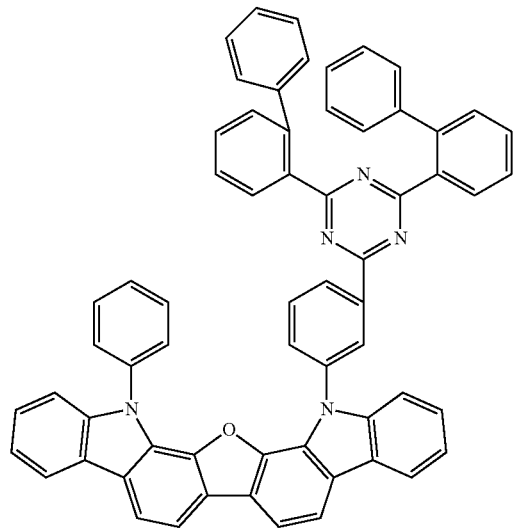
[114]
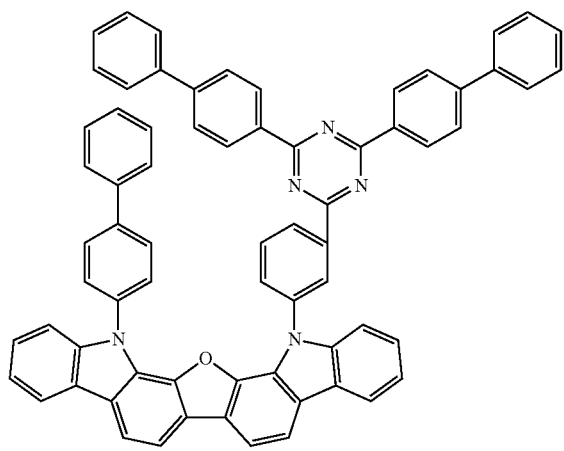
[115]
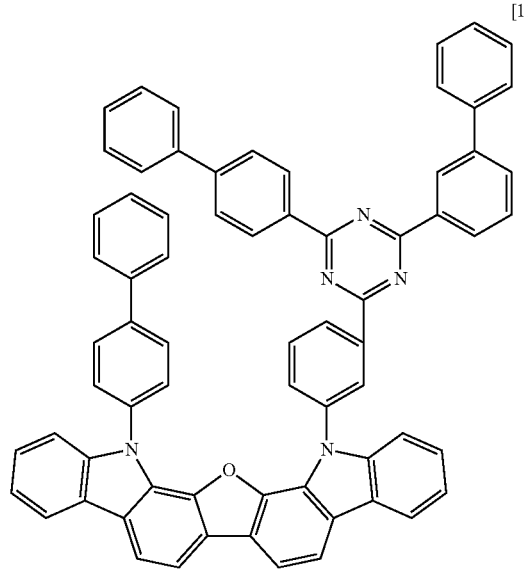
[116]
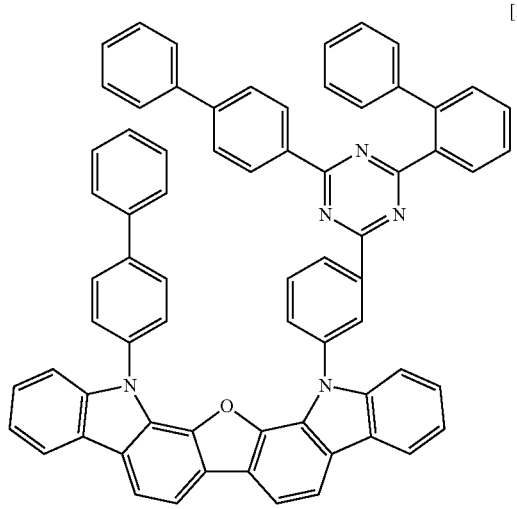
[117]
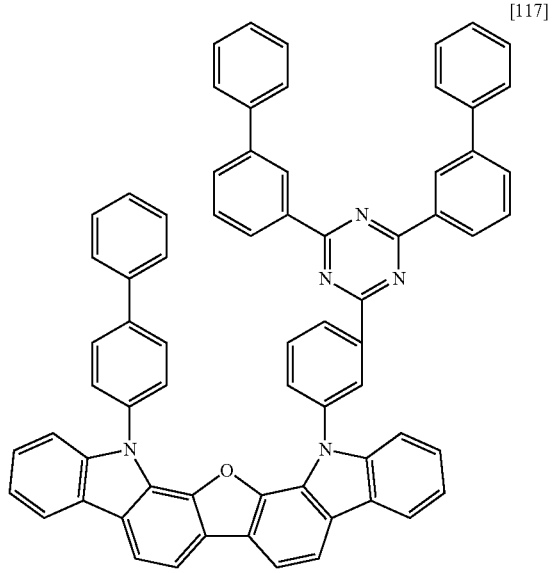
[118]
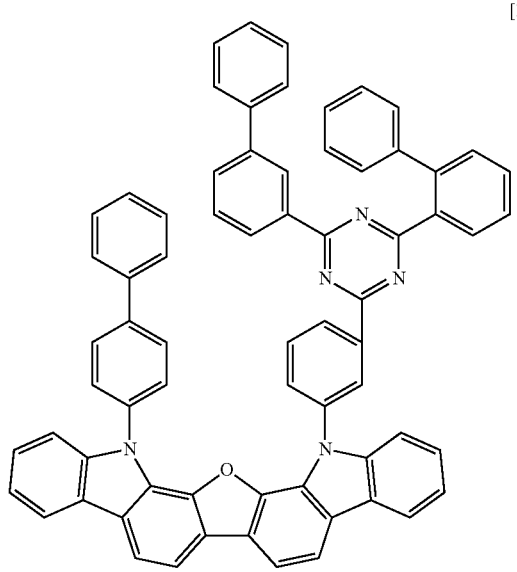

-continued
[119]
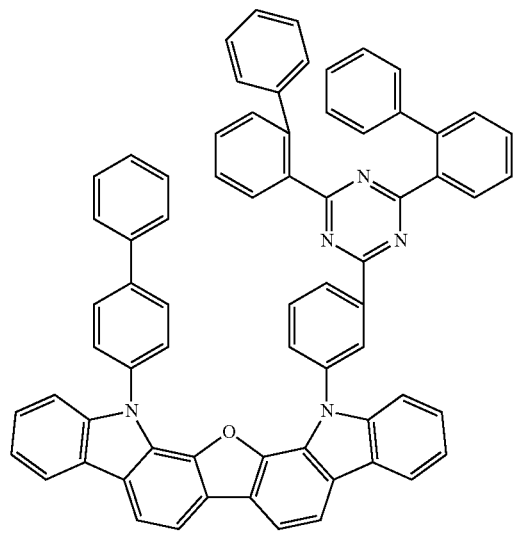
[120]
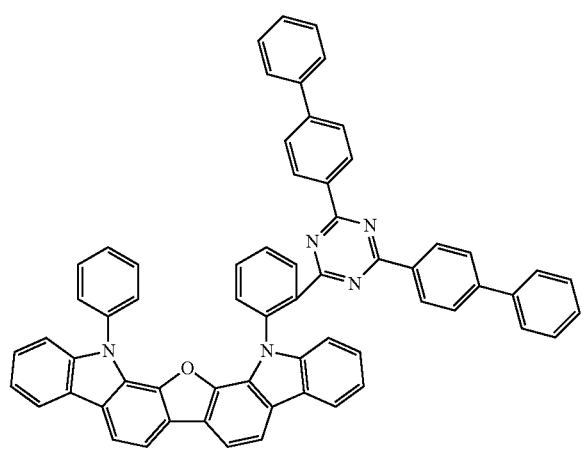
[121]
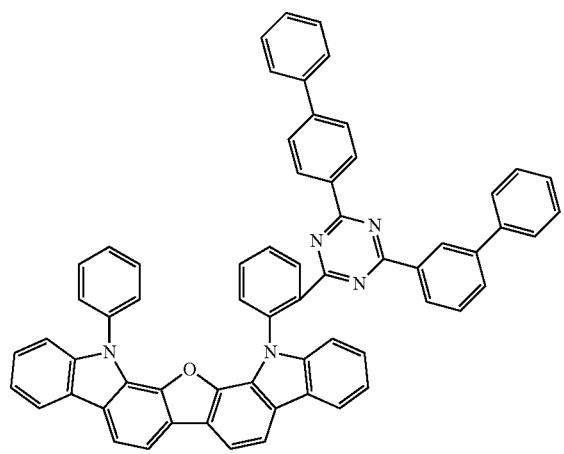
-continued
[122]
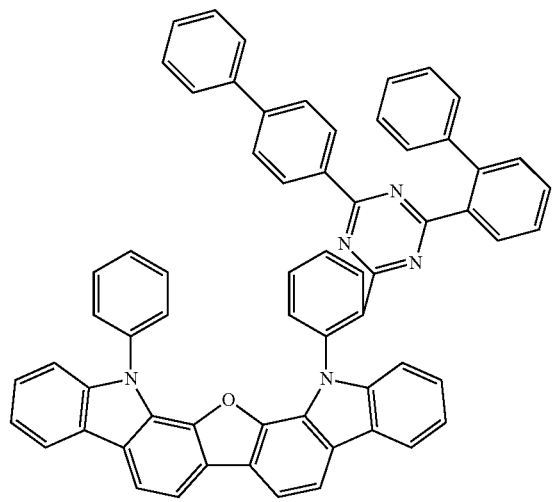
[123]
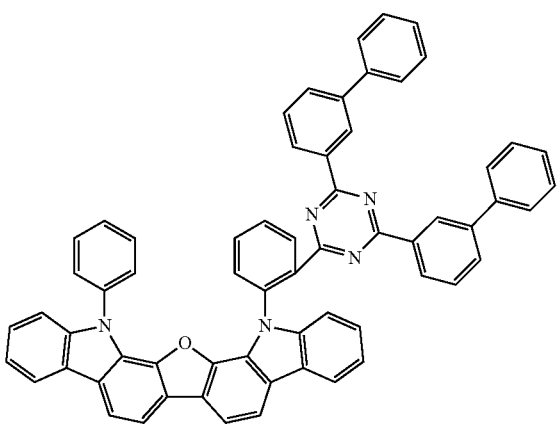
[124]
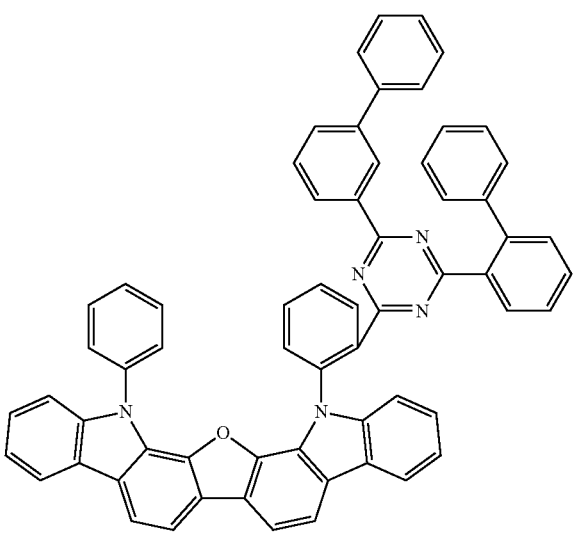

[125]
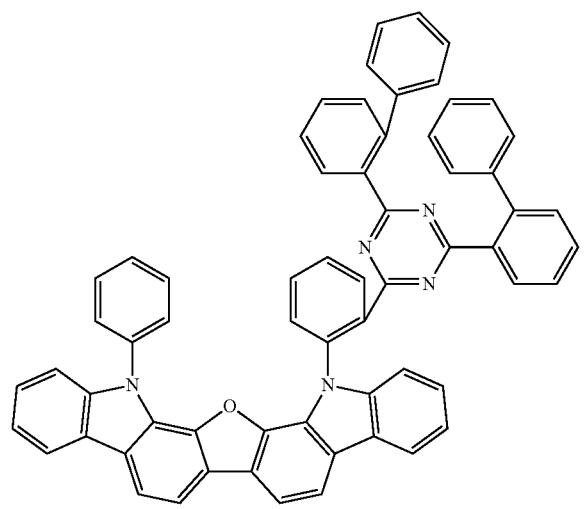
[126]
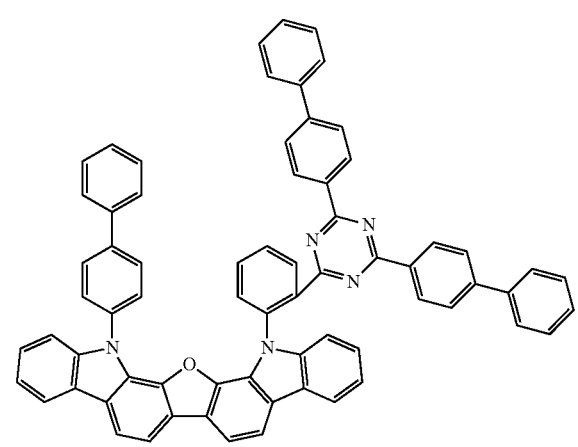
[127]
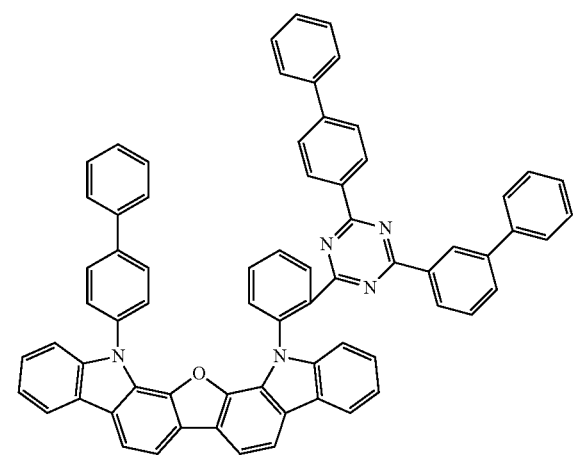
[128]
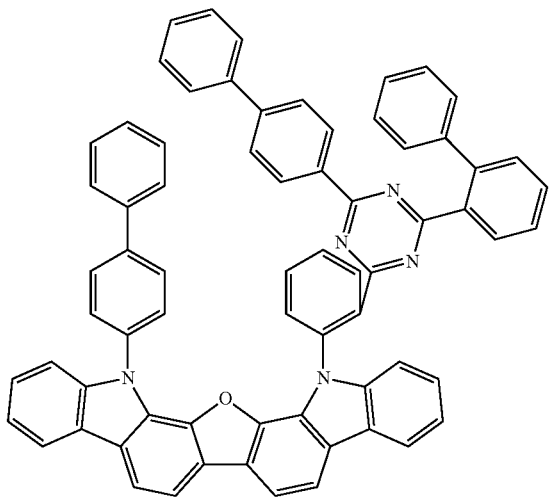
[129]
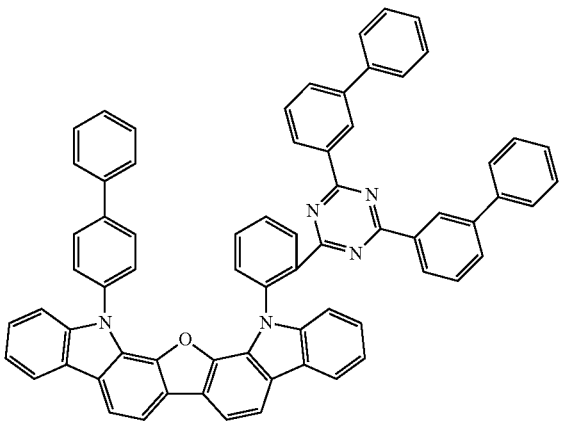
[130]
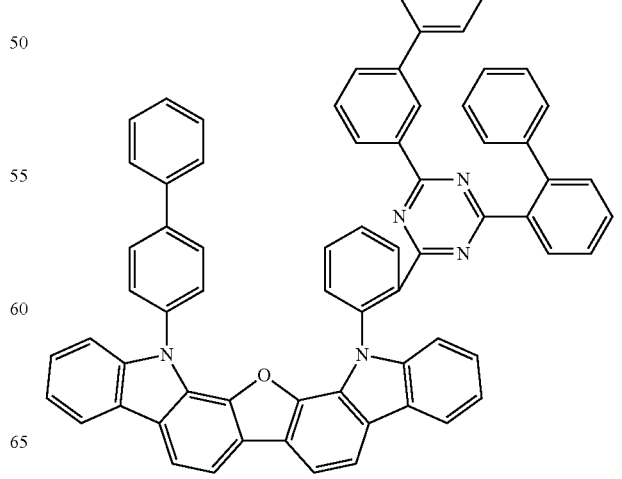

-continued
[131]
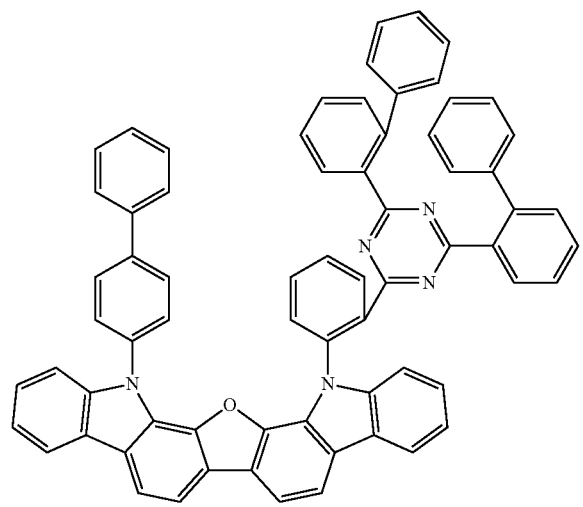
[132]
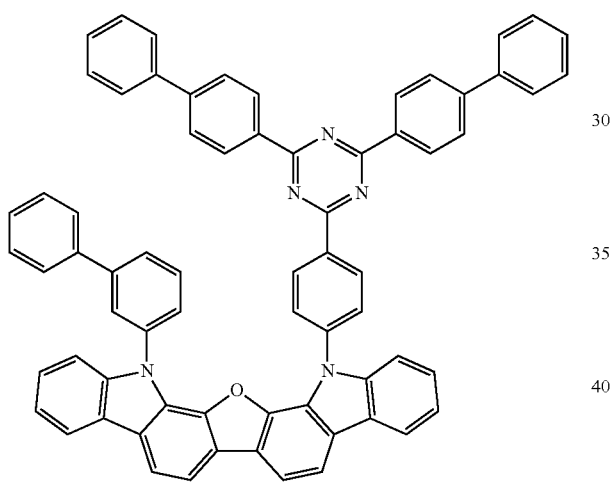
[133]
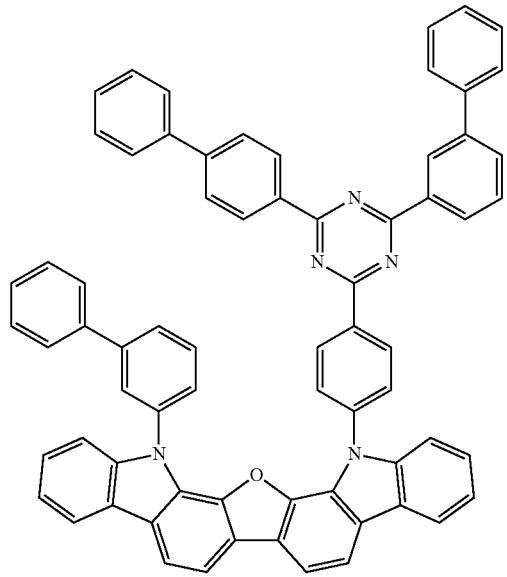
-continued
[134]
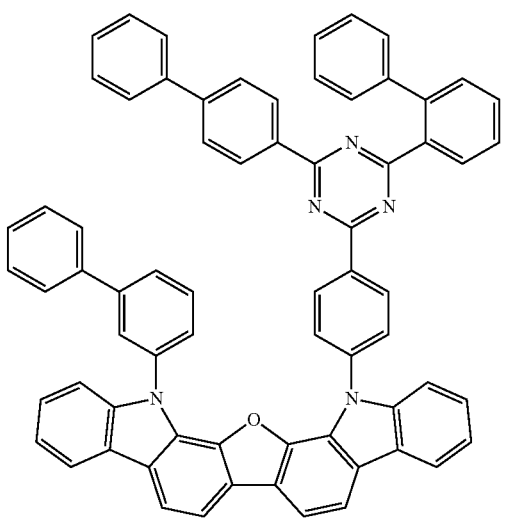
[135]
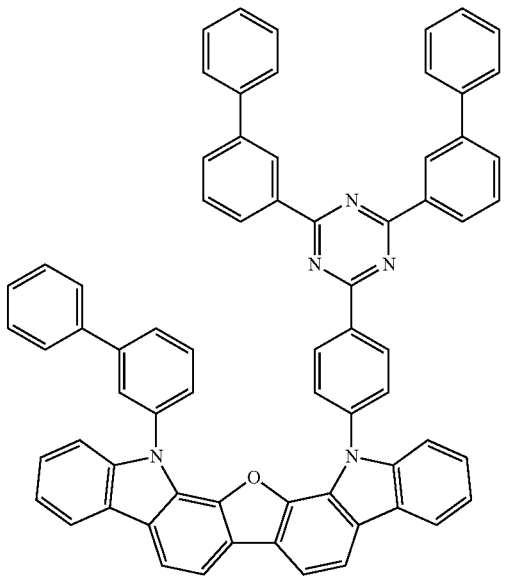

[136]
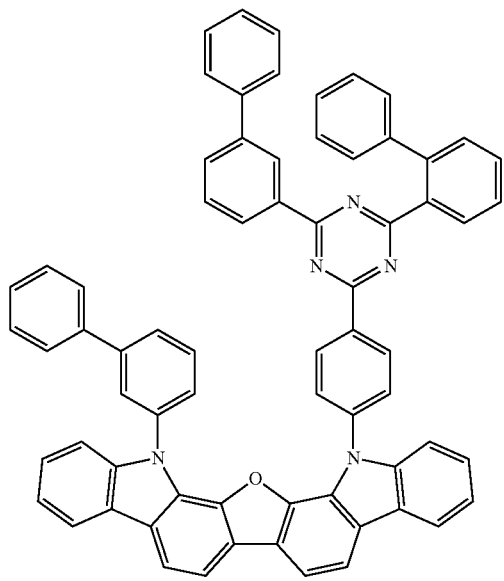
[137]
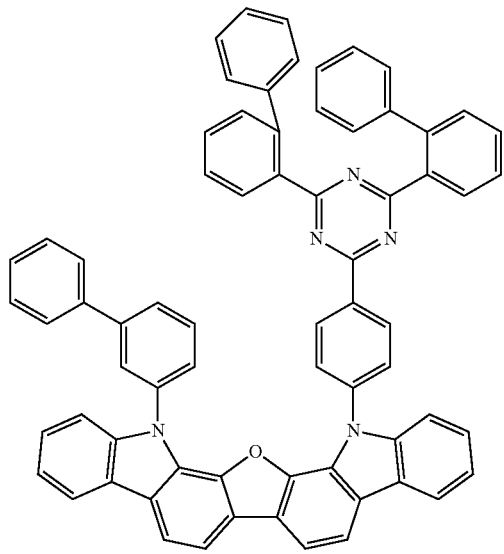
[138]
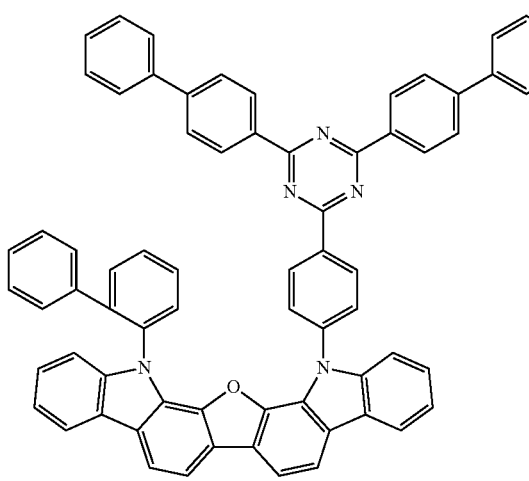
[139]
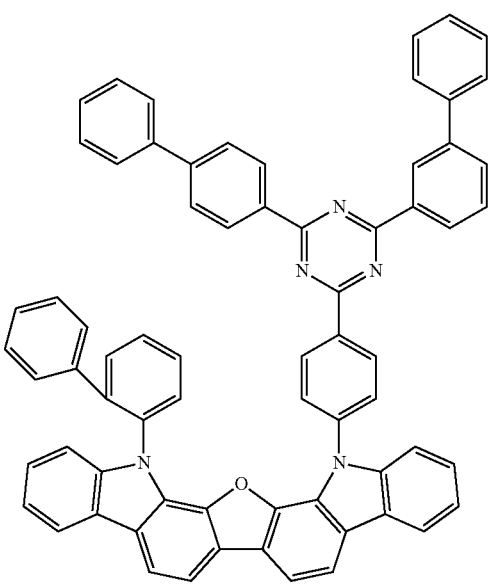
[140]
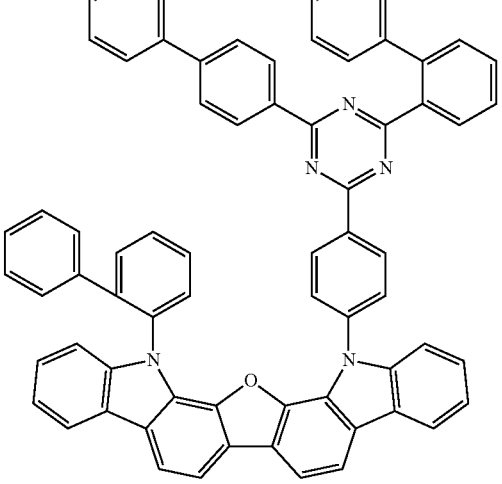

[141]
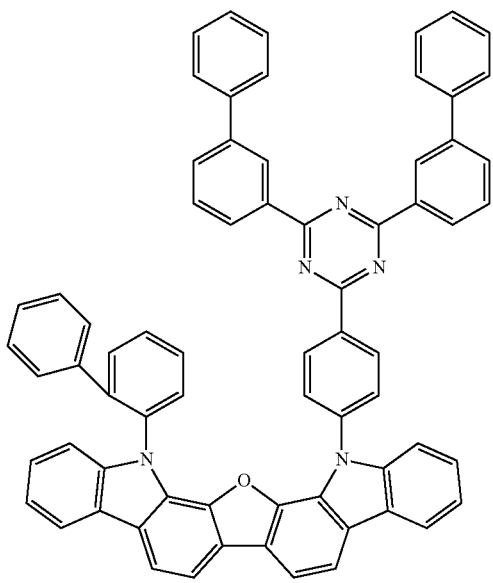
[142]
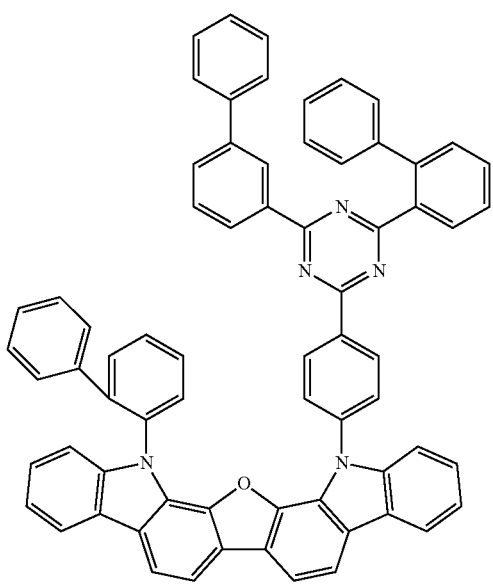
[143]
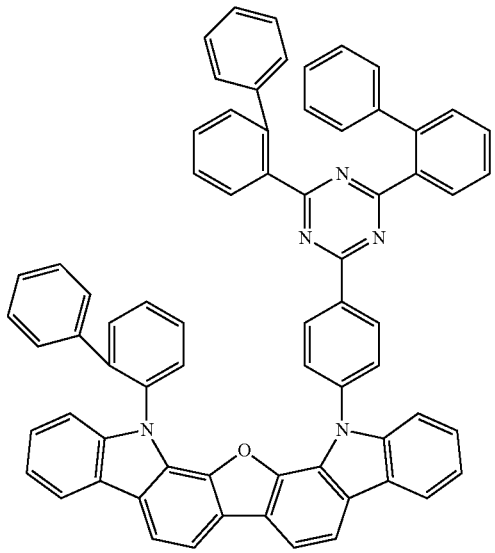
[144]
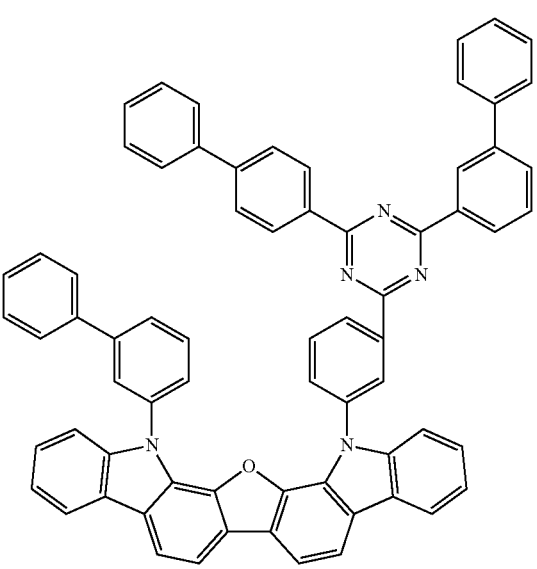
[145]

[146]
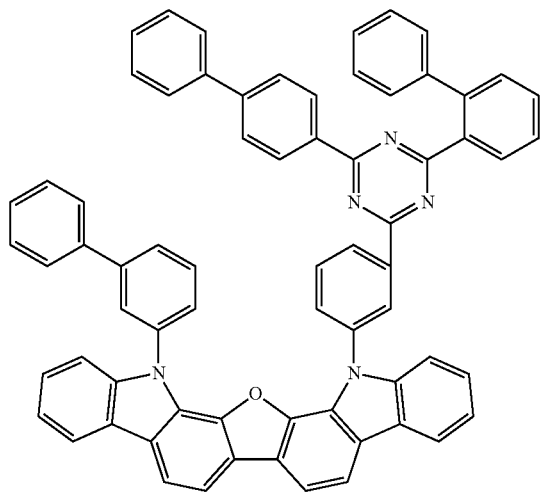
[147]
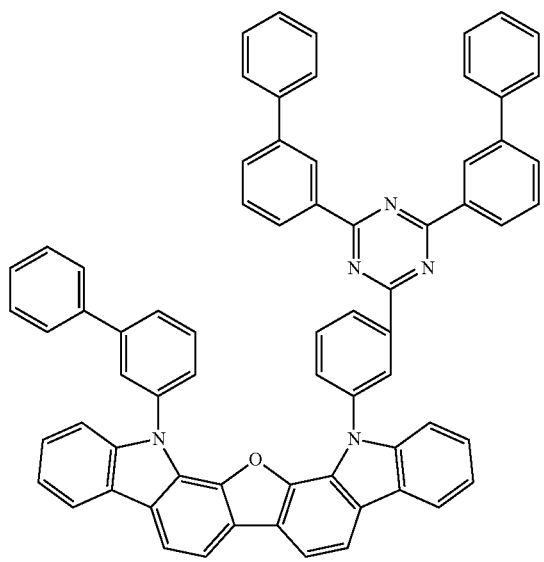
[148]
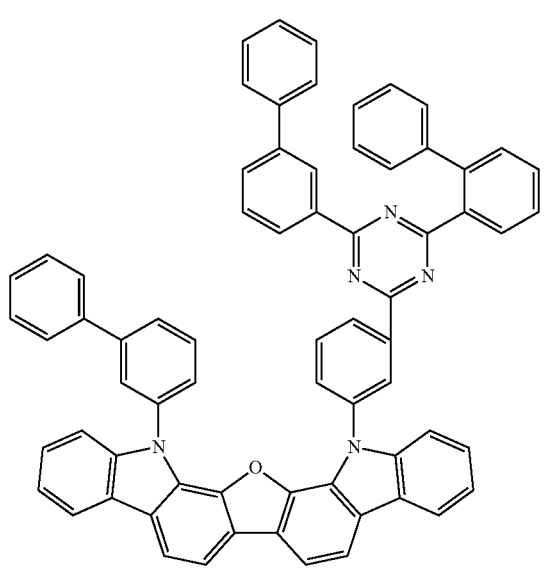
[149]
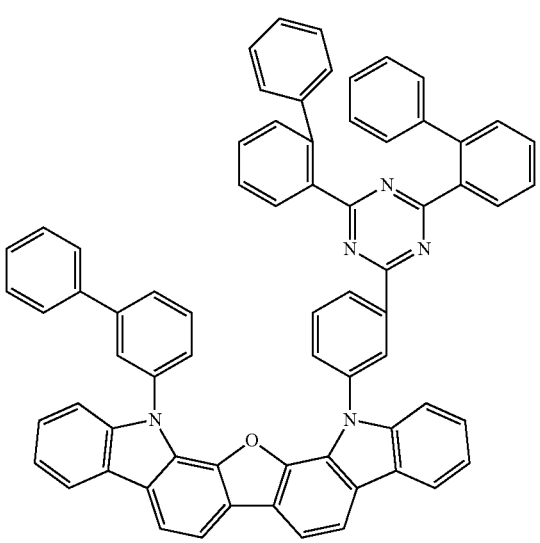
[150]
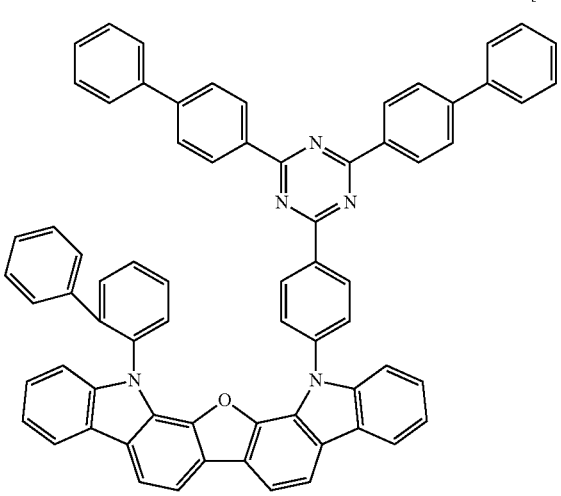
[151]
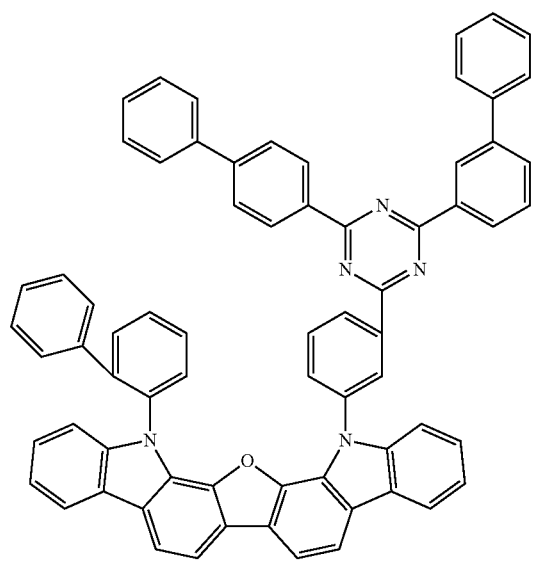

[152]
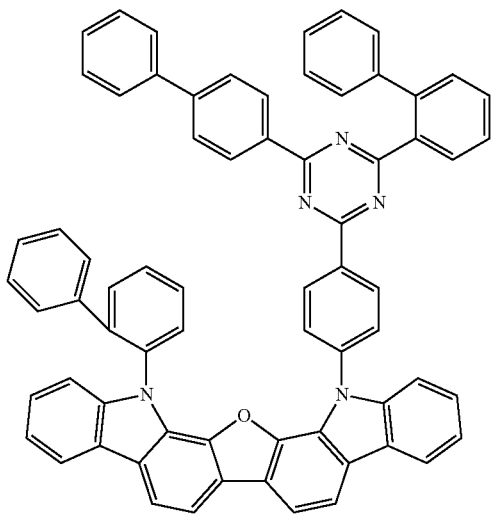
[153]
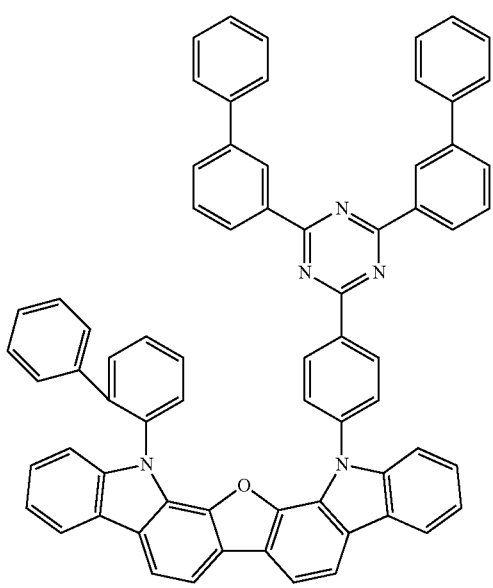
[154]
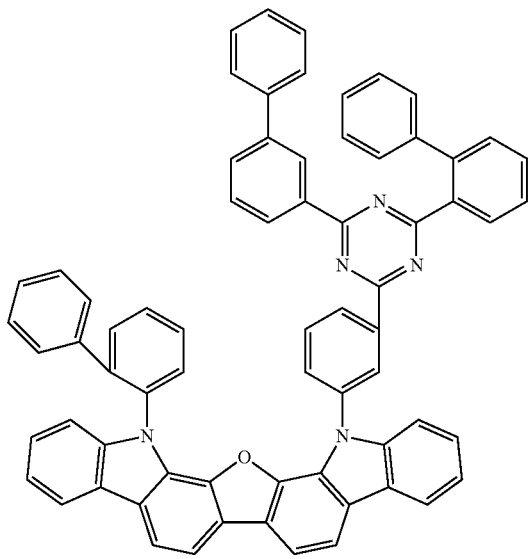
[155]
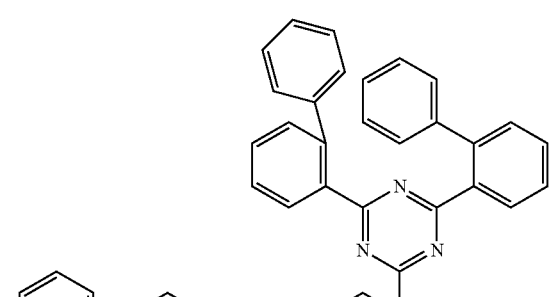
[156]
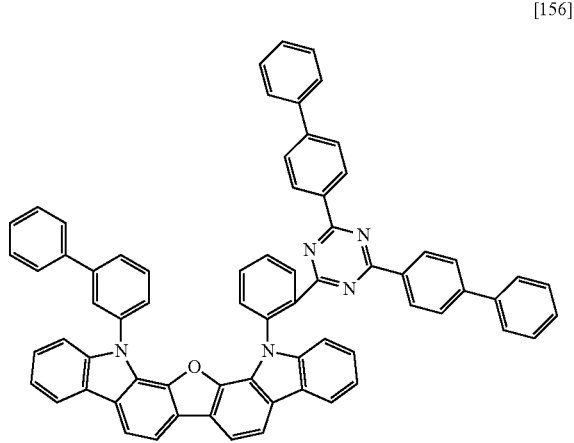

281
-continued
[157]
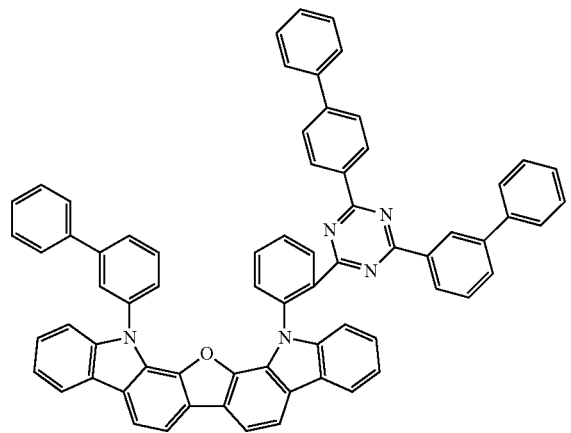
[158]
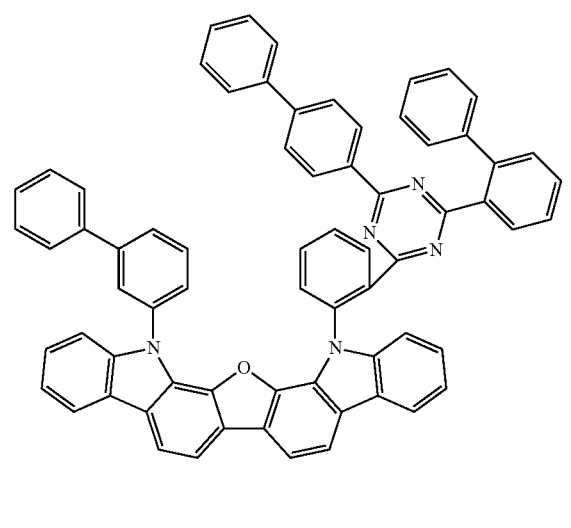
[159]
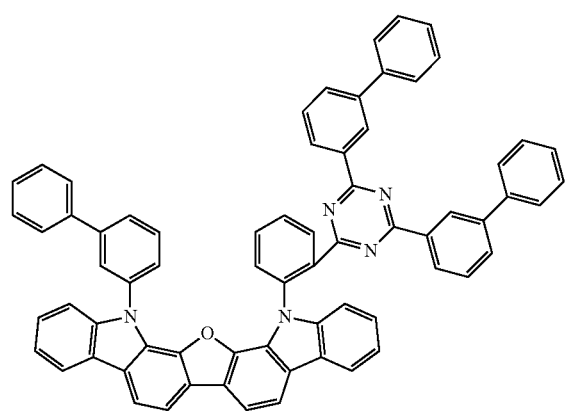
282
-continued
[160]
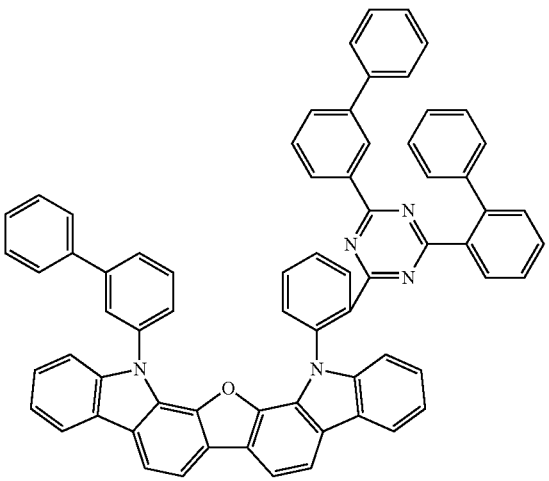
[161]
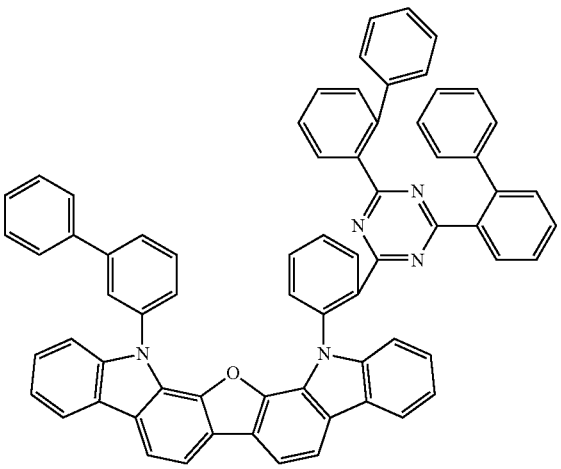
[162]
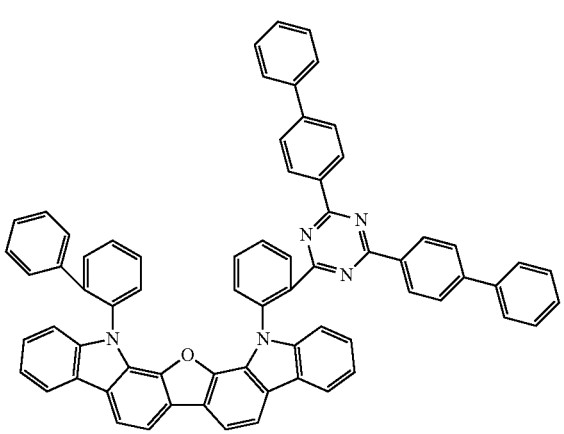

[163]
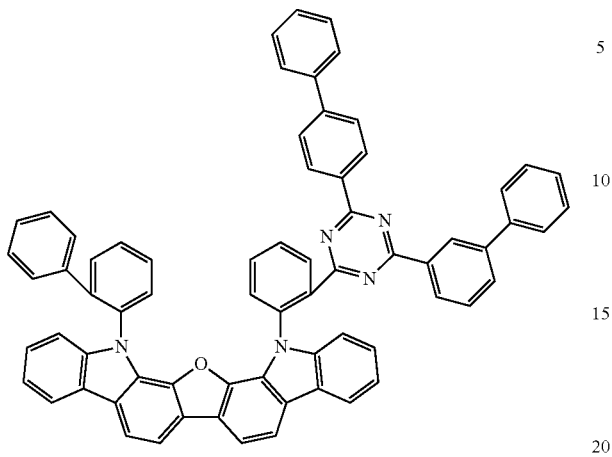
[164]
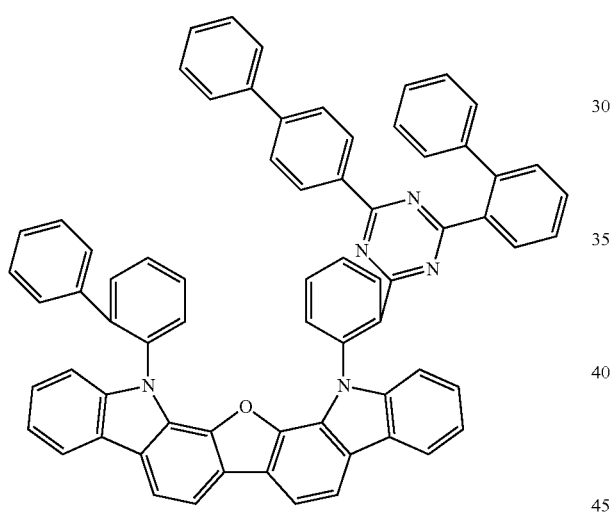
[165]
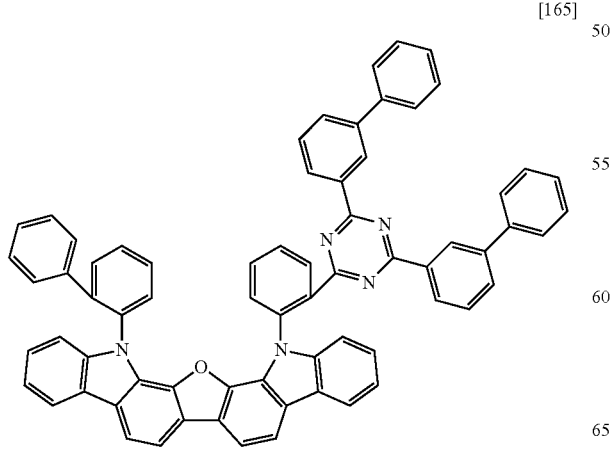
[166]
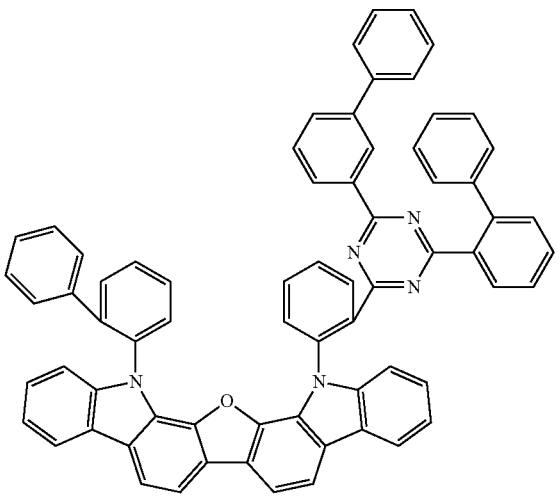
[167]
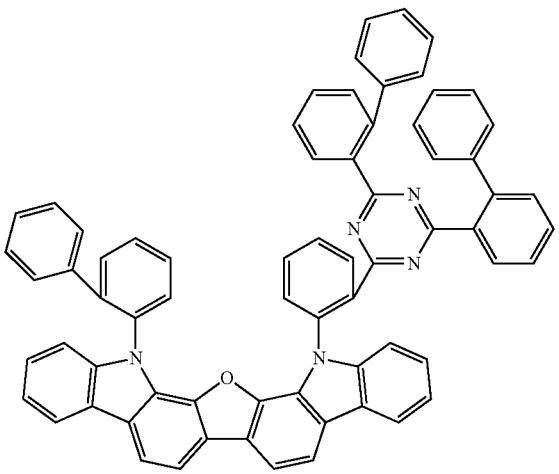
[168]
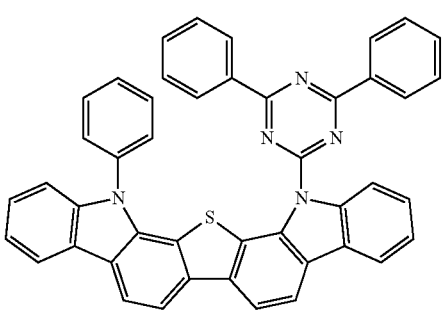

-continued
[169]
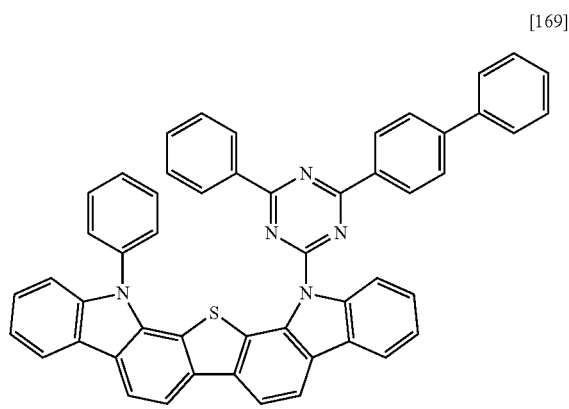
[170]
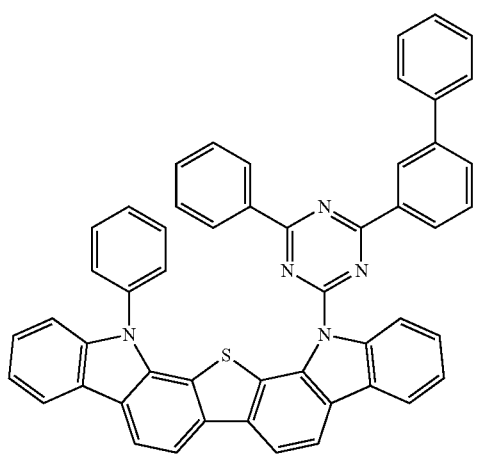
[171]
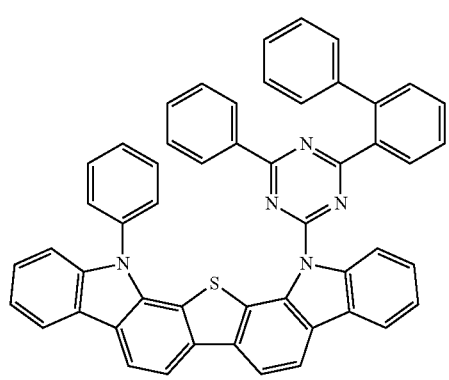
[172]
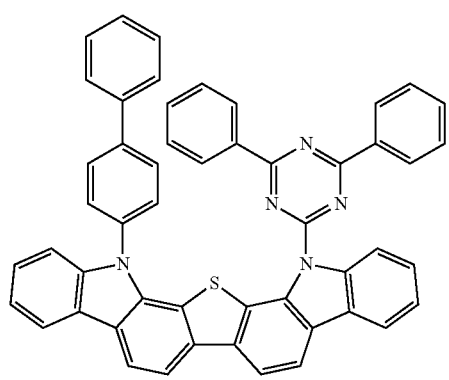
-continued
[173]
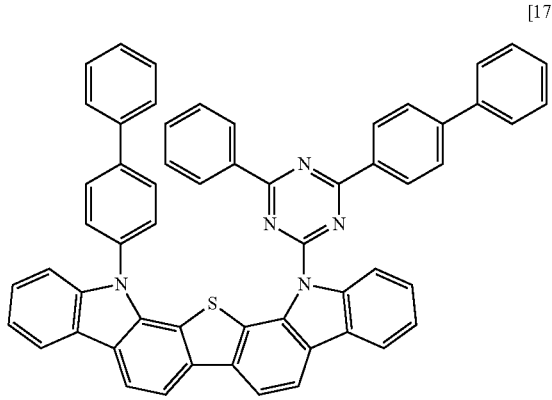
[174]
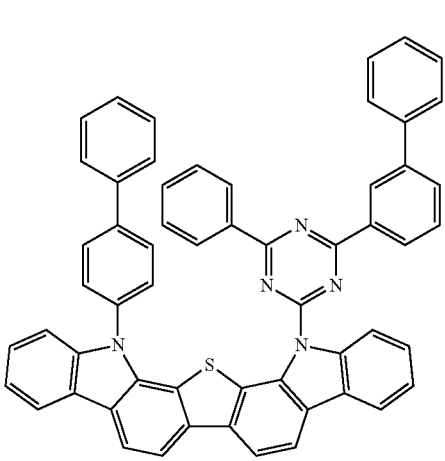
[175]
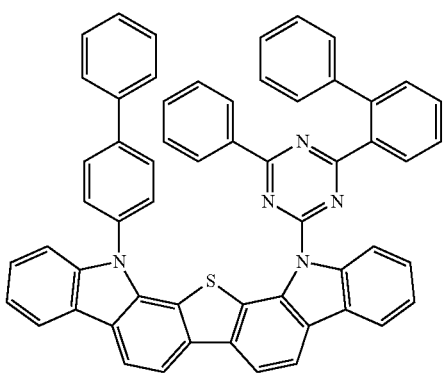
[176]
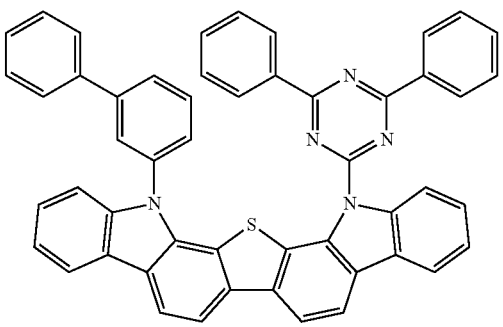

[177]
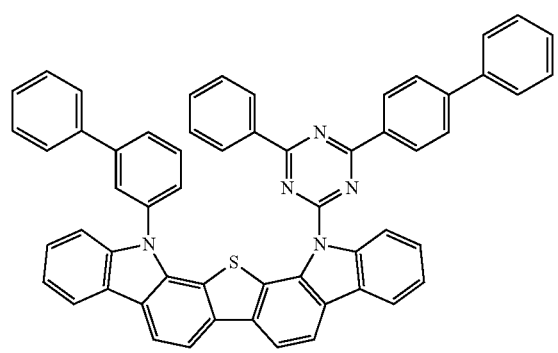
[178]
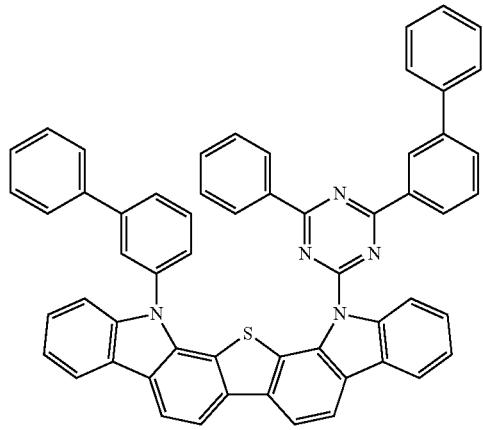
[179]
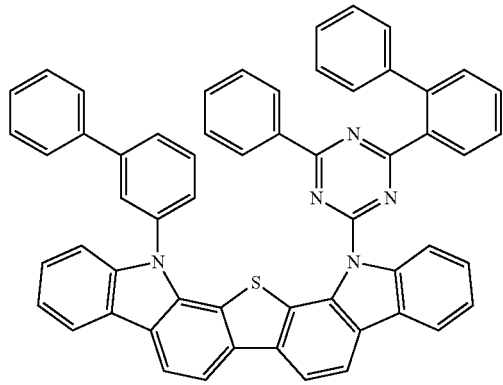
[180]
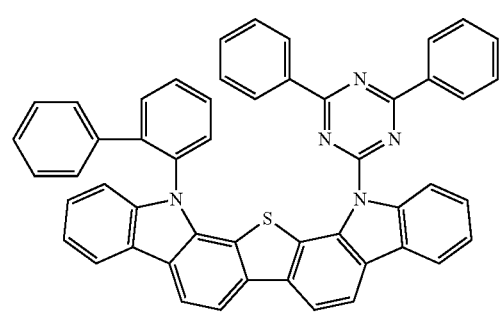
[181]
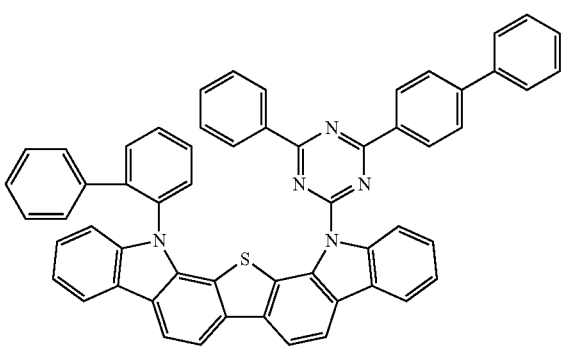
[182]
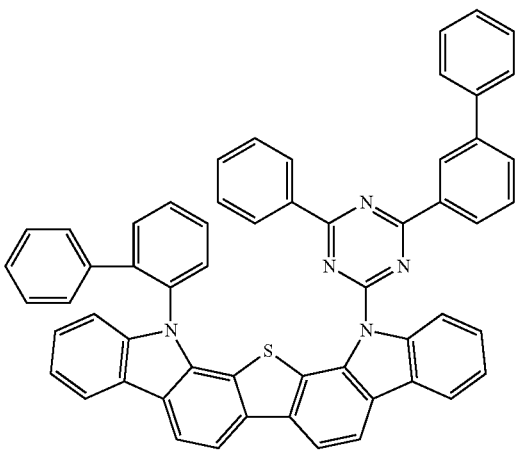
[183]
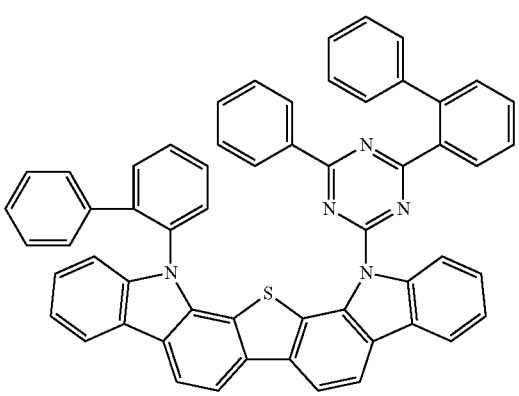
[184]
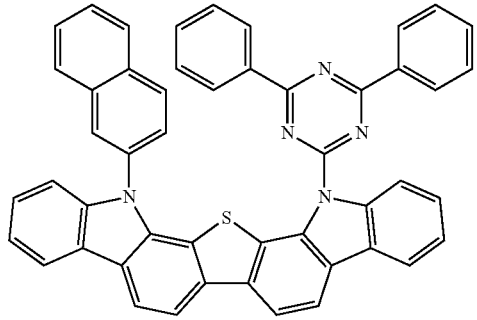

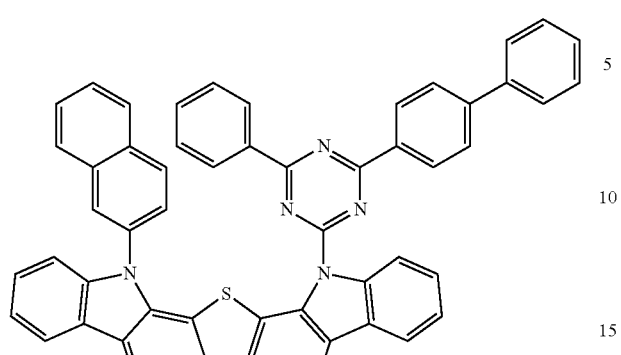
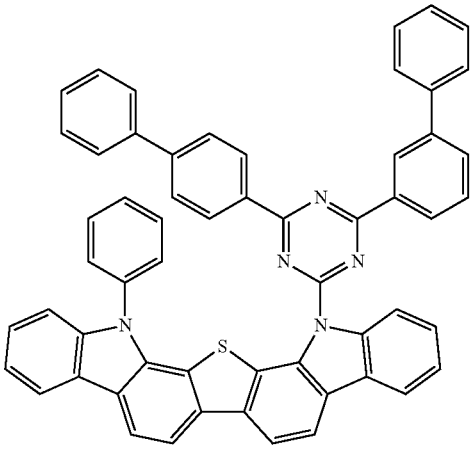
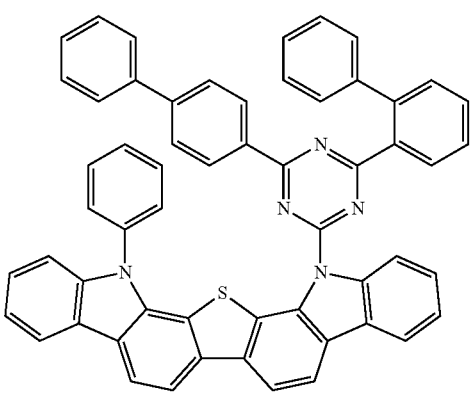
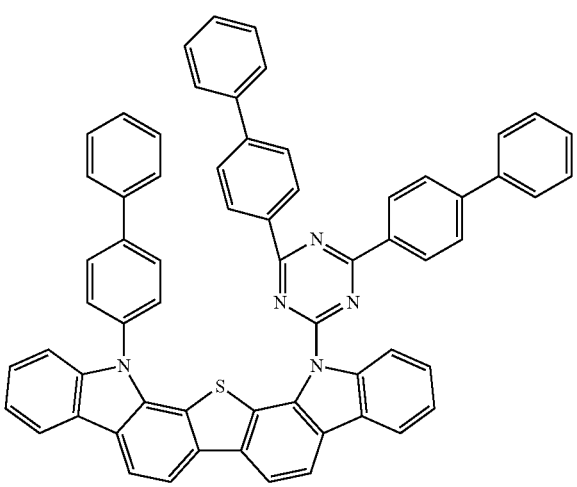

[192]
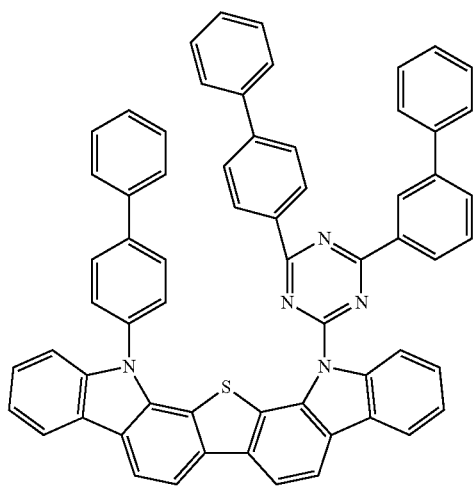
[193]
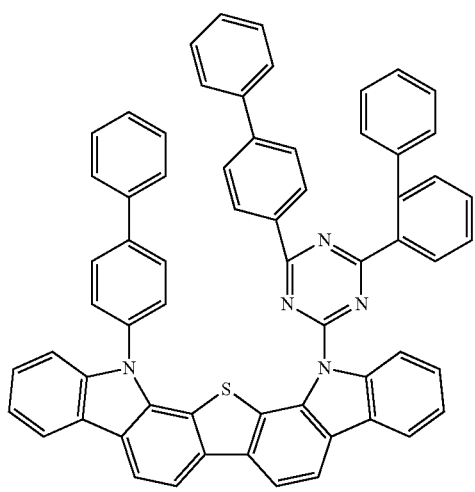
[194]
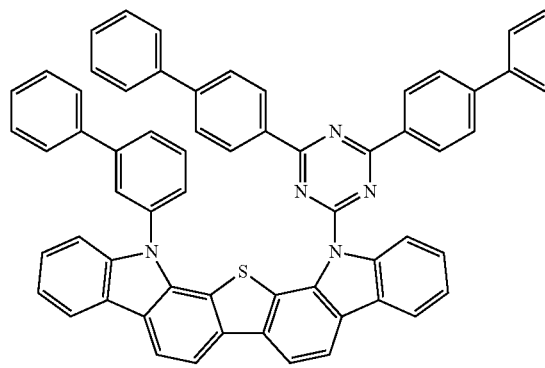
[195]
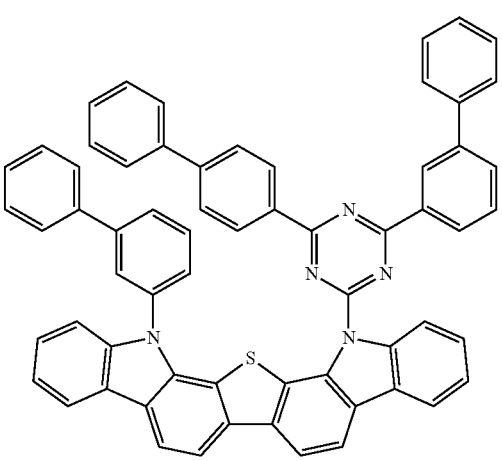
[196]
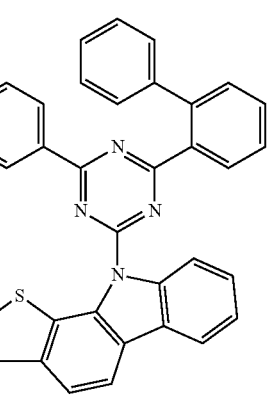
[197]
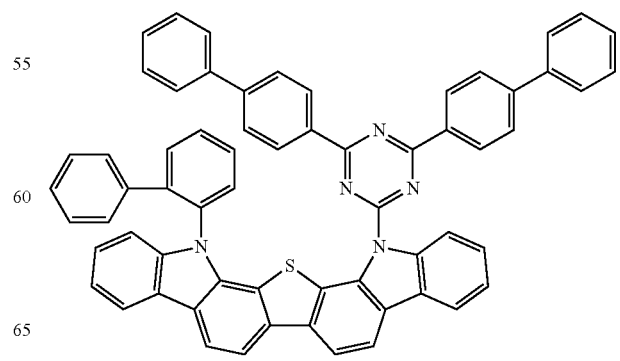

[198]
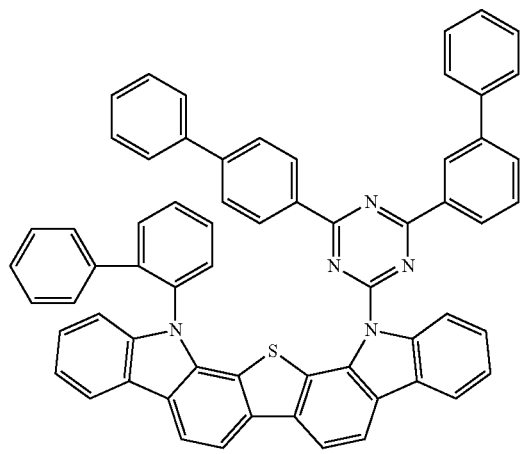
[199]
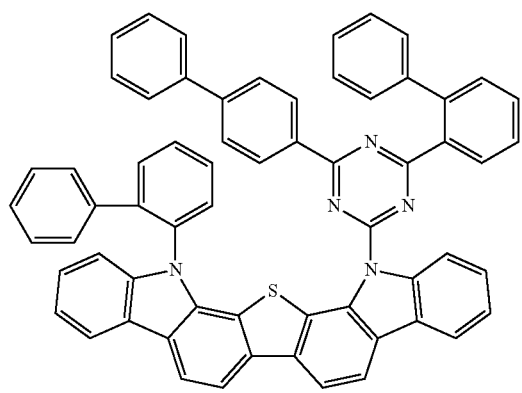
[200]
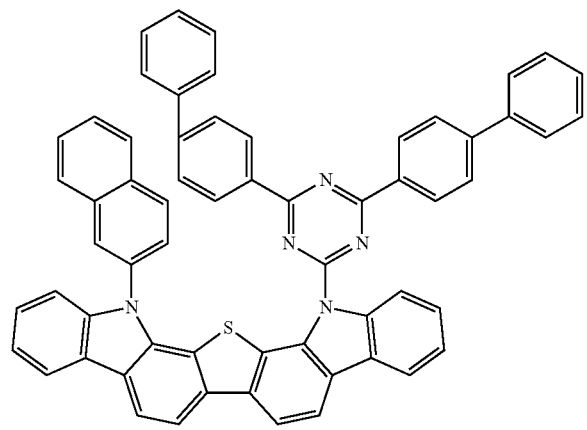
[201]
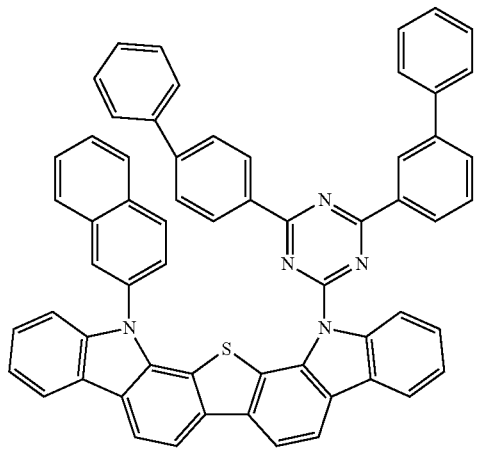
[202]
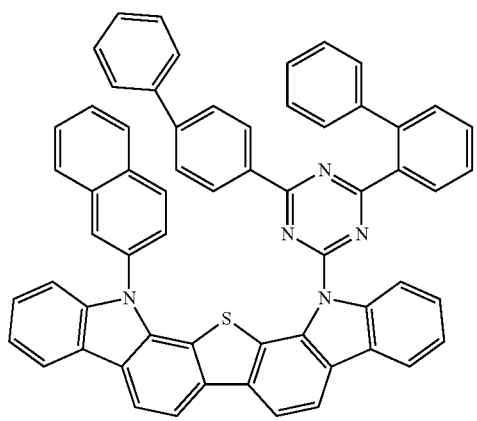
[203]
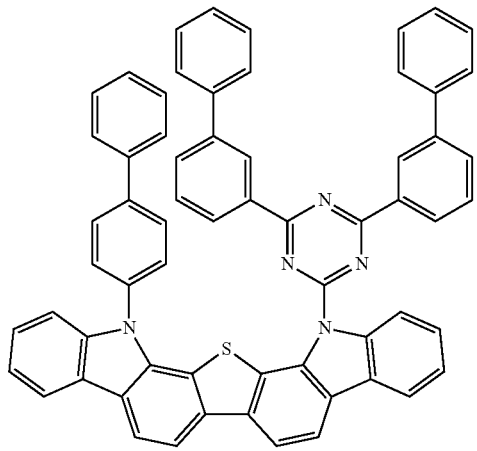

[204]
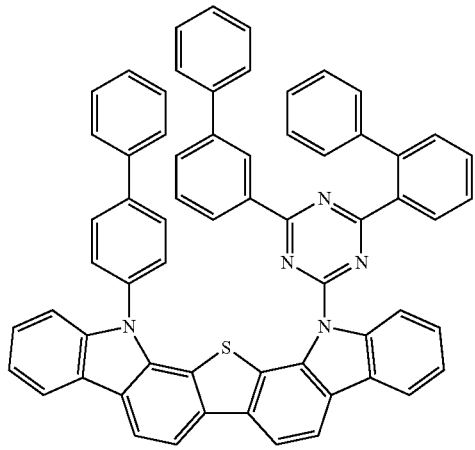
[205]
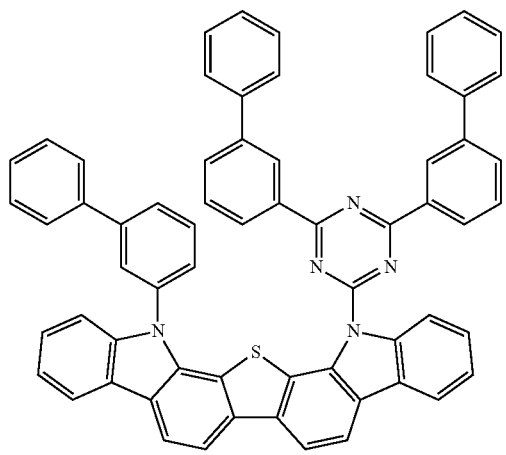
[206]
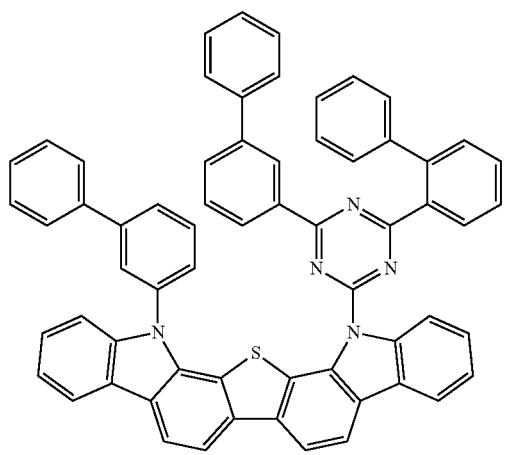
[207]
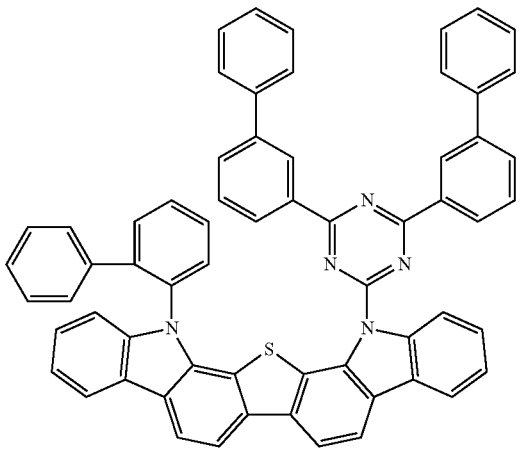
[208]
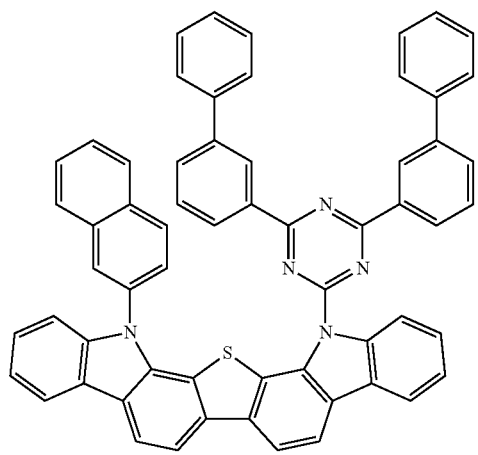
[209]

[210]
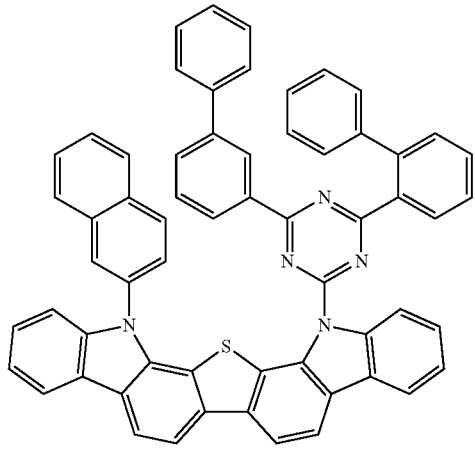
[211]
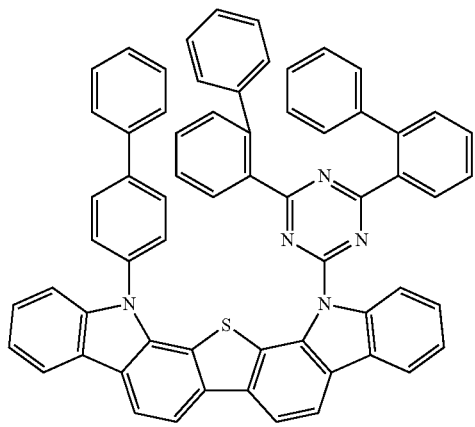
[212]
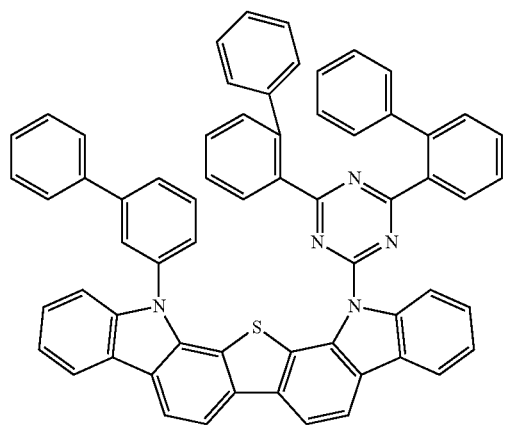
[213]
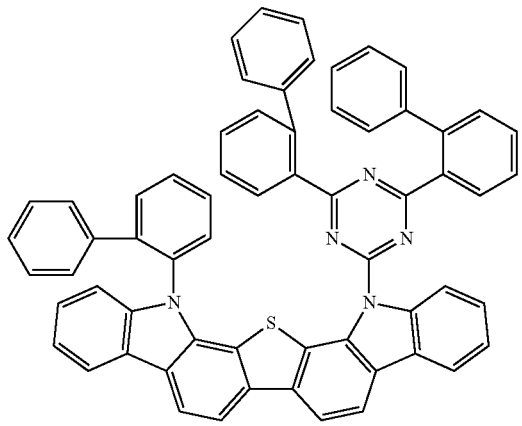
[214]
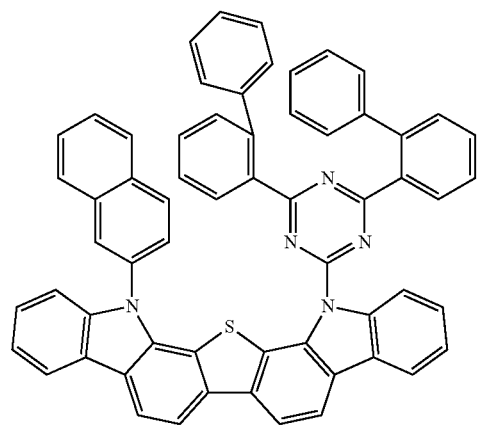
[215]
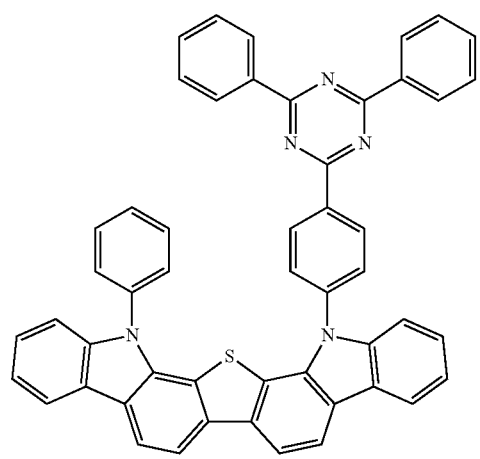

[216]
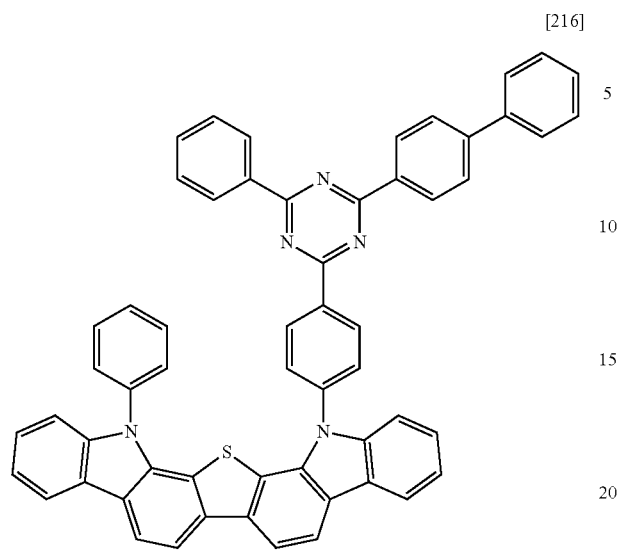
[217]
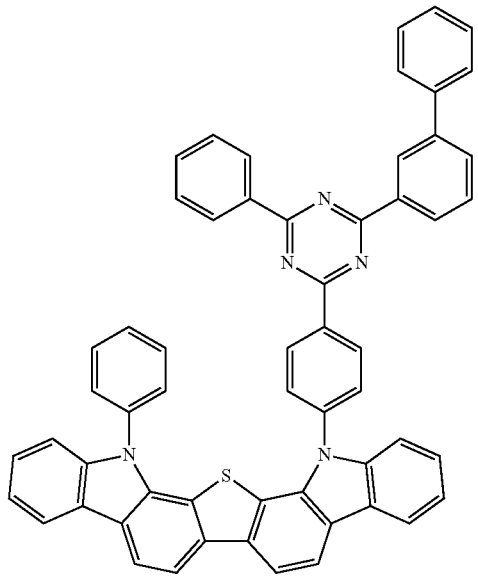
[218]
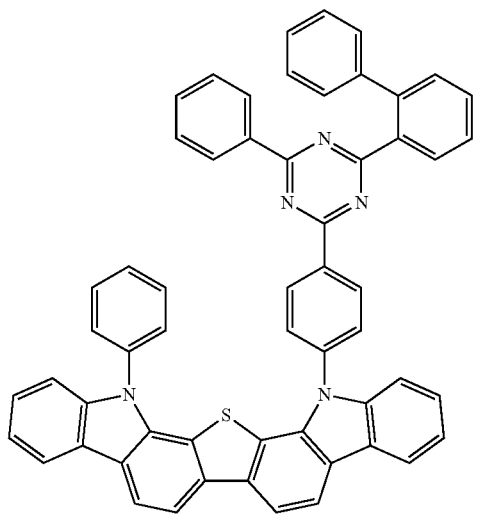
[219]
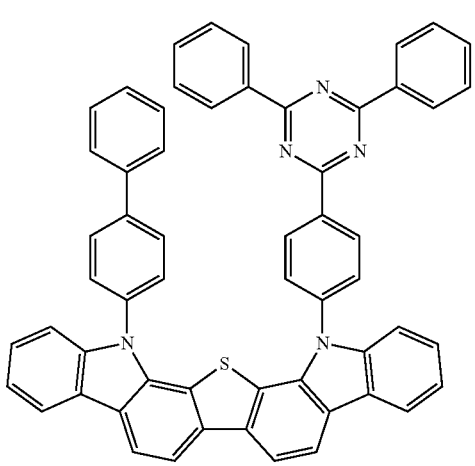
[220]
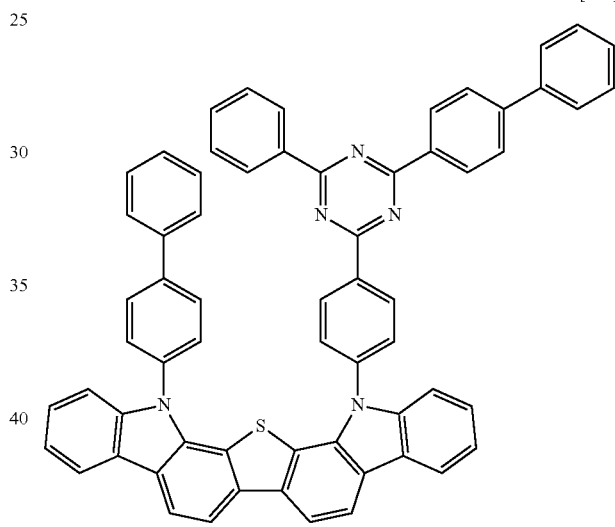
[221]
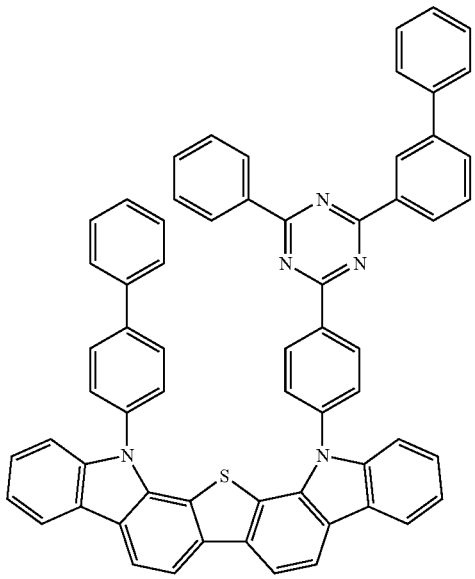

-continued
[222]
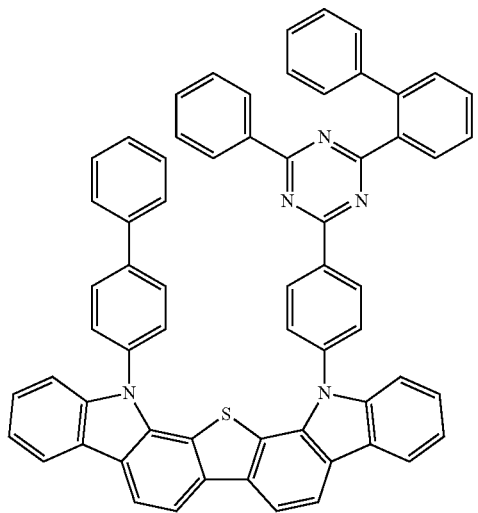
[223]
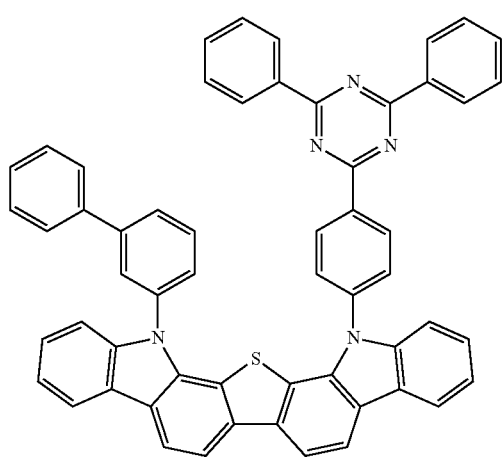
[224]
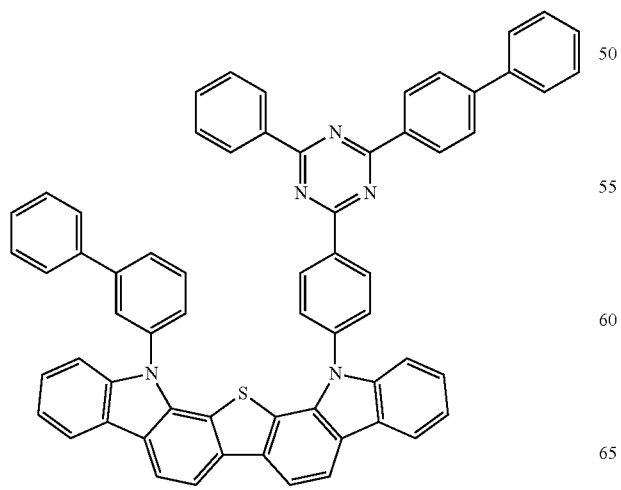
-continued
[225]
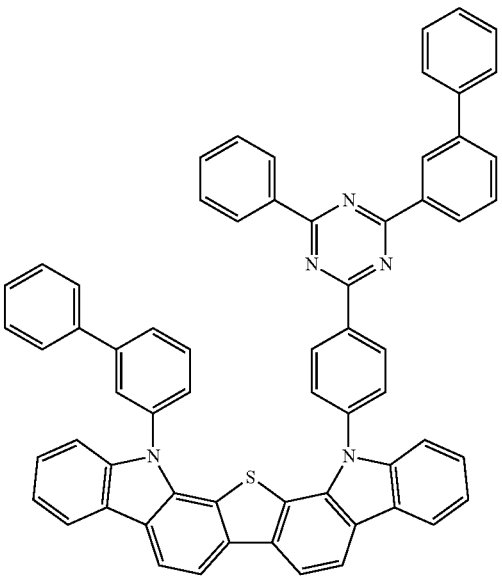
[226]
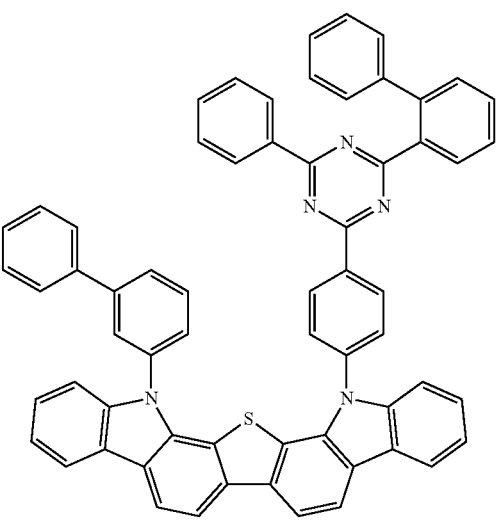
[227]
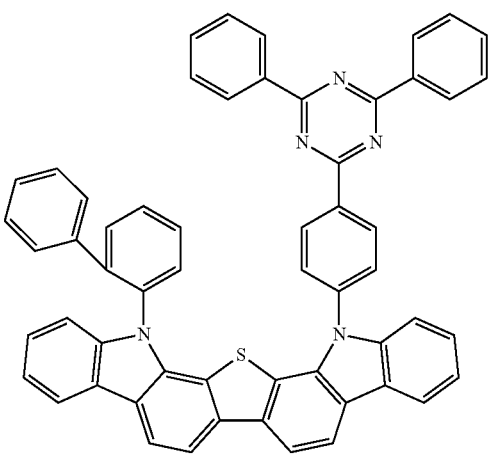

[228]
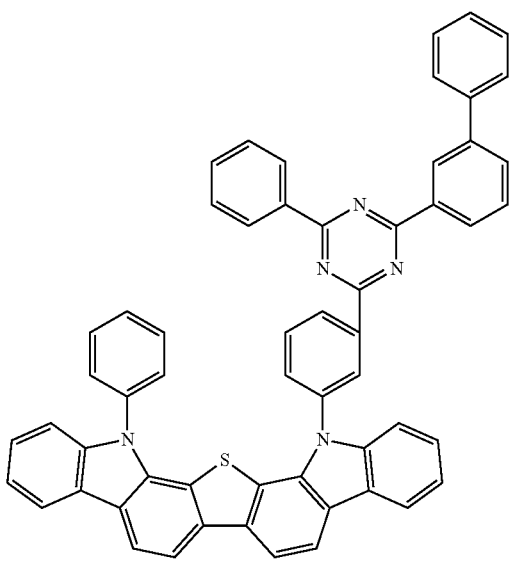
[229]
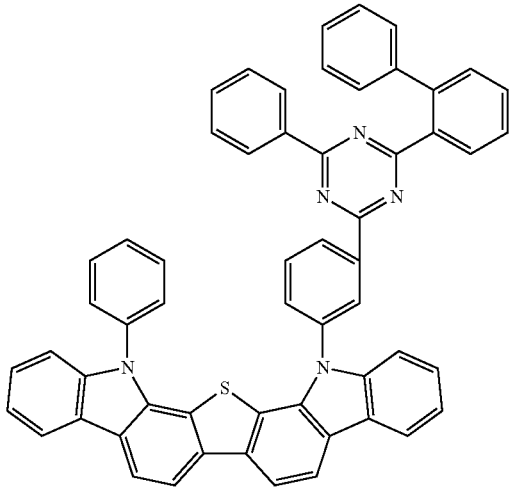
[230]
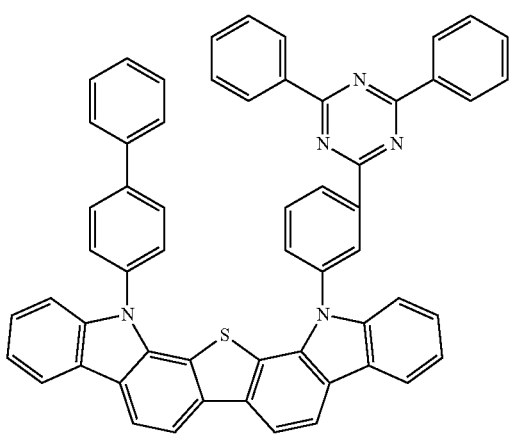
[231]
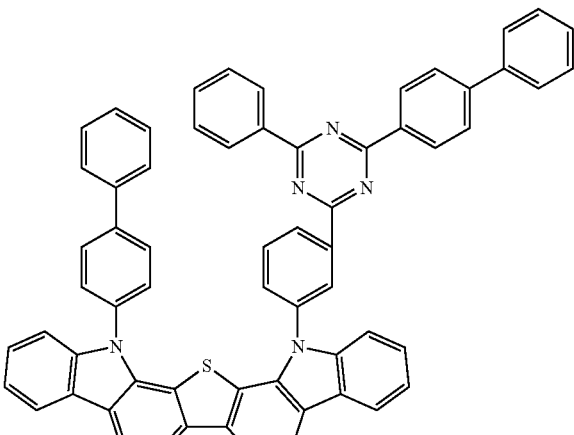
[232]
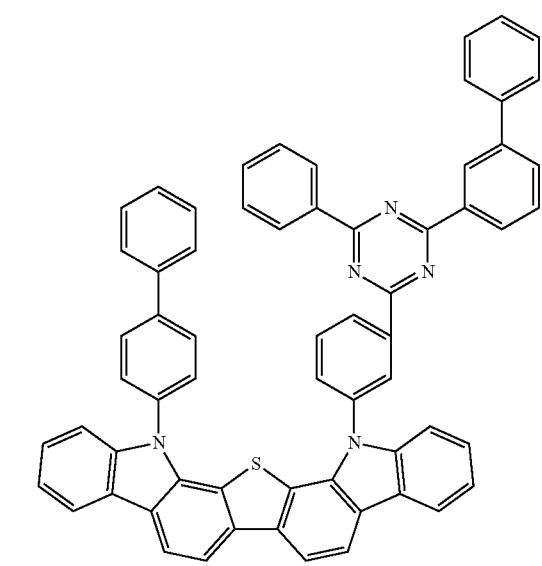
[233]
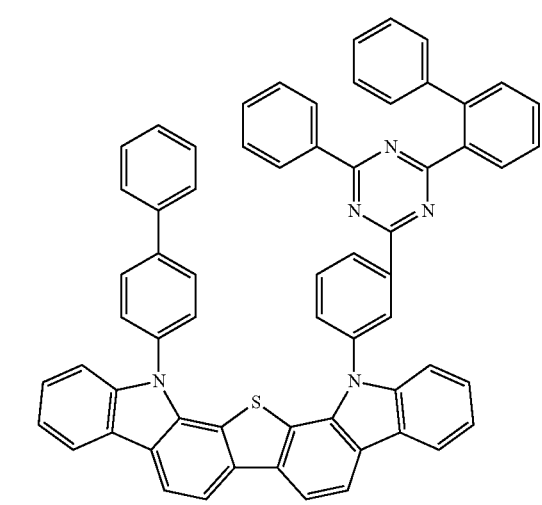

[234]
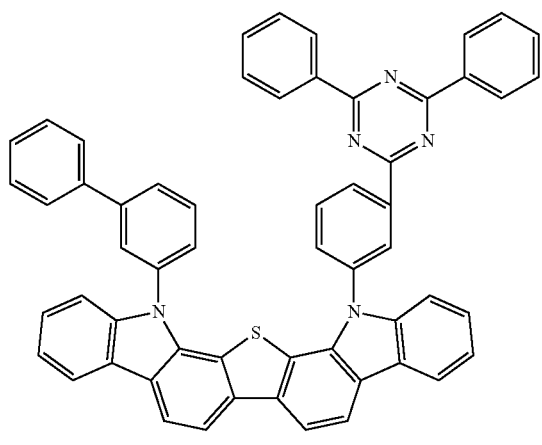
[235]
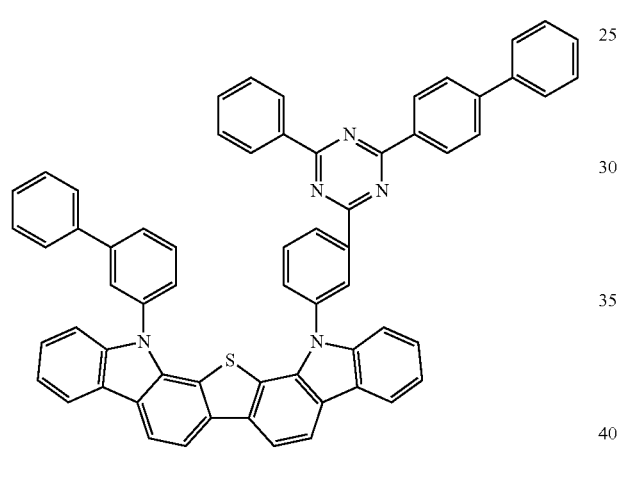
[236]
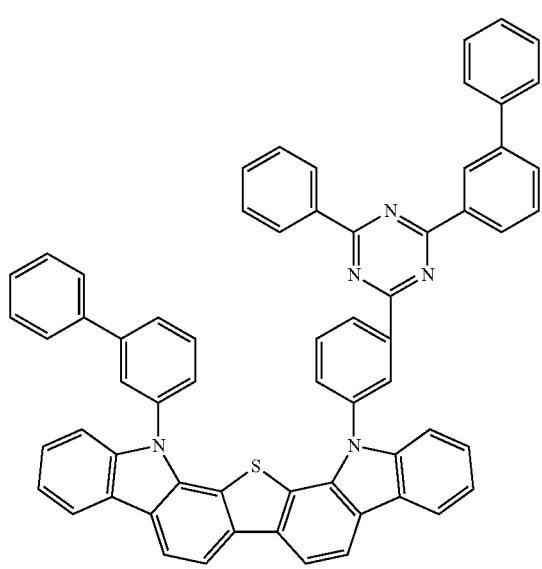
[237]
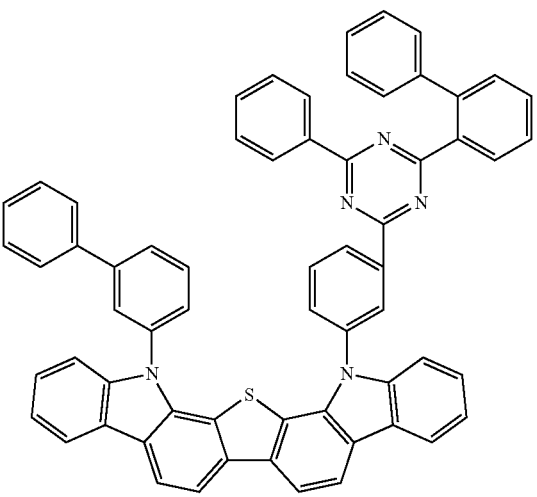
[238]
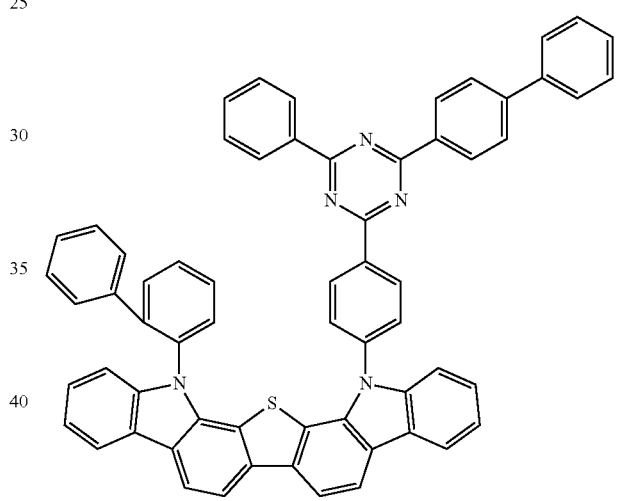
[239]
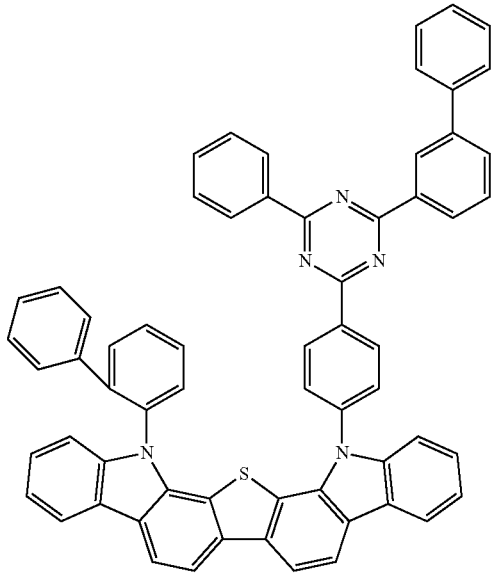

[240]
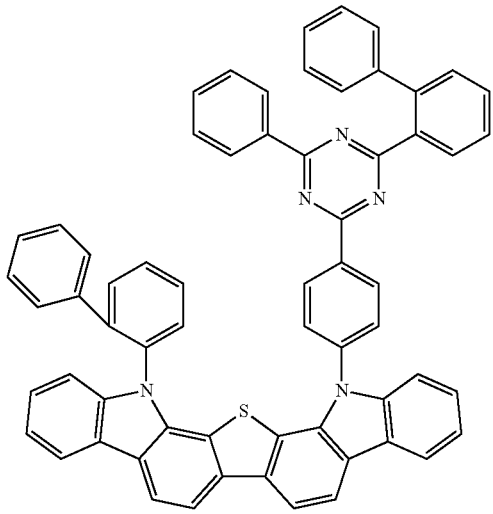
[241]
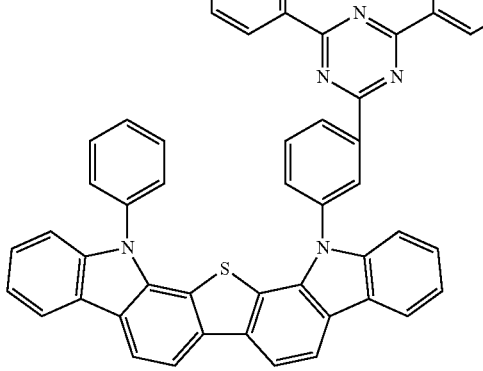
[242]
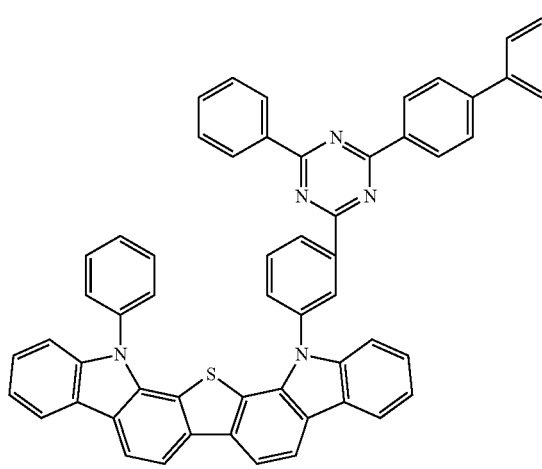
[243]
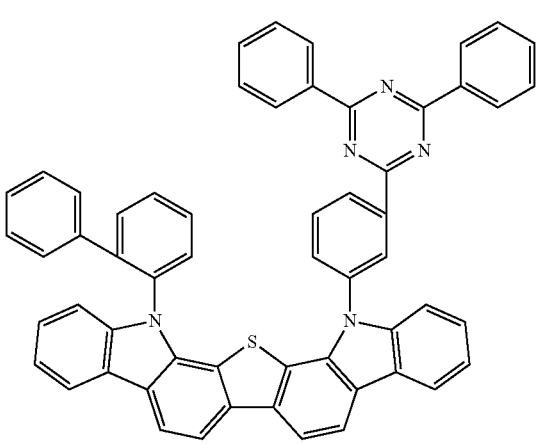
[244]
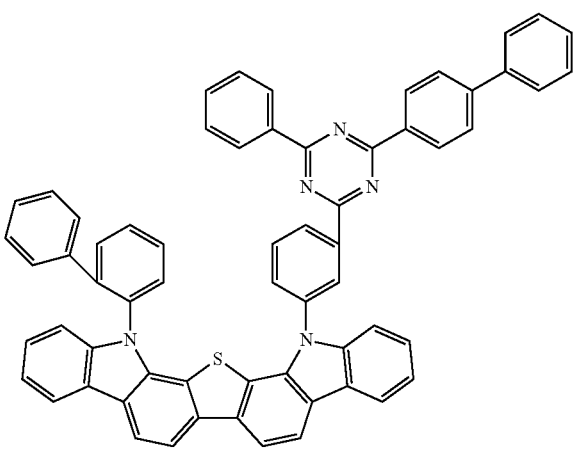
[245]
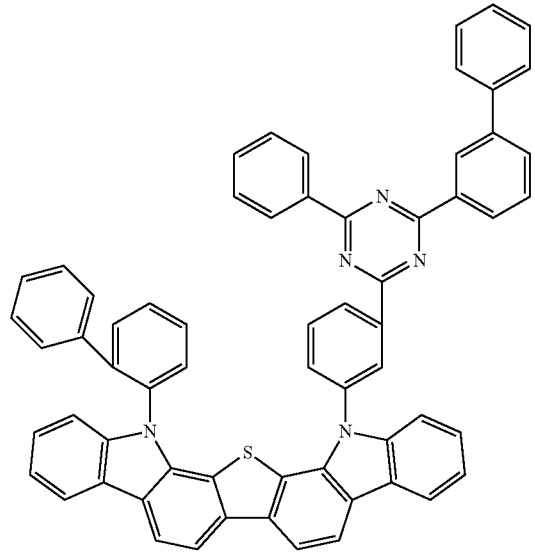

[246]
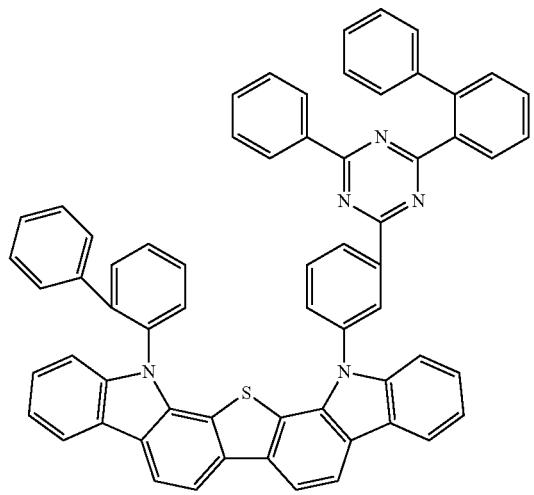
[247]
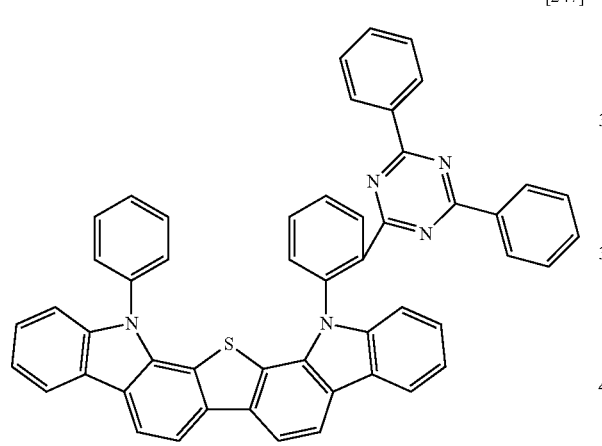
[248]
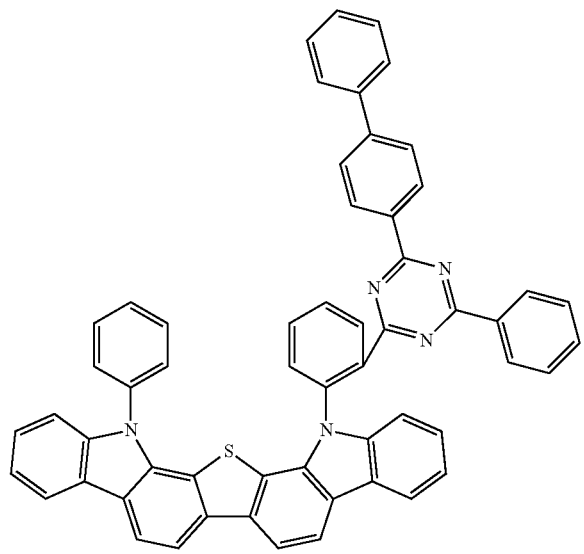
[249]
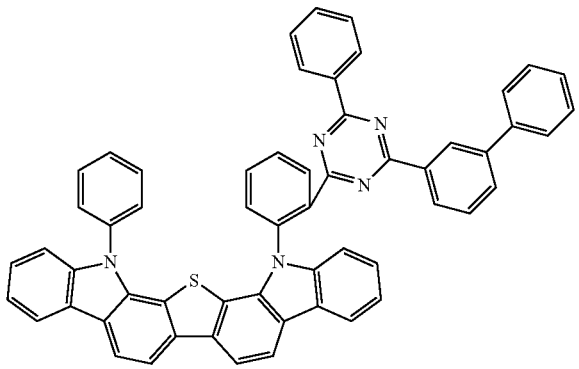
[250]
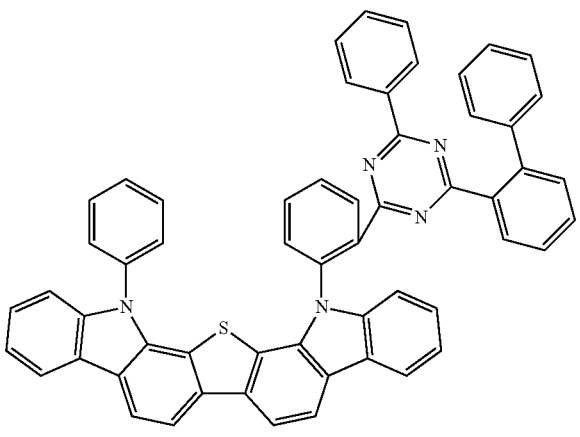
[251]
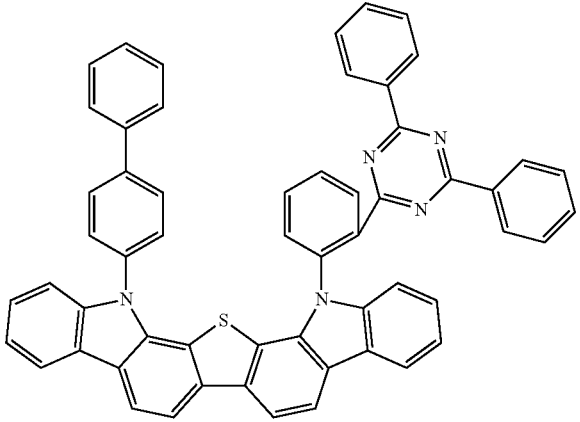

[252]
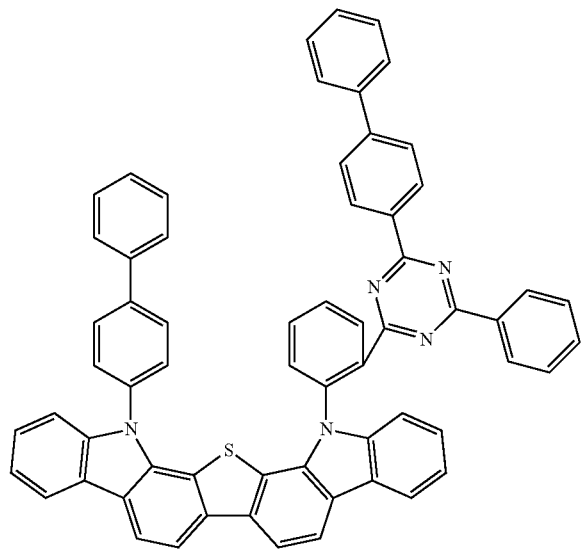
[253]
[254]
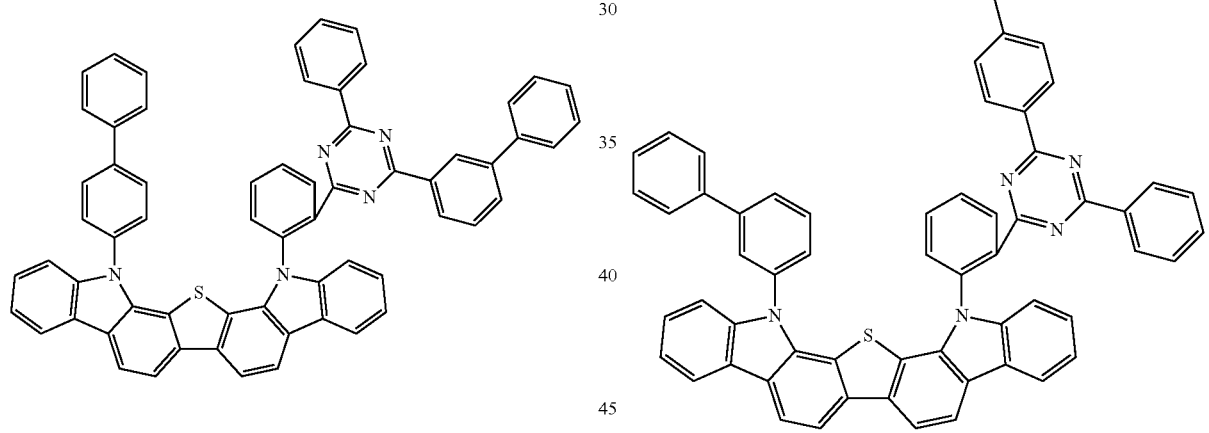
[255]
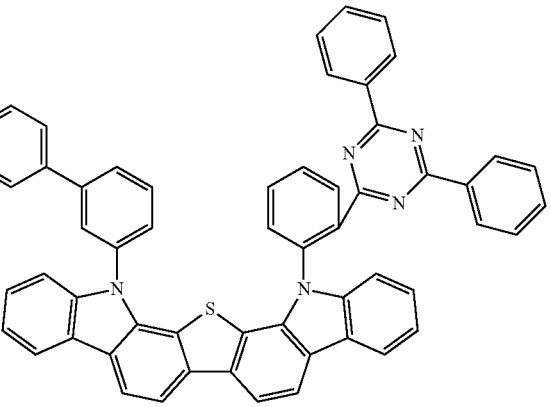
[256]
[257]
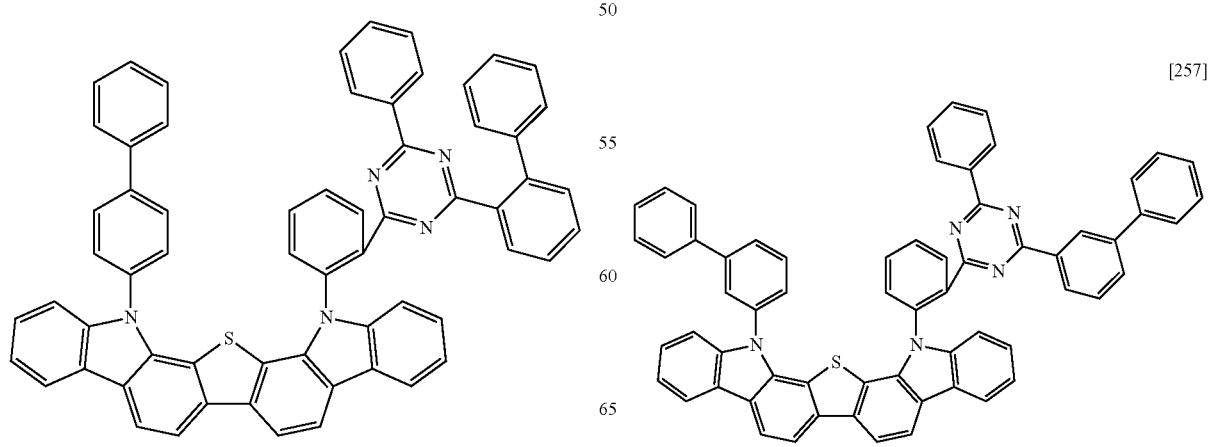

[258]
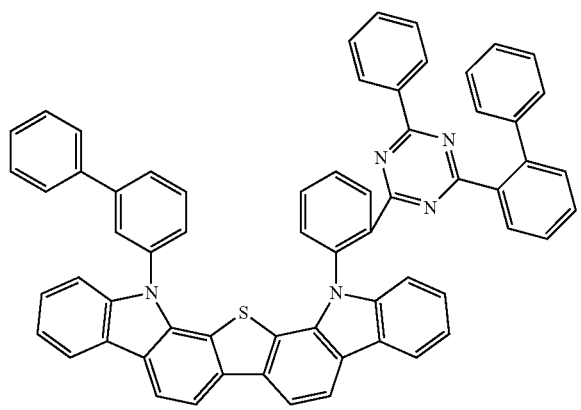
[259]
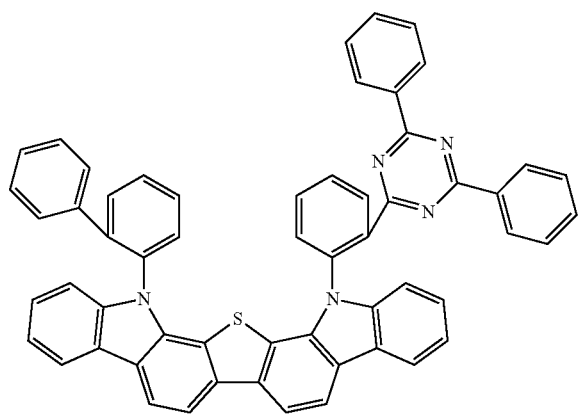
[260]
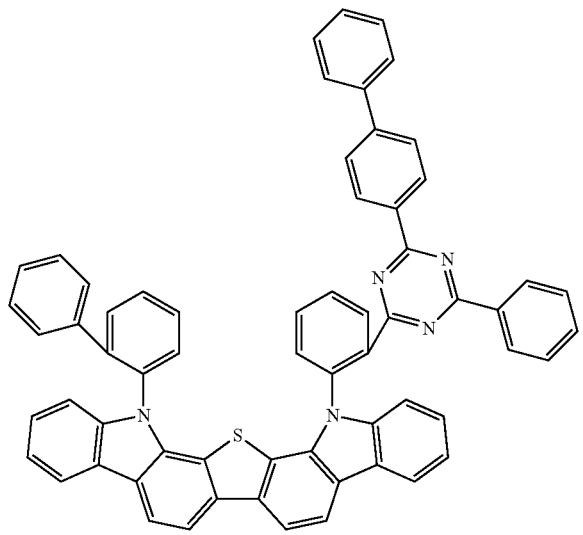
[261]
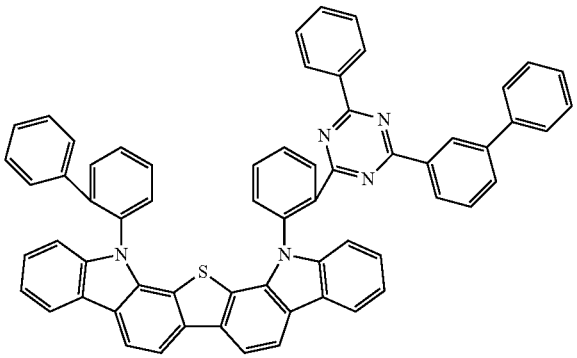
[262]
[263]
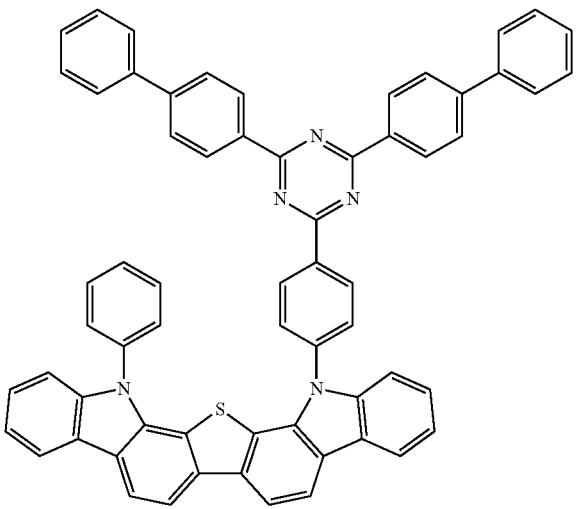

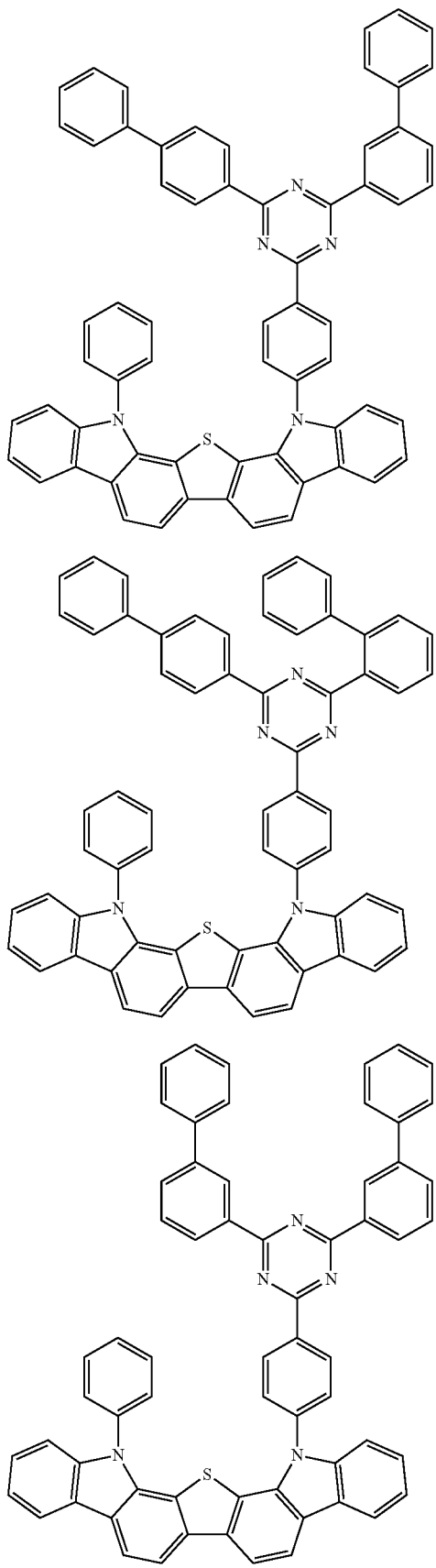
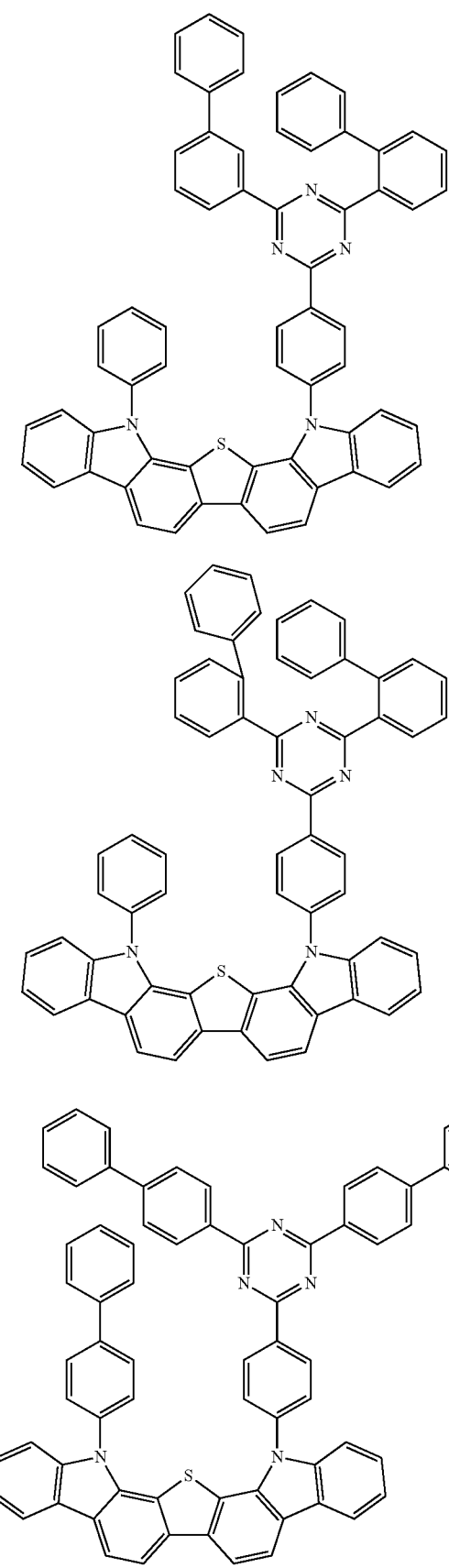

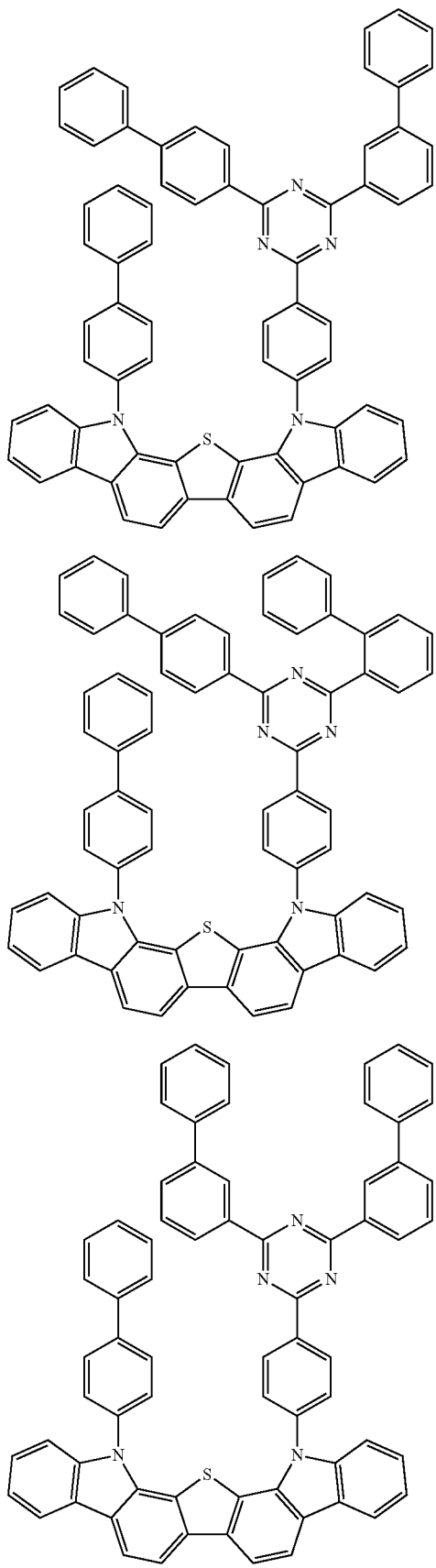
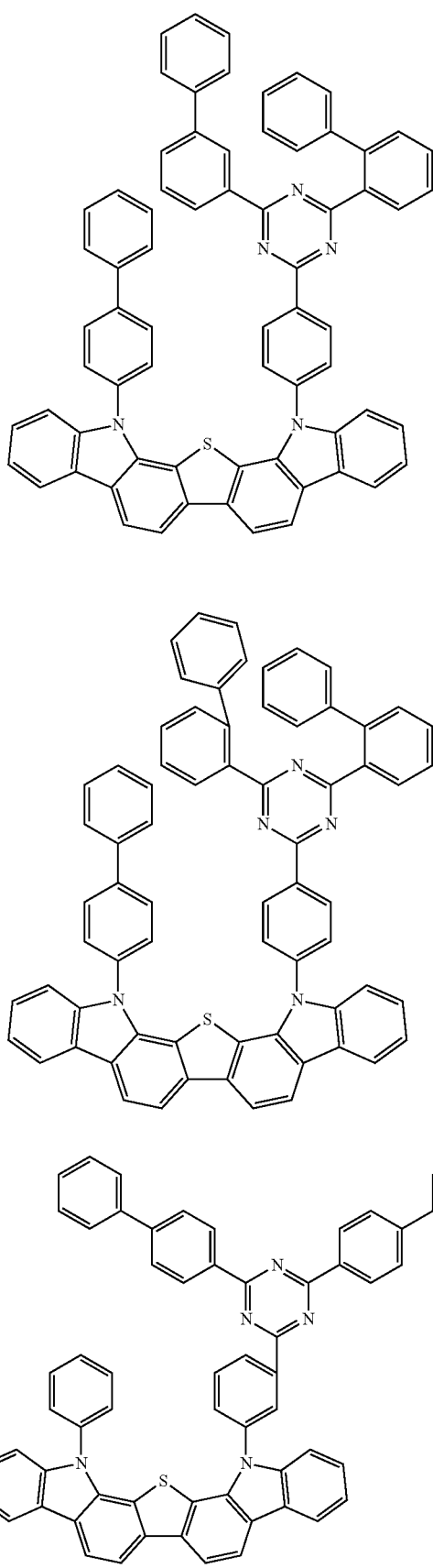

[276]
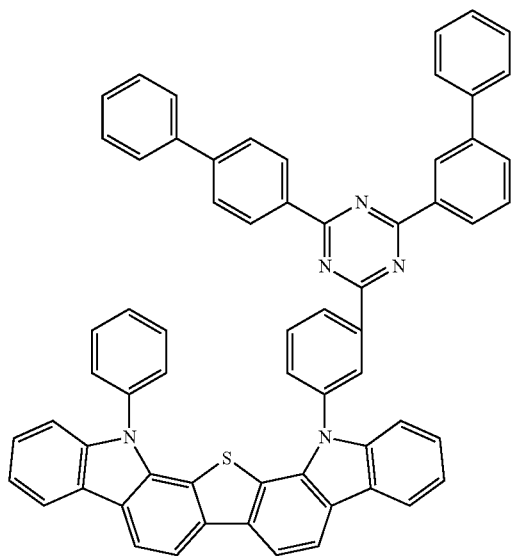
[277]
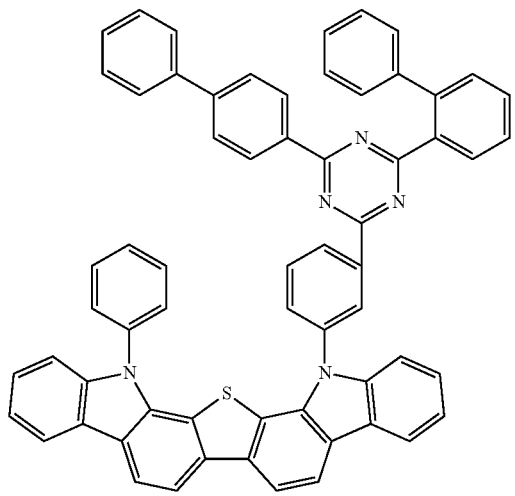
[278]
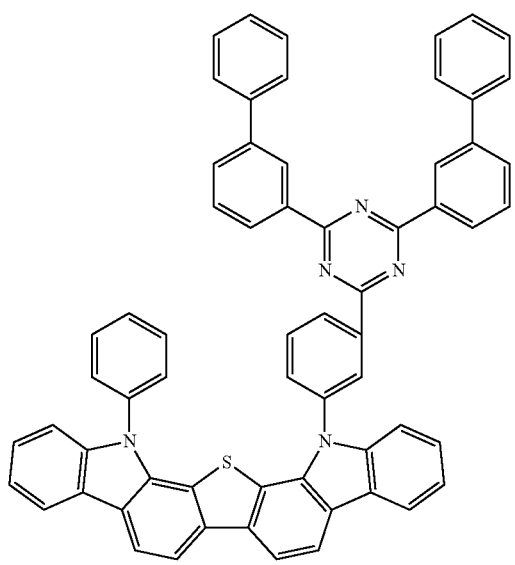
[279]
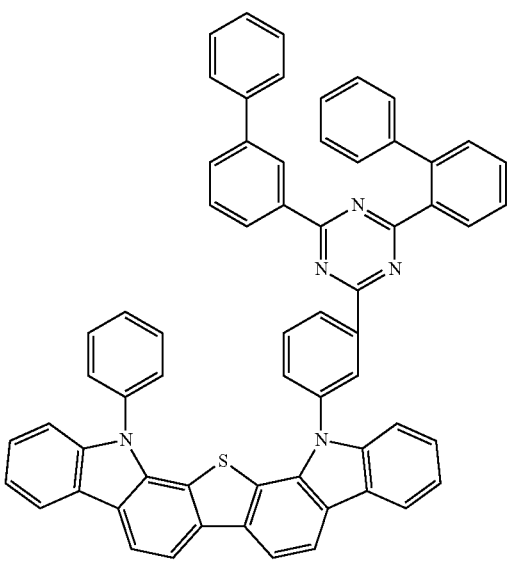
[280]
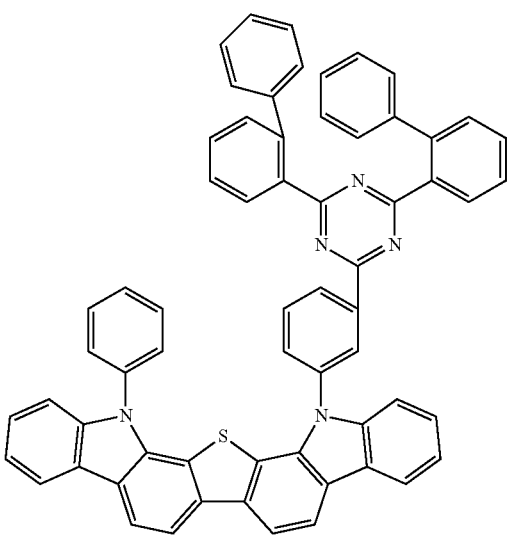
[281]
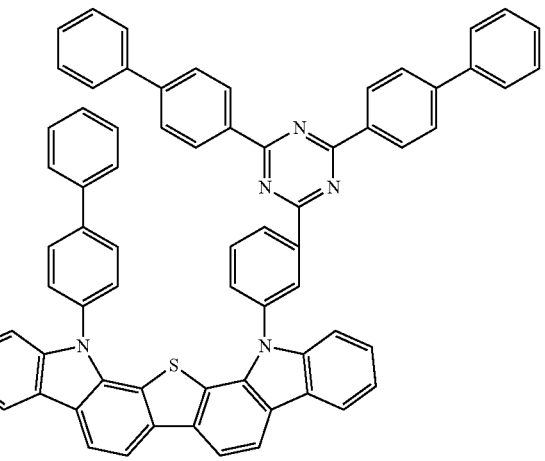

[282]
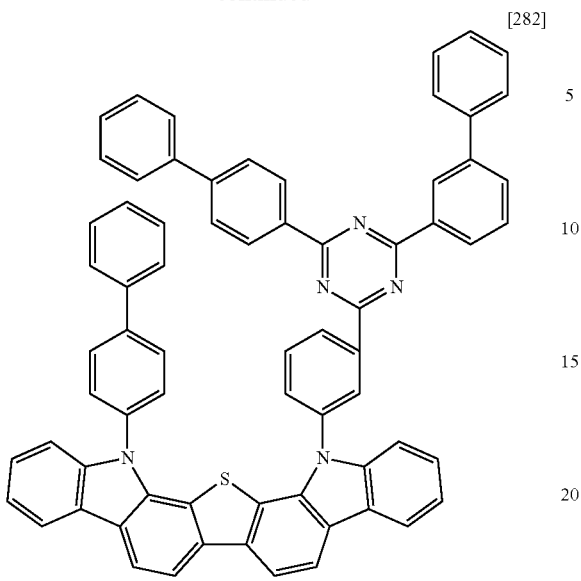
[283]
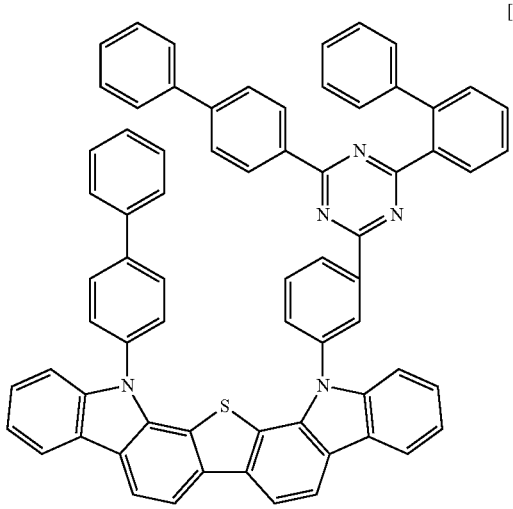
[284]
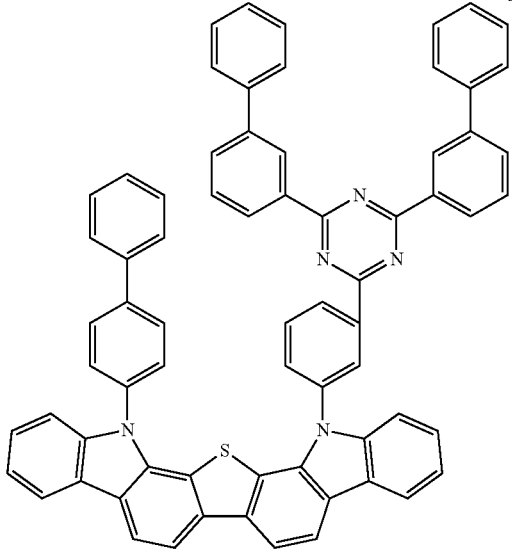
[285]
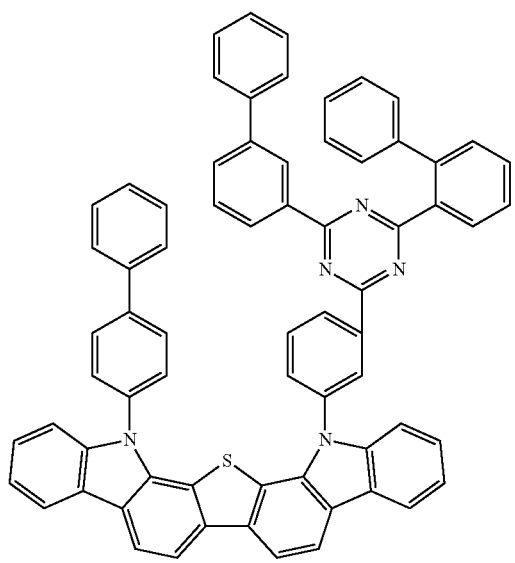
[286]
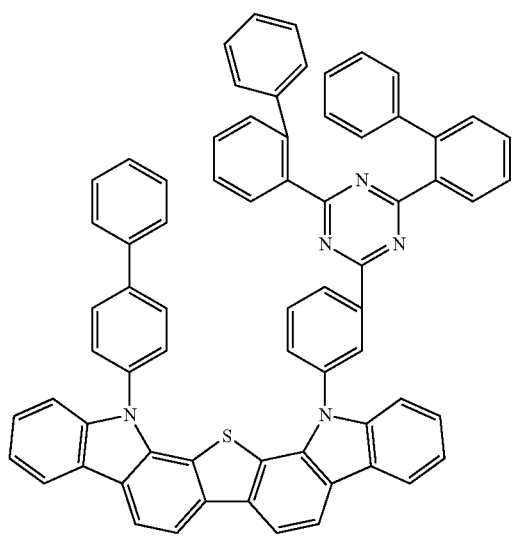
[287]
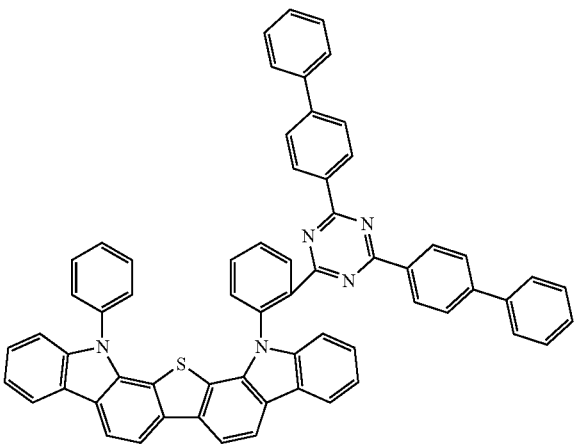

[287]
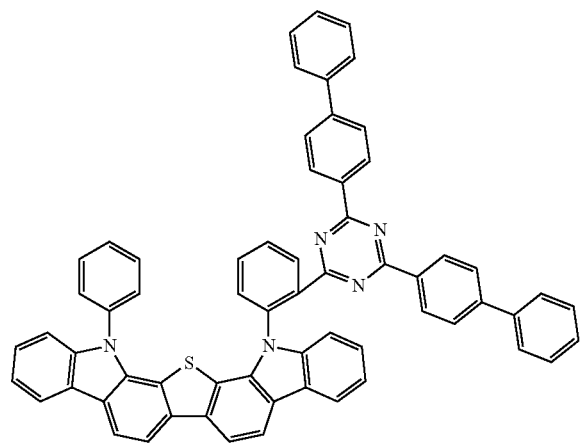
[288]
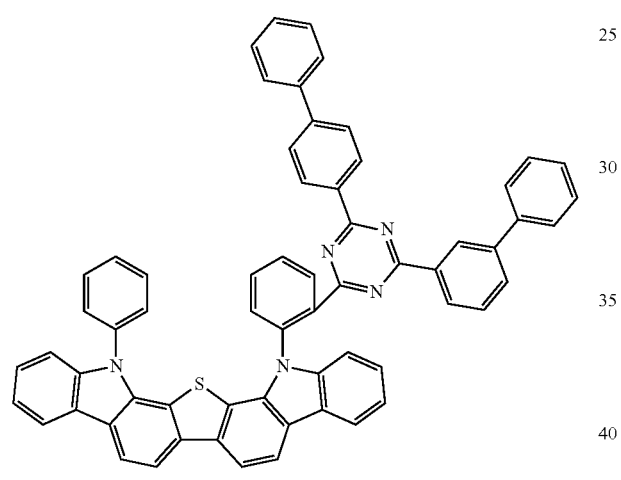
[289]
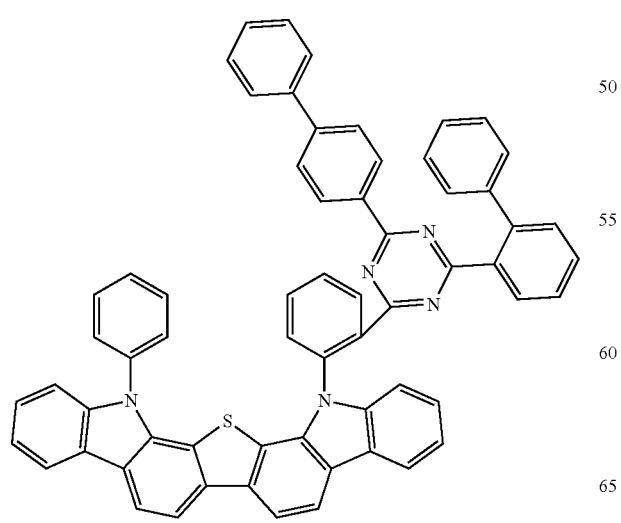
[290]
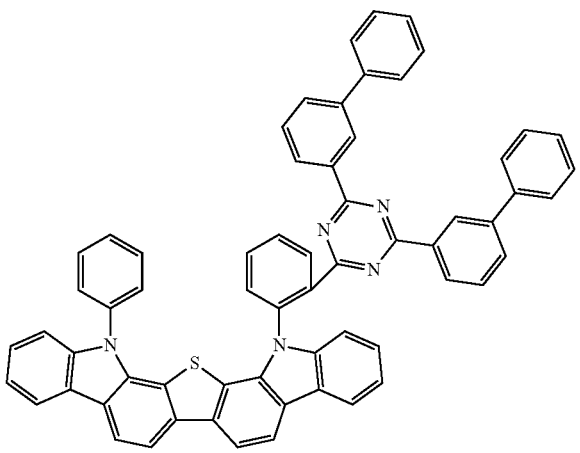
[291]
[292]
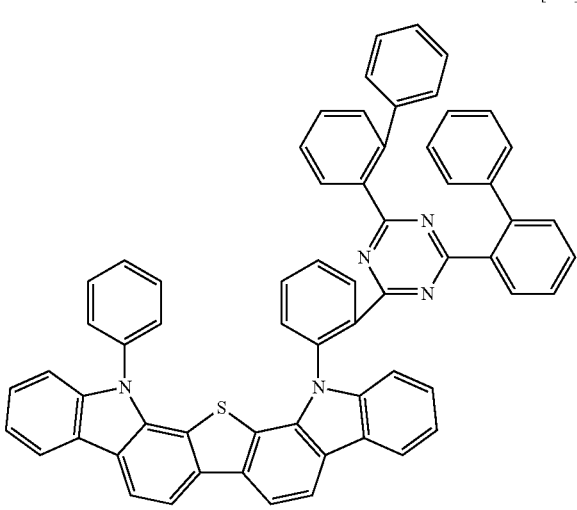

325
-continued
[293]
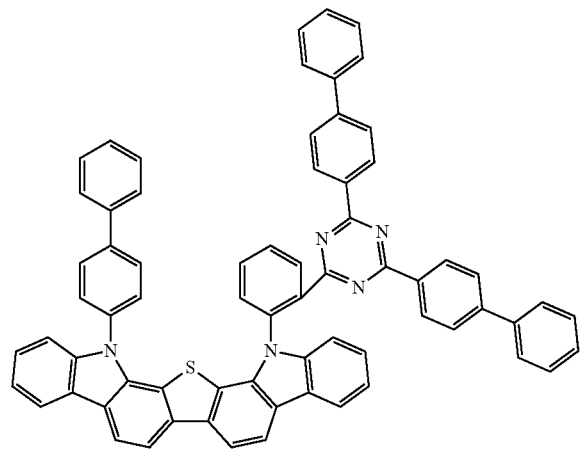
[294]
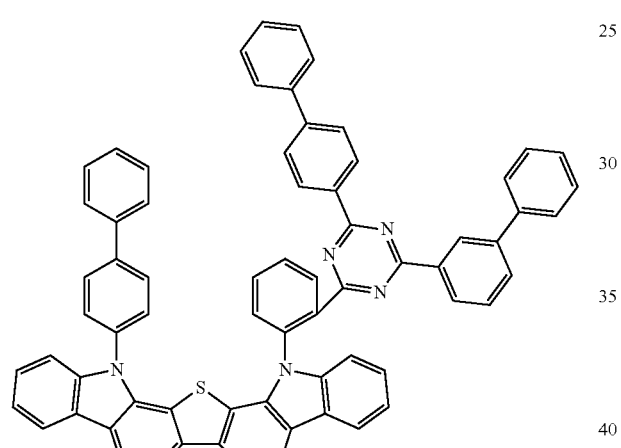
[295]
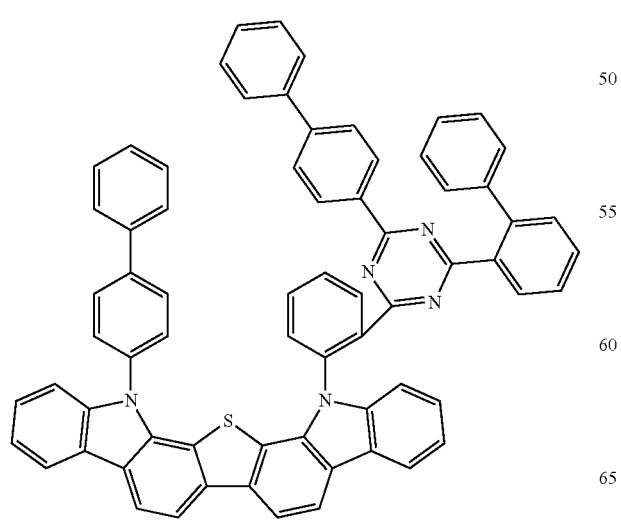
326
-continued
[296]
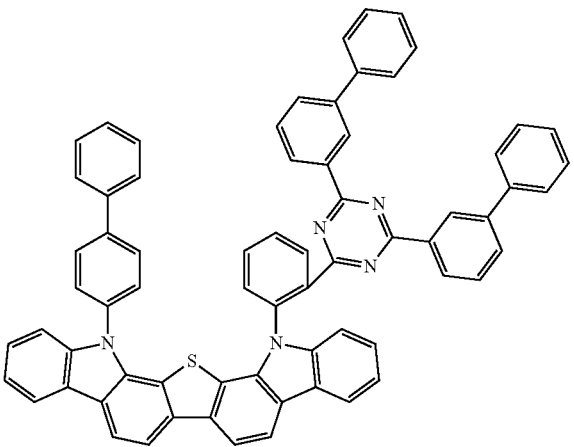
[297]
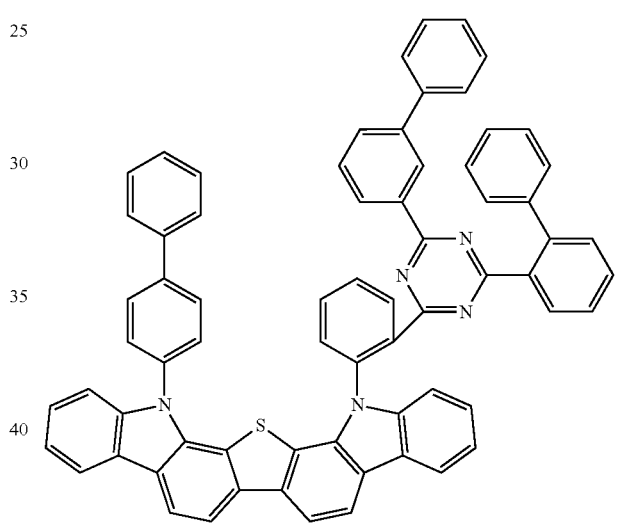
[298]
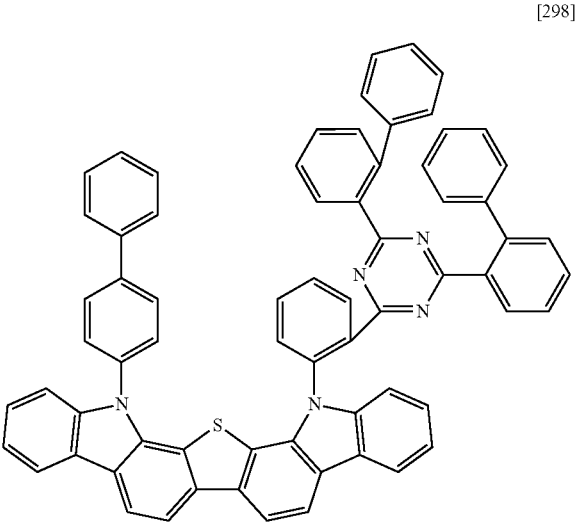

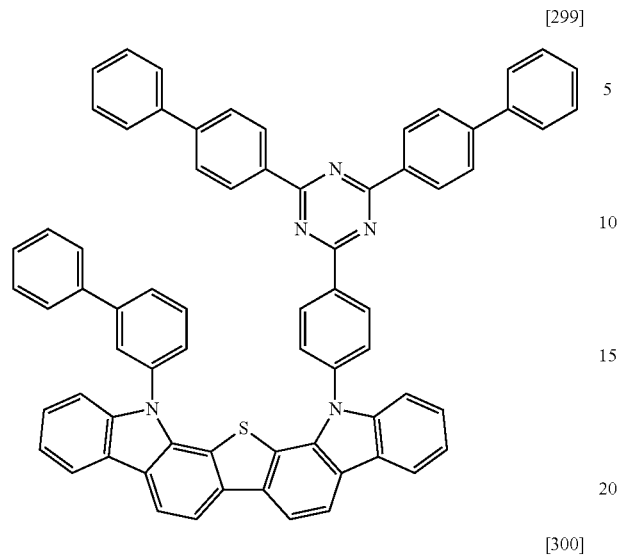
[299]
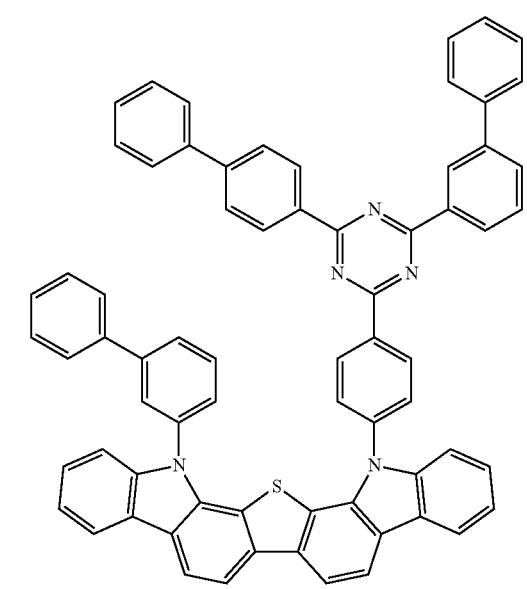
[300]
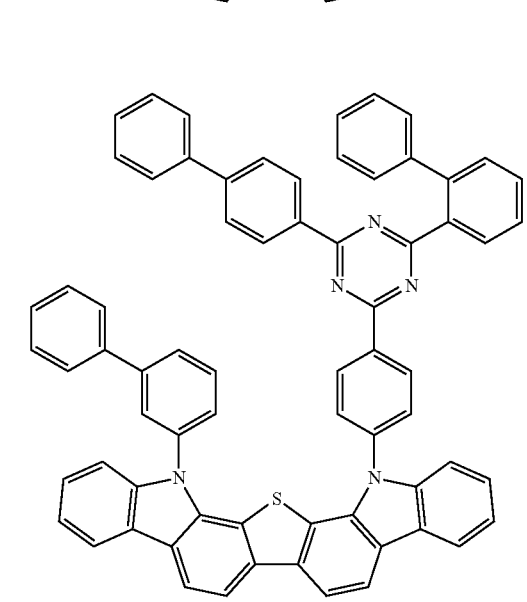
[301]
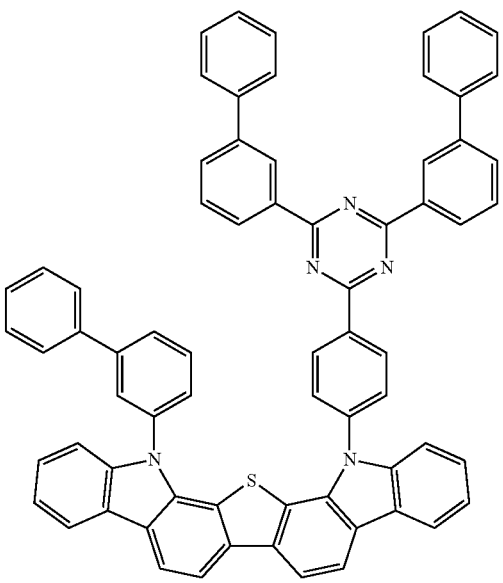
[302]
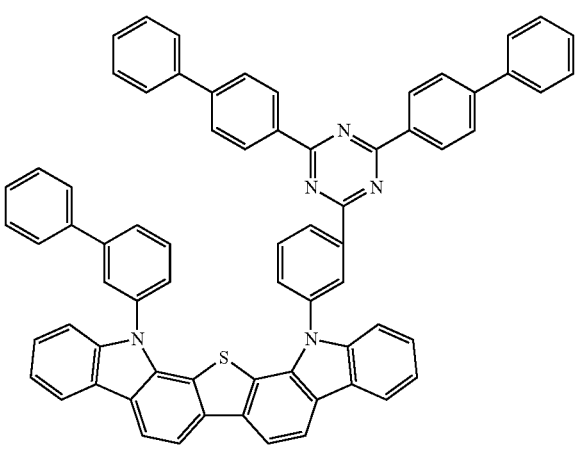
[303]
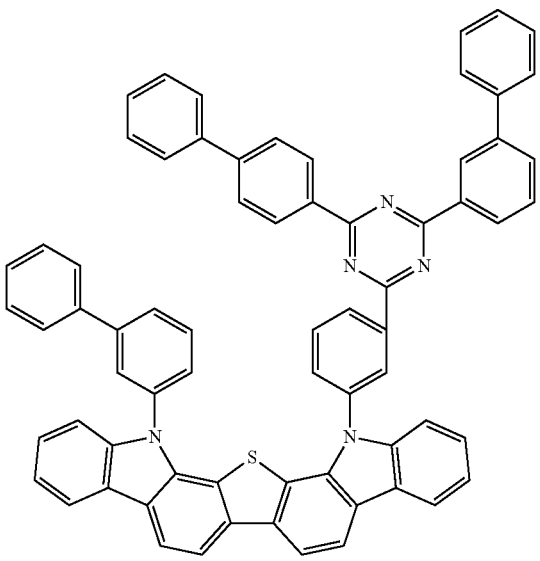
[304]

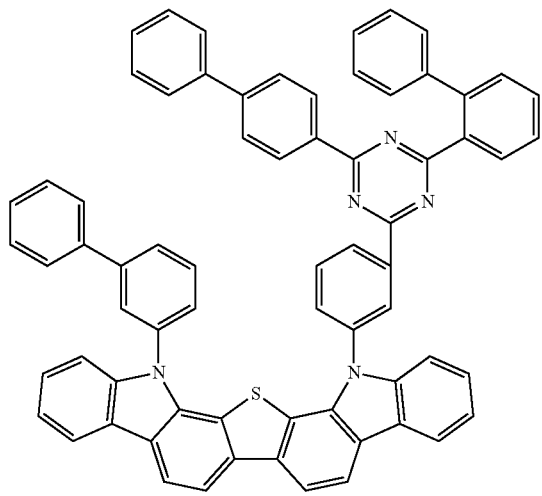
[305]
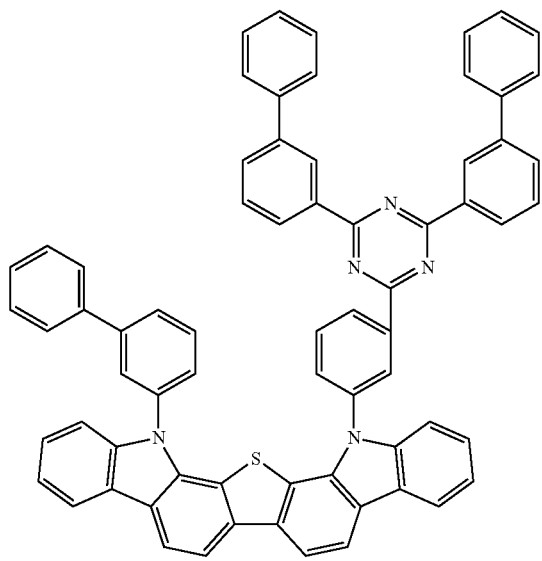
[306]
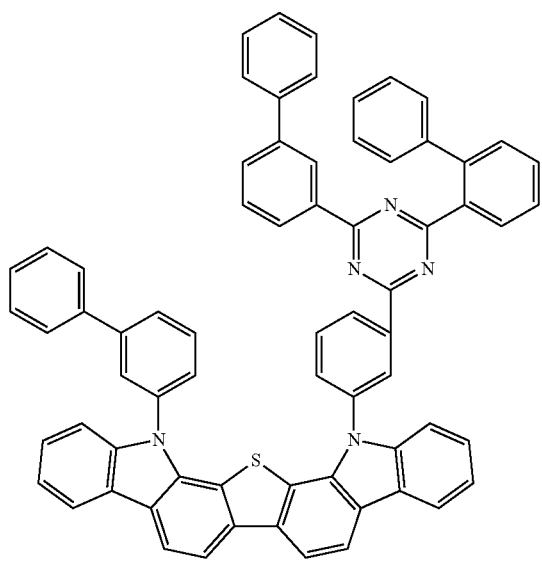
[307]
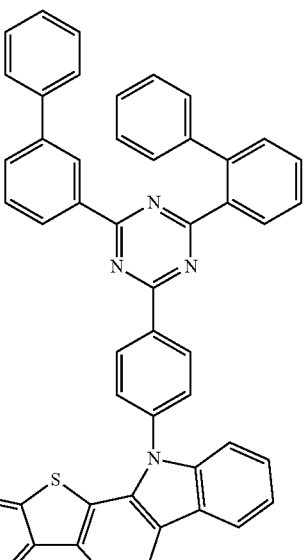
[308]
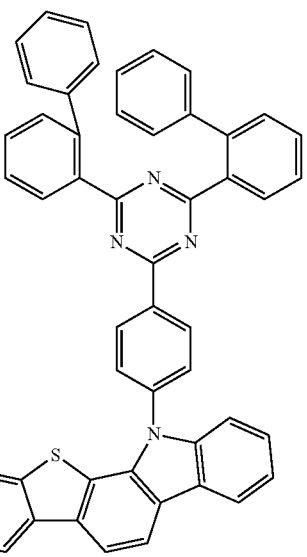
[309]

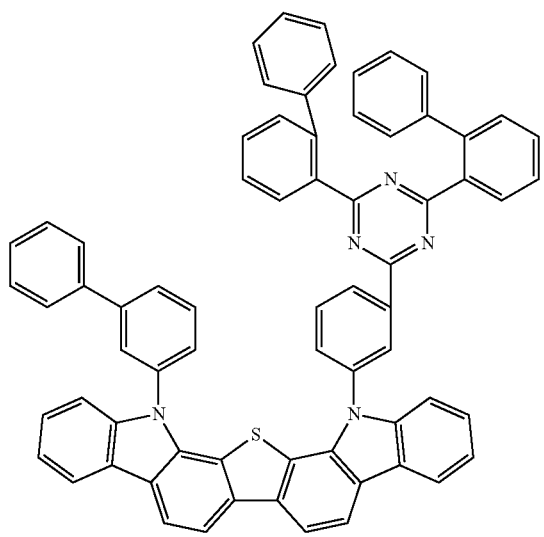
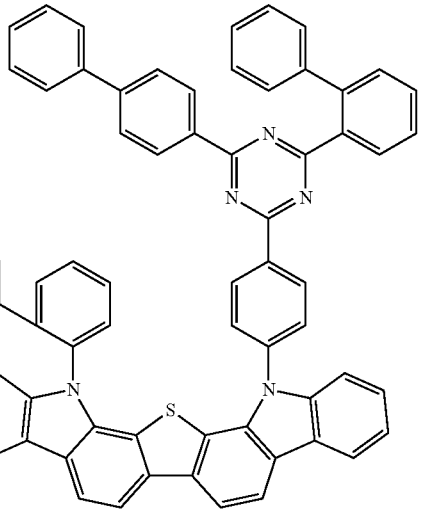
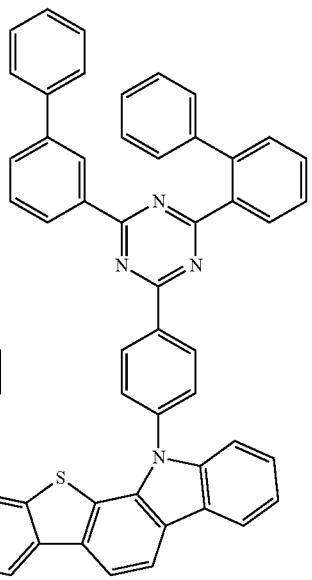
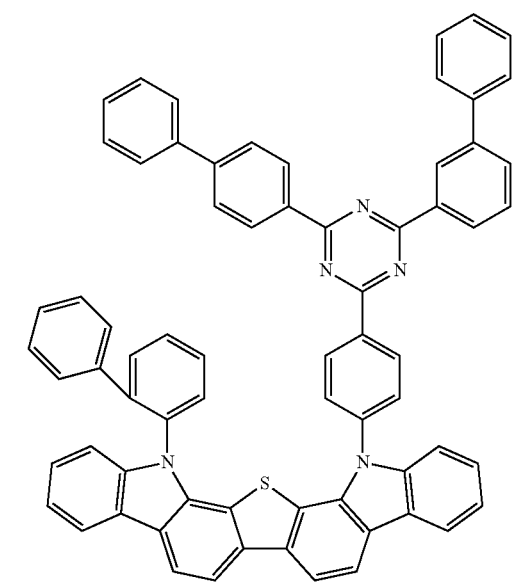

333
-continued
[316]
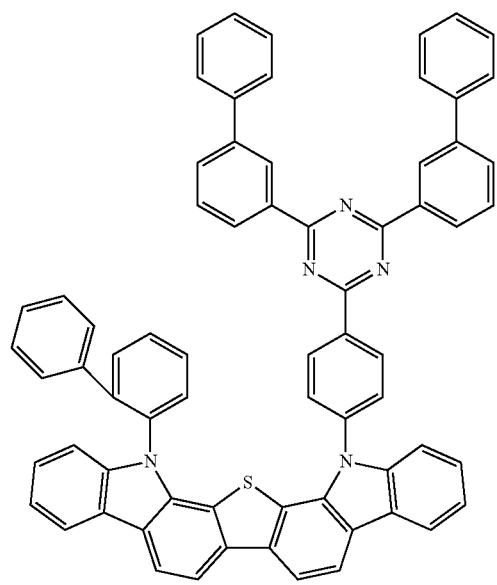
[317]
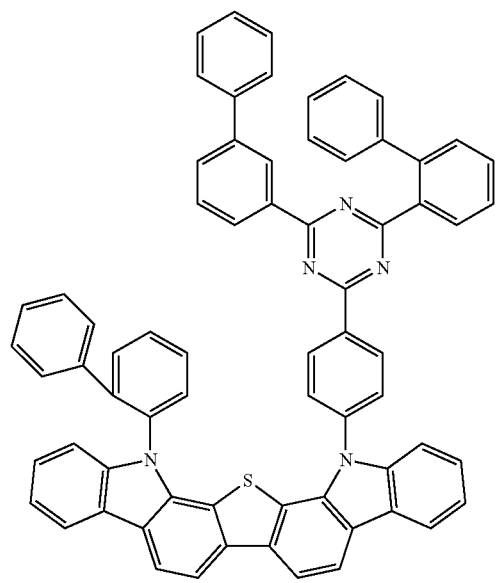
[318]
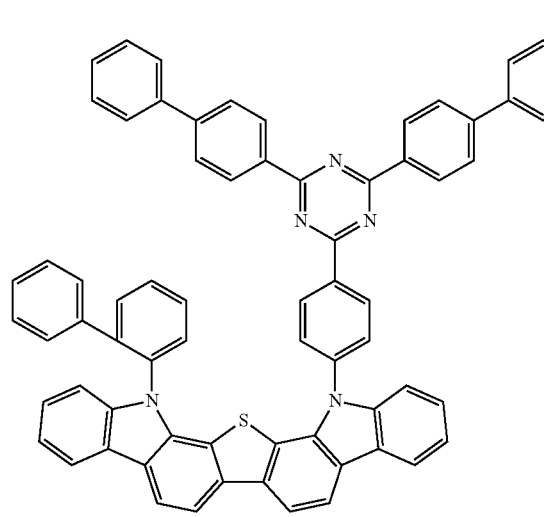
334
-continued
[319]
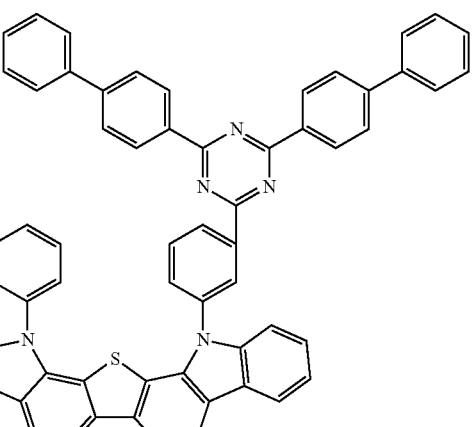
[320]
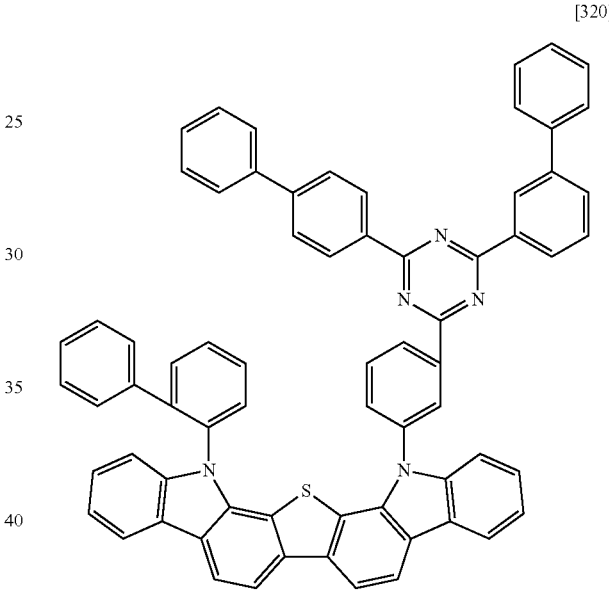
[321]
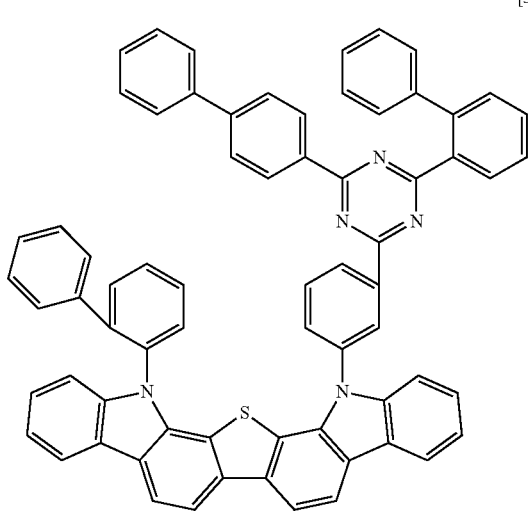

[322]
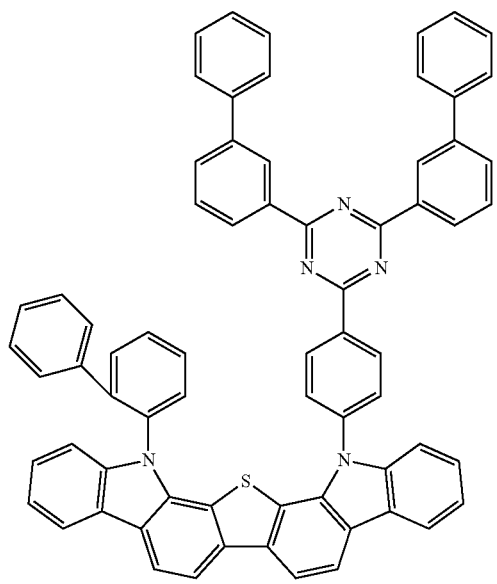
[323]
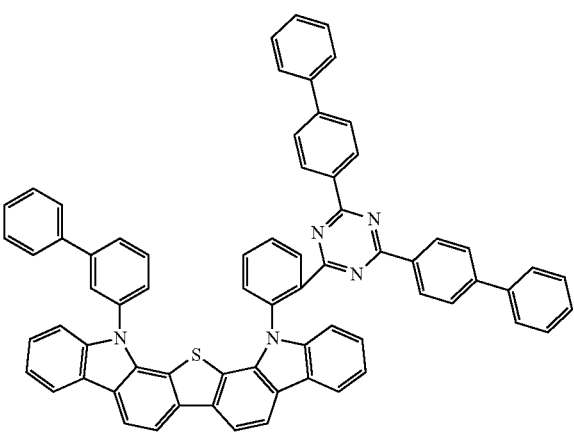
[324]
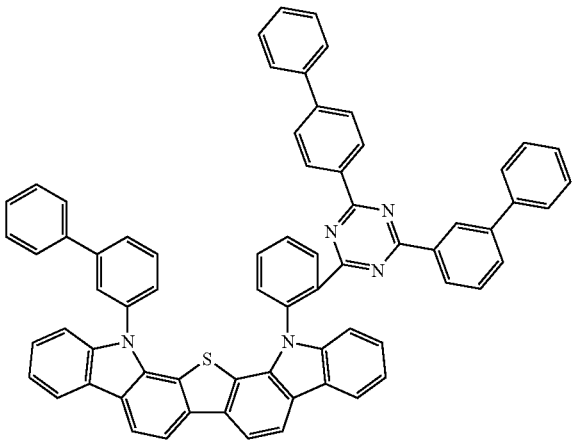
[325]
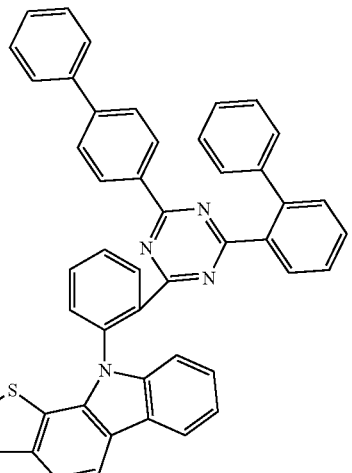
[326]
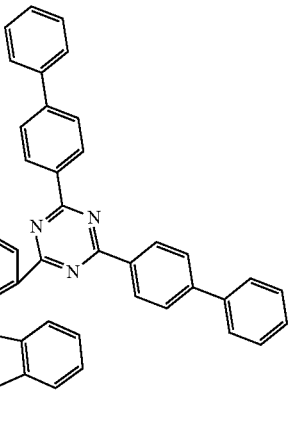
[327]
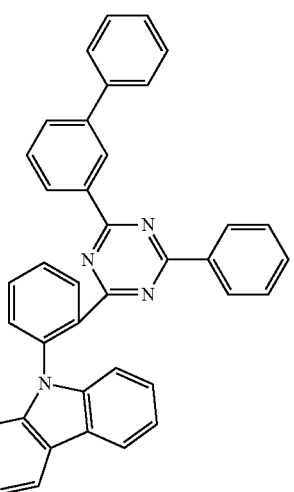

[328]
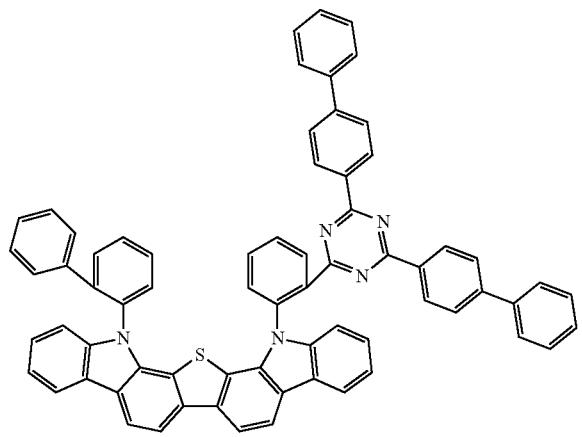
[329]
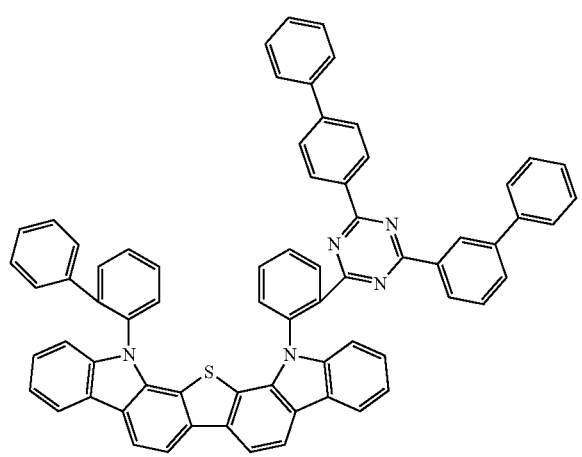
[330]
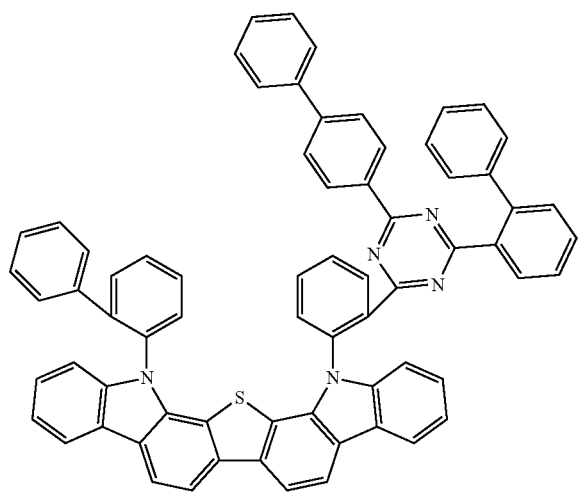
[331]
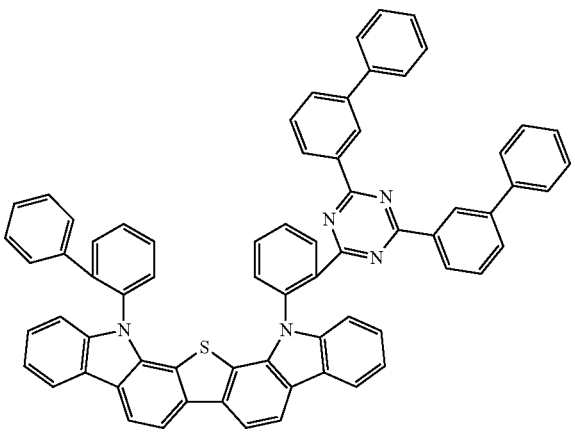
[332]
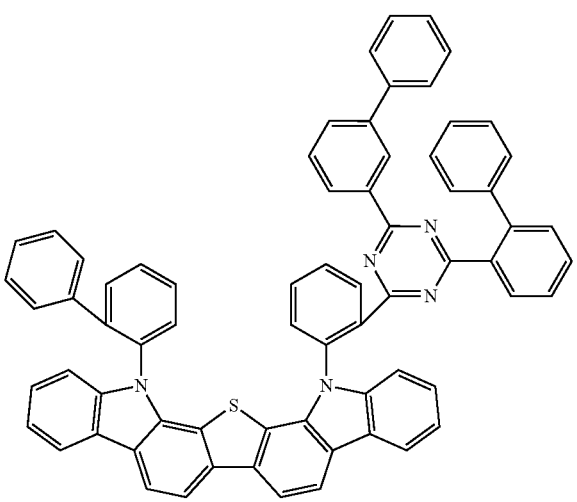
[333]
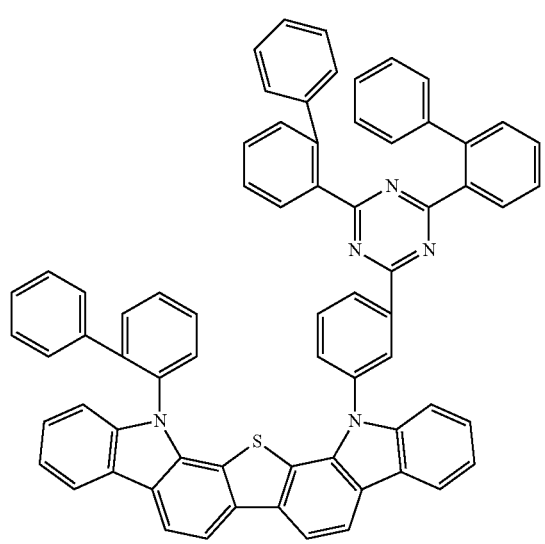

-continued

[334]

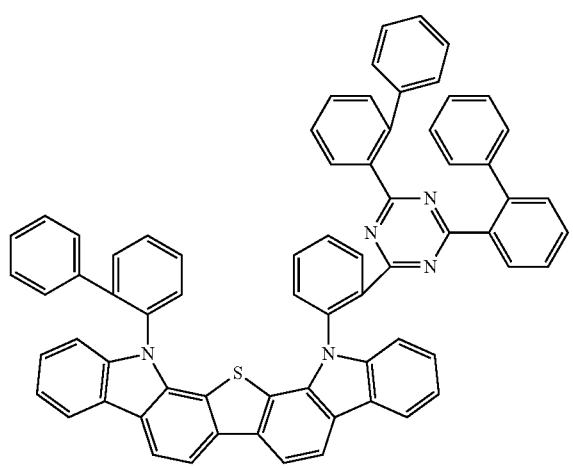

[Chemical Formula 3]

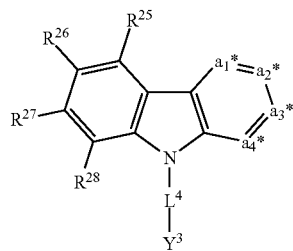

[Chemical Formula 4]

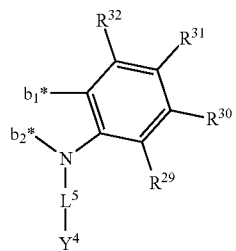

in Chemical Formula 3 and Chemical Formula 4, $Y^3$ and $Y^4$ are each independently a substituted or unsubstituted C6 to C20 aryl group or a substituted or unsubstituted C2 to C30 heterocyclic group, two adjacent ones of $a_1{}^*$ to $a_4{}^*$ of Chemical Formula 3 are linking carbons linked at $b_1{}^*$ and $b_2{}^*$ of Chemical Formula 4, the remaining two of $a_1{}^*$ to $a_4{}^*$ of Chemical Formula 3, not linked at $b_1{}^*$ and $b_2{}^*$ of Chemical Formula 4, are each independently C-$L^a$-$R^b$, $L^a$, $L^4$, and $L^5$ are each independently a single bond or a substituted or unsubstituted C6 to C20 arylene group, and $R^b$ and $R^{25}$ to $R^{32}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

8. The composition as claimed in claim 7, wherein:

the second compound is represented by Chemical Formula 2,

Chemical Formula 2 is represented by Chemical Formula 2-8:

7. A composition for an organic optoelectronic device, the composition comprising a first compound and a second compound, wherein:

the first compound is the compound for an organic optoelectronic device as claimed in claim 1, and the second compound is represented by Chemical Formula 2; or a combination of Chemical Formula 3 and Chemical Formula 4:

[Chemical Formula 2]

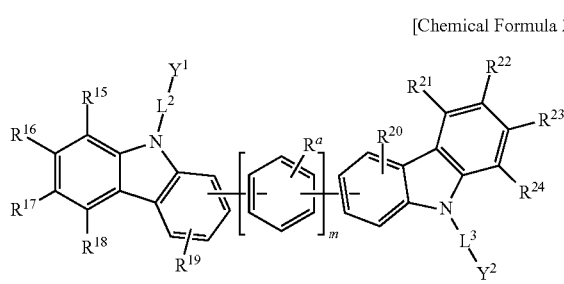

in Chemical Formula 2, $Y^1$ and $Y^2$ are each independently a substituted or unsubstituted C6 to C20 aryl group or a substituted or unsubstituted C2 to C30 heterocyclic group, $L^2$ and $L^3$ are each independently a single bond, or a substituted or unsubstituted C6 to C20 arylene group, $R^a$ and $R^{15}$ to $R^{24}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group, and m is an integer of 0 to 2;

[Chemcial Formula 2-8]

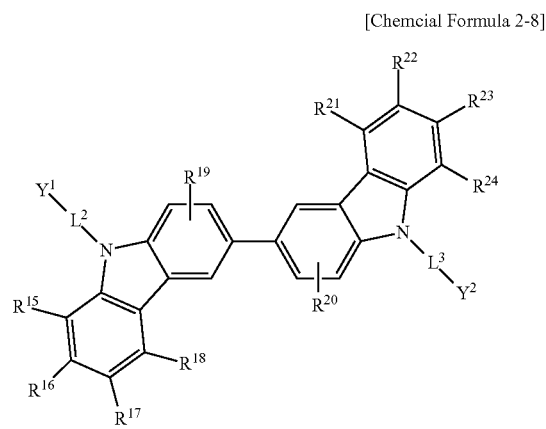

in Chemical Formula 2-8,
$R^{15}$ to $R^{24}$ are each independently hydrogen or a substituted or unsubstituted C6 to C12 aryl group, and
moieties *-$L^2$-$Y^1$ and *-$L^3$-$Y^2$ are each independently a moiety of Group II,
[Group II]
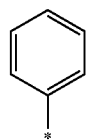
C-1
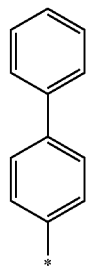
C-2
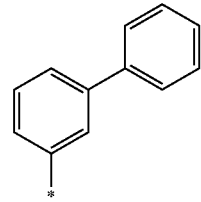
C-3
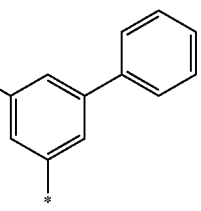
C-4
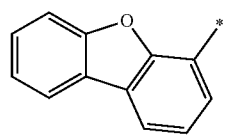
C-5
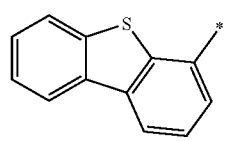
C-6
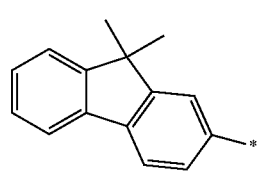
C-7
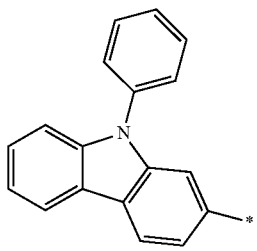
C-8
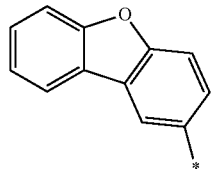
C-9
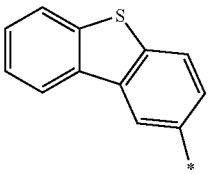
C-10
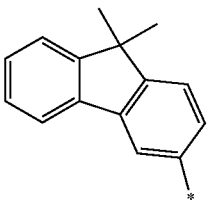
C-11
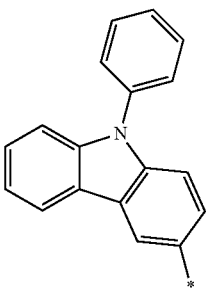
C-12
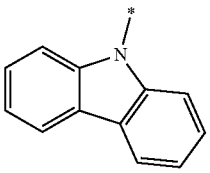
C-13
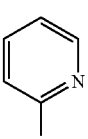
C-14
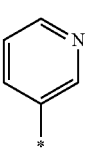
C-15

C-16 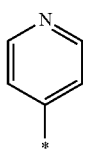
C-17 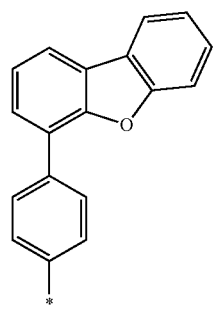
C-18 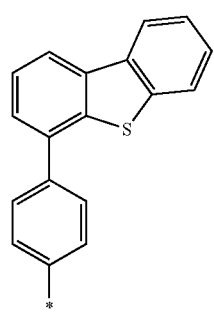
C-19 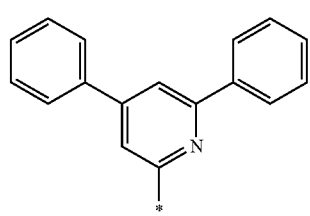
C-20 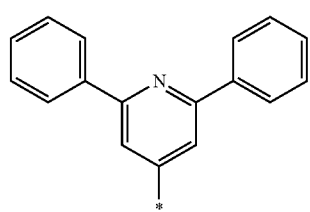
C-21 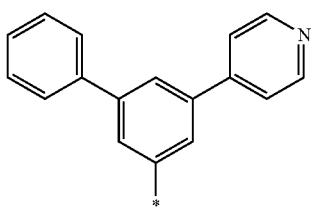
C-22 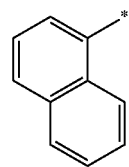
C-23 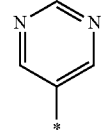
C-24 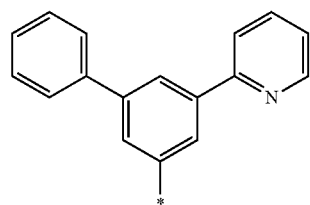
C-25 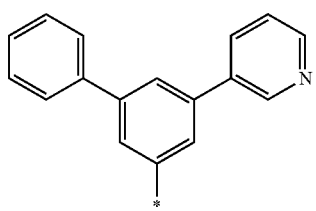
C-26 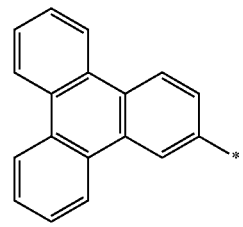
C-27 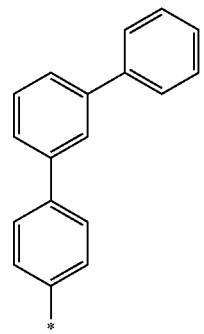
C-28 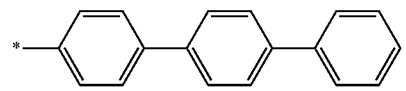
C-29 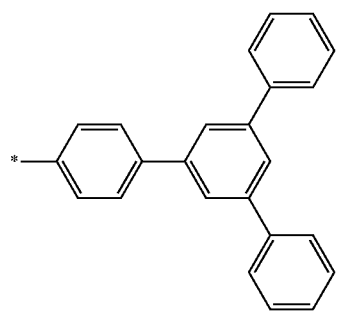

-continued

C-30

C-31

C-32

C-33

* is a linking point.

9. The composition as claimed in claim 7, wherein:
the second compound is represented by a combination of Chemical Formula 3 and Chemical Formula 4,
the combination of Chemical Formula 3 and Chemical Formula 4 is represented by Chemical Formula 3C:

[Chemical Formula 3C]

wherein, in Chemical Formula 3C,
$L^{a3}$ and $L^{a4}$ are each a single bond,
$L^4$ and $L^5$ are each independently a single bond or a substituted or unsubstituted C6 to C12 arylene group,
$R^{25}$ to $R^{32}$, $R^{b3}$, and $R^{b4}$ are each hydrogen, and
$Y^3$ and $Y^4$ are each independently a substituted or unsubstituted phenyl group, a substituted or unsubstituted naphthyl group, or a substituted or unsubstituted biphenyl group.

10. An organic optoelectronic device, comprising:
an anode and a cathode facing each other, and
at least one organic layer between the anode and the cathode,
wherein the at least one organic layer includes the composition for an organic optoelectronic device as claimed in claim 7.

11. The organic optoelectronic device as claimed in claim 10, wherein:
the at least one organic layer includes a light emitting layer, and
the light emitting layer includes the composition for an organic optoelectronic device.

12. A display device comprising the organic optoelectronic device as claimed in claim 10.

13. An organic optoelectronic device, comprising:
an anode and a cathode facing each other, and
at least one organic layer between the anode and the cathode,
wherein the at least one organic layer includes the compound for an organic optoelectronic device as claimed in claim 1.

14. The organic optoelectronic device as claimed in claim 13, wherein:
the at least one organic layer includes a light emitting layer, and
the light emitting layer includes the compound for an organic optoelectronic device.

15. A display device comprising the organic optoelectronic device as claimed in claim 10.

16. A composition for an organic optoelectronic device, the composition comprising a first compound and a second compound, wherein:
the first compound is represented by Chemical Formula 1:

[Chemical Formula 1]

in Chemical Formula 1,
X is O or S,
$L^1$ is a single bond or a substituted or unsubstituted C6 to C20 arylene group,
$R^1$ to $R^{12}$ are each independently hydrogen, deuterium, a substituted or unsubstituted C1 to C30 alkyl group, or a substituted or unsubstituted C6 to C20 aryl group,
$R^{13}$ and $R^{14}$ are each independently a substituted or unsubstituted C6 to C30 aryl group, a substituted or unsubstituted dibenzofuranyl group, or a substituted or unsubstituted dibenzothiophenyl group, and
$Ar^1$ is a substituted or unsubstituted C6 to C30 aryl group, and
the second compound is represented by Chemical Formula 2; or a combination of Chemical Formula 3 and Chemical Formula 4:

[Chemical Formula 2]

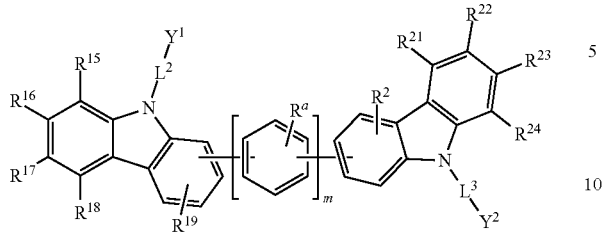

in Chemical Formula 2,
$Y^1$ and $Y^2$ are each independently a substituted or unsubstituted C6 to C20 aryl group or a substituted or unsubstituted C2 to C30 heterocyclic group,
$L^2$ and $L^3$ are each independently a single bond, or a substituted or unsubstituted C6 to C20 arylene group,
$R^a$ and $R^{15}$ to $R^{24}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group, and
m is an integer of 0 to 2;

[Chemical Formula 3]

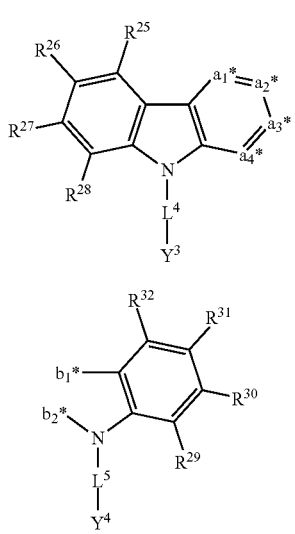

[Chemical Formula 4]

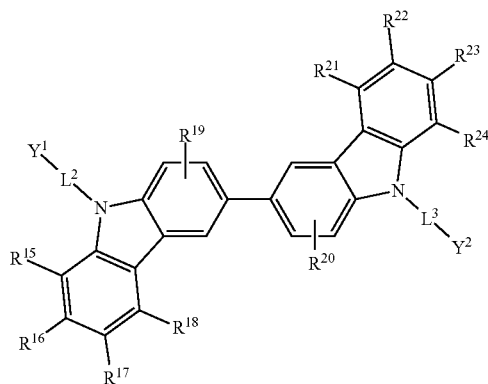

in Chemical Formula 3 and Chemical Formula 4,
$Y^3$ and $Y^4$ are each independently a substituted or unsubstituted C6 to C20 aryl group or a substituted or unsubstituted C2 to C30 heterocyclic group,
two adjacent ones of $a_1^*$ to $a_4^*$ of Chemical Formula 3 are linking carbons linked at $b_1^*$ and $b_2^*$ of Chemical Formula 4,
the remaining two of $a_1^*$ to $a_4^*$ of Chemical Formula 3, not linked at $b_1^*$ and $b_2^*$ of Chemical Formula 4, are each independently $C$-$L^a$-$R^b$,
$L^a$, $L^4$, and $L^5$ are each independently a single bond or a substituted or unsubstituted C6 to C20 arylene group, and
$R^b$ and $R^{25}$ to $R^{32}$ are each independently hydrogen, deuterium, a cyano group, a halogen, a substituted or unsubstituted amino group, a substituted or unsubstituted C1 to C30 alkyl group, a substituted or unsubstituted C6 to C30 aryl group, or a substituted or unsubstituted C2 to C30 heterocyclic group.

17. The composition as claimed in claim 16, wherein:
the second compound is represented by Chemical Formula 2,
Chemical Formula 2 is represented by Chemical Formula 2-8:

[Chemical Formula 2-8]

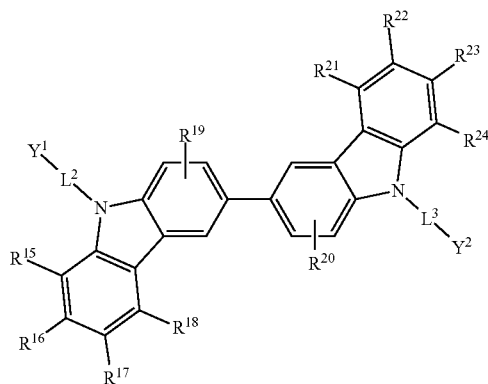

in Chemical Formula 2-8,
$R^{15}$ to $R^{24}$ are each independently hydrogen or a substituted or unsubstituted C6 to C12 aryl group, and
moieties *-$L^2$-$Y^1$ and *-$L^3$-$Y^2$ are each independently a moiety of Group II,

[Group II]

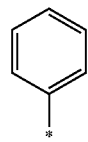
C-1

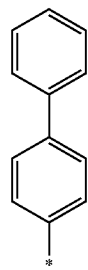
C-2

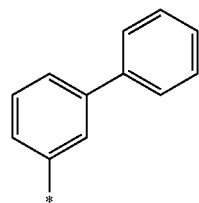
C-3

-continued

C-4

C-5

C-6

C-7

C-8

C-9

C-10

C-11

-continued

C-12

C-13

C-14

C-15

C-16

C-17

C-18

C-19
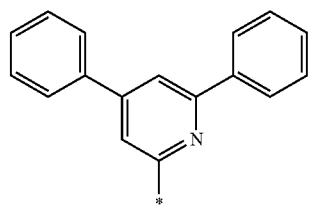
C-20
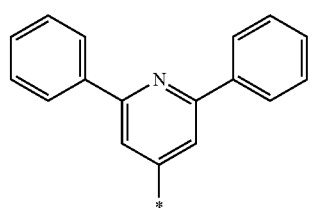
C-21
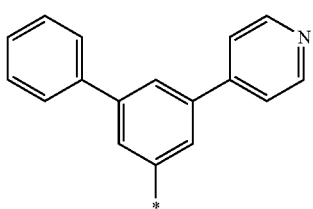
C-22
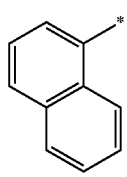
C-23
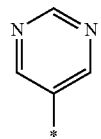
C-24
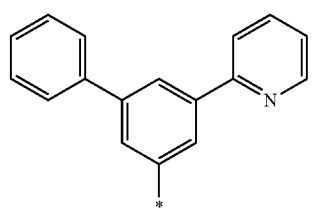
C-25
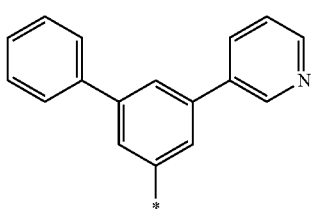
C-26
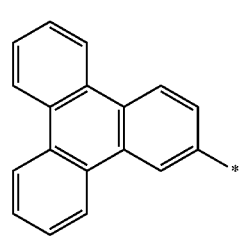
C-27
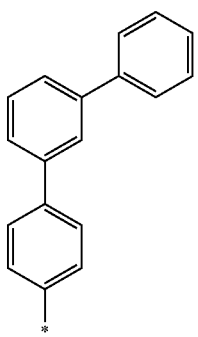
C-28
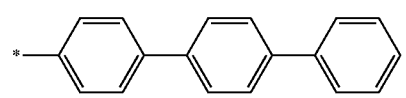
C-29
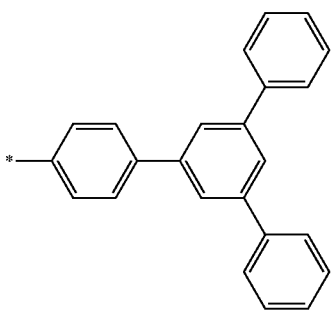
C-30
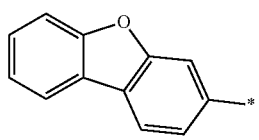
C-31
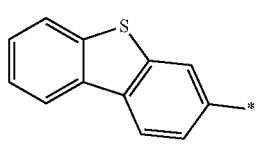
C-32
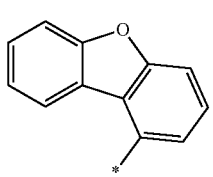
C-33
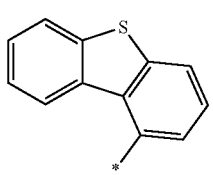
* is a linking point.
18. The composition as claimed in claim 16, wherein:
the second compound is represented by a combination of Chemical Formula 3 and Chemical Formula 4, the combination of Chemical Formula 3 and Chemical Formula 4 is represented by Chemical Formula 3C:

[Chemical Formula 3C]

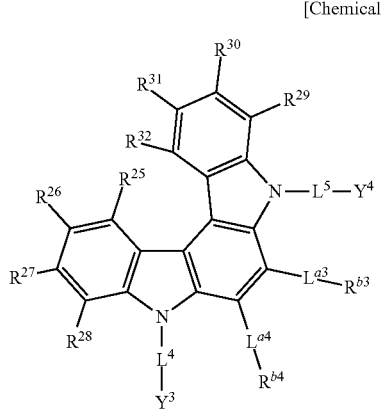

wherein, in Chemical Formula 3C, $L^{a3}$ and $L^{a4}$ are each a single bond, $L^4$ and $L^5$ are each independently a single bond or a substituted or unsubstituted C6 to C12 arylene group, $R^{25}$ to $R^{32}$, $R^{b3}$, and $R^{b4}$ are each hydrogen, and $Y^3$ and $Y^4$ are each independently a substituted or unsubstituted phenyl group, a substituted or unsubstituted naphthyl group, or a substituted or unsubstituted biphenyl group.

19. An organic optoelectronic device, comprising:

an anode and a cathode facing each other, and at least one organic layer between the anode and the cathode, wherein the at least one organic layer includes the composition for an organic optoelectronic device as claimed in claim 16.

20. A display device comprising the organic optoelectronic device as claimed in claim 19.

* * * * *